United States Patent
Binggeli et al.

(10) Patent No.: US 7,645,753 B2
(45) Date of Patent: *Jan. 12, 2010

(54) BENZOTHIAZOLE, THIAZOLOPYRIDINE, BENZOOXAZOLE AND OXAZOLOPYRIDINE DERIVATIVES

(75) Inventors: Alfred Binggeli, Binningen (CH); Andreas Dominik Christ, Arlesheim (CH); Luke Gideon Granville Green, Basel (CH); Wolfgang Guba, Muellheim (DE); Hans-Peter Maerki, Basel (CH); Rainer Eugen Martin, Basel (CH); Peter Mohr, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 580 days.

This patent is subject to a terminal disclaimer.

(21) Appl. No.: 11/366,516

(22) Filed: Mar. 2, 2006

(65) Prior Publication Data
US 2006/0205718 A1    Sep. 14, 2006

(30) Foreign Application Priority Data
Mar. 9, 2005    (EP)    .................................. 05101815

(51) Int. Cl.
*A61K 31/541*   (2006.01)
*A61K 31/5377*  (2006.01)
*A61K 31/4743*  (2006.01)
*A61K 31/4741*  (2006.01)
*C07D 498/02*   (2006.01)
*C07D 491/02*   (2006.01)

(52) U.S. Cl. .................. 514/227.8; 514/233.2; 514/301; 514/302; 546/114; 546/115; 544/60; 544/125

(58) Field of Classification Search ............... 546/114, 546/115; 544/60, 125; 514/227.8, 233.2, 514/301, 302
See application file for complete search history.

(56) References Cited
U.S. PATENT DOCUMENTS

2007/0093521 A1*  4/2007  Binggeli et al. ............. 514/301

FOREIGN PATENT DOCUMENTS

| EP | 0 184 257 A1 | 6/1986 |
| EP | 1 086 086 | 3/2001 |
| WO | WO 99/52875 | 10/1999 |
| WO | WO 2004/014885 A1 | 2/2004 |

OTHER PUBLICATIONS

Contour-Galcera, M.-O., et al., Bioorganic & Medicinal Chemistry Letters, vol. 11, No. 5, pp. 741-745 (2001).
Joslin's Diabetes Mellitus 13th Ed. (Eds. C. R. Kahn, G. C. Weir), Lea & Febiger, Malvern, PA, pp. 240-264.
H. E. Lebovitz, 1994, Oral antidiabetic agents. Joslin's Diabetes Mellitus 13th Ed. (Eds. C. R. Kahn, G. C. Weir), Lea & Febiger, Malvern, PA, pp. 508-529.
C. J. Bailey, M. R. C. Path, R. C. Turner *N. Engl. J. Med.* 1996, 334, 574-579.
G. L.Plosker, D. Faulds *Drugs* 1999, 57, 409-438.
Y. Zambre, et. al., Inhibition of human pancreatic islet insulin release by receptor-selective somatostatin analogs directed to somatostatin receptor subtype 5 in *Biochem. Pharmacol.* 1999, 57, 1159-1164.
S. P. Fagan, et. al., Insulin secretion is inhibited by subtype five somatostatin receptor in the mouse in *Surgery* 1998, 124, 254-258.
M. Norman, et. al., Sulfonylurea receptor knockout causes glucose intolerance in mice that is not alleviated by concomitant somatostatin subtype receptor 5 knockout in *Ann. Surg.* 2002, 235, 767-774.
T.A. Tirone, et. al., Pancreatic somatostatin inhibits insulin secretion via SSTR-5 in the isolated perfused mouse pancreas model in *Pancreas* 2003, 26, e67-73.
M. Z. Strowski, et. al., Somatostatin receptor subtype 5 regulates insulin secretion and glucose homeostasis in *Mol. Endocrinol.* 2003, 17, 93-106.
K. Cejvan, et. al., Intra-islet somatostatin regulates glucagon release via type 2 somatostatin receptors in rats in *Diabetes* 2003, 52, 1176-1181.
M. Z. Strowski, et. al., Somatostatin inhibits insulin and glucagon secretion via two receptor subtypes: an in vitro study of pancreatic islets from somatostatin receptor 2 knockout mice in *Endocrinology* 2000, 141, 111-117.
E. Näslund, et. al., *Int. J. Obes.* 1999, 23, 304-311.
J.-P. Gutzwiller, et. al., *Gut* 1999, 44, 81-88.
J.-P. Gutzwiller, et. al., *Am. J. Physiol.* 1999, 276, R1541-1544.

(Continued)

*Primary Examiner*—D. Margaret Seaman
*Assistant Examiner*—Niloofar Rahmani
(74) *Attorney, Agent, or Firm*—George W. Johnston; Dennis P. Tramaloni; Samuel H. Megerditchian

(57) ABSTRACT

This invention is concerned with compounds of the formula

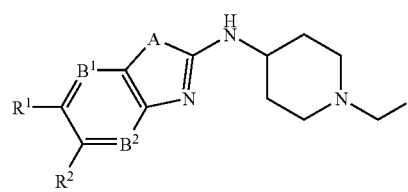

I wherein A, $B^1$, $B^2$, $R^1$, $R^2$ and G are as defined in the description and claims, and pharmaceutically acceptable salts thereof. The invention further relates to pharmaceutical compositions containing such compounds, to a process for their preparation and to their use for the treatment and/or prevention of diseases which are associated with the modulation of SST receptors subtype 5.

27 Claims, No Drawings

OTHER PUBLICATIONS

M. D. Turton, et. al., *Nature* 1996, 379, 69-72.
A. Flint, et. al., *J. Clin. Invest.* 1998, 101, 515-520.
M. B. Toft-Nielsen, et. al., *Diabetes Care* 1999, 22, 1137-1143.
L. Hansen, et. al., *Am. J. Phys.* 2000, 278, E1010-1018.
D. G. Burrin, et. al., *Domest. Anim. Endocrinol.* 2003, 24, 103-122.
K. V. Haderslev, et. al., *Scand. J. Gastroenterol.* 2002, 37, 392-398.
P. B. Jeppesen *J. Nutr.* 2003, 133, 3721-3724.
T. Talme, et. al., *Clin. Exp. Immunol.* 2001, 125, 71-79.
D. Ferone, et. al., *Dig. Liver Dis.* 2004, 36, S68-77.
C. E. Ghamrawy, et. al., *Peptides* 1999, 20, 305-311.

* cited by examiner

BENZOTHIAZOLE, THIAZOLOPYRIDINE, BENZOOXAZOLE AND OXAZOLOPYRIDINE DERIVATIVES

PRIORITY TO RELATED APPLICATIONS

This application claims the benefit of European Application No. 05101815.8, filed Mar. 9, 2005, which is hereby incorporated by reference in its entirety.

FIELD OF THE INVENTION

The present invention is directed to novel benzothiazole, thiazolopyridine, benzooxazole and oxazolopyridine derivatives, their manufacture, pharmaceutical compositions containing them and their use as medicaments. The active compounds of the present invention are useful in the prevention and/or treatment of diabetes mellitus and other disorders.

The present invention is preferably directed to compounds of formula I:

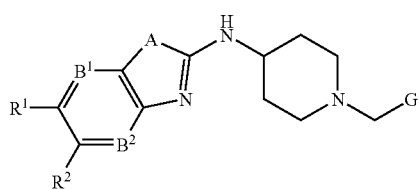

and pharmaceutically acceptable salts thereof.

The compounds of formula I possess pharmaceutical activity, in particular they are modulators of somatostatin receptor activity. More particularly, the compounds are antagonists of the somatostatin receptor subtype 5 (SSTR5).

All documents cited or relied upon herein are expressly incorporated herein by reference.

BACKGROUND OF THE INVENTION

Diabetes mellitus is a systemic disease characterized by metabolic disorders involving insulin, carbohydrates, fats and proteins, and disorders in the structure and function of blood vessels. The primary symptom of acute diabetes is hyperglycemia, often accompanied by glucosuria, the presence in urine of large amounts of glucose, and polyuria, the excretion of large volumes of urine. Additional symptoms arise in chronic diabetes, including degeneration of the walls of blood vessels. Although many different human organs are affected by these vascular changes, the eyes and kidneys appear to be the most susceptible. As such, long-standing diabetes mellitus, even when treated with insulin, is a leading cause of blindness.

There are three recognized types of diabetes mellitus. Type I diabetes or insulin dependent diabetes mellitus (IDDM) is typically of juvenile onset; ketosis develops early in life with much more severe symptoms and has a near-certain prospect of later vascular involvement. Control of Type I diabetes is difficult and requires exogenous insulin administration. Type II diabetes or non-insulin dependent diabetes mellitus (NIDDM) is ketosis-resistant, generally develops later in life, is milder and has a more gradual onset. Gestational diabetes is related to type II diabetes and associated with an increased risk of later development of that disease. Type III diabetes is malnutrition-related diabetes.

NIDDM is a condition that poses a major threat to the health of the citizens of the western world. NIDDM accounts for over 85% of diabetes incidence worldwide and about 160 million people are suffering from NIDDM. The incidence is expected to increase considerably within the next decades, especially in developing countries. NIDDM is associated with morbidity and premature mortality resulting from serious complications, e.g. cardiovascular disease (G. C. Weir, J. L. Leahy, 1994, Pathogenesis of non-insulin dependent (Type II) diabetes mellitus. Joslin's Diabetes Mellitus 13th Ed. (Eds. C. R. Kahn, G. C. Weir), Lea & Febiger, Malvern, Pa., pp. 240-264). NIDDM is characterized by both fasting and post-prandial hyperglycemia resulting from abnormalities in insulin secretion and insulin action (G. C. Weir et al., vide supra).

The hyperglycemia in patients suffering from NIDDM can usually be initially treated by dieting, but eventually most NIDDM patients have to take oral antidiabetic agents and/or insulin injections to normalize their blood glucose levels. The introduction of orally effective hypoglycemic agents was an important development in the treatment of hyperglycemia by lowering blood glucose levels. Currently, the most widely used oral antidiabetic agents are the sulfonylureas, which act by increasing the secretion of insulin from the pancreas (H. E. Lebovitz, 1994, Oral antidiabetic agents. Joslin's Diabetes Mellitus 13th Ed. (Eds. C. R. Kahn, G. C. Weir), Lea & Febiger, Malvern, Pa., pp. 508-529), the biguanides (e.g., metformin) which act on the liver and periphery by unknown mechanisms (C. J. Bailey, M. R. C. Path, R. C. Turner *N. Engl. J. Med.* 1996, 334, 574-579) and the thiazolidinediones (e.g., rosiglitazone/Avandia®) which enhance the effects of insulin at peripheral target sites (G. L. Plosker, D. Faulds *Drugs* 1999, 57, 409-438). These existing therapies which comprise a wide variety of biguanide, sulfonylurea and thiazolidinedione derivatives have been used clinically as hypoglycemic agents. However, all three classes of compound have side effects. The biguanides, for example metformin, are unspecific and in certain cases has been associated with lactic acidosis, and need to be given over a longer period of time, i.e. they are not suitable for acute administration (Bailey et al., vide supra). The sulfonylureas, though having good hypoglycemic activity, require great care during use because they frequently cause serious hypoglycemia and are most effective over a period of about ten years. The thiazolidinediones may cause weight gain following chronic administration (Plosker and Faulds, vide supra) and troglitazone has been associated with the occurrence of serious hepatic dysfunction.

Thus, there is a significant and rising need for antidiabetic drugs that have novel mechanisms of action, thereby avoiding side effects produced by known therapies. The hormone somatostatin (SST) is primarily produced in the intestinal tract and in the pancreas. In addition it acts as a neurotransmitter. The hormone is involved through its receptors in the regulation of several other hormones and in immunoregulation. In particular, SST suppresses the secretion of insulin by pancreatic β cells and the secretion of glucagon-like peptide 1 (GLP-1) by L cells. GLP-1 in turn is one of the most potent stimulators of insulin production and secretion and is a trophic factor for β cells. β and L cells express SST receptor subtype 5 (SSTR5) and agonizing this receptor suppresses insulin and GLP-1 secretion in humans and in animal models (e.g., Y. Zambre, Z. Ling, M.-C. Chen, X. Hou, C.-W. Woon, M. Culler, J. E. Taylor, D. H. Coy, C. van Schravendijk, F. Schuit, D. G. Pipeleers and D. L. Eizirik, *Inhibition of human pancreatic islet insulin release by receptor-selective somatostatin analogs directed to somatostatin receptor subtype 5* in *Biochem. Pharmacol.* 1999, 57, 1159-1164; S. P. Fagan, A.

Azizzadeh, S. Moldovan, M. K. Ray, T. E. Adrian, X. Ding, D. H. Coy and F. C. Brunicardi, *Insulin secretion is inhibited by subtype five somatostatin receptor in the mouse* in *Surgery* 1998, 124, 254-258; M. Norman, S. Moldovan, V. Seghers, X.-P. Wang, F. J. DeMayo and F. C. Brunicardi, *Sulfonylurea receptor knockout causes glucose intolerance in mice that is not alleviated by concomitant somatostatin subtype receptor 5 knockout* in *Ann. Surg.* 2002, 235, 767-774; T. A. Tirone, M. A. Norman, S. Moldovan, F. J. DeMayo, X.-P. Wang, F. C. Brunicardi, *Pancreatic somatostatin inhibits insulin secretion via SSTR-5 in the isolated perfused mouse pancreas model* in *Pancreas* 2003, 26, e67-73; M. Z. Strowski, M. Köhler, H. Y. Chen, M. E. Trumbauer, Z. Li, D. Szalkowski, S. Gopal-Truter, J. K. Fisher, J. M. Schaeffer, A. D. Blake, B. B. Zhang, H. A. Wilkinson, *Somatostatin receptor subtype 5 regulates insulin secretion and glucose homeostasis* in *Mol. Endocrinol.* 2003, 17, 93-106).

Consequently, antagonizing the effect of SST would lead to higher plasma insulin concentrations. In patients suffering from impaired glucose tolerance and NIDDM, a higher plasma insulin concentration would moderate the dangerous hyperglycemia and accordingly reduce the risk of tissue damage. If such SSTR5 antagonists are sufficiently selective over the other four SST receptors, little influence is expected on secretion of other hormones. Particularly, selectivity over SST receptor subtype 2 avoids influences on glucagon secretion (K. Cejvan, D. H. Coy, S. Efendic, *Intra-islet somatostatin regulates glucagon release via type 2 somatostatin receptors in rats* in *Diabetes* 2003, 52, 1176-1181; M. Z. Strowski, R. M. Parmar, A. D. Blake, J. M. Schaeffer, *Somatostatin inhibits insulin and glucagon secretion via two receptor subtypes: an in vitro study of pancreatic islets from somatostatin receptor 2 knockout mice* in *Endocrinology* 2000, 141, 111-117). Advantageous over established therapies is the dual mechanism of action to increase insulin secretion: directly on pancreatic β cells and indirectly through GLP-1 release from L cells. Additionally, SSTR5 knockout mice demonstrated higher insulin sensitivity than littermates (Strowski, Kohler et al, vide supra). Therefore, SSTR5 antagonists could have the potential to beneficially influence insulin resistance in patients with NIDDM. In summary, SSTR5 antagonists are expected to beneficially influence NIDDM, the underlying impaired fasting glucose and impaired glucose tolerance, as well as complications of long-standing, insufficiently controlled diabetes mellitus.

GLP-1 is known as an endogenous regulator of food intake reducing appetite as shown in laboratory animals, healthy volunteers and patients with NIDDM (E. Näslund, B. Barkeling, N. King, M. Gutniak, J. E. Blundell, J. J. Holst, S. Rössner, P. M. Hellström *Int. J. Obes.* 1999, 23, 304-311; J.-P. Gutzwiller, B. Göke, J. Drewe, P. Hildebrand, S. Ketterer, D. Handschin, R. Winterhalder, D. Conen, C. Beglinger *Gut* 1999, 44, 81-88; J.-P. Gutzwiller, J. Drewe, B. Göke, H. Schmidt, B. Rohrer, J. Lareida, C. Beglinger *Am. J. Physiol.* 1999, 276, R1541-1544; M. D. Turton, D. O'Shea, I. Gunn, S. A. Beak, C. M. Edwards, K. Meeran, S. J. Choi, G. M. Taylor, M. M. Heath, P. D. Lambert, J. P. Wilding, D. M. Smith, M. A. Ghatei, J. Herbert, S. R. Bloom *Nature* 1996, 379, 69-72; A. Flint, A. Raben, A. Astrup, J. J. Holst *J. Clin. Invest.* 1998, 101, 515-520; M. B. Toft-Nielsen, S. Madsbad, J. J. Holst *Diabetes Care* 1999, 22, 1137-1143); thus, elevated GLP-1 will also counteract obesity, a typical condition associated with and leading to NIDDM.

GLP-1 is co-secreted with GLP-2 that is, consequently, also regulated by SST through SSTR5 (L. Hansen, B. Hartmann, T. Bisgaard, H. Mineo, P. N. Jørgensen, J. J. Holst *Am. J. Phys.* 2000, 278, E1010-1018). GLP-2 is enterotrophic and beneficial in patients with malabsorption of certain origins, such as short bowel syndrome (D. G. Burrin, B. Stoll, X. Guan *Domest. Anim. Endocrinol.* 2003, 24, 103-122; K. V. Haderslev, P. B. Jeppesen, B. Hartmann, J. Thulesen, H. A. Sorensen, J. Graff, B. S. Hansen, F. Tofteng, S. S. Poulsen, J. L. Madsen, J. J. Holst, M. Staun, P. B. Mortensen *Scand. J. Gastroenterol.* 2002, 37, 392-398; P. B. Jeppesen *J. Nutr.* 2003, 133, 3721-3724).

Moreover, there is increasing evidence for a role of SST on immune cells and expression of SSTR5 on activated T lymphocytes (T. Talme, J. Ivanoff, M. Hägglund, R. J. J. van Neerven, A. Ivanoff, K. G. Sundqvist *Clin. Exp. Immunol.* 2001, 125, 71-79; D. Ferone, P. M. van Hagen, C. Semino, V. A. Dalm, A. Barreca, A. Colao, S. W. J. Lamberts, F. Minuto, L. J. Hofland *Dig. Liver Dis.* 2004, 36, S68-77, C. E. Ghamrawy, C. Rabourdin-Combe, S. Krantic *Peptides* 1999, 20, 305-311). Consequently, SSTR5 antagonists could also prove valuable in treating diseases characterized by a disturbed immune system, such as inflammatory bowel disease.

There is a need, therefore, for selective, directly acting SSTR5 antagonists. Such antagonists are useful as therapeutically active substances, particularly in the treatment and/or prevention of diseases which are associated with the modulation of SST receptors subtype 5.

SUMMARY OF THE INVENTION

In one embodiment of the present invention, provided is a compound of the formula I:

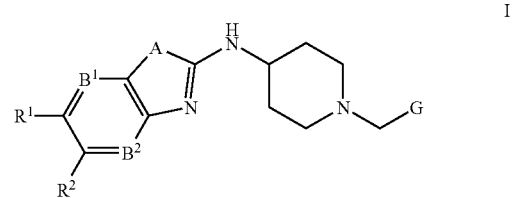

wherein
A is S or O;
$B^1$ is $CR^3$ and $B^2$ is $CR^4$, or
$B^1$ is N and $B^2$ is $CR^4$, or
$B^1$ is $CR^3$ and $B^2$ is N;
one of $R^1$ and $R^2$ is selected from hydrogen or halogen and the other one of $R^1$ and $R^2$ is selected from the group consisting of hydrogen, halogen, cyano, $-NR^5R^6$, $-CONR^7R^8$, $-NHCOR^9$, $-SO_2NR^{10}R^{11}$, $-SO_2R^2$, $-NHSO_2R^{13}$, halogen-$C_{1-7}$-alkoxy and nitro;
$R^5$ and $R^6$ independently from each other are selected from the group consisting of hydrogen, $C_{1-7}$-alkyl and $C_{3-7}$-cycloalkyl;
$R^7$ is selected from the group consisting of hydrogen, $C_{1-7}$-alkyl and $C_{3-7}$-cycloalkyl;
$R^8$ is selected from the group consisting of hydrogen, $C_{1-7}$-alkyl, $C_{3-7}$-cycloalkyl, unsubstituted phenyl, phenyl substituted by one to three groups selected from the group consisting of $C_{1-7}$-alkyl, $C_{3-7}$-cycloalkyl, $C_{1-7}$-alkoxy, halogen-$C_{1-7}$-alkyl and halogen, unsubstituted thienyl, thienyl substituted by one or two groups selected from the group consisting of $C_{1-7}$-alkyl and $C_{3-7}$-cycloalkyl, unsubstituted thiazolyl, thiazolyl substituted by one or two groups selected from $C_{1-7}$-alkyl and $C_{3-7}$-cycloalkyl, $C_{1-7}$-alkyl substituted with a group selected from the group consisting of $C_{3-7}$-cycloalkyl, unsubstituted phenyl, phenyl substituted by one to three groups selected from the group consisting of $C_{1-7}$-alkyl, $C_{3-7}$-cycloalkyl, $C_{1-7}$-alkoxy, halogen-$C_{1-7}$-alkyl and halogen, unsubstituted thienyl, thienyl substituted by one or two groups selected from $C_{1-7}$-alkyl and $C_{3-7}$-cycloalkyl, unsubstituted thiazolyl and thiazolyl substituted by one or two groups selected from $C_{1-7}$-alkyl and $C_{3-7}$-cycloalkyl; or $R^7$ and $R^8$ together with the nitrogen atom they are attached to form a morpholine ring;

$R^9$ is selected from the group consisting of $C_{1-7}$-alkyl, $C_{3-7}$-cycloalkyl, halogen-$C_{1-7}$-alkyl unsubstituted phenyl, phenyl substituted by one to three groups selected from the group consisting of $C_{1-7}$-alkyl, $C_{3-7}$-cycloalkyl, $C_{1-7}$-alkoxy, halogen-$C_{1-7}$-alkyl and halogen, unsubstituted heteroaryl, and heteroaryl substituted by one or two groups selected from the group consisting of $C_{1-7}$-alkyl, $C_{3-7}$-cycloalkyl, $C_{1-7}$-alkoxy, halogen-$C_{1-7}$-alkyl and halogen;

$R^{10}$ and $R^{11}$ independently from each other are selected from the group consisting of hydrogen, $C_{1-7}$-alkyl and $C_{3-7}$-cycloalcyl;

$R^{12}$ is $C_{1-7}$-alkyl or $C_{3-7}$-cycloalkyl;

$R^{13}$ is selected from the group consisting of $C_{1-7}$-alkyl, $C_{3-7}$-cycloalkyl, unsubstituted phenyl, phenyl substituted by one to three groups selected from the group consisting of $C_{1-7}$-alkyl, $C_{3-7}$-cycloalkyl, $C_{1-7}$-alkoxy, halogen-$C_{1-7}$-alkyl and halogen, unsubstituted heteroaryl, and heteroaryl substituted by one or two groups selected from the group consisting of $C_{1-7}$-alkyl, $C_{3-7}$-cycloalkyl, $C_{1-7}$-alkoxy, halogen-$C_{1-7}$-alkyl and halogen;

$R^3$ is selected from the group consisting of hydrogen, —$CONR^7R^8$ and —$CO_2R^a$;

$R^a$ is hydrogen or $C_{1-7}$-alkyl;

$R^4$ is hydrogen, and

G is

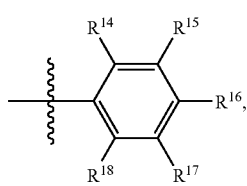

G1

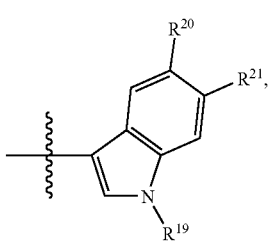

G2

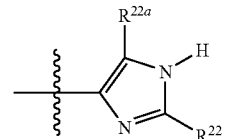

G3

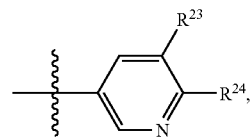

G4

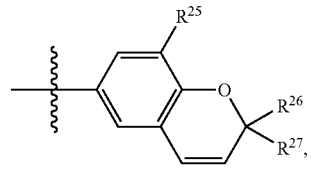

G5

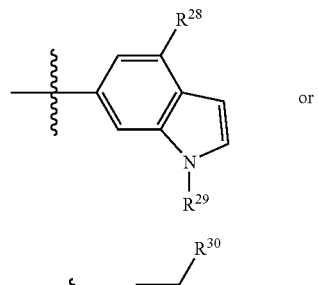

G6 or

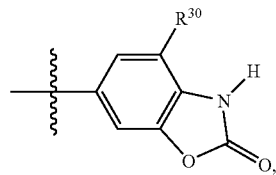

G7 wherein $R^{14}$ is selected from the group consisting of hydrogen, hydroxy, $C_{1-7}$-alkoxy and halogen;

$R^{15}$ is selected from the group consisting of $C_{1-7}$-alkoxy, $C_{2-7}$-alkenyloxy, $C_{3-7}$-cycloalkyloxy, —$NR^{31}R^{32}$, halogen-$C_{1-7}$-alkoxy, $C_{1-7}$-alkoxy-$C_{1-7}$-alkoxy, $C_{1-7}$-alkoxy-$C_{1-7}$-alkyl, and hydrogen, provided that not both of $R^{14}$ and $R^{15}$ are hydrogen;

$R^{31}$ and $R^{32}$ independently from each other are hydrogen or $C_{1-7}$-alkyl;

$R^{16}$ is selected from the group consisting of hydrogen, $C_{1-7}$-alkyl, halogen-$C_{1-7}$-alkyl, hydroxy, $C_{1-7}$-alkoxy, hydroxy-$C_{1-7}$-alkoxy, $C_{3-7}$-cycloalkyloxy, halogen, —$NR^{33}R^{34}$, $C_{1-7}$-alkylthio, pyrrolo, triazolo, —$CO_2R^{35}$, —$NHCOR^{35}$, —$OSO_2R^{35}$, —$SOR^{35}$, —$SO_2R^{35}$, unsubstituted phenyl, and phenyl substituted by halogen-$C_{1-7}$-alkyl or halogen;

$R^{33}$ and $R^{34}$ independently from each other are hydrogen or $C_{1-7}$-alkyl;

$R^{35}$ is $C_{1-7}$-alkyl;

or $R^{15}$ and $R^{16}$ together with the carbon atoms to which they are attached to form a phenyl ring;

$R^{17}$ is selected from the group consisting of hydrogen, hydroxy, $C_{1-7}$-alkoxy, halogen-$C_{1-7}$-alkoxy, hydroxy-$C_{1-7}$-alkoxy, nitro, —$NR^{36}R^{37}$, —$NHCOR^{38}$, —$NHSO_2R^{38}$, —SOR$^{38}$, —SO$_2$R$^{38}$, —O-tetrahydropyranyl, pyridyl, morpholinyl, thiomorpholinyl and 1,1-dioxothiomorpholinyl;

R$^{36}$ and R$^{37}$ independently from each other are hydrogen or C$_{1-7}$-alkyl;

R$^{38}$ is C$_{1-7}$-alkyl;

R$^{18}$ is selected from the group consisting of hydrogen, halogen, pyridyl, hydroxy, C$_{1-7}$-alkoxy and benzyloxy;

or R$^{17}$ and R$^{18}$ together with the carbon atoms to which they are attached to form a phenyl ring;

R$^{19}$ is C$_{1-7}$-alkyl or —CO$_2$R$^{39}$;

R$^{39}$ is C$_{1-7}$-alkyl;

R$^{20}$ and R$^{21}$ independently from each other are hydrogen or C$_{1-7}$-alkoxy, R$^{22}$ is phenyl unsubstituted or substituted by C$_{1-7}$-alkyl or —NHCOR$^{38}$;

R$^{22a}$ is hydrogen or C$_{1-7}$-alkyl;

R$^{23}$ and R$^{24}$ are hydrogen or C$_{1-7}$-alkoxy, provided that at least one of R$^{23}$ and R$^{24}$ is C$_{1-7}$-alkoxy;

R$^{25}$ is C$_{1-7}$-alkoxy;

R$^{26}$ and R$^{27}$ independently from each other are C$_{1-7}$-alkyl;

R$^{28}$ is C$_{1-7}$-alkoxy;

R$^{29}$ is hydrogen or C$_{1-7}$-alkyl;

R$^{30}$ is C$_{1-7}$-alkoxy;

and pharmaceutically acceptable salts thereof.

In another embodiment of the present invention, provided is a process for the manufacture of a compound according to formula I, comprising the steps of: reacting a compound of the general formula

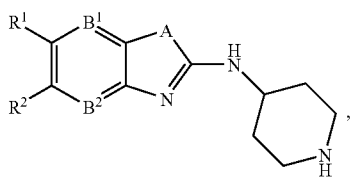

II wherein A, B$^1$, B$^2$, R$^1$ and R$^2$ are as defined above, with an aldehyde of the formula

III wherein G is as defined above, by employing a reducing agent to obtain a compound of the formula

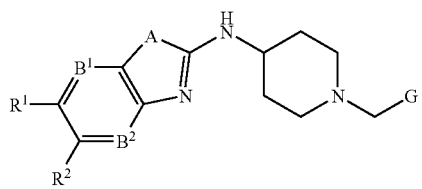

I and, if desired, converting the compound of formula I into a pharmaceutically acceptable salt.

In a further embodiment of the present invention, provided is a pharmaceutical composition, comprising a therapeutically effective amount of a compound according to formula I and a pharmaceutically acceptable carrier and/or adjuvant.

In a yet another embodiment of the present invention, provided is a method for the treatment and/or prevention of diseases which are associated with the modulation of SST receptors subtype 5, comprising the step of administering a therapeutically effective amount of a compound according to formula I to a human being or animal in need thereof.

DETAILED DESCRIPTION

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "C$_{1-7}$-alkyl", alone or in combination, signifies a straight-chain or branched-chain alkyl group with 1 to 7 carbon atoms, preferably a straight or branched-chain alkyl group with 1 to 4 carbon atoms. Examples of straight-chain and branched C$_1$-C$_7$ alkyl groups are methyl, ethyl, propyl, isopropyl, butyl, isobutyl, tert.-butyl, the isomeric pentyls, the isomeric hexyls and the isomeric heptyls, preferably methyl and ethyl and most preferred the groups specifically exemplified herein.

The term "cycloalkyl" or "C$_{3-7}$-cycloalkyl" denotes a saturated carbocyclic group containing from 3 to 7 carbon atoms, such as cyclopropyl, cyclobutyl, cyclopentyl, cyclohexyl or cycloheptyl.

The term "alkoxy" refers to the group R'—O—, wherein R' is alkyl. The term "lower alkoxy" or "C$_{1-7}$-alkoxy"refers to the group R'—O—, wherein R' is lower alkyl and the term "lower alkyl" has the previously given significance. Examples of lower alkoxy groups are e.g., methoxy, ethoxy, n-propoxy, isopropoxy, n-butoxy, iso-butoxy, sec-butoxy and tert-butoxy, preferably methoxy and ethoxy and most preferred the groups specifically exemplified herein.

The term "lower alkoxyalkyl" or "C$_{1-7}$-alkoxy-C$_{1-7}$-alkyl" refers to lower alkyl groups as defined above wherein at least one of the hydrogen atoms of the lower alkyl group is replaced by an alkoxy group as defined above. Among the preferred lower alkoxyalkyl groups are methoxymethyl, methoxyethyl and ethoxymethyl.

The term "lower alkoxyalkoxy" or "C$_{1-7}$-alkoxy-C$_{1-7}$-alkoxy" refers to lower alkoxy groups as defined above wherein at least one of the hydrogen atoms of the lower alkoxy group is replaced by an alkoxy group as defined above. Among the preferred lower alkoxyalkoxy groups are 2-methoxy-ethoxy and 3-methoxy-propoxy.

The term "halogen" refers to fluorine, chlorine, bromine and iodine, with fluorine, chlorine and bromine being preferred.

The term "lower halogenalkyl" or "halogen-C$_{1-7}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with trifluoromethyl being especially preferred.

The term "lower halogenalkoxy" or "halogen-C$_{1-7}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluormethoxy and chloromethoxy, with trifluoromethoxy being especially preferred.

The term "lower hydroxyalkoxy" or hydroxy-$C_{1-7}$-alkoxy" refers to lower alkoxy groups as defined above wherein at least one of the hydrogen atoms of the lower alkoxy group is replaced by a hydroxy group. Examples of lower hydroxyalkoxy groups are hydroxymethoxy or hydroxyethoxy.

The term "alkylthio" or "$C_{1-7}$-alkylthio" refers to the group R'—S—, wherein R' is lower alkyl and the term "lower alkyl" has the previously given significance. Alternatively, this group can also be named as "alkylsulfanyl" or "$C_{1-7}$-alkylsulfanyl". Examples of alkylthio groups are e.g. methylsulfanyl or ethylsulfanyl.

The term "heteroaryl" refers to an aromatic 5- or 6-membered ring which can comprise 1, 2 or 3 atoms selected from nitrogen, oxygen and/or sulphur such as furyl, pyrrolyl, thienyl, 1H-imidazolyl, 2H-imidazolyl, 4H-imidazolyl, 1H-pyrazolyl, 3H-pyrazolyl, 4H-pyrazolyl, 1,2-oxazolyl (isoxazolyl), 1,3-oxazolyl, 1H-[1,2,4]triazolyl, 4H-[1,2,4]triazolyl, 1H-[1,2,3]triazolyl, 2H-[1,2,3]triazolyl, 4H-[1,2,3]triazolyl, [1,2,4]oxadiazolyl, [1,3,4]oxadiazolyl, [1,2,3]oxadiazolyl, 1H-tetrazolyl, 2H-tetrazolyl, [1,2,3,4]oxatriazolyl, [1,2,3,5]oxatriazolyl, 1,3-thiazolyl, 1,2-thiazolyl(isothiazolyl), 1H-pentazolyl, pyridyl, pyrazinyl, pyrimidinyl, pyridazinyl, indolyl, quinolinyl and their dihydro derivatives. The term "heteroaryl" further refers to bicyclic aromatic groups comprising two 5- or 6-membered rings, in which one or both rings can contain 1, 2 or 3 atoms selected from nitrogen, oxygen or sulphur such as e.g., indole or quinoline, or partially hydrogenated bicyclic aromatic groups such as e.g., indolinyl. Preferred heteroaryl groups are pyrrolyl and [1,2,4]oxadiazolyl. A heteroaryl group may optionally be mono- or multiply-substituted, particularly mono- or di-substituted by $C_{1-7}$-alkyl, $C_{3-7}$-cycloalkyl, $C_{1-7}$-alkoxy, halogen-$C_{1-7}$-alkyl or halogen. Preferred heteroaryl groups are e.g., thienyl, thiazolyl and imidazolyl, which can optionally be substituted as described above, preferably with $C_{1-7}$-alkyl.

The term "triazolo" means a group selected from 1H-[1,2,4]triazolyl, 4H-[1,2,4]triazolyl, 1H-[1,2,3]triazolyl, 2H-[1,2,3]triazolyl and 4H-[1,2,3]triazolyl. Preferred is 1H-[1,2,4]triazolyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g., hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In detail, the present invention relates to the general formula I

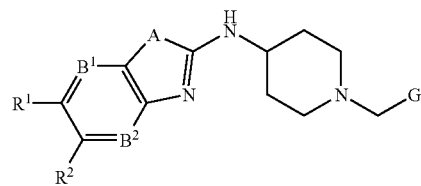

I wherein
A is S or O;
$B^1$ is $CR^3$ and $B^2$ is $CR^4$, or
  $B^1$ is N and $B^2$ is $CR^4$, or
  $B^1$ is $CR^3$ and $B^2$ is N;

one of $R^1$ and $R^2$ is selected from hydrogen or halogen and the other one of $R^1$ and $R^2$ is selected from the group consisting of hydrogen, halogen, cyano, —$NR^5R^6$, —$CONR^7R^8$, —$NHCOR^9$, —$SO_2NR^{10}R^{11}$, —$SO_2R^{12}$, —$NHSO_2R^{13}$, halogen-$C_{1-7}$-alkoxy and nitro;

$R^5$ and $R^6$ independently from each other are selected from the group consisting of hydrogen, $C_{1-7}$-alkyl and $C_{3-7}$-cycloalkyl;

$R^7$ is selected from the group consisting of hydrogen, $C_{1-7}$-alkyl and $C_{3-7}$-cycloalkyl;

$R^8$ is selected from the group consisting of hydrogen, $C_{1-7}$-alkyl, $C_{3-7}$-cycloalkyl, unsubstituted phenyl, phenyl substituted by one to three groups selected from the group consisting of $C_{1-7}$-alkyl, $C_{3-7}$-cycloalkyl, $C_{1-7}$-alkoxy, halogen-$C_{1-7}$-alkyl and halogen, unsubstituted thienyl, thienyl substituted by one or two groups selected from the group consisting of $C_{1-7}$-alkyl and $C_{3-7}$-cycloalkyl, unsubstituted thiazolyl, thiazolyl substituted by one or two groups selected from $C_{1-7}$-alkyl and $C_{3-7}$-cycloalkyl, $C_{1-7}$-alkyl substituted with a group selected from the group consisting of $C_{3-7}$-cycloalkyl, unsubstituted phenyl, phenyl substituted by one to three groups selected from the group consisting of $C_{1-7}$-alkyl, $C_{3-7}$-cycloalkyl, $C_{1-7}$-alkoxy, halogen-$C_{1-7}$-alkyl and halogen, unsubstituted thienyl, substituted thienyl substituted by one or two groups selected from $C_{1-7}$-alkyl and $C_{3-7}$-cycloalkyl, unsubstituted thiazolyl and thiazolyl substituted by one or two groups selected from $C_{1-7}$-alkyl and $C_{3-7}$-cycloalkyl; or $R^7$ and $R^8$ together with the nitrogen atom they are attached to form a morpholine ring;

$R^9$ is selected from the group consisting of $C_{1-7}$-alkyl, $C_{3-7}$-cycloallyl, halogen-$C_{1-7}$-alkyl unsubstituted phenyl, phenyl substituted by one to three groups selected from the group consisting of $C_{1-7}$-alkyl, $C_{3-7}$-cycloalkyl, $C_{1-7}$-alkoxy, halogen-$C_{1-7}$-alkyl and halogen, unsubstituted heteroaryl and heteroaryl substituted by one or two groups selected from the group consisting of $C_{1-7}$-alkyl, $C_{3-7}$-cycloalkyl, $C_{1-7}$-alkoxy, halogen-$C_{1-7}$-alkyl and halogen;

$R^{10}$ and $R^{11}$ independently from each other are selected from the group consisting of hydrogen, $C_{1-7}$-alkyl and $C_{3-7}$-cycloalkyl;

$R^{12}$ is $C_{1-7}$-alkyl or $C_{3-7}$-cycloalkyl;

$R^{13}$ is selected from the group consisting of $C_{1-7}$-alkyl, $C_{3-7}$-cycloalkyl, unsubstituted phenyl, phenyl substituted by one to three groups selected from the group consisting of $C_{1-7}$-alkyl, $C_{3-7}$-cycloalkyl, $C_{1-7}$-alkoxy, halogen-$C_{1-7}$-alkyl and halogen, unsubstituted heteroaryl and heteroaryl substituted by one or two groups selected from the group consisting of $C_{1-7}$-alkyl, $C_{3-7}$-cycloalkyl, $C_{1-7}$-alkoxy, halogen-$C_{1-7}$-alkyl and halogen;

$R^3$ is selected from the group consisting of hydrogen, —$CONR^7R^8$ and —$CO_2R^a$;

$R^a$ is hydrogen or $C_{1-7}$-alkyl;

$R^4$ is hydrogen, and

G is selected from the groups

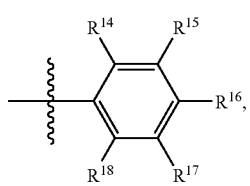

G1

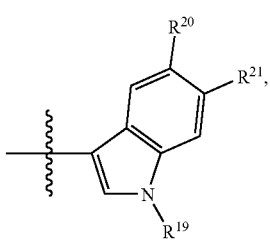

G2

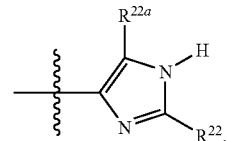

G3

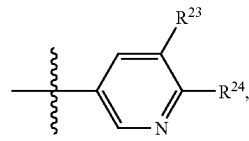

G4

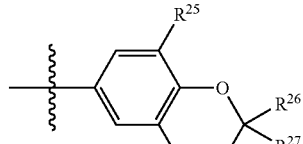

G5

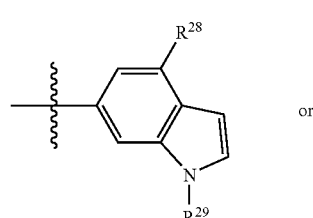

G6 or

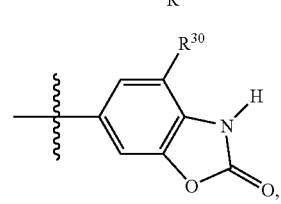

G7 wherein $R^{14}$ is selected from the group consisting of hydrogen, hydroxy, $C_{1-7}$-alkoxy and halogen;

$R^{15}$ is selected from the group consisting of $C_{1-7}$-alkoxy, $C_{2-7}$-alkenyloxy, $C_{3-7}$-cycloalkyloxy, —$NR^{31}R^{32}$, halogen-$C_{1-7}$-alkoxy, $C_{1-7}$-alkoxy-$C_{1-7}$-alkoxy, $C_{1-7}$-alkoxy-$C_{1-7}$-alkyl, and hydrogen, provided that not both of $R^{14}$ and $R^{15}$ are hydrogen;

$R^{31}$ and $R^{32}$ independently from each other are hydrogen or $C_{1-7}$-alkyl;

$R^{16}$ is selected from the group consisting of hydrogen, $C_{1-7}$-alkyl, halogen-$C_{1-7}$-alkyl, hydroxy, $C_{1-7}$-alkoxy, hydroxy-$C_{1-7}$-alkoxy, $C_{3-7}$-cycloalkyloxy, halogen, —$NR^{33}R^{34}$, $C_{1-7}$-alkylthio, pyrrolo, triazolo, —$CO_2R^{35}$, —$NHCOR^{35}$, —$OSO_2R^3$, —$SOR^{35}$, —$SO_2R^{35}$, unsubstituted phenyl and phenyl substituted by halogen-$C_{1-7}$-alkyl or halogen;

$R^{33}$ and $R^{34}$ independently from each other are hydrogen or $C_{1-7}$-alkyl;

$R^{35}$ is $C_{1-7}$-alkyl;

or $R^{15}$ and $R^{16}$ together with the carbon atoms to which they are attached to form a phenyl ring;

$R^{17}$ is selected from the group consisting of hydrogen, hydroxy, $C_{1-7}$-alkoxy, halogen-$C_{1-7}$-alkoxy, hydroxy-$C_{1-7}$-alkoxy, nitro, —$NR^{36}R^{37}$, —$NHCOR^{38}$, —$NHSO_2R^{38}$, —SOR$^{38}$, —SO$_2$R$^{38}$, —O-tetrahydropyranyl, pyridyl, morpholinyl, thiomorpholinyl and 1,1-dioxothiomorpholinyl;

R$^{36}$ and R$^{37}$ independently from each other are hydrogen or C$_{1-7}$-alkyl;

R$^{38}$ is C$_{1-7}$-alkyl;

R$^{18}$ is selected from the group consisting of hydrogen, halogen, pyridyl, hydroxy, C$_{1-7}$-alkoxy and benzyloxy;

or R$^{17}$ and R$^{18}$ together with the carbon atoms to which they are attached to form a phenyl ring;

R$^{19}$ is C$_{1-7}$-alkyl or —CO$_2$R$^{39}$;

R$^{39}$ is C$_{1-7}$-alkyl;

R$^{20}$ and R$^{21}$ independently from each other are hydrogen or C$_{1-7}$-alkoxy;

R$^{22}$ is phenyl unsubstituted or substituted by C$_{1-7}$-alkyl or —NHCOR$^{38}$;

R$^{22a}$ is hydrogen or C$_{1-7}$-alkyl;

R$^{23}$ and R$^{24}$ are hydrogen or C$_{1-7}$-alkoxy, provided that at least one of R$^{23}$ and R$^{24}$ is C$_{1-7}$-alkoxy;

R$^{25}$ is C$_{1-7}$-alkoxy;

R$^{26}$ and R$^{27}$ independently from each other are C$_{1-7}$-alkyl;

R$^{28}$ is C$_{1-7}$-alkoxy;

R$^{29}$ is hydrogen or C$_{1-7}$-alkyl;

R$^{30}$ is C$_{1-7}$-alkoxy;

and pharmaceutically acceptable salts thereof.

Preferred compounds of formula I according to the present invention are those, wherein A is S or O;

B$^1$ is CR$^3$ and B$^2$ is CR$^4$, or

B$^1$ is N and B$^2$ is CH, or

B$^1$ is CH and B$^2$ is N;

one of R$^1$ and R$^2$ is selected from hydrogen or halogen and the other one of R$^1$ and R$^2$ is selected from the group consisting of hydrogen, halogen, —NR$^5$R$^6$, —CONR$^7$R$^8$, —NHCOR$^9$, —SO$_2$NR$^{10}$R$^{11}$, —SO$_2$R$^{12}$, —NHSO$_2$R$^{13}$, halogen-C$_{1-7}$-alkoxy and nitro;

R$^5$ and R$^6$ independently from each other are selected from the group consisting of hydrogen, C$_{1-7}$-alkyl and C$_{3-7}$-cycloalkyl;

R$^7$ is selected from the group consisting of hydrogen, C$_{1-7}$-alkyl and C$_{3-7}$-cycloalkyl;

R$^8$ is selected from the group consisting of hydrogen, C$_{1-7}$-alkyl, C$_{3-7}$-cycloalkyl, unsubstituted phenyl or phenyl substituted by one to three groups selected from C$_{1-7}$-alkyl, C$_{3-7}$-cycloalkyl, C$_{1-7}$-alkoxy, halogen-C$_{1-7}$-alkyl or halogen, unsubstituted thienyl or thienyl substituted by one or two groups selected from C$_{1-7}$-alkyl or C$_{3-7}$-cycloalkyl, unsubstituted thiazolyl or thiazolyl substituted by one or two groups selected from C$_{1-7}$-alkyl or C$_{3-7}$-cycloalkyl, C$_{1-7}$-alkyl substituted with a group selected from the group consisting of C$_{3-7}$-cycloalkyl, unsubstituted phenyl or phenyl substituted by one to three groups selected from C$_{1-7}$-alkyl, C$_{3-7}$-cycloalkyl, C$_{1-7}$-alkoxy, halogen-C$_{1-7}$-alkyl or halogen, unsubstituted thienyl or substituted thienyl substituted by one or two groups selected from C$_{1-7}$-alkyl or C$_{3-7}$-cycloalkyl, unsubstituted thiazolyl and thiazolyl substituted by one or two groups selected from C$_{1-7}$-alkyl or C$_{3-7}$-cycloalkyl; or R$^7$ and R$^8$ together with the nitrogen atom they are attached to form a morpholine ring;

R$^9$ is selected from the group consisting of C$_{1-7}$-alkyl, C$_{3-7}$-cycloalkyl, halogen-C$_{1-7}$-alkyl, unsubstituted phenyl, phenyl substituted by one to three groups selected from the group consisting of C$_{1-7}$-alkyl, C$_{3-7}$-cycloalkyl, C$_{1-7}$-alkoxy, halogen-C$_{1-7}$-alkyl and halogen, unsubstituted heteroaryl and heteroaryl substituted by one or two groups selected from C$_{1-7}$-alkyl, C$_{3-7}$-cycloalkyl, C$_{1-7}$-alkoxy, halogen-C$_{1-7}$-alkyl or halogen;

R$^{10}$ and R$^{11}$ independently from each other are selected from the group consisting of hydrogen, C$_{1-7}$-alkyl and C$_{3-7}$-cycloalkyl;

R$^{12}$ is C$_{1-7}$-alkyl or C$_{3-7}$-cycloalkyl;

R$^{13}$ is selected from the group consisting of C$_{1-7}$-alkyl, C$_{3-7}$-cycloalkyl, unsubstituted phenyl, phenyl substituted by one to three groups selected from C$_{1-7}$-alkyl, C$_{3-7}$-cycloalkyl, C$_{1-7}$-alkoxy, halogen-C$_{1-7}$-alkyl or halogen, unsubstituted heteroaryl and heteroaryl substituted by one or two groups selected from C$_{1-7}$-alkyl, C$_{3-7}$-cycloalkyl, C$_{1-7}$-alkoxy, halogen-C$_{1-7}$-alkyl or halogen;

R$^3$ is hydrogen or —CONR$^7$R$^8$;

R$^4$ is hydrogen, and

G is selected from the groups

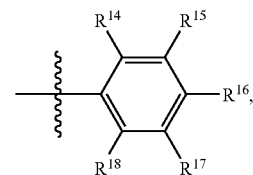

G1

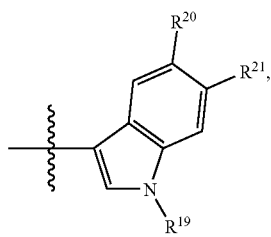

G2

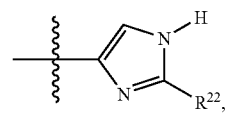

G3a

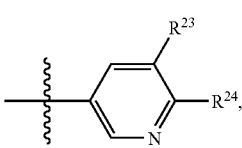

G4

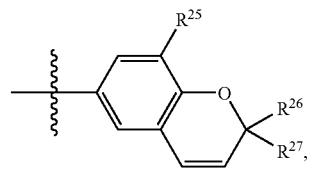

G5

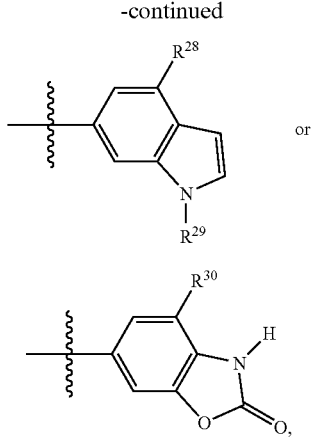

wherein
R$^{14}$ is selected from the group consisting of hydrogen, hydroxy, C$_{1-7}$-alkoxy and halogen;
R$^{15}$ is selected from the group consisting of C$_{1-7}$-alkoxy, C$_{2-7}$-alkenyloxy, C$_{3-7}$-cycloalkyloxy, —NR$^{31}$R$^{32}$, halogen-C$_{1-7}$-alkoxy, C$_{1-7}$-alkoxy-C$_{1-7}$-alkoxy, C$_{1-7}$-alkoxy-C$_{1-7}$-alkyl, and hydrogen, provided that not both of R$^{14}$ and R$^{15}$ are hydrogen;
R$^{31}$ and R$^{32}$ independently from each other are hydrogen or C$_{1-7}$-alkyl;
R$^{16}$ is selected from the group consisting of hydrogen, C$_{1-7}$-alkyl, halogen-C$_{1-7}$-alkyl, hydroxy, C$_{1-7}$-alkoxy, hydroxy-C$_{1-7}$-alkoxy, C$_{3-7}$-cycloalkyloxy, halogen, —NR$^{33}$R$^{34}$, C$_{1-7}$-alkylthio, pyrrolo, —CO$_2$R$^{35}$, —NHCOR$^{35}$, —OSO$_2$R$^{35}$, —SOR$^{35}$ and —SO$_2$R$^{35}$;
R$^{33}$ and R$^{34}$ independently from each other are hydrogen or C$_{1-7}$-alkyl;
R$^{35}$ is C$_{1-7}$-alkyl; or R$^{15}$ and R$^{16}$ together with the carbon atoms to which they are attached to form a phenyl ring;
R$^{17}$ is selected from the group consisting of hydrogen, hydroxy, C$_{1-7}$-alkoxy, halogen-C$_{1-7}$-alkoxy, hydroxy-C$_{1-7}$-alkoxy, nitro, —NR$^{36}$R$^{37}$, —NHCOR$^{38}$, —NHSO$_2$R$^{38}$, —SOR$^{38}$, —SO$_2$R$^{38}$, —O-tetrahydropyranyl, pyridyl, morpholinyl, thiomorpholinyl and 1,1-dioxothiomorpholinyl;
R$^{36}$ and R$^{37}$ independently from each other are hydrogen or C$_{1-7}$-alkyl;
R$^{38}$ is C$_{1-7}$-alkyl;
R$^{18}$ is selected from the group consisting of hydrogen, halogen, pyridyl, hydroxy, C$_{1-7}$-alkoxy and benzyloxy;

or R$^{17}$ and R$^{18}$ together with the carbon atoms to which they are attached to form a phenyl ring;
R$^{19}$ is C$_{1-7}$-alkyl or —CO$_2$R$^{39}$;
R$^{39}$ is C$_{1-7}$-alkyl;
R$^{20}$ and R$^{21}$ independently from each other are hydrogen or C$_{1-7}$-alkoxy,
R$^{22}$ is phenyl;
R$^{23}$ and R$^{24}$ are hydrogen or C$_{1-7}$-alkoxy, provided that at least one of R$^{23}$ and R$^{24}$ is C$_{1-7}$-alkoxy;
R$^{25}$ is C$_{1-7}$-alkoxy;
R$^{26}$ and R$^{27}$ independently from each other are C$_{1-7}$-alkyl;
R$^{28}$ is C$_{1-7}$-alkoxy;
R$^{29}$ is hydrogen or C$_{1-7}$-alkyl;
R$^{30}$ is C$_{1-7}$-alkoxy;

and pharmaceutically acceptable salts thereof.

Preferred compounds of formula I of the present invention are also those, wherein A is O.

Also preferred are compounds of formula I, wherein A is S.

Furthermore, compounds of formula I according to the present invention are preferred, wherein B$^1$ is CR$^3$ and B$^2$ is CR$^4$ and wherein R$^3$ is hydrogen or —CONR$^7$R$^8$ and R$^4$ is hydrogen.

In addition, compounds of formula in accordance of the invention are preferred, wherein B$^1$ is CR$^3$ and B$^2$ is CR$^4$ and wherein R$^4$ is hydrogen and R$^3$ is CO$_2$R$^a$ with R$^a$ being hydrogen or C$_{1-7}$-alkyl.

More preferably, compounds of formula I are those, wherein B$^1$ is CR$^3$, B$^2$ is CR$^4$ and R$^3$ and R$^4$ are hydrogen.

Another group of preferred compounds of formula I are those, wherein R$^4$ is hydrogen and R$^3$ is —CONR$^7$R$^8$, wherein R$^7$ is selected from the group consisting of hydrogen, C$_{1-7}$-alkyl and C$_{3-7}$-cycloalkyl;
R$^8$ is selected from the group consisting of hydrogen, C$_{1-7}$-alkyl, C$_{3-7}$-cycloalkyl, unsubstituted phenyl or phenyl substituted by one to three groups selected from C$_{1-7}$-alkyl, C$_{3-7}$-cycloalkyl, C$_{1-7}$-alkoxy, halogen-C$_{1-7}$-alkyl or halogen, unsubstituted thienyl or thienyl substituted by one or two groups selected from C$_{1-7}$-alkyl or C$_{3-7}$-cycloalkyl, unsubstituted thiazolyl or thiazolyl substituted by one or two groups selected from C$_{1-7}$-alkyl or C$_{3-7}$-cycloalkyl, C$_{1-7}$-alkyl substituted with a group selected from the group consisting of $_{3-7}$-cycloalkyl, unsubstituted phenyl or phenyl substituted by one to three groups selected from C$_{1-7}$-alkyl, C$_{3-7}$-cycloalkyl, C$_{1-7}$-alkoxy, halogen-C$_{1-7}$-alkyl or halogen, unsubstituted thienyl or substituted thienyl substituted by one or two groups selected from C$_{1-7}$-alkyl or C$_{3-7}$-cycloalkyl, unsubstituted thiazolyl and thiazolyl substituted by one or two groups selected from C$_{1-7}$-alkyl or C$_{3-7}$-cycloalkyl; or
R$^7$ and R$^8$ together with the nitrogen atom they are attached to form a morpholine ring.

Within this group, compounds of formula I are especially preferred, wherein R$^3$ is —CONR$^7$R$^8$, R$^7$ is hydrogen and R$^8$ is unsubstituted thiazolyl or thiazolyl substituted by one or two groups selected from C$_{1-7}$-alkyl or C$_{3-7}$-cycloalkyl.

Also preferred are compounds of formula I according to the present invention, wherein B$^1$ is N and B$^2$ is CH, with those compounds, wherein B$^1$ is N, B$^2$ is CH and A is S being more preferred, and with those compounds, wherein B$^1$ is N, B$^2$ is CH, A is S and R$^1$ and R$^2$ are hydrogen, being especially preferred.

Furthermore, compounds of formula I according to the present invention are preferred, wherein B$^1$ is CH and B$^2$ is N. More preferably, B$^1$ is CH, B$^2$ is N and A is O. Especially preferred are those compounds of formula 1, wherein B$^1$ is CH, B$^2$ is N, A is O and R$^1$ and R$^2$ are hydrogen.

Compounds of formula I of the present invention, wherein R$^1$ and R$^2$ are hydrogen, are especially preferred.

Furthermore, compounds of formula I are preferred, wherein one of R$^1$ and R$^2$ is selected from hydrogen or halogen and the other one of R$^1$ and R$^2$ is selected from the group consisting of halogen, —NR$^5$R$^6$, —NHCOR$^9$, —SO$_2$NR$^{10}$R$^{11}$, —SO$_2$R$^{12}$, —NHSO$_2$R$^{13}$, halogen-C$_{1-7}$-alkoxy and nitro.

Preferably, R$^5$ and R$^6$ are hydrogen.

$R^9$ is preferably selected from the group consisting of $C_{1-7}$-alkyl, $C_{3-7}$-cycloalkyl, halogen-$C_{1-7}$-alkyl, unsubstituted heteroaryl and heteroaryl substituted by one or two groups selected from $C_{1-7}$-alkyl, $C_{3-7}$-cycloalkyl, $C_{1-7}$-alkoxy, halogen-$C_{1-7}$-alkyl or halogen.

Preferably, $R^{10}$ and $R^{11}$ independently from each other are hydrogen or $C_{1-7}$-alkyl.

Preferred $R^{12}$ is $C_{1-7}$-alkyl.

$R^{13}$ is preferably selected from the group consisting of unsubstituted phenyl, phenyl substituted by one to three groups selected from $C_{1-7}$-alkyl, $C_{3-7}$-cycloalkyl, $C_{1-7}$-alkoxy, halogen-$C_{1-7}$-alkyl or halogen, unsubstituted heteroaryl and heteroaryl substituted by one or two groups selected from $C_{1-7}$-alkyl, $C_{3-7}$-cycloalkyl, $C_{1-7}$-alkoxy, halogen-$C_{1-7}$-alkyl or halogen.

Especially preferred are compounds of formula I, wherein one of $R^1$ and $R^2$ is selected from hydrogen or halogen and the other one of $R^1$ and $R^2$ is selected from the group consisting of —NHCOR$^9$, —SO$_2$NR$^{10}$R$^{11}$, —SO$_2$R$^2$, and —NHSO$_2$R$^{13}$.

Also preferred are compounds of formula I, wherein one of $R^1$ and $R^2$ is selected from hydrogen or halogen and the other one of $R^1$ and $R^2$ is —CONR$^7$R$^8$, with those compounds, wherein $R^7$ and $R^8$ are hydrogen, being especially preferred.

Furthermore, preferred compounds of formula I according to the present invention are those, wherein G is

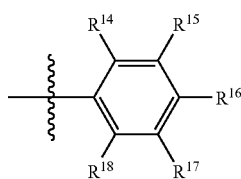

G1 and wherein $R^{14}$ is selected from the group consisting of hydrogen, hydroxy, $C_{1-7}$-alkoxy and halogen;

$R^{15}$ is selected from the group consisting of $C_{1-7}$-alkoxy, $C_{2-7}$-alkenyloxy, $C_{3-7}$-cycloalkyloxy, —NR$^{31}$R$^{32}$, halogen-$C_{1-7}$-alkoxy, $C_{1-7}$-alkoxy-$C_{1-7}$-alkoxy, $C_{1-7}$-alkoxy-$C_{1-7}$-alkyl, and hydrogen, provided that not both of $R^{14}$ and $R^{15}$ are hydrogen;

$R^{31}$ and $R^{32}$ independently from each other are hydrogen or $C_{1-7}$-alkyl;

$R^{16}$ is selected from the group consisting of hydrogen, $C_{1-7}$-alkyl, halogen-$C_{1-7}$-alkyl, hydroxy, $C_{1-7}$-alkoxy, hydroxy-$C_{1-7}$-alkoxy, $C_{3-7}$-cycloalkyloxy, halogen, —NR$^{33}$R$^{34}$, $C_{1-7}$-alkylthio, pyrrolo, triazolo, —CO$_2$R$^{35}$, —NHCOR$^{35}$, —OSO$_2$R$^3$, —SOR$^{35}$, —SO$_2$R$^{35}$, unsubstituted phenyl and phenyl substituted by halogen-$C_{1-7}$-alkyl or halogen;

$R^{33}$ and $R^{34}$ independently from each other are hydrogen or $C_{1-7}$-alkyl;

$R^{35}$ is $C_{1-7}$-alkyl;

or $R^{15}$ and $R^{16}$ together with the carbon atoms to which they are attached to form a phenyl ring;

$R^{17}$ is selected from the group consisting of hydrogen, hydroxy, $C_{1-7}$-alkoxy, halogen-$C_{1-7}$-alkoxy, hydroxy-$C_{1-7}$-alkoxy, nitro, —NR$^{36}$R$^{37}$, —NHCOR$^{38}$, —NHSO$_2$R$^{38}$, —SOR$^{38}$, —SO$_2$R$^{38}$, —O-tetrahydropyranyl, pyridyl, morpholinyl, thiomorpholinyl and 1,1-dioxothiomorpholinyl;

$R^{36}$ and $R^{37}$ independently from each other are hydrogen or $C_{1-7}$-alkyl;

$R^{38}$ is $C_{1-7}$-alkyl;

$R^{18}$ is selected from the group consisting of hydrogen, halogen, pyridyl, hydroxy, $C_{1-7}$-alkoxy and benzyloxy;

or $R^{17}$ and $R^{18}$ together with the carbon atoms to which they are attached to form a phenyl ring.

Preferred $R^{14}$ is hydrogen.

$R^{15}$ is preferably selected from the group consisting of $C_{1-7}$-alkoxy, $C_{2-7}$-alkenyloxy, $C_{3-7}$-cycloalkyloxy, halogen-$C_{1-7}$-alkoxy, hydroxy-$C_{1-7}$-alkoxy and $C_{1-7}$-alkoxy-$C_{1-7}$-alkyl.

Especially preferred are those compounds of formula I, wherein $R^{15}$ is $C_{1-7}$-alkoxy, with those compounds, wherein $R^{15}$ is ethoxy, being most preferred.

Preferred are compounds of formula I, wherein $R^{16}$ is selected from the group consisting of hydrogen, $C_{1-7}$-alkyl, halogen-$C_{1-7}$-alkyl, hydroxy, $C_{1-7}$-alkoxy, hydroxy-$C_{1-7}$-alkoxy, $C_{3-7}$-cycloalkyloxy, halogen, —NR$^{33}$R$^{34}$, $C_{1-7}$-alkylthio, pyrrolo, —CO$_2$R$^{35}$, —NHCOR$^{35}$, —OSO$_2$R$^{35}$, —SOR$^{35}$ and —SO$_2$R$^{35}$.

Especially preferred are those compounds of formula I, wherein $R^{16}$ is selected from the group consisting of hydrogen, $C_{1-7}$-alkyl, halogen-$C_{1-7}$-alkyl, $C_{1-7}$-alkoxy, halogen, —NR$^{33}$R$^{34}$ and pyrrolo. Preferably, $R^{33}$ and $R^{34}$ independently from each other are hydrogen or $C_{1-7}$-alkyl.

Especially preferred are compounds of formula I, wherein $R^{16}$ is pyrrolo.

Further preferred compounds of formula I of the present invention are those, wherein $R^{17}$ is selected from the group consisting of hydrogen, $C_{1-7}$-alkoxy and —O-tetrahydropyranyl.

$R^{18}$ is preferably hydrogen or pyridyl.

Also preferred are compounds of the present invention, wherein G is a group selected from

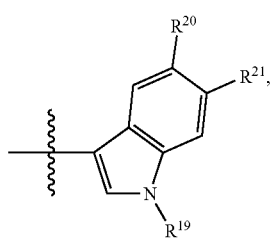

G2

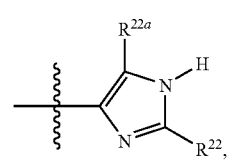

G3

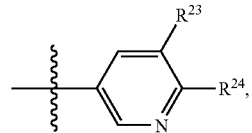

G4

-continued

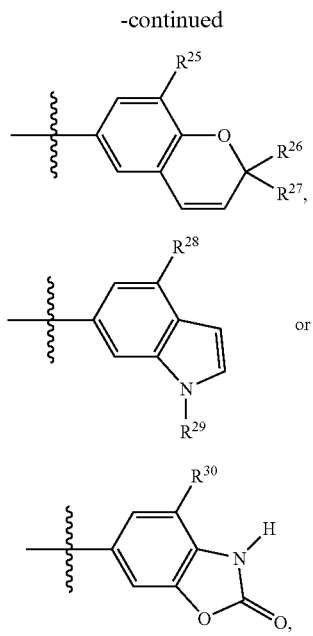

and wherein
R$^{19}$ is C$_{1-7}$-alkyl or —CO$_2$R$^{39}$;
R$^{39}$ is C$_{1-7}$-alkyl;
R$^{20}$ and R$^{21}$ independently from each other are hydrogen or C$_{1-7}$-alkoxy;
R$^{22}$ is phenyl;
R$^{23}$ and R$^{24}$ are hydrogen or C$_{1-7}$-alkoxy, provided that at least one of R$^{23}$ and R$^{24}$ is C$_{1-7}$-alkoxy;
R$^{25}$ is C$_{1-7}$-alkoxy;
R$^{26}$ and R$^{27}$ independently from each other are C$_{1-7}$-alkyl;
R$^{28}$ is C$_{1-7}$-alkoxy;
R$^{29}$ is hydrogen or C$_{1-7}$-alkyl; and
R$^{30}$ is C$_{1-7}$-alkoxy.

Especially preferred are compounds of formula I, wherein G is

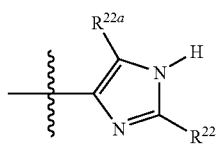

and R$^{22}$ is phenyl unsubstituted or substituted by C$_{1-7}$-alkyl or —NHCOR$^{38}$ and R$^{22a}$ is hydrogen or C$_{1-7}$-alkyl. R$^{38}$ is C$_{1-7}$-alkyl, preferably methyl. Preferably, R$^{22a}$ is hydrogen or methyl, most preferred is hydrogen.

Examples of preferred compounds of formula I are the following:
benzothiazol-2-yl-[1-(2-ethoxy-naphthalen-1-ylmethyl)-piperidin-4-yl]-amine,
benzothiazol-2-yl-[1-(1,4-dimethoxy-naphthalen-2-ylmethyl)-piperidin-4-yl]-amine,
4-[4-(benzothiazol-2-ylamino)-piperidin-1-ylmethyl]-2-methoxy-phenol,
benzothiazol-2-yl-[1-(3,4-dimethoxy-benzyl)-piperidin-4-yl]-amine,
4-[4-(benzothiazol-2-ylamino)-piperidin-1-ylmethyl]-2-ethoxy-phenol,
benzothiazol-2-yl-[1-(3-ethoxy-4-methoxy-benzyl)-piperidin-4-yl]-amine,
benzothiazol-2-yl-[1-(3-ethoxy-4-isopropoxy-benzyl)-piperidin-4-yl]-amine,
benzothiazol-2-yl-[1-(4-methoxy-3-propoxy-benzyl)-piperidin-4-yl]-amine,
benzothiazol-2-yl-{1-[3-(2-fluoro-ethoxy)-4-methoxy-benzyl]-piperidin-4-yl}-amine,
benzothiazol-2-yl-[1-(3,5-dimethoxy-benzyl)-piperidin-4-yl]-amine,
benzothiazol-2-yl-[1-(2,4-dimethoxy-benzyl)-piperidin-4-yl]-amine,
2-[4-(benzothiazol-2-ylamino)-piperidin-1-ylmethyl]-6-methoxy-phenol,
benzothiazol-2-yl-[1-(3,4,5-trimethoxy-benzyl)-piperidin-4-yl]-amine,
benzothiazol-2-yl-[1-(2-benzyloxy-4,5-dimethoxy-benzyl)-piperidin-4-yl]-amine,
benzothiazol-2-yl-[1-(3,5-diethoxy-4-pyrrol-1-yl-benzyl)-piperidin-4-yl]-amine,
benzothiazol-2-yl-[1-(1-methyl-1H-indole-3-ylmethyl)-piperidin-4-yl]-amine,
3-[4-(benzothiazol-2-ylamino)-piperidin-1-ylmethyl]-indole-1-carboxylic acid tert-butyl ester,
benzothiazol-2-yl-[1-(2-phenyl-3H-imidazol-4-ylmethyl)-piperidin-4-yl]-amine,
(6-chloro-benzothiazol-2-yl)-[1-(1,4-dimethoxy-naphthalen-2-ylmethyl)-piperidin-4-yl]-amine,
(6-chloro-benzothiazol-2-yl)-[1-(3,4-dimethoxy-benzyl)-piperidin-4-yl]-amine,
(6-chloro-benzothiazol-2-yl)-[1-(3-ethoxy-4-methyl-benzyl)-piperidin-4-yl]-amine,
(6-chloro-benzothiazol-2-yl)-[1-(4-chloro-3-ethoxy-benzyl)-piperidin-4-yl]-amine,
4-[4-(6-chloro-benzothiazol-2-ylamino)-piperidin-1-ylmethyl]-2-ethoxy-phenol,
(6-chloro-benzothiazol-2-yl)-[1-(3-ethoxy-4-methoxy-benzyl)-piperidin-4-yl]-amine,
(6-chloro-benzothiazol-2-yl)-{1-[3-(2-fluoro-ethoxy)-4-methoxy-benzyl]-piperidin-4-yl}-amine,
4-[4-(6-chloro-benzothiazol-2-ylamino)-piperidin-1-ylmethyl]-2-ethoxy-5-fluoro-phenol,
(6-chloro-benzothiazol-2-yl)-[1-(2-phenyl-1H-imidazol-4-ylmethyl)-piperidin-4-yl]-amine,
[1-(2-ethoxy-naphthalen-1-ylmethyl)-piperidin-4-yl]-thiazolo[5,4-b]pyridin-2-yl-amine,
[1-(1,4-dimethoxy-naphthalen-2-ylmethyl)-piperidin-4-yl]-thiazolo[5,4-b]pyridin-2-yl-amine,
[1-(4-chloro-3-ethoxy-benzyl)-piperidin-4-yl]-thiazolo[5,4-b]pyridin-2-yl-amine,
[1-(3-ethoxy-4-methoxy-benzyl)-piperidin-4-yl]-thiazolo[5,4-b]pyridin-2-yl-amine,
[1-(4-methoxy-3-propoxy-benzyl)-piperidin-4-yl]-thiazolo[5,4-b]pyridin-2-yl-amine,
{1-[3-(2-fluoro-ethoxy)-4-methoxy-benzyl]-piperidin-4-yl}-thiazolo[5,4-b]pyridin-2-yl-amine,
[1-(3-isobutoxy-4-methoxy-benzyl)-piperidin-4-yl]-thiazolo[5,4-b]pyridin-2-yl-amine,
2-{2-isopropoxy-5-[4-(thiazolo[5,4-b]pyridin-2-ylamino)-piperidin-1-ylmethyl]-phenoxy}-ethanol,
[1-(2,5-dimethoxy-benzyl)-piperidin-4-yl]-thiazolo[5,4-b]pyridin-2-yl-amine,
benzooxazol-2-yl-[1-(2-ethoxy-naphthalen-1-ylmethyl)-piperidin-4-yl]-amine,
benzooxazol-2-yl-[1-(1,4-dimethoxy-naphthalen-2-ylmethyl)-piperidin-4-yl]-amine,
benzooxazol-2-yl-[1-(3,4-dimethoxy-benzyl)-piperidin-4-yl]-amine,
benzooxazol-2-yl-[1-(3-ethoxy-4-methyl-benzyl)-piperidin-4-yl]-amine, benzooxazol-2-yl-[1-(4-chloro-3-ethoxy-benzyl)-piperidin-4-yl]-amine,
benzooxazol-2-yl-[1-(3-ethoxy-4-fluoro-benzyl)-piperidin-4-yl]-amine,
benzooxazol-2-yl-[1-(3-ethoxy-4-trifluoromethyl-benzyl)-piperidin-4-yl]-amine,
4-[4-(benzooxazol-2-ylamino)-piperidin-1-ylmethyl]-2-ethoxy-phenol,
benzooxazol-2-yl-[1-(3-ethoxy-4-methoxy-benzyl)-piperidin-4-yl]-amine,
benzooxazol-2-yl-[1-(3,4-diethoxy-benzyl)-piperidin-4-yl]-amine,
benzooxazol-2-yl-[1-(3-ethoxy-4-isopropoxy-benzyl)-piperidin-4-yl]-amine,
benzooxazol-2-yl-[1-(4-cyclopropoxy-3-ethoxy-benzyl)-piperidin-4-yl]-amine,
benzooxazol-2-yl-{1-[3-ethoxy-4-(1-ethyl-propoxy)-benzyl]-piperidin-4-yl}-amine,
benzooxazol-2-yl-{1-[3-ethoxy-4-(3-methyl-but-2-enyloxy)-benzyl]-piperidin-4-yl}-amine,
benzooxazol-2-yl-[1-(3-cyclopentyloxy-4-methoxy-benzyl)-piperidin-4-yl]-amine,
[1-(3-allyloxy-4-methoxy-benzyl)-piperidin-4-yl]-benzooxazol-2-yl-amine,
benzooxazol-2-yl-[1-(4-methoxy-3-propoxy-benzyl)-piperidin-4-yl]-amine,
benzooxazol-2-yl-{1-[3-(2-fluoro-ethoxy)-4-methoxy-benzyl]-piperidin-4-yl}-amine,
benzooxazol-2-yl-[1-(3-butoxy-4-methoxy-benzyl)-piperidin-4-yl]-amine,
benzooxazol-2-yl-[1-(3-isobutoxy-4-methoxy-benzyl)-piperidin-4-yl]-amine,
4-[4-(benzooxazol-2-ylamino)-piperidin-1-ylmethyl]-2-ethoxy-5-fluoro-phenol,
2-{4-[4-(benzooxazol-2-ylamino)-piperidin-1-ylmethyl]-2-ethoxy-5-fluoro-phenoxy}-ethanol,
benzooxazol-2-yl-[1-(3,4,5-trimethoxy-benzyl)-piperidin-4-yl]-amine,
benzooxazol-2-yl-[1-(2,4,5-trimethoxy-benzyl)-piperidin-4-yl]-amine,
benzooxazol-2-yl-[1-(2-benzyloxy-4,5-dimethoxy-benzyl)-piperidin-4-yl]-amine,
benzooxazol-2-yl-[1-(2,3,4-trimethoxy-benzyl)-piperidin-4-yl]-amine,
benzooxazol-2-yl-[1-(8-ethoxy-2,2-dimethyl-2H-chromen-6-ylmethyl)-piperidin-4-yl]-amine,
benzooxazol-2-yl-{1-[3-ethoxy-5-(2,2,2-trifluoro-ethoxy)-benzyl]-piperidin-4-yl}-amine,
benzooxazol-2-yl-{1-[3-ethoxy-5-(tetrahydro-pyran-4-yloxy)-benzyl]-piperidin-4-yl}-amine,
benzooxazol-2-yl-[1-(3,5-diethoxy-4-fluoro-benzyl)-piperidin-4-yl]-amine,
4-[4-(benzooxazol-2-ylamino)-piperidin-1-ylmethyl]-2,6-diethoxy-benzoic acid ethyl ester,
[1-(4-amino-3,5-diethoxy-benzyl)-piperidin-4-yl]-benzooxazol-2-yl-amine,
N-{4-[4-(benzooxazol-2-ylamino)-piperidin-1-ylmethyl]-2,6-diethoxy-phenyl}-acetamide,
[1-(3-amino-5-ethoxy-4-iodo-benzyl)-piperidin-4-yl]-benzooxazol-2-yl-amine,
N-{5-[4-(benzooxazol-2-ylamino)-piperidin-1-ylmethyl]-3-ethoxy-2-iodo-phenyl}-acetamide,
benzooxazol-2-yl-[1-(4-ethoxy-1H-indol-6-ylmethyl)-piperidin-4-yl]-amine,
benzooxazol-2-yl-[1-(5-ethoxy-6-methoxy-pyridin-3-ylmethyl)-piperidin-4-yl]-amine,
benzooxazol-2-yl-[1-(3-ethylamino-4-methoxy-benzyl)-piperidin-4-yl]-amine,
benzooxazol-2-yl-[1-(2-phenyl-3H-imidazol-4-ylmethyl)-piperidin-4-yl]-amine,
(5-chloro-benzooxazol-2-yl)-[1-(3-ethoxy-4-methyl-benzyl)-piperidin-4-yl]-amine,
(5-chloro-benzooxazol-2-yl)-[1-(4-chloro-3-ethoxy-benzyl)-piperidin-4-yl]-amine,
4-[4-(5-chloro-benzooxazol-2-ylamino)-piperidin-1-ylmethyl]-2-ethoxy-phenol,
(5-chloro-benzooxazol-2-yl)-[1-(3-ethoxy-4-methoxy-benzyl)-piperidin-4-yl]-amine,
(5-chloro-benzooxazol-2-yl)-[1-(4-methoxy-3-propoxy-benzyl)-piperidin-4-yl]-amine,
(5-chloro-benzooxazol-2-yl)-{1-[3-(2-fluoro-ethoxy)-4-methoxy-benzyl]-piperidin-4-yl}-amine,
(5-chloro-benzooxazol-2-yl)-[1-(3,5-diethoxy-benzyl)-piperidin-4-yl]-amine,
(5-chloro-benzooxazol-2-yl)-[1-(3,5-diethoxy-4-fluoro-benzyl)-piperidin-4-yl]-amine,
(5-chloro-benzooxazol-2-yl)-[1-(3,5-diethoxy-4-pyrrol-1-yl-benzyl)-piperidin-4-yl]-amine,
(6-chloro-benzooxazol-2-yl)-[1-(3,4-dimethoxy-benzyl)-piperidin-4-yl]-amine,
(6-chloro-benzooxazol-2-yl)-[1-(3-ethoxy-4-methyl-benzyl)-piperidin-4-yl]-amine,
(6-chloro-benzooxazol-2-yl)-[1-(4-chloro-3-ethoxy-benzyl)-piperidin-4-yl]-amine,
4-[4-(6-chloro-benzooxazol-2-ylamino)-piperidin-1-ylmethyl]-2-ethoxy-phenol,
(6-chloro-benzooxazol-2-yl)-[1-(4-methoxy-3-propoxy-benzyl)-piperidin-4-yl]-amine,
(6-chloro-benzooxazol-2-yl)-{1-[3-(2-fluoro-ethoxy)-4-methoxy-benzyl]-piperidin-4-yl}-amine,
(6-chloro-benzooxazol-2-yl)-[1-(3-isobutoxy-4-methoxy-benzyl)-piperidin-4-yl]-amine,
(6-chloro-benzooxazol-2-yl)-[1-(3,5-diethoxy-benzyl)-piperidin-4-yl]-amine,
(6-chloro-benzooxazol-2-yl)-[1-(3,5-diethoxy-4-fluoro-benzyl)-piperidin-4-yl]-amine,
2-[1-(3-ethoxy-4-methyl-benzyl)-piperidin-4-ylamino]-benzooxazole-5-sulfonic acid amide,
2-[1-(4-chloro-3-ethoxy-bezyl)-piperidin-4-ylamino]-benzooxazole-5-sulfonic acid amide,
2-[1-(3-ethoxy-4-fluoro-benzyl)-piperidin-4-ylamino]-benzooxazole-5-sulfonic acid amide,
2-[1-(3-ethoxy-4-trifluoromethyl-benzyl)-piperidin-4-ylamino]-benzooxazole-5-sulfonic acid amide,
2-[1-(3-ethoxy-4-hydroxy-benzyl)-piperidin-4-ylamino]-benzooxazole-5-sulfonic acid amide,
2-[1-(3-ethoxy-4,5-dihydroxy-benzyl)-piperidin-4-ylamino]-benzooxazole-5-sulfonic acid amide,
2-[1-(3-ethoxy-4-methoxy-benzyl)-piperidin-4-ylamino]-benzooxazole-5-sulfonic acid amide,
methanesulfonic acid 2-ethoxy-4-[4-(5-sulfamoyl-benzooxazol-2-ylamino)-piperidin-1-ylmethyl]-phenyl ester,
2-[1-(3,4-diethoxy-benzyl)-piperidin-4-ylamino]-benzooxazole-5-sulfonic acid amide,
2-[1-(4,5-diethoxy-2-hydroxy-benzyl)-piperidin-4-ylamino]-benzooxazole-5-sulfonic acid amide,
2-[1-(3-ethoxy-4-isopropoxy-benzyl)-piperidin-4-ylamino]-benzooxazole-5-sulfonic acid amide,
2-{1-[3-(2-hydroxy-ethoxy)-4-isopropoxy-benzyl]-piperidin-4-ylamino}-benzooxazole-5-sulfonic acid amide,
2-{1-[3-ethoxy-4-(1-ethyl-propoxy)-benzyl]-piperidin-4-ylamino}-benzooxazole-5-sulfonic acid amide,
2-{1-[3-ethoxy-4-(3-methyl-but-2-enyloxy)-benzyl]-piperidin-4-ylamino}-benzooxazole-5-sulfonic acid amide,
2-[1-(3,4-diisopropoxy-benzyl)-piperidin-4-ylamino]-benzooxazole-5-sulfonic acid amide,
2-[1-(4-methoxy-3-propoxy-benzyl)-piperidin-4-ylamino]-benzooxazole-5-sulfonic acid amide,
2-{1-[3-(2-fluoro-ethoxy)-4-methoxy-benzyl]-piperidin-4-ylamino}-benzooxazole-5-sulfonic acid amide, 2-{1-[4-methoxy-3-(2,2,2-trifluoro-ethoxy)-benzyl]-piperidin-4-ylamino}-benzooxazole-5-sulfonic acid amide,
2-[1-(3-isobutoxy-4-methoxy-benzyl)-piperidin-4-ylamino]-benzooxazole-5-sulfonic acid amide,
2-[1-(5-ethoxy-2-fluoro-4-hydroxy-benzyl)-piperidin-4-ylamino]-benzooxazole-5-sulfonic acid amide,
(±)-2-[1-(3-ethanesulfinyl-5-ethoxy-benzyl)-piperidin-4-ylamino]-benzooxazole-5-sulfonic acid amide,
2-[1-(3-ethanesulfonyl-5-ethoxy-benzyl)-piperidin-4-ylamino]-benzooxazole-5-sulfonic acid amide,
2-[1-(3,5-diethoxy-benzyl)-piperidin-4-ylamino]-benzooxazole-5-sulfonic acid amide,
2-[1-(3-ethoxy-5-isobutoxy-benzyl)-piperidin-4-ylamino]-benzooxazole-5-sulfonic acid amide,
2-[1-(3,5-diethoxy-2-fluoro-benzyl)-piperidin-4-ylamino]-benzooxazole-5-sulfonic acid amide,
2-[1-(2-chloro-3,5-diethoxy-benzyl)-piperidin-4-ylamino]-benzooxazole-5-sulfonic acid amide,
2-{1-[3-ethoxy-5-(tetrahydro-pyran-4-yloxy)-benzyl]-piperidin-4-ylamino}-benzooxazole-5-sulfonic acid amide,
2-{1-[3-ethoxy-5-(3-hydroxy-2,2-dimethyl-propoxy)-benzyl]-piperidin-4-ylamino}-benzooxazole-5-sulfonic acid amide,
2-[1-(3,5-diethoxy-4-fluoro-benzyl)-piperidin-4-ylamino]-benzooxazole-5-sulfonic acid amide,
2-[1-(3,5-diethoxy-4-methylsulfanyl-benzyl)-piperidin-4-ylamino]-benzooxazole-5-sulfonic acid amide,
(±)-2-[1-(3,5-diethoxy-4-methanesulfinyl-benzyl)-piperidin-4-ylamino]-benzooxazole-5-sulfonic acid amide,
2-[1-(3,5-diethoxy-4-methanesulfonyl-benzyl)-piperidin-4-ylamino]-benzooxazole-5-sulfonic acid amide,
2-[1-(4-amino-3,5-diethoxy-benzyl)-piperidin-4-ylamino]-benzooxazole-5-sulfonic acid amide,
N-{2,6-diethoxy-4-[4-(5-sulfamoyl-benzooxazol-2-ylamino)-piperidin-1-ylmethyl]-phenyl}-acetamide,
2-[1-(3,5-diethoxy-4-pyrrol-1-yl-benzyl)-piperidin-4-ylamino]-benzooxazole-5-sulfonic acid amide,
2-[1-(8-ethoxy-2,2-dimethyl-2H-chromen-6-ylmethyl)-piperidin-4-ylamino]-benzooxazole-5-sulfonic acid amide,
2-[1-(4-ethoxy-2-oxo-2,3-dihydro-benzooxazol-6-ylmethyl)-piperidin-4-ylamino]-benzooxazole-5-sulfonic acid amide,
N-{2-chloro-3-ethoxy-5-[4-(5-sulfamoyl-benzooxazol-2-ylamino)-piperidin-1-ylmethyl]-phenyl}-acetamide,
N-{3-ethoxy-2-iodo-5-[4-(5-sulfamoyl-benzooxazol-2-ylamino)-piperidin-1-ylmethyl]-phenyl}-acetamide,
2-[1-(3-ethoxy-4-iodo-5-methoxymethoxy-benzyl)-piperidin-4-ylamino]-benzooxazole-5-sulfonic acid amide,
2-{1-[4-chloro-3-(1,1-dioxo-1λ⁶-thiomorpholin-4-yl)-5-ethoxy-benzyl]-piperidin-4-ylamino}-benzooxazole-5-sulfonic acid amide,
2-[1-(4-ethoxy-1H-indol-6-ylmethyl)-piperidin-4-ylamino]-benzooxazole-5-sulfonic acid amide,
2-[1-(3-ethylamino-4-methoxy-benzyl)-piperidin-4-ylamino]-benzooxazole-5-sulfonic acid amide,
2-[1-(3,4-dimethoxy-benzyl)-piperidin-4-ylamino]-benzooxazole-5-sulfonic acid dimethylamide,
2-[1-(3-ethoxy-4-methyl-benzyl)-piperidin-4-ylamino]-benzooxazole-5-sulfonic acid dimethylamide,
2-[1-(4-chloro-3-ethoxy-benzyl)-piperidin-4-ylamino]-benzooxazole-5-sulfonic acid dimethylamide,
2-[1-(3-ethoxy-4-fluoro-benzyl)-piperidin-4-ylamino]-benzooxazole-5-sulfonic acid dimethylamide,
2-[1-(3-ethoxy-4-trifluoromethyl-benzyl)-piperidin-4-ylamino]-benzooxazole-5-sulfonic acid dimethylamide,
2-[1-(3-ethoxy-4-hydroxy-benzyl)-piperidin-4-ylamino]-benzooxazole-5-sulfonic acid dimethylamide,
2-[1-(3-ethoxy-4-methoxy-benzyl)-piperidin-4-ylamino]-benzooxazole-5-sulfonic acid dimethylamide,
methanesulfonic acid 4-[4-(5-dimethylsulfamoyl-benzooxazol-2-ylamino)-piperidin-1-ylmethyl]-2-ethoxy-phenyl ester,
2-[1-(3-ethoxy-4-isopropoxy-benzyl)-piperidin-4-ylamino]-benzooxazole-5-sulfonic acid dimethylamide,
2-[1-(4-methoxy-3-propoxy-benzyl)-piperidin-4-ylamino]-benzooxazole-5-sulfonic acid dimethylamide,
2-{1-[3-(2-fluoro-ethoxy)-4-methoxy-benzyl]-piperidin-4-ylamino}-benzooxazole-5-sulfonic acid dimethylamide,
2-{1-[4-methoxy-3-(2,2,2-trifluoro-ethoxy)-benzyl]-piperidin-4-ylamino}-benzooxazole-5-sulfonic acid dimethylamide,
2-[1-(3-isobutoxy-4-methoxy-benzyl)-piperidin-4-ylamino]-benzooxazole-5-sulfonic acid dimethylamide,
2-{1-[4-methoxy-3-(2-methoxy-ethoxy)-benzyl]-piperidin-4-ylamino}-benzooxazole-5-sulfonic acid dimethylamide,
2-[1-(5-ethoxy-2-fluoro-4-hydroxy-benzyl)-piperidin-4-ylamino]-benzooxazole-5-sulfonic acid dimethylamide,
2-[1-(2,4,5-trimethoxy-benzyl)-piperidin-4-ylamino]-benzooxazole-5-sulfonic acid dimethylamide,
2-[1-(2-benzyloxy-4,5-dimethoxy-benzyl)-piperidin-4-ylamino]-benzooxazole-5-sulfonic acid dimethylamide,
2-[1-(3,5-diethoxy-benzyl)-piperidin-4-ylamino]-benzooxazole-5-sulfonic acid dimethylamide,
2-{1-[3-ethoxy-5-(tetrahydro-pyran-4-yloxy)-benzyl]-piperidin-4-ylamino}-benzooxazole-5-sulfonic acid dimethylamide,
2-[1-(3,5-diethoxy-4-fluoro-benzyl)-piperidin-4-ylamino]-benzooxazole-5-sulfonic acid dimethylamide,
2-[1-(4-amino-3,5-diethoxy-benzyl)-piperidin-4-ylamino]-benzooxazole-5-sulfonic acid dimethylamide,
N-{4-[4-(5-dimethylsulfamoyl-benzooxazol-2-ylamino)-piperidin-1-ylmethyl]-2,6-diethoxy-phenyl}-acetamide,
2-[1-(3,5-diethoxy-4-pyrrol-1-yl-benzyl)-piperidin-4-ylamino]-benzooxazole-5-sulfonic acid dimethylamide,
2-[1-(3-amino-5-ethoxy-4-iodo-benzyl)-piperidin-4-ylamino]-benzooxazole-5-sulfonic acid dimethylamide,
N-{5-[4-(5-dimethylsulfamoyl-benzooxazol-2-ylamino)-piperidin-1-ylmethyl]-3-ethoxy-2-iodo-phenyl}-acetamide,
2-[1-(3-ethoxy-4-hydroxy-5-nitro-benzyl)-piperidin-4-ylamino]-benzooxazole-5-sulfonic acid dimethylamide,
2-[1-(3-ethoxy-4-methoxy-5-nitro-benzyl)-piperidin-4-ylamino]-benzooxazole-5-sulfonic acid dimethylamide,
2-[1-(4-ethoxy-2-oxo-2,3-dihydro-benzooxazol-6-ylmethyl)-piperidin-4-ylamino]-benzooxazole-5-sulfonic acid dimethylamide,
2-[1-(4-ethoxy-1H-indol-6-ylmethyl)-piperidin-4-ylamino]-benzooxazole-5-sulfonic acid dimethylamide,
5-chloro-2-[1-(3-ethoxy-4-methyl-benzyl)-piperidin-4-ylamino]-benzooxazole-6-sulfonic acid amide,
5-chloro-2-[1-(4-chloro-3-ethoxy-benzyl)-piperidin-4-ylamino]-benzooxazole-6-sulfonic acid amide,
5-chloro-2-[1-(3-ethoxy-4-fluoro-benzyl)-piperidin-4-ylamino]-benzooxazole-6-sulfonic acid amide,
5-chloro-2-[1-(3-ethoxy-4-trifluoromethyl-benzyl)-piperidin-4-ylamino]-benzooxazole-6-sulfonic acid amide,
5-chloro-2-[1-(3-ethoxy-4-hydroxy-benzyl)-piperidin-4-ylamino]-benzooxazole-6-sulfonic acid amide,
5-chloro-2-[1-(3-ethoxy-4-methoxy-benzyl)-piperidin-4-ylamino]-benzooxazole-6-sulfonic acid amide,
methanesulfonic acid 4-[4-(5-chloro-6-sulfamoyl-benzooxazol-2-ylamino)-piperidin-1-ylmethyl]-2-ethoxy-phenyl ester,
5-chloro-2-[1-(3-ethoxy-isopropoxy-benzyl)-piperidin-4-ylamino]-benzooxazole-6-sulfonic acid amide,
2-[1-(3-allyloxy-4-methoxy-benzyl)-piperidin-4-ylamino]-5-chloro-benzooxazole-6-sulfonic acid amide,
5-chloro-2-[1-(4-methoxy-3-propoxy-benzyl)-piperidin-4-ylamino]-benzooxazole-6-sulfonic acid amide, 5-chloro-2-{1-[3-(2-fluoro-ethoxy)-4-methoxy-benzyl]-piperidin-4-ylamino}-benzooxazole-6-sulfonic acid amide,
5-chloro-2-[1-(5-ethoxy-2-fluoro-4-hydroxy-benzyl)-piperidin-4-ylamino]-benzooxazole-6-sulfonic acid amide,
5-chloro-2-[1-(3,5-diethoxy-benzyl)-piperidin-4-ylamino]-benzooxazole-6-sulfonic acid amide,
5-chloro-2-[1-(3,5-diethoxy-2-fluoro-benzyl)-piperidin-4-ylamino]-benzooxazole-6-sulfonic acid amide,
5-chloro-2-[1-(2-chloro-3,5-diethoxy-benzyl)-piperidin-4-ylamino]-benzooxazole-6-sulfonic acid amide,
5-chloro-2-[1-(3,5-diethoxy-4-fluoro-benzyl)-piperidin-4-ylamino]-benzooxazole-6-sulfonic acid amide,
N-{4-[4-(5-chloro-6-sulfamoyl-benzooxazol-2-ylamino)-piperidin-1-ylmethyl]-2,6-diethoxy-phenyl}-acetamide,
5-chloro-2-[1-(3,5-diethoxy-4-pyrrol-1-yl-benzyl)-piperidin-4-ylamino]-benzooxazole-6-sulfonic acid amide,
2-[1-(3-amino-5-ethoxy-4-iodo-benzyl)-piperidin-4-ylamino]-5-chloro-benzooxazole-6-sulfonic acid amide,
N-{5-[4-(5-chloro-6-sulfamoyl-benzooxazol-2-ylamino)-piperidin-1-ylmethyl]-3-ethoxy-2-iodo-phenyl}-acetamide,
5-chloro-2-[1-(4-ethoxy-2-oxo-2,3-dihydro-benzooxazol-6-ylmethyl)-piperidin-4-ylamino]-benzooxazole-6-sulfonic acid amide,
5-chloro-2-[1-(3-ethylamino-4-methoxy-benzyl)-piperidin-4-ylamino]-benzooxazole-6-sulfonic acid amide,
5-chloro-2-[1-(5-methoxy-1H-indol-2-ylmethyl)-piperidin-4-ylamino]-benzooxazole-6-sulfonic acid amide,
(5-ethanesulfonyl-benzooxazol-2-yl)-[1-(3-ethoxy-benzyl)-piperidin-4-yl]-amine,
(5-ethanesulfonyl-benzooxazol-2-yl)-[1-(3-ethoxy-4-methyl-benzyl)-piperidin-4-yl]-amine,
[1-(4-chloro-3-ethoxy-benzyl)-piperidin-4-yl]-(5-ethanesulfonyl-benzooxazol-2-yl)-amine,
(5-ethanesulfonyl-benzooxazol-2-yl)-[1-(3-ethoxy-4-fluoro-benzyl)-piperidin-4-yl]-amine,
(5-ethanesulfonyl-benzooxazol-2-yl)-[1-(3-ethoxy-4-trifluoromethyl-benzyl)-piperidin-4-yl]-amine,
4-[4-(5-ethanesulfonyl-benzooxazol-2-ylamino)-piperidin-1-ylmethyl]-2-ethoxy-phenol,
(5-ethanesulfonyl-benzooxazol-2-yl)-[1-(3-ethoxy-4-methoxy-benzyl)-piperidin-4-yl]-amine,
(5-ethanesulfonyl-benzooxazol-2-yl)-[1-(3-ethoxy-4-isopropoxy-benzyl)-piperidin-4-yl]-amine,
(5-ethanesulfonyl-benzooxazol-2-yl)-[1-(4-methoxy-3-propoxy-benzyl)-piperidin-4-yl]-amine,
(5-ethanesulfonyl-benzooxazol-2-yl)-{1-[3-(2-fluoro-ethoxy)-4-methoxy-benzyl]-piperidin-4-yl}-amine,
(5-ethanesulfonyl-benzooxazol-2-yl)-[1-(3-isobutoxy-4-methoxy-benzyl)-piperidin-4-yl]-amine,
4-[4-(5-ethanesulfonyl-benzooxazol-2-ylamino)-piperidin-1-ylmethyl]-2-ethoxy-5-fluoro-phenol,
[1-(3,5-diethoxy-benzyl)-piperidin-4-yl]-(5-ethanesulfonyl-benzooxazol-2-yl)-amine,
(5-ethanesulfonyl-benzooxazol-2-yl)-{1-[3-ethoxy-5-(tetrahydro-pyran-4-yloxy)-benzyl]-piperidin-4-yl}-amine,
[1-(3,5-diethoxy-2-fluoro-benzyl)-piperidin-4-yl]-(5-ethanesulfonyl-benzooxazol-2-yl)-amine,
[1-(2-chloro-3,5-diethoxy-benzyl)-piperidin-4-yl]-(5-ethanesulfonyl-benzooxazol-2-yl)-amine,
[1-(3,5-diethoxy-4-fluoro-benzyl)-piperidin-4-yl]-(5-ethanesulfonyl-benzooxazol-2-yl)-amine,
[1-(3,5-diethoxy-4-pyrrol-1-yl-benzyl)-piperidin-4-yl]-(5-ethanesulfonyl-benzooxazol-2-yl)-amine,
4-[4-(5-ethanesulfonyl-benzooxazol-2-ylamino)-piperidin-1-ylmethyl]-2-ethoxy-6-nitro-phenol,
(5-ethanesulfonyl-benzooxazol-2-yl)-[1-(3-ethoxy-4-methoxy-5-nitro-benzyl)-piperidin-4-yl]-amine,
[1-(3-amino-5-ethoxy-4-iodo-benzyl)-piperidin-4-yl]-(5-ethanesulfonyl-benzooxazol-2-yl)-amine,
(5-ethanesulfonyl-benzooxazol-2-yl)-[1-(5-ethoxy-6-methoxy-pyridin-3-ylmethyl)-piperidin-4-yl]-amine,
(5-ethanesulfonyl-benzooxazol-2-yl)-[1-(3-ethylamino-4-methoxy-benzyl)-piperidin-4-yl]-amine,
(5-ethanesulfonyl-benzooxazol-2-yl)-[1-(5-methoxy-1H-indol-2-ylmethyl)-piperidin-4-yl]-amine,
[1-(4-chloro-3-ethoxy-benzyl)-piperidin-4-yl]-(5-trifluoromethoxy-benzooxazol-2-yl)-amine,
[1-(3-ethoxy-4-methoxy-benzyl)-piperidin-4-yl]-(5-trifluoromethoxy-benzooxazol-2-yl)-amine,
[1-(3,5-diethoxy-4-fluoro-benzyl)-piperidin-4-yl]-(5-trifluoromethoxy-benzooxazol-2-yl)-amine,
[1-(3-ethoxy-4-methyl-benzyl)-piperidin-4-yl]-(5-nitro-benzooxazol-2-yl)-amine,
[1-(4-chloro-3-ethoxy-benzyl)-piperidin-4-yl]-(5-nitro-benzooxazol-2-yl)-amine,
[1-(3-ethoxy-4-fluoro-benzyl)-piperidin-4-yl]-(5-nitro-benzooxazol-2-yl)-amine,
2-ethoxy-4-[4-(5-nitro-benzooxazol-2-ylamino)-piperidin-1-ylmethyl]-phenol,
[1-(3-ethoxy-4-methoxy-benzyl)-piperidin-4-yl]-(5-nitro-benzooxazol-2-yl)-amine,
[1-(3-ethoxy-4-isopropoxy-benzyl)-piperidin-4-yl]-(5-nitro-benzooxazol-2-yl)-amine,
{1-[3-(2-fluoro-ethoxy)-4-methoxy-benzyl]-piperidin-4-yl}-(5-nitro-benzooxazol-2-yl)-amine,
[1-(4-methoxy-3-propoxy-benzyl)-piperidin-4-yl]-(5-nitro-benzooxazol-2-yl)-amine,
2-ethoxy-5-fluoro-4-[4-(5-nitro-benzooxazol-2-ylamino)-piperidin-1-ylmethyl]-phenol,
[1-(3,5-diethoxy-benzyl)-piperidin-4-yl]-(5-nitro-benzooxazol-2-yl)-amine,
[1-(3,5-diethoxy-4-fluoro-benzyl)-piperidin-4-yl]-(5-nitro-benzooxazol-2-yl)-amine,
[1-(3,5-diethoxy-4-pyrrol-1-yl-benzyl)-piperidin-4-yl]-(5-nitro-benzooxazol-2-yl)-amine,
[1-(5-methoxy-1H-indol-2-ylmethyl)-piperidin-4-yl]-(5-nitro-benzooxazol-2-yl)-amine,
$N^2$-[1-(4-chloro-3-ethoxy-benzyl)-piperidin-4-yl]-benzooxazole-2,5-diamine,
$N^2$-[1-(3-ethoxy-4-isopropoxy-benzyl)-piperidin-4-yl]-benzooxazole-2,5-diamine,
$N^2$-[1-(3,5-diethoxy-4-fluoro-benzyl)-piperidin-4-yl]-benzooxazole-2,5-diamine,
[1-(3-ethoxy-4-methyl-benzyl)-piperidin-4-yl]-oxazolo[4,5-b]pyridin-2-yl-amine,
[1-(4-chloro-3-ethoxy-benzyl)-piperidin-4-yl]-oxazolo[4,5-b]pyridin-2-yl-amine,
[1-(3-ethoxy-4-fluoro-benzyl)-piperidin-4-yl]-oxazolo[4,5-b]pyridin-2-yl-amine,
2-ethoxy-4-[4-(oxazolo[4,5-b]pyridin-2-ylamino)-piperidin-1-ylmethyl]-phenol,
[1-(3-ethoxy-4-methoxy-benzyl)-piperidin-4-yl]-oxazolo[4,5-b]pyridin-2-yl-amine,
[1-(3,5-diethoxy-benzyl)-piperidin-4-yl]-oxazolo[4,5-b]pyridin-2-yl-amine,
[1-(3,5-diethoxy-4-fluoro-benzyl)-piperidin-4-yl]-oxazolo[4,5-b]pyridin-2-yl-amine,
[1-(3,5-diethoxy-4-pyrrol-1-yl-benzyl)-piperidin-4-yl]-oxazolo[4,5-b]pyridin-2-yl-amine,
(5-ethanesulfonyl-benzooxazol-2-yl)-[1-(5-ethoxy-4-methoxy-2-pyridin-4-yl-benzyl)-piperidin-4-yl]-amine,
N-{2-[1-(3-ethoxy-4-methoxy-benzyl)-piperidin-4-ylamino]-benzooxazol-5-yl}-acetamide,
N-{2-[1-(3-ethoxy-4-methoxy-benzyl)-piperidin-4-ylamino]-benzooxazol-5-yl}-propionamide cyclobutanecarboxylic acid{2-[1-(3-ethoxy-4-methoxy-benzyl)-piperidin-4-ylamino]-benzooxazol-5-yl}-amide,
N-{2-[1-(3-ethoxy-4-methoxy-benzyl)-piperidin-4-ylamino]-benzooxazol-5-yl}-2,2,2-trifluoro-acetamide, 3,5-dimethyl-isoxazole-4-carboxylic acid {2-[1-(3-ethoxy-4-methoxy-benzyl)-piperidin-4-ylamino]-benzooxazol-5-yl}-amide,
N-{2-[1-(3-ethoxy-4-methoxy-benzyl)-piperidin-4-ylamino]-benzooxazol-5-yl}-methanesulfonamide,
N-{2-[1-(3-ethoxy-4-methoxy-benzyl)-piperidin-4-ylamino]-benzooxazol-5-yl}-benzenesulfonamide,
3,5-dimethyl-isoxazole-4-sulfonic acid{2-[1-(3-ethoxy-4-methoxy-benzyl)-piperidin-4-ylamino]-benzooxazol-5-yl}-amide,
2,3-dimethyl-3H-imidazole-4-sulfonic acid{2-[1-(3-ethoxy-4-methoxy-benzyl)-piperidin-4-ylamino]-benzooxazol-5-yl}-amide,
1-methyl-1H-imidazole-4-sulfonic acid{2-[1-(3-ethoxy-4-methoxy-benzyl)-piperidin-4-ylamino]-benzooxazol-5-yl}-amide,
2-[1-(3-ethoxy-4-methoxy-benzyl)-piperidin-4-ylamino]-benzooxazole-7-carboxylic acid dimethylamide,
2-[1-(3-ethoxy-4-methoxy-benzyl)-piperidin-4-ylamino]-benzooxazole-7-carboxylic acid diethylamide,
2-[1-(3-ethoxy-4-methoxy-benzyl)-piperidin-4-ylamino]-benzooxazole-7-carboxylic acid cyclopropylmethyl-amide,
{2-[1-(3-ethoxy-4-methoxy-benzyl)-piperidin-4-ylamino]-benzooxazol-7-yl}-morpholin-4-yl-methanone,
2-[1-(3-ethoxy-4-methoxy-benzyl)-piperidin-4-ylamino]-benzooxazole-7-carboxylic acid (thiophen-3-ylmethyl)-amide,
2-[1-(3-ethoxy-4-methoxy-benzyl)-piperidin-4-ylamino]-benzooxazole-7-carboxylic acid benzylamide,
2-[1-(3-ethoxy-4-methoxy-benzyl)-piperidin-4-ylamino]-benzooxazole-7-carboxylic acid (4-methyl-thiazol-2-yl)-amide,
2-[1-(3-ethoxy-4-methoxy-benzyl)-piperidin-4-ylamino]-benzooxazole-7-carboxylic acid (5-methyl-thiazol-2-yl)-amide,
2-[1-(3-ethoxy-4-methoxy-benzyl)-piperidin-4-ylamino]-benzooxazole-7-carboxylic acid diethylamide,
2-[1-(3-ethoxy-4-methoxy-benzyl)-piperidin-4-ylamino]-benzooxazole-7-carboxylic acid cyclopropylmethyl-amide,
{2-[1-(3-ethoxy-4-methoxy-benzyl)-piperidin-4-ylamino]-benzooxazol-7-yl}-morpholin-4-yl-methanone,
2-[1-(3-ethoxy-4-methoxy-benzyl)-piperidin-4-ylamino]-benzooxazole-7-carboxylic acid (thiophen-3-ylmethyl)-amide,
2-[1-(3-ethoxy-4-methoxy-benzyl)-piperidin-4-ylamino]-benzooxazole-7-carboxylic acid benzylamide,
2-[1-(3-ethoxy-4-methoxy-benzyl)-piperidin-4-ylamino]-benzooxazole-7-carboxylic acid (4-methyl-thiazol-2-yl)-amide,
2-[1-(3-ethoxy-4-methoxy-benzyl)-piperidin-4-ylamino]-benzooxazole-7-carboxylic acid (5-methyl-thiazol-2-yl)-amide,
cyclobutanecarboxylic acid{2-[1-(3-ethoxy-4-methyl-benzyl)-piperidin-4-ylamino]-benzooxazol-5-yl}-amide,
cyclobutanecarboxylic acid{2-[1-(4-chloro-3-ethoxy-benzyl)-piperidin-4-ylamino]-benzooxazol-5-yl}-amide,
cyclobutanecarboxylic acid{2-[1-(3-ethoxy-4-fluoro-benzyl)-piperidin-4-ylamino]-benzooxazol-5-yl}-amide,
cyclobutanecarboxylic acid{2-[1-(3-ethoxy-4-trifluoromethyl-benzyl)-piperidin-4-ylamino]-benzooxazol-5-yl}-amide,
cyclobutanecarboxylic acid{2-[1-(3-ethoxy-4-hydroxy-benzyl)-piperidin-4-ylamino]-benzooxazol-5-yl}-amide,
methanesulfonic acid 4-{4-[5-(cyclobutanecarbonyl-amino)-benzooxazol-2-ylamino]-piperidin-1-ylmethyl}-2-ethoxy-phenyl ester,
cyclobutanecarboxylic acid (2-{1-[3-(2-fluoro-ethoxy)-4-methoxy-benzyl]-piperidin-4-ylamino}-benzooxazol-5-yl)-amide,
cyclobutanecarboxylic acid{2-[1-(3-isobutoxy-4-methoxy-benzyl)-piperidin-4-ylamino]-benzooxazol-5-yl}-amide,
cyclobutanecarboxylic acid{2-[1-(3-ethoxy-5-isobutoxy-benzyl)-piperidin-4-ylamino]-benzooxazol-5-yl}-amide,
cyclobutanecarboxylic acid (2-{1-[3-ethoxy-5-(tetrahydro-pyran-4-yloxy)-benzyl]-piperidin-4-ylamino}-benzooxazol-5-yl)-amide,
cyclobutanecarboxylic acid (2-{1-[3-ethoxy-5-(3-hydroxy-2,2-dimethyl-propoxy)-benzyl]-piperidin-4-ylamino}-benzooxazol-5-yl)-amide,
cyclobutanecarboxylic acid{2-[1-(3,5-diethoxy-4-fluoro-benzyl)-piperidin-4-ylamino]-benzooxazol-5-yl}-amide,
(±)-cyclobutanecarboxylic acid{2-[1-(3,5-diethoxy-4-methanesulfinyl-benzyl)-piperidin-4-ylamino]-benzooxazol-5-yl}-amide,
cyclobutanecarboxylic acid{2-[1-(4-amino-3,5-diethoxy-benzyl)-piperidin-4-ylamino]-benzooxazol-5-yl}-amide,
cyclobutanecarboxylic acid{2-[1-(4-acetylamino-3,5-diethoxy-benzyl)-piperidin-4-ylamino]-benzooxazol-5-yl}-amide,
cyclobutanecarboxylic acid{2-[1-(3,5-diethoxy-4-pyrrol-1-yl-benzyl)-piperidin-4-ylamino]-benzooxazol-5-yl}-amide,
cyclobutanecarboxylic acid{2-[1-(4-ethoxy-2-oxo-2,3-dihydro-benzooxazol-6-ylmethyl)-piperidin-4-ylamino]-benzooxazol-5-yl}-amide,
cyclobutanecarboxylic acid{2-[1-(3-acetylamino-5-ethoxy-4-iodo-benzyl)-piperidin-4-ylamino]-benzooxazol-5-yl}-amide,
1-methyl-1H-imidazole-4-sulfonic acid{2-[1-(3-ethoxy-4-methyl-benzyl)-piperidin-4-ylamino]-benzooxazol-5-yl}-amide,
1-methyl-1H-imidazole-4-sulfonic acid{2-[1-(4-chloro-3-ethoxy-benzyl)-piperidin-4-ylamino]-benzooxazol-5-yl}-amide,
1-methyl-1H-imidazole-4-sulfonic acid{2-[1-(3-ethoxy-4-fluoro-benzyl)-piperidin-4-ylamino]-benzooxazol-5-yl}-amide,
1-methyl-1H-imidazole-4-sulfonic acid{2-[1-(3-ethoxy-4-trifluoromethyl-benzyl)-piperidin-4-ylamino]-benzooxazol-5-yl}-amide,
1-methyl-1H-imidazole-4-sulfonic acid{2-[1-(3-ethoxy-4-hydroxy-benzyl)-piperidin-4-ylamino]-benzooxazol-5-yl}-amide,
methanesulfonic acid 2-ethoxy-4-{4-[5-(1-methyl-1H-imidazole-4-sulfonylamino)-benzooxazol-2-ylamino]-piperidin-1-ylmethyl}-phenyl ester,
1-methyl-1H-imidazole-4-sulfonic acid (2-1 {-[3-(2-fluoro-ethoxy)-4-methoxy-benzyl]-piperidin-4-ylamino}-benzooxazol-5-yl)-amide,
1-methyl-1H-imidazole-4-sulfonic acid{2-[1-(3-isobutoxy-4-methoxy-benzyl)-piperidin-4-ylamino]-benzooxazol-5-yl}-amide,
methyl-1H-imidazole-4-sulfonic acid{2-[1-(3-ethoxy-5-isobutoxy-benzyl)-piperidin-4-ylamino]-benzooxazol-5-yl}-amide,
1-methyl-1H-imidazole-4-sulfonic acid (2-{1-[3-ethoxy-5-(tetrahydro-pyran-4-yloxy)-benzyl]-piperidin-4-ylamino}-benzooxazol-5-yl)-amide,
1-methyl-1H-imidazole-4-sulfonic acid (2-{1-[3-ethoxy-5-(3-hydroxy-2,2-dimethyl-propoxy)-benzyl]-piperidin-4-ylamino}-benzooxazol-5-yl)-amide,
1-methyl-1H-imidazole-4-sulfonic acid{2-[1-(3,5-diethoxy-4-fluoro-benzyl)-piperidin-4-ylamino]-benzooxazol-5-yl}-amide, 1-methyl-1H-imidazole-4-sulfonic acid{2-[1-(4-amino-3,5-diethoxy-benzyl)-piperidin-4-ylamino]-benzooxazol-5-yl}-amide,
N-(2,6-diethoxy-4-{4-[5-(1-methyl-1H-imidazole-4-sulfonylamino)-benzooxazol-2-ylamino]-piperidin-1-ylmethyl}-phenyl)-acetamide,
1-methyl-1H-imidazole-4-sulfonic acid{2-[1-(4-ethoxy-2-oxo-2,3-dihydro-benzooxazol-6-ylmethyl)-piperidin-4-ylamino]-benzooxazol-5-yl}-amide,
N-(3-ethoxy-2-iodo-5-{4-[5-(1-methyl-1H-imidazole-4-sulfonylamino)-benzooxazol-2-ylamino]-piperidin-1-ylmethyl}-phenyl)-acetamide,
benzooxazol-2-yl-[1-(3,5-diisopropoxy-benzyl)-piperidin-4-yl]-amine
2-[1-(3-cyclopentyloxy-4-methoxy-benzyl)-piperidin-4-ylamino]-benzooxazole-5-sulfonic acid amide,
2-[1-(3,5-diethoxy-4-methoxy-benzyl)-piperidin-4-ylamino]-benzooxazole-5-sulfonic acid amide,
[1-(3-ethoxy-4-methyl-benzyl)-piperidin-4-yl]-oxazolo[5,4-b]pyridin-2-yl-amine,
[1-(4-chloro-3-ethoxy-benzyl)-piperidin-4-yl]-oxazolo[5,4-b]pyridin-2-yl-amine,
[1-(3-ethoxy-4-methoxy-benzyl)-piperidin-4-yl]-oxazolo[5,4-b]pyridin-2-yl-amine,
[1-(3,5-diethoxy-4-fluoro-benzyl)-piperidin-4-yl]-oxazolo[5,4-b]pyridin-2-yl-amine,
[1-(4-amino-3,5-diethoxy-benzyl)-piperidin-4-yl]-oxazolo[5,4-b]pyridin-2-yl-amine,
2-[1-(3,5-diethoxy-4-fluoro-benzyl)-piperidin-4-ylamino]-benzooxazole-5-carbonitrile,
2-[1-(3,5-diethoxy-4-pyrrol-1-yl-benzyl)-piperidin-4-ylamino]-benzooxazole-5-carbonitrile,
2-[1-(3,5-diethoxy-4-[1,2,4]triazol-1-yl-benzyl)-piperidin-4-ylamino]-benzooxazole-5-carbonitrile,
2-[1-(3-ethoxy-4-methoxy-benzyl)-piperidin-4-ylamino]-benzooxazole-5-carboxylic acid amide,
2-[1-(3,5-diethoxy-4-fluoro-benzyl)-piperidin-4-ylamino]-benzooxazole-5-carboxylic acid amide,
2-[1-(3,5-diethoxy-4-pyrrol-1-yl-benzyl)-piperidin-4-ylamino]-benzooxazole-5-carboxylic acid amide,
2-[1-(3-ethoxy-4-methyl-benzyl)-piperidin-4-ylamino]-benzooxazole-7-carboxylic acid methyl ester,
2-[1-(4-chloro-3-ethoxy-benzyl)-piperidin-4-ylamino]-benzooxazole-7-carboxylic acid methyl ester,
2-[1-(3-ethoxy-4-fluoro-benzyl)-piperidin-4-ylamino]-benzooxazole-7-carboxylic acid methyl ester,
2-[1-(3,5-diethoxy-4-fluoro-benzyl)-piperidin-4-ylamino]-benzooxazole-7-carboxylic acid methyl ester,
2-[1-(4-ethoxy-1H-indol-6-ylmethyl)-piperidin-4-ylamino]-benzooxazole-7-carboxylic acid methyl ester,
2-{1-[4-chloro-3-(2-fluoro-ethoxy)-benzyl]-piperidin-4-ylamino}-benzooxazole-7-carboxylic acid methyl ester,
2-{1-[3-(2-fluoro-ethoxy)-4-methyl-benzyl]-piperidin-4-ylamino}-benzooxazole-7-carboxylic acid methyl ester,
2-{1-[4-fluoro-3-(2-fluoro-ethoxy)-benzyl]-piperidin-4-ylamino}-benzooxazole-7-carboxylic acid methyl ester,
2-[1-(2-ethoxy-4'-fluoro-biphenyl-4-ylmethyl)-piperidin-4-ylamino]-benzooxazole-7-carboxylic acid methyl ester,
2-[1-(2-ethoxy-4'-trifluoromethyl-biphenyl-4-ylmethyl)-piperidin-4-ylamino]-benzooxazole-7-carboxylic acid methyl ester,
2-[1-(3-ethoxy-4-methyl-benzyl)-piperidin-4-ylamino]-benzooxazole-7-carboxylic acid;
compound with acetic acid,
2-[1-(4-chloro-3-ethoxy-benzyl)-piperidin-4-ylamino]-benzooxazole-7-carboxylic acid,
2-[1-(3-ethoxy-4-fluoro-benzyl)-piperidin-4-ylamino]-benzooxazole-7-carboxylic acid,
2-{1-[4-chloro-3-(2-fluoro-ethoxy)-benzyl]-piperidin-4-ylamino}-benzooxazole-7-carboxylic acid,
2-{1-[3-(2-fluoro-ethoxy)-4-methyl-benzyl]-piperidin-4-ylamino}-benzooxazole-7-carboxylic acid,
2-{1-[4-fluoro-3-(2-fluoro-ethoxy)-benzyl]-piperidin-4-ylamino}-benzooxazole-7-carboxylic acid,
2-[1-(2-ethoxy-4'-fluoro-biphenyl-4-ylmethyl)-piperidin-4-ylamino]-benzooxazole-7-carboxylic acid,
benzooxazol-2-yl-[1-(5-methyl-2-phenyl-1H-imidazol-4-ylmethyl)-piperidin-4-yl]-amine,
benzooxazol-2-yl-[1-(5-methyl-2-m-tolyl-1H-imidazol-4-ylmethyl)-piperidin-4-yl]-amine,
N-(3-{4-[4-(benzooxazol-2-ylamino)-piperidin-1-ylmethyl]-5-methyl-1H-imidazol-2-yl}-phenyl)-acetamide, and pharmaceutically acceptable salts thereof.

Particularly preferred compounds of formula I of the present invention are the following:
[1-(4-chloro-3-ethoxy-benzyl)-piperidin-4-yl]-thiazolo[5,4-b]pyridin-2-yl-amine,
benzooxazol-2-yl-[1-(3-ethoxy-4-methoxy-benzyl)-piperidin-4-yl]-amine,
benzooxazol-2-yl-{1-[3-ethoxy-5-(tetrahydro-pyran-4-yloxy)-benzyl]-piperidin-4-yl}-amine,
benzooxazol-2-yl-[1-(3,5-diethoxy-4-fluoro-benzyl)-piperidin-4-yl]-amine,
benzooxazol-2-yl-[1-(2-phenyl-3H-imidazol-4-ylmethyl)-piperidin-4-yl]-amine,
2-[1-(3-ethoxy-4-methyl-benzyl)-piperidin-4-ylamino]-benzooxazole-5-sulfonic acid amide,
2-[1-(3-ethoxy-4-fluoro-benzyl)-piperidin-4-ylamino]-benzooxazole-5-sulfonic acid amide,
2-[1-(3-ethoxy-4-trifluoromethyl-benzyl)-piperidin-4-ylamino]-benzooxazole-5-sulfonic acid amide,
2-[1-(3-ethoxy-4-methoxy-benzyl)-piperidin-4-ylamino]-benzooxazole-5-sulfonic acid amide,
2-[1-(3,5-diethoxy-4-fluoro-benzyl)-piperidin-4-ylamino]-benzooxazole-5-sulfonic acid amide,
2-[1-(4-amino-3,5-diethoxy-benzyl)-piperidin-4-ylamino]-benzooxazole-5-sulfonic acid amide,
2-[1-(3,5-diethoxy-4-pyrrol-1-yl-benzyl)-piperidin-4-ylamino]-benzooxazole-5-sulfonic acid amide,
5-chloro-2-[1-(4-chloro-3-ethoxy-benzyl)-piperidin-4-ylamino]-benzooxazole-6-sulfonic acid amide,
5-chloro-2-[1-(3-ethoxy-4-trifluoromethyl-benzyl)-piperidin-4-ylamino]-benzooxazole-6-sulfonic acid amide,
[1-(4-chloro-3-ethoxy-benzyl)-piperidin-4-yl]-(5-ethanesulfonyl-benzooxazol-2-yl)-amine,
[1-(4-chloro-3-ethoxy-benzyl)-piperidin-4-yl]-oxazolo[4,5-b]pyridin-2-yl-amine,
[1-(3,5-diethoxy-benzyl)-piperidin-4-yl]-oxazolo[4,5-b]pyridin-2-yl-amine,
[1-(3,5-diethoxy-4-pyrrol-1-yl-benzyl)-piperidin-4-yl]-oxazolo[4,5-b]pyridin-2-yl-amine,
(5-ethanesulfonyl-benzooxazol-2-yl)-[1-(5-ethoxy-4-methoxy-2-pyridin-4-yl-benzyl)-piperidin-4-yl]-amine,
3,5-dimethyl-isoxazole-4-sulfonic acid{2-[1-(3-ethoxy-4-methoxy-benzyl)-piperidin-4-ylamino]-benzooxazol-5-yl}-amide,
2-[1-(3-ethoxy-4-methoxy-benzyl)-piperidin-4-ylamino]-benzooxazole-7-carboxylic acid (4-methyl-thiazol-2-yl)-amide,
2-[1-(3-ethoxy-4-methoxy-benzyl)-piperidin-4-ylamino]-benzooxazole-7-carboxylic acid (5-methyl-thiazol-2-yl)-amide,
cyclobutanecarboxylic acid{2-[1-(3-ethoxy-4-methyl-benzyl)-piperidin-4-ylamino]-benzooxazol-5-yl}-amide,
1-methyl-1H-imidazole-4-sulfonic acid{2-[1-(4-chloro-3-ethoxy-benzyl)-piperidin-4-ylamino]-benzooxazol-5-yl}-amide,
benzooxazol-2-yl-[1-(3,5-diisopropoxy-benzyl)-piperidin-4-yl]-amine,

[1-(4-chloro-3-ethoxy-benzyl)-piperidin-4-yl]-oxazolo[5,4-b]pyridin-2-yl-amine,
2-[1-(3,5-diethoxy-4-fluoro-benzyl)-piperidin-4-ylamino]-benzooxazole-5-carboxylic acid amide, and pharmaceutically acceptable salts thereof.

Especially preferred are the following compounds of formula I of the present invention:
2-[1-(3-ethoxy-4-methyl-benzyl)-piperidin-4-ylamino]-benzooxazole-5-sulfonic acid amide,
2-[1-(3-ethoxy-4-fluoro-benzyl)-piperidin-4-ylamino]-benzooxazole-5-sulfonic acid amide,
2-[1-(3-ethoxy-4-trifluoromethyl-benzyl)-piperidin-4-ylamino]-benzooxazole-5-sulfonic acid amide,
2-[1-(3,5-diethoxy-4-fluoro-benzyl)-piperidin-4-ylamino]-benzooxazole-5-sulfonic acid amide,
2-[1-(4-amino-3,5-diethoxy-benzyl)-piperidin-4-ylamino]-benzooxazole-5-sulfonic acid amide,
2-[1-(3,5-diethoxy-4-pyrrol-1-yl-benzyl)-piperidin-4-ylamino]-benzooxazole-5-sulfonic acid amide,
[1-(3,5-diethoxy-4-pyrrol-1-yl-benzyl)-piperidin-4-yl]-oxazolo[4,5-b]pyridin-2-yl-amine,
cyclobutanecarboxylic acid{2-[1-(3-ethoxy-4-methyl-benzyl)-piperidin-4-ylamino]-benzooxazol-5-yl}-amide,
1-methyl-1H-imidazole-4-sulfonic acid{2-[1-(4-chloro-3-ethoxy-benzyl)-piperidin-4-ylamino]-benzooxazol-5-yl}-amide,
benzooxazol-2-yl-[1-(3,5-diisopropoxy-benzyl)-piperidin-4-yl]-amine,
[1-(4-chloro-3-ethoxy-benzyl)-piperidin-4-yl]-oxazolo[5,4-b]pyridin-2-yl-amine,
2-[1-(3,5-diethoxy-4-fluoro-benzyl)-piperidin-4-ylamino]-benzooxazole-5-carboxylic acid amide, and pharmaceutically acceptable salts thereof.

Furthermore, the pharmaceutically acceptable salts of the compounds of formula I individually constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula (I) as defined above, which process comprises reacting a compound of the general formula

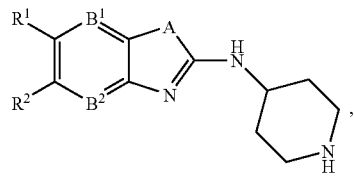

wherein A, $B^1$, $B^2$, $R^1$ and $R^2$ are as defined herein before, with an aldehyde of the formula

wherein G is as defined herein before, by employing a reducing agent to obtain a compound of the formula

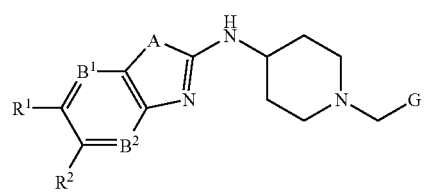

and, if desired, converting the compound of formula I into a pharmaceutically acceptable salt.

The invention further relates to compounds of formula I as defined above, when manufactured according to a process as defined above.

Suitable reducing agents are preferably selected from the group consisting of pyridine-$BH_3$ complex, $NaBH(OAc)_3$ and $NaCNBH_3$. The reaction can be carried out under acidic conditions by using an acid such as acetic acid or formic acid or an Lewis acid (e.g., $Ti(iPrO)_4$, $ZnCl_2$) or under basic conditions (no additive) in a suitable solvent such as dichloromethane, dichloroethane or ethanol (or mixtures thereof) at ambient or elevated temperatures using conventional heating or heating by microwave irradiation.

The conversion of a compound of formula I, wherein $R^1$ or $R^2$ signifies an amino group, into a compound of formula I, wherein $R^1$ or $R^2$ signifies a group such as —$NHCOR^9$ or —$NHSO_2R^3$, is also embraced in the present invention.

As described above, the compounds of formula (I) of the present invention can be used as medicaments for the treatment and/or prevention of diseases which are associated with the modulation of SST receptors subtype 5.

"Diseases which are associated with the modulation of SST receptors subtype 5" are such diseases as diabetes mellitus, particularly type 2 diabetes mellitus, impaired fasting glucose, impaired glucose tolerance, micro- and macrovascular diabetic complications, posttransplantation diabetes mellitus in patients having type 1 diabetes mellitus, gestational diabetes, obesity, inflammatory bowel diseases such as Crohn's disease or ulcerative colitis, malabsorption, autoimmune diseases such as rheumatoid arthritis, osteoarthritis, psoriasis and other skin disorder, and immunodeficiences. Microvascular diabetic complications include diabetic nephropathy and diabetic retinopathy, whereas macrovascular diabetes-associated complications lead to an increased risk for myocardial infarction, stroke and limb amputations.

The use as medicament for the treatment and/or prevention of diabetes mellitus, particularly type 2 diabetes mellitus, impaired fasting glucose or impaired glucose tolerance is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of SST receptors subtype 5.

In another embodiment, the invention relates to a method for the treatment and/or prevention of diseases which are which are associated with the modulation of SST receptors subtype 5, which method comprises administering a compound of formula I to a human or animal. The method for the treatment and/or prevention of diabetes mellitus, particularly type 2 diabetes mellitus, impaired fasting glucose or impaired glucose tolerance, is most preferred.

The invention further relates to the use of compounds as defined above for the treatment and/or prevention of diseases which are associated with the modulation of SST receptors subtype 5.

In addition, the invention relates to the use of compounds as defined above for the preparation of medicaments for the treatment and/or prevention of diseases which are associated with the modulation of SST receptors subtype 5. Preferred examples of such diseases are diabetes mellitus, particularly type 2 diabetes mellitus, impaired fasting glucose or impaired glucose tolerance.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The synthesis of compounds with the general structure I, particularly compounds according to formula Ia to Id, are described in schemes 1 to 6.

The synthesis of compounds of the general formula I, particularly compounds according to formula Ia with A=S can be accomplished according to scheme 1.

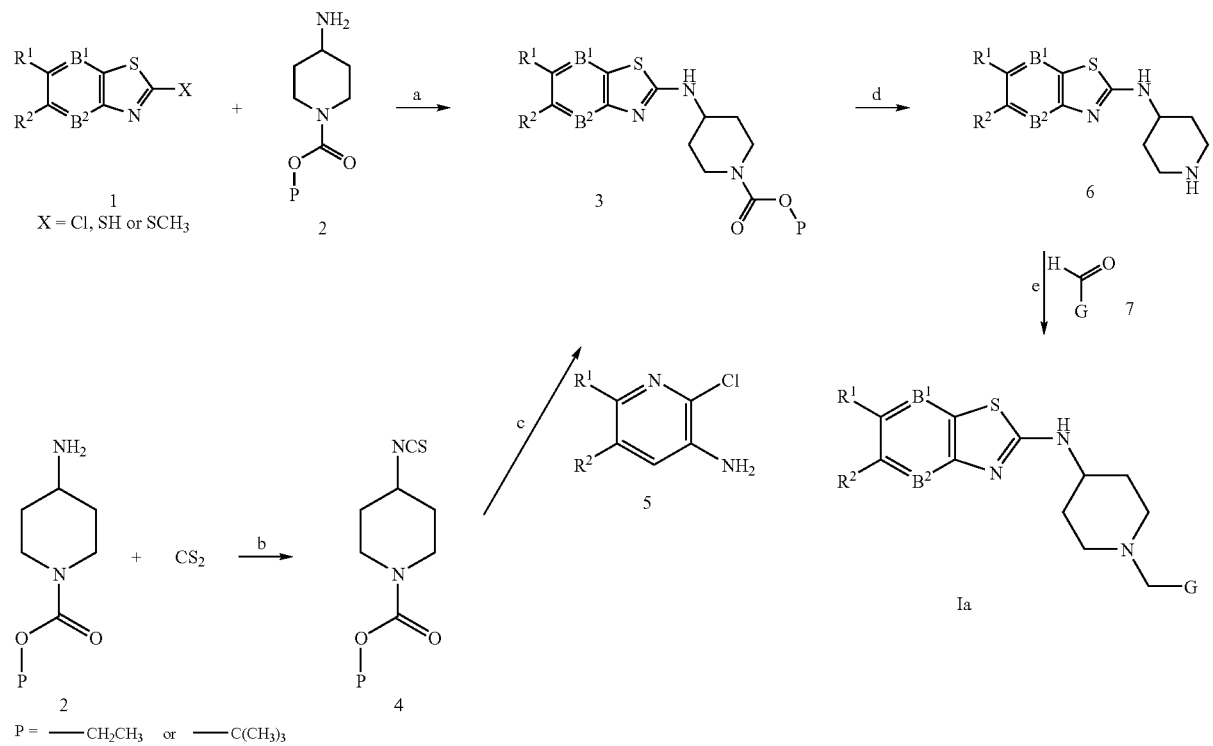

Benzothiazoles or thiazolopyridines of general structure 1 are known or can be prepared by numerous methods known in the art. Reaction of 2-chloro-, 2-mercapto- or 2-methylmercapto-benzothiazoles or thiazolopyridines and suitably protected 4-amino piperidines of formula 2 (for protecting groups see Protective Groups in Organic Synthesis, T. W. Greene, Wiley-Interscience 1999) undergo a nucleophilic replacement reaction at room or elevated temperatures providing piperidines of formula 3 (Scheme 1, step a). Thereby heating can be achieved conventionally or by microwave irradiation using a suitable microwave irradiation apparatus. Furthermore the reaction can be conducted in the presence of or without solvent (typically an aprotic polar solvent such as DMF (dimethylformamide), DMAc (dimethylacetamide) or THF) and in the presence of or without a tertiary amine base such as triethylamine or N-ethyl diisopropylamine. Alternatively, thiazolopyridine piperidines of formula 3 can be prepared by coupling of an appropriately protected 4-isothiocyanato piperidine such as 4, prepared from a suitably protected 4-amino piperidine such as 2 and carbondisulfide (step b), and 2-chloropyridine amines of formula 5 by heating to reflux in a polar solvent such as ethanol or isopropanol (step c; preparation described in EP 184257 A1, Janssen Pharmaceutica). The protecting group can then be removed yielding piperidines of formula 6 (step d) by depending on the group used, e.g, treatment with acid or hydrogenation (see Protective Groups in Organic Synthesis, T. W. Greene, Wiley-Interscience 1999). Target compounds of formula Ia can be obtained by reductive alkylation of piperidines of formula 6 with aldehydes 7 (step e). The piperidines of formula 6 may thereby used either as a salt, e.g., hydrochlorine or hydrobromine salt, or as the corresponding free amine. The reductive alkylation step can be conducted employing a suitable reducing agent such as pyridine-$BH_3$ complex, $NaBH(OAc)_3$ or $NaCNBH_3$ under acidic conditions (e.g., acetic acid, formic acid), by using a Lewis acid (e.g., $Ti(iPrO)_4$, $ZnCl_2$) or under basic conditions (no additive) in a suitable solvent such as dichloromethane, dichloroethane or ethanol (or mixtures thereof) at ambient or elevated temperatures using conventional heating or heating by microwave irradiation.

In a similar manner the synthesis of compounds of formula I having the formula Ib with A=O (benzooxazoles and oxazolopyridines) can be accomplished according to scheme 2.

might be wished to increase the leaving group properties of mercaptane which can be achieved by methylation with methyliodide or dimethylsulfate in a suitable solvent such as THF or N,N-dimethylformamide using conventional heating or heating by microwave irradiation with the addition of a suitable tertiary amine base (e.g., triethylamine, N-ethyl diisopropylamine) or an inorganic base (e.g., $Cs_2CO_3$, $K_2CO_3$; step b).

Scheme 3

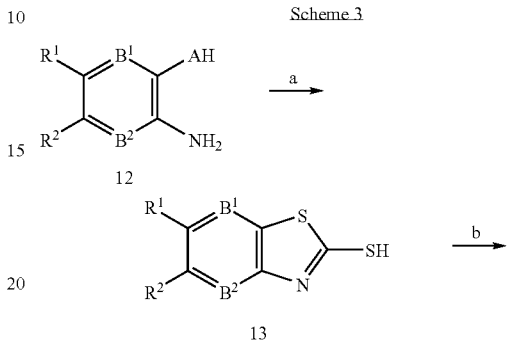

Scheme 2

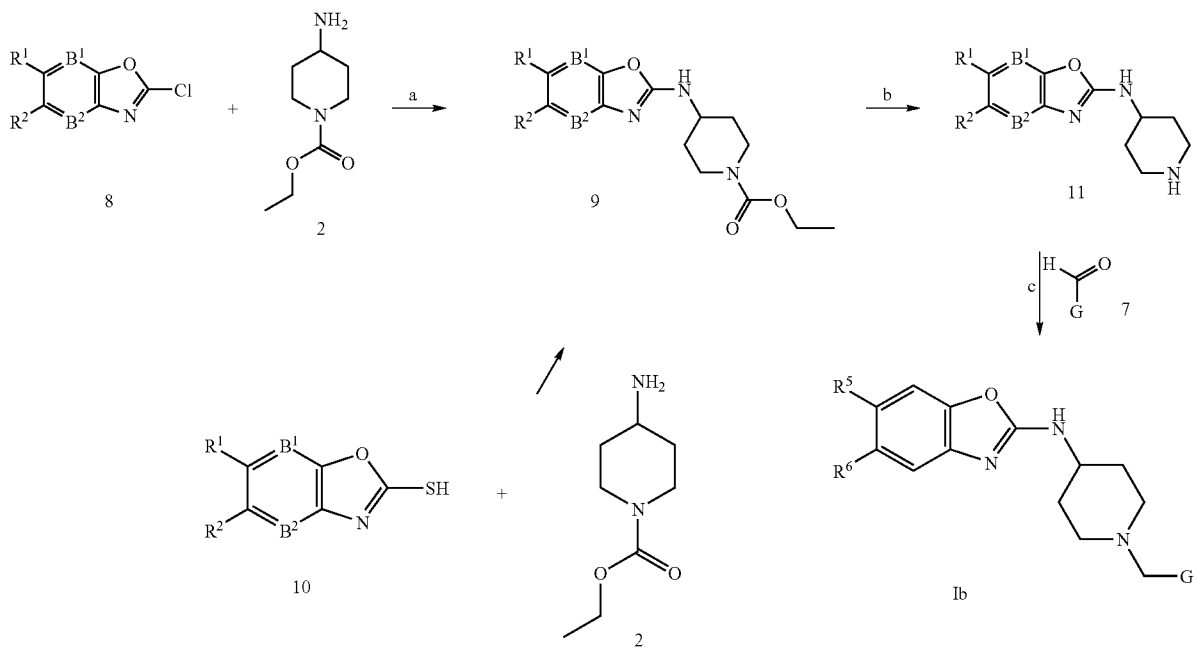

Target compounds of formula Ia or Ib might also be synthesized by direct alkylation of piperidines 6 with alkyl halides in solvents such as N,N-dimethylformamide, dichloromethane or dichloroethane at ambient or elevated temperatures using conventional heating or heating by microwave irradiation with the addition of a suitable tertiary amine base (e.g., triethylamine, N-ethyl diisopropylamine) or an inorganic base (e.g., $Cs_2CO_3$, $K_2CO_3$).

If not commercially available, the preparation of benzothiazoles, thiazolopyridines, benzooxazoles or oxazolopyridines of formulas 1, 8 or 10 can be accomplished by ring closure of suitably decorated aminophenoles or aminothiols of structure 12 (A=O or S) by thiophosgene or potassium ethylxanthogenate in a suitable solvent such as dichloromethane or THF (or mixtures thereof) at ambient or elevated temperatures (Scheme 2, step a). In some cases it -continued

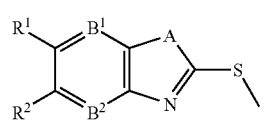

14

In order to obtain further derivatized target compounds of formula Ic or Id the reaction sequence can be conducted in reverse, namely by first performing the reductive alkylation step with a suitable functional group on the benzothiazole, thiazolopyridine, benzooxazole or oxazolopyridine core such as a the nitro (15, Scheme 4) or the carboxylic acid moiety (17, Scheme 5).

The nitro group can be reduced by applying a hydrogen atmosphere in the presence of a transition metal catalysts (e.g., Pd/C) and optionally an acid like HCl or acetic acid at room temperature or elevated temperatures in an alcohol such as methanol or ethanol to provide the corresponding anilines of formula 16 (scheme 4, step a). The compounds of general structure Ic are then obtained by coupling anilines of formula 16 with acid chlorides or sulfonyl chlorides in the presence of a suitable tertiary amine base (e.g., triethylamine, N-ethyl diisopropylamine) and a solvent such as DMF or THF at room or elevated temperatures. Alternatively, amides of structure Ic might also be obtained by coupling of anilines of formula Ic with carboxylic acids employing a suitable coupling agent (e.g., N,N'-carbonyldiimidazole (CDI), 1-(3-dimethylamino-propyl)-3-ethylcarbodiimide (EDCI) or 1-[bis(dimethyl-lamino)methylene]-1H-1,2,3-triazolo[4,5-b]pyridinium-3-oxide hexafluorphosphate (HATU)), typically in DMF or dichloroethane (DCE) at room temperature or elevated temperatures (step b).

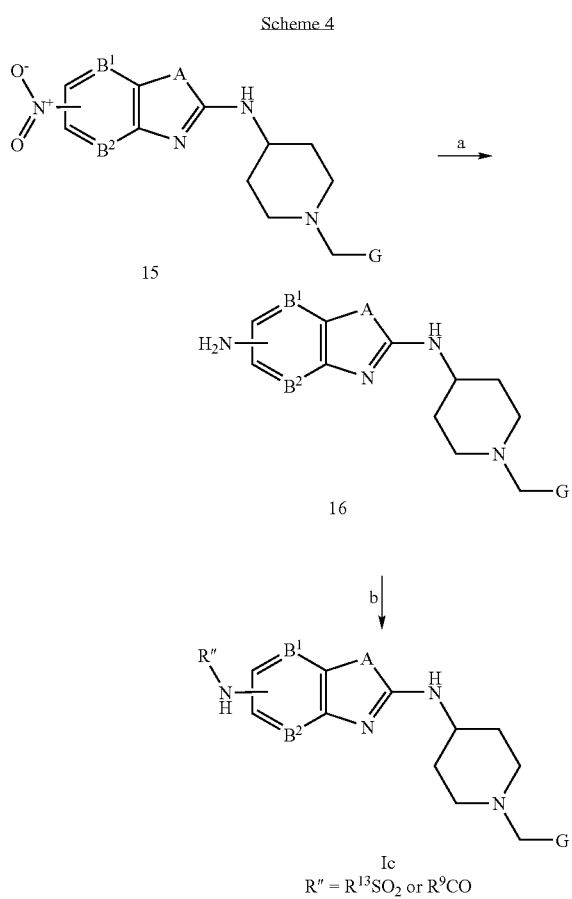

The inverted amides of structure Id can be accomplished by coupling the carboxylic acids of formula 17, obtainable by hydrolyses of the corresponding carboxylic esters with bases such as NaOH or LiOH, with primary or secondary amines employing a suitable coupling agent (e.g., CDI, EDCI or HATU) typically in DMF or DCE at room temperature or elevated temperatures (Scheme 5, step a).

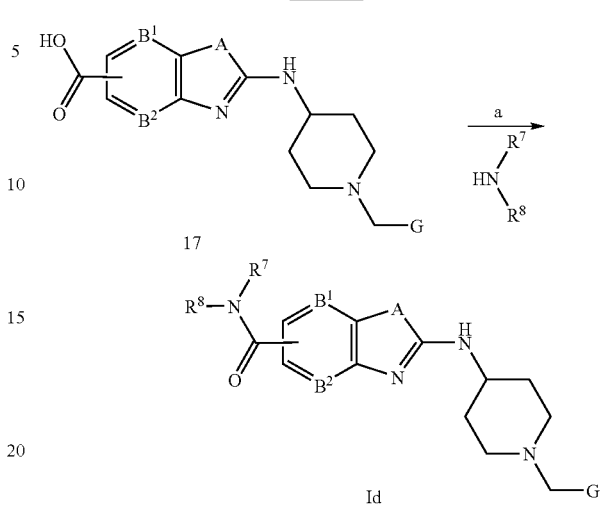

The requisite aldehyde partners are either commercially available or can be derived by alkylation with alkyl halides, alkyl mesylates, alkyl tosylates or alcohols containing any other suitable leaving group in a polar solvent such as DMF or acetone and a suitable base (e.g., $Cs_2CO_3$, $K_2CO_3$) at room temperature or elevated temperatures, by Mitsonobu reaction with alcohols activated by a mixture of triphenylphosphine and diethylazadicarboxylate, or by analogous alkylation of the phenolic carboxylic esters or acids of formula 18 (Scheme 6, step a). Reduction of the esters of formula 19 by a suitable reducing agent (e.g., diisobutylaluminium hydride at low temperature, with $LiAlH_4$ at elevated or ambient temperature) in a solvent such as THF provides the corresponding benzylalcohols of formula 20 (step b). These can then be oxidized to the aldehydes of formula 21, preferably with activated $MnO_2$ as oxidant in dichloromethane (step c). Alternatively the introduction of the side-chain can be accomplished by direct alkylation (sequential for unsymmetrical compounds) of the phenolic benzaldehydes of formula 22 providing the desired compounds of formula 21 directly. A further well-established route towards the synthesis of benzylaldehydes of formula 24 consists in the reduction of the corresponding benzonitriles of formula 23 by a suitable reducing agent such as diisobutylaluminium hydride at low temperature in a non-protic polar solvent (e.g., THF).

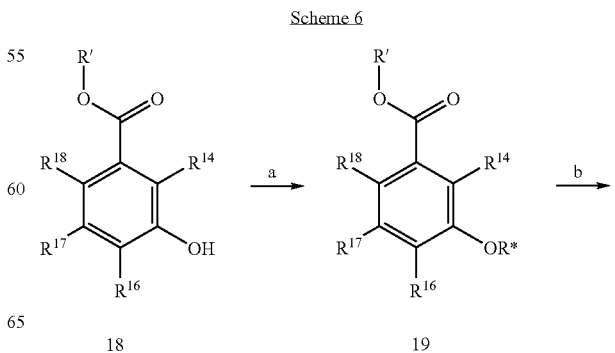

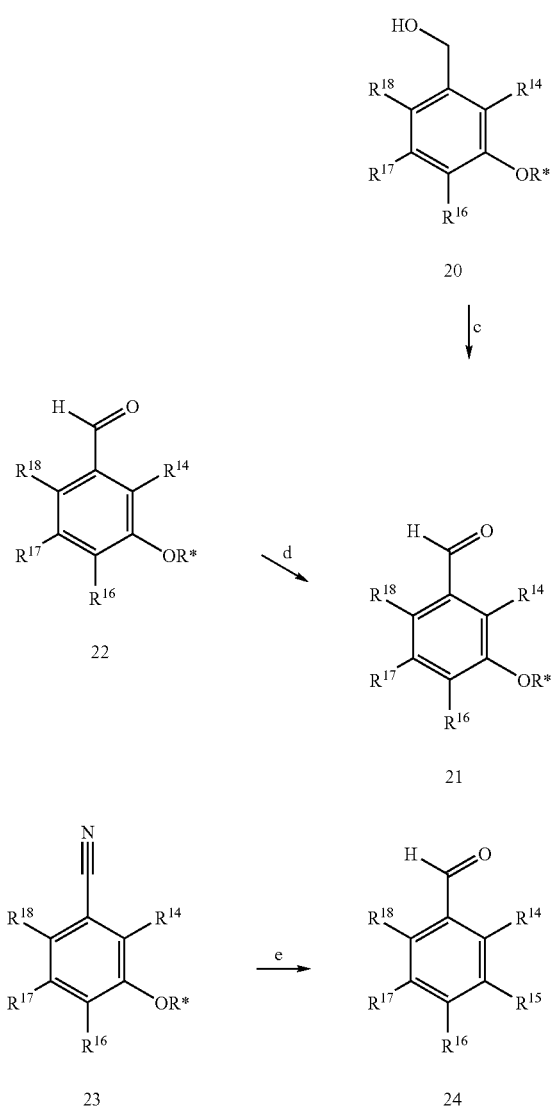

The synthesis of further aldehydes of formula 7 is described in more detail in the examples for intermediates 1 to 52.

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The present invention will be further explained by reference to the following illustrative examples. They are, however, not intended to limit its scope in any manner.

EXAMPLES

Abbreviations

Ar=argon, BINAP=(±)-2,2'-Bis(diphenylphosphino)-1,1'-binaphthalene, CDI=1,2-carbonyldiimidazole, DEAD=diazenedicarboxylic acid diethyl ester, DMAc=dimethylacetamide, DMF=N,N-dimethylformamide, DMSO=dimethyl sulfoxide, EI=electron impact (ionization), ESI=electron spray ionisation, HPLC=high performance liquid chromatography, Hyflo Super Cel®=filtration aid (Fluka), ISN=ion spray negative (mode), ISP=ion spray positive (mode), NMP=N-methylpyrrolidon, NMR=nuclear magnetic resonance, MS=mass spectrum, P=protecting group, py=pyridine, R=any group, rt=room temperature, THF=tetrahydrofuran, TFA=trifluoroacetic acid, X=halogen, Y=any group including heteroatoms and halides.

Example 1

Benzothiazol-2-yl-[1-(2-ethoxy-naphthalen-1-ylm-ethyl)-piperidin-4-yl]-amine

Step 1

4-(Benzothiazol-2-ylamino)-piperidine-1-carboxylic acid ethyl ester

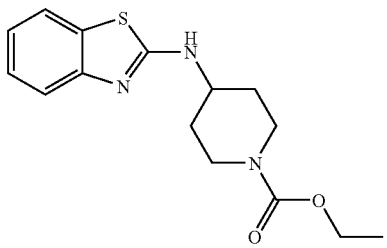

A mixture of 2-chloro-benzothiazole (2.00 g, 12.0 mmol, 1.0 equiv), ethyl 4-amino-1-piperidine carboxylate (2.44 g, 14.0 mmol, 1.2 equiv) and triethylamine (1.79 g, 18.0 mmol, 1.5 equiv) was heated by microwave irradiation to 180° C. for 5 min. To the crude reaction mixture was added dichloromethane (10 mL) and the suspension quickly poured onto tert-butyl methylether (200 mL). The hydrochloric salts of remaining ethyl 4-amino-1-piperidine carboxylate and triethylamine precipitated out and were removed by filtration. The filtrate was evaporated to dryness and the residue purified with column chromatography on silica eluting with dichloromethane/methanol (95:5) to yield 2.7 g (75%) of the title compound as a white solid. $^1$H NMR (300 MHz, DMSO): δ 1.19 (t, J=7.1 Hz, 3H), 1.31-1.44 (m, 2H), 1.96-2.01 (m, 2H), 2.98-3.06 (m, 2H), 3.88-3.98 (m, 3H), 4.04 (q, J=7.1 Hz, 2H), 7.01 (t, J=7.4 Hz, 1H), 7.21 (t, J=7.8 Hz, 1H), 7.39 (d, J=7.4 Hz, 1H), 7.65 (d, J=7.8 Hz, 1H), 8.01 (d, J=7.3 Hz, 1H). MS (ISP): 306.0 [M+H]$^+$.

Step 2

Benzothiazol-2-yl-piperidin-4-yl-amine (Intermediate A)

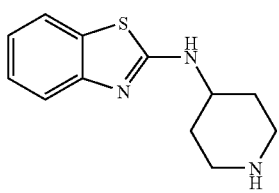

A solution of 4-(benzothiazol-2-ylamino)-piperidine-1-carboxylic acid ethyl ester (3.70 g, 12.0 mmol) in hydrobromic acid 48% in water (20 mL) was heated to reflux. After 18 h hydrobromic acid was removed under reduced pressure and the crude solid dissolved by vigorous stirring in hot methanol (50 mL). The obtained solution was cooled to −20° C. by which a precipitate formed that was removed by filtration. The organic phase was concentrated under reduced pressure, 4 N NaOH (100 mL) added and the solution extracted with dichloromethane (3×100 mL). The combined organic phases were dried over MgSO$_4$ to yield after evaporation of the solvent 1.7 g (61%) of the title compound which was used directly in the following step. $^1$H NMR (300 MHz, DMSO): δ 1.19-1.39 (m, 2H), 1.90-2.00 (m, 2H), 2.92-2.97 (m, 2H), 3.72-3.79 (m, 2H), 6.99 (t, J=8.2 Hz, 1H), 7.20 (t, J=8.2 Hz, 1H), 7.37 (d, J=7.6 Hz, 1H), 7.65 (d, J=7.2 Hz, 1H), 7.95 (d, J=7.2 Hz, 1H). MS (ISP): 233.9 [M+H]$^+$.

Step 3

To a solution of benzothiazol-2-yl-piperidin-4-yl-amine (23.3 mg, 0.1 mmol, 1.0 equiv) and 2-ethoxy-naphthalene-1-carbaldehyde (commercially available, 24.0 mg, 0.12 mmol, 1.2 equiv) in ethanol (2 mL) was added diisopropylethylamine (23.42 µL, 25.9 mg, 0.2 mmol, 2.0 equiv) and acetic acid (18.0 mg, 0.3 mmol, 3.0 equiv) and the mixture stirred at 40° C. After 1 h, sodium cyano borohydride (7.54 mg, 0.12 mmol, 1.2 equiv) was added and the mixture stirred at 40° C. over night. Removal of the solvent under reduced pressure and purification by preparative HPLC on reversed phase eluting with a gradient of acetonitrile/water provided 3.3 mg (8%) of the title compound. MS (ESI): 418.4 [M+H]$^+$.

Synthesis of Benzothiazole and Thiazolopyridine Intermediates B and C to be Used in Table 1

Intermediate B (6-Chloro-benzothiazol-2-yl)-piperidin-4-yl-amine dihydrobromide

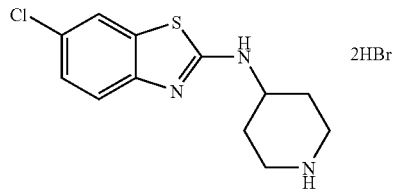

Step 1

4-(6-Chloro-benzothiazol-2-ylamino)-piperidine-1-carboxylic acid ethyl ester

A mixture of 2,6-dichloro-benzothiazole (1.83 g, 8.97 mmol, 1.0 equiv) and ethyl 4-amino-1-piperidine carboxylate (3.09 g, 17.93 mmol, 2.0 equiv) in anhydrous THF (20 mL) was heated to reflux for 12 h. Purification with column chromatography on silica eluting with ethyl acetate/hexane (3:1) yielded 2.5 g (76%) of the title compound. $^1$H NMR (400 MHz, DMSO): δ 1.18 (t, J=7.2 Hz, 3H), 1.33 (br m, 2H), 1.97 (br d, 2H), 3.01 (br s, 2H), 3.90 (br d, 3H), 4.04 (q, J=7.2 Hz, 2H), 7.21 (m, 1H), 7.36 (d, J=8.4 Hz, 1H), 7.78 (s, 1H), 8.16 (d, J=7.2 Hz, 1H). MS (ISP): 340.4 [M+H]$^+$.

Step 2

A solution of 4-(6-chloro-benzothiazol-2-ylamino)-piperidine-1-carboxylic acid ethyl ester (2.60 g, 7.65 mmol) in hydrobromic acid 48% in water (60 mL) was heated to reflux for 18 h. Removal of hydrobromic acid under reduced pressure and precipitation from ethanol (50 mL) provided 3.26 g (99%) of the title compound which was used directly in the next step. $^1$H NMR (400 MHz, DMSO): δ 1.69-1.79 (m, 2H), 2.14-2.17 (m, 2H), 3.01-3.09 (m, 2H), 3.32-3.35 (m, 2H), 4.06 (br s, 1H), 7.31 (dd, J=8.4 Hz, J=2.4 Hz, 1H), 7.42 (d, J=8.4 Hz, 1H), 7.88 (d, J=2.4 Hz, 1H), 8.52 (br s, 1H), 8.62 (br s, 1H), 9.00 (br s, 1H). MS (ISP): 266.0 [M–H]⁻.

Intermediate C

Piperidin-4-yl-thiazolo[5,4-b]pyridin-2-yl-amine dihydrobromide

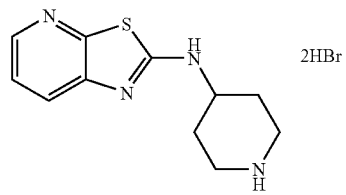

Step 1

4-(Thiazolo[5,4-b]pyridin-2-ylamino)-piperidine-1-carboxylic acid ethyl ester

The title compound was prepared according to European Patent Application EP 0 184 257 A1 (Janssen Pharmaceutica N.V.).

Step 2

A solution of 4-(thiazolo[5,4-b]pyridin-2-ylamino)-piperidine-1-carboxylic acid ethyl ester (3.10 g, 10.1 mmol) in 48% hydrobromic acid in water (50 mL) was heated to reflux. After 18 h the hydrobromic acid was removed under reduced pressure and the crude material directly used in the following reductive alkylation step. MS (ESI): 234.4 [M+H]⁺.

The aldehyde intermediates 1 to 52 were prepared following literature precedents or in analogy to literature precedents or as described below.

Synthesis of Aldehyde Intermediates 1 to 52 to be Used in Tables 1 to 3 and 6 to 8

Intermediate 1

1,4-Dimethoxy-naphthalene-2-carbaldehyde [CAS RN 75965-83-2]

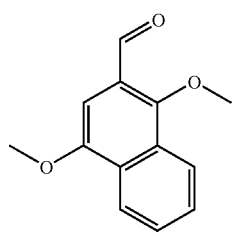

The title compound was prepared by treating (1,4-dimethoxy-naphthalen-2-yl)-methanol (6.5 g, 29.8 mmol, 1.0 equiv, [CAS RN 150556-57-3], prepared as described in C. Flader, J. Liu, R. F. Borch *J. Med. Chem.* 2000, 43, 3157-3167) with activated MnO₂ (25.9 g, 297.8 mmol, 10.0 equiv) in dichloromethane for 4 h, after which time the reaction was filtered through Hyflo Super Cel and concentrated by evaporation of the solvent under reduced pressure affording 5.1 g (81%) of the title compound. ¹H NMR (300 MHz, CDCl₃): δ 4.02 (s, 3H), 4.10 (s, 3H), 7.14 (s, 1H), 7.61-7.65 (m, 2H), 8.18-8.30 (m, 2H), 10.58 (s, 1H).

Intermediate 2

4-Methoxy-3-propoxy-benzaldehyde [CAS RN 5922-56-5]

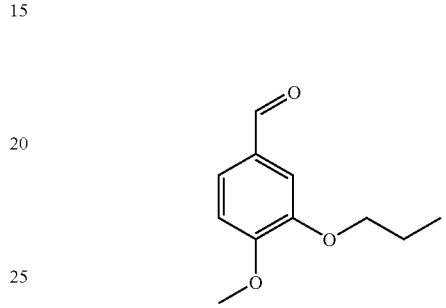

The title compound was prepared by reaction of isovanillin with propyl iodide in DMF with K₂CO₃ as base as described in M. J. Ashton, D. C. Cook, G. Fenton, J.-A. Karlsson, M. N. Palfreyman, D. Raeburn, A. J. Ratcliffe, J. E. Souness, S. Thurairatnam, N. Vicker *J. Med. Chem.* 1994, 37, 1696-1703.

Intermediate 3

3-(2-Fluoro-ethoxy)-4-methoxy-benzaldehyde

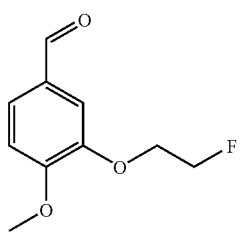

To a solution of 3-hydroxy-4-methoxy-benzaldehyde (10.0 g, 66.0 mmol, 1.0 equiv) in anhydrous DMF (40 mL) was added K₂CO₃ (13.6 g, 99.0 mmol, 1.5 equiv) and 1-bromo-2-fluoro-ethane (9.2 mg, 72.0 mmol, 1.1 equiv) and the mixture stirred at rt for 48 h. The K₂CO₃ was removed by filtration and the organic phase concentrated under reduced pressure. To the crude reaction mixture was added a conc. solution of sodium chloride (100 mL) and the solution extracted with ethyl acetate (3×100 mL). The combined organic phases were dried over MgSO₄ and the product crystallized from a mixture of isopropanol/diethylether to yield 12.69 g (97%) of the title compound. ¹H NMR (300 MHz, DMSO): δ 3.89 (1H), 4.24-4.27 (m, 1H), 4.34-4.37 (m, 1H), 4.67-4.70 (m, 1H), 4.83-4.86 (m, 1H), 7.20 (d, J=8.4 Hz, 1H), 7.43 (d, J=1.9 Hz, 1H), 7.59 (dd, J=8.4 Hz, J=1.9 Hz, 1H), 9.84 (s, 1H). MS (ISP): 198.6 [M+H]⁺.

Intermediate 4

3,5-Diethoxy-4-pyrrol-1-yl-benzaldehyde

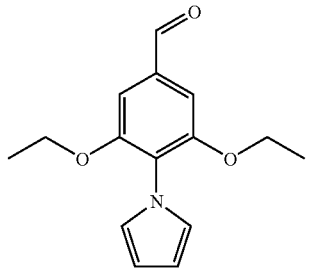

Step 1

3,5-Diethoxy-4-pyrrol-1-yl-benzoic acid ethyl ester

To a solution of 4-amino-3,5-diethoxy-benzoic acid ethyl ester (3.0 g, 11.84 mmol, 1.0 equiv; prepared as described in I. Kompis, A. Wick *Helv. Chim. Acta* 1977, 60, 3025-3034) in heptane (10 mL) and conc. acetic acid (0.2 mL) was added 2,5-dimethoxy-tetrahydro-furan (1.88 g, 14.21 mmol, 1.2 equiv). After heating to reflux for 5 h, a Dean-Stark apparatus was attached and the reaction mixture heated for an additional time period of 5 h. Filtration of the crude reaction mixture and crystallisation at 0° C. from heptane provided 2.94 g (82%) of the title compound. $^1$H NMR (300 MHz, DMSO): δ 1.15 (t, J=7.0 Hz, 6H), 1.27 (t, J=7.1 Hz, 3H), 3.98 (q, J=7.0 Hz, 4H), 4.28 (q, J=7.1 Hz, 2H), 6.07-6.08 (m, 2H), 6.73-6.74 (m, 2H), 7.22 (s, 2H). $^{13}$C NMR (75 MHz, DMSO): δ 14.11, 14.35, 61.06, 64.57, 106.87, 107.64, 122.61, 123.33, 129.29, 153.75, 165.06. MS (ISP): 303.4 [M+H]$^+$.

Step 2

To a solution of 3,5-diethoxy-4-pyrrol-1-yl-benzoic acid ethyl ester (1.51 g, 4.98 mmol, 1.0 equiv) in toluene (5 mL) was added slowly over a time period of 15 min under slight cooling to 20° C. a solution of diisobutylaluminium hydride (8.9 mL, 12.45 mmol, 2.5 equiv; 20% solution in toluene). After 1 h, the excess hydride was quenched by cautious addition of water (10 mL) and a 28% solution of sodium hydoxide (2 mL). The mixture was stirred for 30 min and the organic phase filtered over Hyflo Super Cel. The aqueous layer was extracted with toluene (2×50 mL), the combined organic phases washed with a sat. solution of sodium chloride (2×50 mL) and concentrated by evaporation under reduced pressure to afford 1.30 g (100%) of (3,5-diethoxy-4-pyrrol-1-yl-phenyl)-methanol. The crude alcohol (1.30 g, 4.98 mmol, 1.0 equiv) was dissolved in toluene (20 mL) and activated MnO$_2$ (7.79 g, 89.5 mmol, 18.0 equiv) was added. The reaction mixture was heated to reflux for 7 h, after which time the reaction was filtered through Hyflo Super Cel and concentrated yielding 1.15 g (89% yield) of the title compound. $^1$H NMR (300 MHz, DMSO): δ 1.17 (t, J=7.0 Hz, 6H), 4.02 (q, J=7.0 Hz, 4H), 6.08-6.09 (m, 2H), 6.75-6.76 (m, 2H), 7.25 (s, 2H), 9.89 (s, 1H). MS (ISP): 260.1 [M+H]$^+$.

Intermediate 5

Ethoxy-4-methyl-benzaldehyde [CAS RN 157143-20-9]

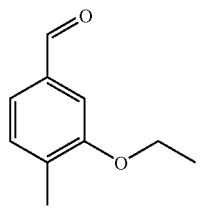

The title compound was prepared by reaction of commercially available 3-hydroxy-4-methyl-benzaldehyde with ethyl iodide in analogy to the preparation of intermediate 2 (4-methoxy-3-propoxy-benzaldehyde).

Intermediate 6

Chloro-3-ethoxy-benzaldehyde [CAS RN 85259-46-7]

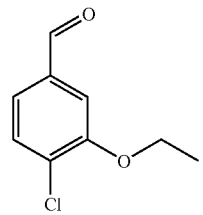

To a solution of 4-chloro-3-hydroxy-benzoic acid (3.0 g, 17.4 mmol, 1.0 equiv) in DMF (15 mL) was added K$_2$CO$_3$ (4.81 g, 34.8 mmol, 2.0 equiv) and ethyl iodide (4.03 mL, 5.97 g, 38.2 mmol, 2.2 equiv). The reaction mixture was stirred for 6 h at rt, diluted with water (20 mL) and extracted with ethyl acetate (3×50 mL). The organic phases were dried over Na$_2$SO$_4$ and concentrated to afford 3.6 g (91%) of 4-chloro-3-ethoxy-benzoic acid ethyl ester. The crude ester was then dissolved in THF (20 mL) and cooled to −78° C. under Ar. A solution of diisobutylaluminium hydride (95 mL, 95.0 mmol, 6.0 equiv; 1 M solution in THF) was slowly added over a time period of 15 min, the cooling bath removed on completion of addition and the reaction allowed to reach 0° C. After 1 h, the reaction was cooled to −78° C. and the excess hydride quenched by cautious addition of a solution of 1 M HCl (10 mL). The mixture was brought to rt, the organic phase separated and the aqueous layer extracted with ethyl acetate (3×100 mL). The combined organic phases were dried over Na$_2$SO$_4$ and concentrated by evaporation under reduced pressure to afford 2.94 g (100%) of 4-chloro-3-ethoxy-benzyl alcohol. The crude alcohol (2.94 g, 15.75 mmol, 1.0 equiv) was dissolved in dichloromethane (15 mL) and activated MnO$_2$ (5.48 g, 63.0 mmol, 4.0 equiv) was added. The reaction mixture was stirred for 16 h, after which time the reaction was filtered through Hyflo Super Cel and concentrated. The residue was purified by flash column chromatography on silica eluting with heptane/ethyl acetate (4:1) to yield 1.51 g (52% yield) of the title compound. $^1$H NMR (300 MHz, CDCl$_3$): δ

1.51 (t, J=7.1 Hz, 3H), 4.19 (q, J=7.1 Hz, 2H), 7.37-7.42 (m, 2H), 7.55 (d, J=9.0 Hz, 1H), 9.94 (s, 1H).

Intermediate 7

Ethoxy-2-fluoro-4-hydroxy-benzaldehyde [CAS RN 3766000-65-6]

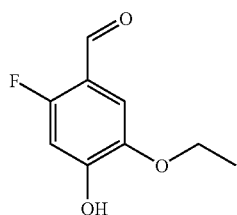

The title compound was prepared according to WO 01/090 051 A1 (Hoffmann-La Roche A G).

Intermediate 8

3-Isobutoxy-4-methoxy-benzaldehyde [CAS RN 57724-26-2]

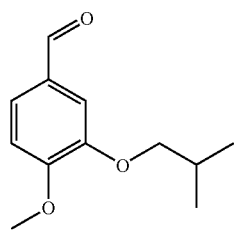

The title compound was prepared by reaction of isovanillin with 1-bromo-2-methyl propane as described in WO 04/000 806 A1 (Elbion AG).

Intermediate 9

3-(2-Hydroxy-ethoxy)-4-isopropoxy-benzaldehyde

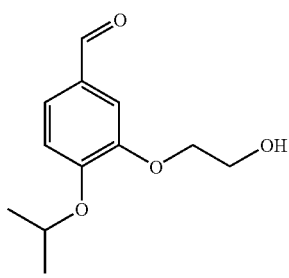

The title compound was prepared analogously to intermediate 2 (4-methoxy-3-propoxy-benzaldehyde) by reaction of 3-hydroxy-4-isopropoxy-benzaldehyde ([CAS RN 94283-73-5], F. R. Hewgill, M. C. Pass *Australian J. Chem.* 1985, 38, 537-554) with 2-bromo-ethanol in DMF using $K_2CO_3$ as base. MS (ISP): 224.2 [M+H]$^+$.

Intermediate 10

3-Ethoxy-4-fluoro-benzaldehyde

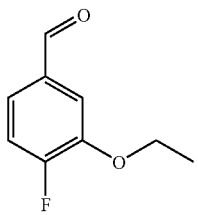

The title compound was prepared according to the procedure described for the synthesis of intermediate 6 (4-chloro-3-ethoxy-benzaldehyde) starting from 4-fluoro-3-hydroxy-benzoic acid in 73% overall yield after purification by flash column chromatography on silica eluting with hexane/ethyl acetate (10:1). $^1$H NMR (300 MHz, DMSO): δ 1.32 (t, J=7.0 Hz, 3H), 4.12 (q, J=7.0 Hz, 2H), 7.34-7.41 (m, 1H), 7.47-7.56 (m, 2H), 9.87 (s, 1H). MS (ISP): 186.1 [M+NH$_4$]$^+$.

Intermediate 11

3-Ethoxy-4-trifluoromethyl-benzaldehyde

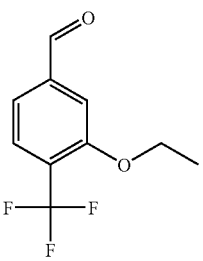

Step 1

Ethoxy-2-nitro-4-trifluoromethyl-phenylamine

To ethanol (500 mL) was added potassium metal (ca. 21 g, ca. 537 mmol, ca. 2.24 equiv) and the vigorous reaction had to be cooled with an ice bath. Stirring was continued until all potassium metal was dissolved. Solid commercially available 5-chloro-2-nitro-4-trifluoromethyl-phenylamine (57.74 g, 240 mmol, 1.0 equiv, [CAS RN 35375-74-7]) was added in one portion and the resulting dark red mixture was stirred at 55-60° C. for 4 d. The warm reaction mixture was slowly poured into water (ca. 2000 mL), the pH adjusted with a solution of 1 M HCl to 2, the yellow precipitate filtered off, washed with water and dried in air at 60° C. to give 57.81 g (96%) of the title compound as a yellow solid which was used without further purification. MS (ISN): 249.0 [M−H]$^-$.

Step 2

Bromo-5-ethoxy-2-nitro-4-trifluoromethyl-benzene

Solid 5-ethoxy-2-nitro-4-trifluoromethyl-phenylamine from step 1 (57.81 g, 231 mmol, 1.0 equiv) was added slowly over 15 min to a rapidly stirred mixture of tert-butyl nitrite (45.8 mL, 347 mmol, 1.5 equiv) and anhydrous copper(II) bromide (77.4 g, 347 mmol, 1.5 equiv) in acetonitrile (462 mL), which was heated to 65° C. in an oil bath. Stirring at 65° C. was continued for 30 min, the reaction mixture was cooled to 23° C., poured into a solution of 1 M HCl, saturated with solid sodium chloride, extracted with tert-butyl methylether and dried over MgSO$_4$. Removal of the solvent by evaporation under reduced pressure left a dark brown oil (74.5 g), which was purified by flash column chromatography on silica eluting with heptane/ethyl acetate (4:1) yielding 63.03 g (87%) of the title compound as a yellow solid. MS (EI): 313.0 [M]$^+$ and 315.0 [M$^+$2]$^+$.

Step 3

Ethoxy-2-nitro-4-trifluoromethyl-benzonitrile

A mixture of 1-bromo-5-ethoxy-2-nitro-4-trifluoromethyl-benzene (61.81 g, 197 mmol, 1.0 equiv) and CuCN (18.51 g, 207 mmol, 1.05 equiv) in NMP (197 mL) was heated to 150° C. for 30 min. After cooling to 23° C. it was poured into 1 M HCl, extracted with tert-butyl methylether, washed with a sat. solution of sodium chloride and the organic phases dried over Na$_2$SO$_4$. Removal of the solvent by evaporation under reduced pressure left a brown oil, which was purified by flash column chromatography on silica eluting with heptane/ethyl acetate (4:1) providing 46.73 g (91%) of the title compound as a yellow solid. MS (EI): 260.1 [M]$^+$.

Step 4

Amino-5-ethoxy-4-trifluoromethyl-benzonitrile

Iron powder (40.96 g, 733 mmol, 1.0 equiv) was added in small portions over 5 min to a stirred suspension of finely grinded 5-ethoxy-2-nitro-4-trifluoromethyl-benzonitrile (42.79 g, 164.5 mmol, 4.5 equiv) in methanol (85 mL) and conc. HCl (102 mL) which was cooled with a water bath to keep the internal temperature at 40-50° C. The resulting mixture was stirred for an additional hour at ca. 50° C. and then poured into ice cold water (700 mL). The precipitate was filtered, washed with water, dried, and dissolved in boiling ethanol (800 mL). Activated carbon (ca. 10 g) was added, the mixture refluxed for 45 min, the hot solution filtered and the organic phase evaporated under reduced pressure to dryness to leave 31.8 g (84%) of the title compound as a yellow solid which was used without further purification. MS (EI): 230.1 [M]$^+$.

Step 5

Ethoxy-4-trifluoromethyl-benzonitrile

To a solution of 2-amino-5-ethoxy-4-trifluoromethyl-benzonitrile (31.62 g, 137.4 mmol, 1.0 equiv) in anhydrous THF (410 mL) was added isoamyl nitrite (40.4 mL, 302 mmol, 2.2 equiv) and the mixture was heated to reflux for 16 h. The solvent was removed by evaporation under reduced pressure to give an orange oil which was dissolved in a sat. solution of NaHCO$_3$ and extracted three times with diethyl ether. The combined organic phases were washed with 1 N HCl and a sat. solution of sodium chloride and the organic phases dried over Na$_2$SO$_4$. Removal of the solvent by evaporation under reduced pressure left an orange oil which was purified by double Kugelrohr distillation (up to 160° C. bath temperature at 1.5 mbar) yielding 25.1 g (85%) of the title compound as a light yellow solid upon solidification. MS (EI): 185.1 [M]$^+$.

Step 6

To a solution of 3-ethoxy-4-trifluoromethyl-benzonitrile (0.65 g, 3.02 mmol, 1.0 equiv) in toluene (10 mL) at −10° C. under Ar was slowly added diisobutylaluminium hydride (2.75 mL, 2.36 g, 3.32 mmol, 1.1 equiv, 20% solution in toluene) over a time period of 30 min. After 1 h, the excess hydride was quenched by cautious addition of a solution of 1 M HCl (10 mL) and the crude reaction mixture extracted with ethyl acetate (3×50 mL). The combined organic phases were dried over MgSO$_4$ and the solvent removed by evaporation under reduced pressure to yield 0.52 g (79%) of the title compound. $^1$H NMR (300 MHz, CDCl$_3$): δ 1.41 (t, J=7.0 Hz, 3H), 4.14 (q, J=7.0 Hz, 2H), 7.40 (s, 1H), 7.42 (d, J=8.1 Hz, 1H), 7.68 (d, J=8.1 Hz, 1H), 9.96 (s, 1H). $^{19}$F NMR (282 MHz, DMSO): δ −63.12.

Intermediate 12

Cyclopropoxy-3-ethoxy-benzaldehyde

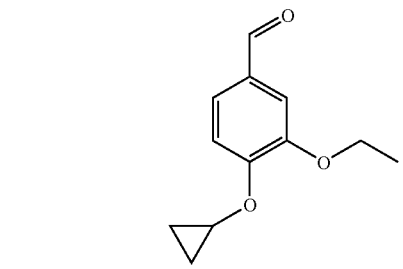

The title compound was prepared analogously to intermediate 2 (4-methoxy-3-propoxy-benzaldehyde) by reaction of 3-ethoxy-4-hydroxy-benzaldehyde with cyclopropyl bromide in DMF using K$_2$CO$_3$ as base. MS (ISP): 206.9 [M+H]$^+$.

Intermediate 13

3-Ethoxy-4-(1-ethyl-propoxy)-benzaldehyde

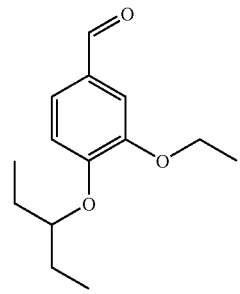

The title compound was prepared analogously to intermediate 2 (4-methoxy-3-propoxy-benzaldehyde) by reaction of 3-ethoxy-4-hydroxy-benzaldehyde with 3-bromo-pentane in DMF using K$_2$CO$_3$ as base. MS (ISP): 237.1 [M+H]$^+$.

Intermediate 14

3-Ethoxy-4-(3-methyl-but-2-enyloxy)-benzaldehyde

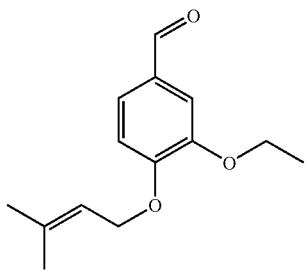

The title compound was prepared analogously to intermediate 2 (4-methoxy-3-propoxy-benzaldehyde) by reaction of 3-ethoxy-4-hydroxy-benzaldehyde with 1-bromo-3-methyl-2-butene in DMF using $K_2CO_3$ as base. MS (ISN): 233.1 [M−H]⁻.

Intermediate 15

3-Allyloxy-4-methoxy-benzaldehyde [CAS RN 225939-36-6]

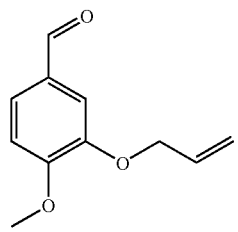

The title compound was prepared analogously to intermediate 2 (4-methoxy-3-propoxy-benzaldehyde) by reaction of 3-hydroxy-4-methoxy-benzaldehyde with allylbromide in DMF using $K_2CO_3$ as base (see also A. W. White, R. Almassy, A. H. Calvert, N. J. Curtin, R. J. Griffin, Z. Hostomsky, K. Maegley, D. R. Newell, S. Srinivasan, B. T. Golding *J. Med. Chem.* 2000, 43, 4084-4097).

Intermediate 16

3-Butoxy-4-methoxy-benzaldehyde

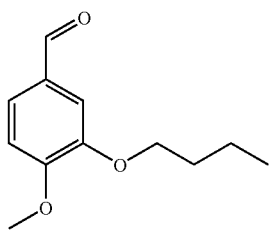

The title compound was prepared analogously to intermediate 2 (4-methoxy-3-propoxy-benzaldehyde) by reaction of 3-hydroxy-4-methoxy-benzaldehyde with 4-bromo-butane in DMF using $K_2CO_3$ as base. MS (ISP): 209.1 [M+H]⁺.

Intermediate 17

Ethoxy-2-fluoro-4-(2-hydroxy-ethoxy)-benzaldehyde [CAS RN 376600-66-7]

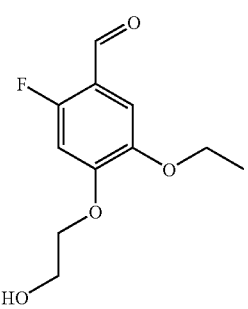

The title compound was prepared according to WO 01/090 051 (Hoffmann-La Roche A G).

Intermediate 18

Ethoxy-2,2-dimethyl-2H-chromene-6-carbaldehyde [CAS RN 210404-30-9]

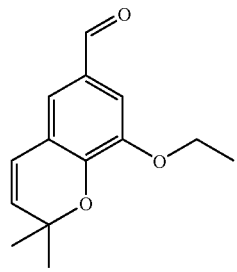

The title compound was prepared according to WO 01/083 476 A1 (Hoffmann-La Roche A G).

Intermediate 19

3-Ethoxy-5-(2,2,2-trifluoro-ethoxy)-benzaldehyde

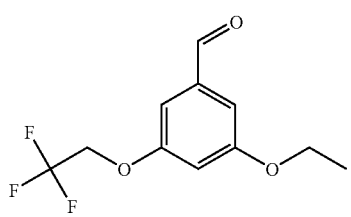

Step 1

3-Ethoxy-5-(2,2,2-trifluoro-ethoxy)-benzoic acid methyl ester

A mixture of 3-ethoxy-5-hydroxy-benzoic acid methyl ester (1.5 g, 7.65 mmol, 1.0 equiv; prepared as described in WO 99/05123 A1, Astra Pharmaceuticals Ltd.), 2,2,2-trifluoroethyl iodide (2.25 mL, 4.82 g, 22.94 mmol, 3.0 equiv) and cesium carbonate (4.98 g, 15.29 mmol, 2.0 equiv) was heated to 130° C. under microwave irradiation for 20 min. The crude reaction mixture was filtered over Hyflo Super Cel and extracted with dichloromethane (3×50 mL). The combined organic phases were dried over MgSO$_4$, the solvent removed by evaporation under reduced pressure and the crude material purified by flash column chromatography on silica eluting with a gradient of heptane/dichloromethane (1:1→0:1) yielding 0.89 g (42%) of the title compound. $^1$H NMR (300 MHz, CDCl$_3$): δ 1.35 (t, J=7.0 Hz, 3H), 3.84 (s, 3H), 4.00 (q, J=7.0 Hz, 2H), 4.30 (q, J=8.1 Hz, 2H), 6.62-6.63 (m, 1H), 7.10-7.11 (m, 1H), 7.19-7.21 (m, 1H). MS (ISP): 279.0 [M+H]$^+$.

Step 2

To a solution of 3-ethoxy-5-(2,2,2-trifluoro-ethoxy)-benzoic acid methyl ester (0.8 g, 2.88 mmol, 1.0 equiv) in anhydrous THF (20 mL) was added lithium aluminium hydride (0.273 g, 7.19 mmol, 2.5 equiv) and the reaction mixture stirred at rt for 4 h. The crude reaction mixture was filtered over Hyflo Super Cel, the filtrate extracted with diethyl ether (3×50 mL) and the combined organic phases dried over MgSO$_4$ providing 0.75 g (99%) of the benzyl alcohol. The crude reaction product (0.75 g, 3.0 mmol, 1.0 equiv) was dissolved in THF (20 mL) and activated MnO$_2$ (2.61 g, 30.00 mmol, 10.0 equiv) was added. After stirring at rt for 3 h, the reaction mixture was filtered over Hyflo Super Cel and the solvent removed by evaporation under reduced pressure. A conc. solution of sodium chloride (100 mL) was added, the mixture extracted with ethyl acetate (3×100 mL) and the combined organic phases dried over MgSO$_4$. Purification of the crude material with column chromatography on silica eluting with heptane/ethyl acetate (4:1) provided 0.54 g (72%) of the title compound. $^1$H NMR (300 MHz, CDCl$_3$): δ 1.35 (t, J=7.0 Hz, 3H), 4.00 (q, J=7.0 Hz, 2H), 4.31 (q, J=8.1 Hz, 2H), 6.66-6.67 (m, 1H), 6.91-6.92 (m, 1H), 6.99-7.00 (m, 1H).

Intermediate 20

3-Ethoxy-5-(tetrahydro-pyran-4-yloxy)-benzaldehyde

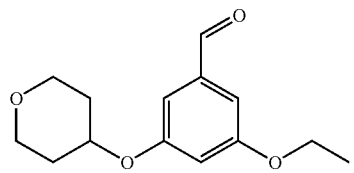

Step 1

3-Ethoxy-5-(tetrahydro-pyran-4-yloxy)-benzoic acid methyl ester

To a mixture of triphenylphosphine (1.18 g, 4.49 mmol, 1.1 equiv) and DEAD (0.76 mL, 0.85 g, 4.89 mmol, 1.2 equiv) in anhydrous THF (10 mL) was added 3-ethoxy-5-hydroxy-benzoic acid methyl ester (0.8 g, 4.08 mmol, 1.0 equiv; prepared as described in WO 99/05123 A1, Astra Pharmaceuticals Ltd.) and tetrahydro-pyran-4-ol (0.42 g, 4.08 mmol, 1.0 equiv), dissolved in THF (10 mL), at 0° C. under Ar. After stirring for 6 h, the solvent was partially removed by evaporation under reduced pressure, water (50 mL) added and the reaction mixture extracted with ethyl acetate (3×50 mL). The combined organic phases were dried over MgSO$_4$, the solvent removed by evaporation under reduced pressure and the crude material yielding 0.64 g (56%) of the title compound which was directly used in the next step. $^1$H NMR (300 MHz, CDCl$_3$): δ 1.32 (t, J=7.0 Hz, 3H), 1.67-1.72 (m, 2H), 1.91-1.97 (m, 2H), 3.48-3.53 (m, 2H), 3.81 (s, 3H), 3.85-3.91 (m, 2H), 3.96 (q, J=7.0 Hz, 2H), 4.40-4.44 (m, 1H), 6.56-6.58 (m, 1H), 7.08-7.10 (m, 2H). $^{13}$C NMR (75 MHz, CDCl$_3$): δ 14.59, 31.68, 51.99, 63.69, 64.89, 71.86, 107.82, 108.06, 109.09, 131.98, 158.17, 160.05, 166.61. MS (ISP): 281.2 [M+H]$^+$.

Step 2

To a solution of 3-ethoxy-5-(tetrahydro-pyran-4-yloxy)-benzoic acid methyl ester (0.64 g, 2.28 mmol, 1.0 equiv) in anhydrous THF (20 mL) was added lithium aluminium hydride (0.217 g, 5.71 mmol, 2.5 equiv) and the reaction mixture stirred at rt for 4 h. The crude reaction mixture was filtered over Hyflo Super Cel, the filtrate extracted with diethyl ether (3×50 mL) and the combined organic phases dried over MgSO$_4$ providing 0.56 g (100%) of the benzyl alcohol. The crude reaction product (0.56 g, 2.22 mmol, 1.0 equiv) was dissolved in THF (20 mL) and activated MnO$_2$ (1.93 g, 22.2 mmol, 10.0 equiv) was added. After stirring at rt for 3 h, the reaction mixture was filtered over Hyflo Super Cel and the solvent removed by evaporation under reduced pressure. A conc. solution of sodium chloride (100 mL) was added, the mixture extracted with ethyl acetate (3×100 mL) and the combined organic phases dried over MgSO$_4$ providing 0.46 g (83%) of the title compound. $^1$H NMR (300 MHz, CDCl$_3$): δ 1.34 (t, J=7.0 Hz, 3H), 1.66-1.76 (m, 2H), 1.91-1.98 (m, 2H), 3.46-3.53 (m, 2H), 3.85-3.92 (m, 2H), 3.98 (q, J=7.0 Hz, 2H), 4.41-4.47 (m, 1H), 6.62-6.63 (m, 1H), 6.89-6.91 (m, 2H), 9.79 (s, 1H). $^{13}$C NMR (75 MHz, CDCl$_3$): δ 14.62, 31.67, 63.90, 64.96, 72.02, 107.96, 108.68, 109.44, 138.49, 158.85, 160.71, 191.72. MS (ISP): 251.1 [M+H]$^+$.

Intermediate 21

3,5-Diethoxy-4-fluoro-benzaldehyde

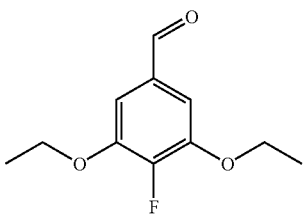

Step 1 tert-Butyl-(4-fluoro-benzyloxy)-dimethyl-silane

To a solution of (4-fluoro-phenyl)-methanol (12.16 g, 96.4 mmol, 1.0 equiv) in anhydrous DMF (50 mL) at 0° C. under Ar was added imidazole (7.22 g, 106.1 mmol, 1.1 equiv) and tert-butyl-chloro-dimethyl-silane (15.99 g, 106.1 mmol, 1.1 equiv). After the addition was completed the cooling bath was removed and the reaction stirred for 18 h at rt. The reaction mixture was poured on ice, extracted with ethyl acetate (2×100 mL) and the combined organic phases washed with a sat. solution of sodium carbonate (2×100 mL) and sodium chloride (2×100 mL). The organic phase was dried over $Na_2SO_4$, concentrated by evaporation under reduced pressure yielding a brown oil that was purified by high vacuum distillation (bp 32-35° C. at 0.1 mbar) to give 23.0 g (99%) of the title compound. $^1$H NMR (400 MHz, $CDCl_3$): δ 0.00 (s, 6H), 0.84 (s, 9H), 4.60 (s, 2H), 6.89-6.94 (m, 2H), 7.16-7.20 (m, 2H). MS (EI): 183.1 [M-tert-Bu]$^+$.

Step 2

5-(tert-Butyl-dimethyl-silanyloxymethyl)-2-fluoro-phenol

To a solution of tert-butyl-(4-fluoro-benzyloxy)-dimethyl-silane (5.00 g, 20.8 mmol, 1.0 equiv) in anhydrous THF (20 mL) was added at −78° C. under Ar a solution of sec-BuLi (17.6 mL, 22.8 mmol, 1.1 equiv, 1.3 M solution in hexane) within 30 min. Then a solution of trimethyl borate (2.37 mL, 2.20 g, 20.8 mmol, 1.0 equiv) in anhydrous THF (7.5 mL) was added slowly within 30 min and the cooling bath removed. A solution of conc. acetic acid (2.78 mL, 1.87 g, 31.2 mmol, 1.5 equiv) was slowly added followed by addition of a solution of 35% hydrogen peroxide in water (2.0 mL, 2.23 g, 22.9 mmol, 1.1 equiv) and the reaction mixture kept at 0° C. for 30 min. After stirring at rt for an additional 4 h, the reaction was extracted with diethyl ether (2×100 mL) and the combined organic phases washed with a solution of 10% NaOH (2×100 mL) and a sat. solution of sodium chloride (2×100 mL). The organic phase was dried over $Na_2SO_4$, concentrated by evaporation under reduced pressure and the crude material purified with column chromatography on silica eluting with hexane/ethyl acetate (19:1) providing 4.80 g (90%) of the title compound. $^1$H NMR (400 MHz, $CDCl_3$): δ 0.00 (s, 6H), 0.84 (s, 9H), 4.56 (s, 2H), 4.97 (br s, 1H), 6.68-6.72 (m, 1H), 6.87-6.94 (m, 2H). MS (EI): 256.2 [M]$^+$.

Step 3

2-(tert-Butyl-dimethyl-silanyloxy)-4-(tert-butyl-dimethyl-silanyloxymethyl)-1-fluoro-benzene To a solution of 5-(tert-butyl-dimethyl-silanyloxymethyl)-2-fluoro-phenol (4.60 g, 17.9 mmol, 1.0 equiv) in anhydrous DMF (20 mL) at 0° C. under Ar was added imidazole (1.34 g, 19.7 mmol, 1.1 equiv) and tert-butyl-chloro-dimethyl-silane (2.97 g, 19.7 mmol, 1.1 equiv). After the addition was completed the cooling bath was removed and the reaction stirred for 18 h at rt. The reaction mixture was poured on ice, extracted with ethyl acetate (2×100 mL) and the combined organic phases washed with a sat. solution of sodium carbonate (2×100 mL) and sodium chloride (2×100 mL). The organic phase was dried over $Na_2SO_4$ and concentrated by evaporation under reduced pressure yielding 4.50 g (68%) of the title compound. $^1$H NMR (400 MHz, $CDCl_3$): δ 0.00 (s, 6H), 0.10 (s, 6H), 0.85 (s, 9H), 0.92 (s, 9H), 4.55 (s, 2H), 6.71-6.74 (m, 1H), 6.80-6.83 (m, 1H), 6.87-6.92 (m, 1H). MS (EI): 370.2 [M]$^+$.

Step 4

3-(tert-Butyl-dimethyl-silanyloxy)-5-(tert-butyl-dimethyl-silanyloxymethyl)-2-fluoro-phenol To a solution of 2-(tert-butyl-dimethyl-silanyloxy)-4-(tert-butyl-dimethyl-silanyloxymethyl)-1-fluoro-benzene (23.70 g, 63.9 mmol, 1.0 equiv) in anhydrous THF (130 mL) was added at −78° C. under Ar a solution of sec-BuLi (54.5 mL, 71.6 mmol, 1.1 equiv, 1.3 M solution in hexane) within 30 min. Then a solution of trimethyl borate (7.13 mL, 6.64 g, 63.9 mmol, 1.0 equiv) in anhydrous THF (30 mL) was added slowly within 30 min and the cooling bath removed. A solution of conc. acetic acid (5.49 mL, 5.76 g, 95.9 mmol, 1.5 equiv) was slowly added followed by addition of a solution of 35% hydrogen peroxide in water (6.2 mL, 6.83 g, 70.3 mmol, 1.1 equiv) and the reaction mixture kept at 0° C. for 30 min. After stirring at rt for an additional 4 h, the reaction was extracted with diethyl ether (2×100 mL) and the combined organic phases washed with a solution of 10% NaOH (2×100 mL) and a sat. solution of sodium chloride (2×100 mL). The organic phase was dried over $Na_2SO_4$, concentrated by evaporation under reduced pressure and the crude material purified with column chromatography on silica eluting with hexane/ethyl acetate (19:1) providing 15.80 g (64%) of the title compound. $^1$H NMR (400 MHz, $CDCl_3$): δ 0.00 (s, 6H), 0.10 (s, 6H), 0.85 (s, 9H), 0.91 (s, 9H), 4.50 (s, 2H), 4.93 (br s, 1H), 6.37 (d, J=5.6 Hz, 1H), 6.47 (d, J=5.6 Hz, 1H). MS (EI): 329.2 [M-tert-Bu]$^+$.

Step 5 tert-Butyl-(3,5-diethoxy-4-fluoro-benzyloxy)-dimethyl-silane

To a solution of 3-(tert-butyl-dimethyl-silanyloxy)-5-(tert-butyl-dimethyl-silanyloxymethyl)-2-fluoro-phenol (5.80 g, 15.0 mmol, 1.0 equiv) in DMF (60 mL) was added $K_2CO_3$ (4.56 g, 33.0 mmol, 2.2 equiv) and ethyl bromide (2.46 mL, 3.60 g, 33.0 mmol, 2.2 equiv) and the reaction mixture stirred under Ar at 60° C. for 5 h. The $K_2CO_3$ was removed by filtration, the crude reaction mixture concentrated by evaporation under reduced pressure, the residue extracted with ethyl acetate (3×100 mL), the combined organic phases washed with water (2×100 ml) and dried over $Na_2SO_4$. The solvent was removed by evaporation under reduced pressure and the crude material purified with column chromatography on silica eluting with hexane/ethyl acetate (99:1) providing 3.10 g (63%) of the title compound. $^1$H NMR (400 MHz, $CDCl_3$): δ 0.00 (s, 6H), 0.85 (s, 9H), 1.33 (t, J=7.0 Hz, 6H), 4.00 (q, J=7.0 Hz, 4H), 4.55 (s, 2H), 6.47 (d, J=6.8 Hz, 2H). MS (ISP): 329.3 [M+H]$^+$.

Step 6

(3,5-Diethoxy-4-fluoro-phenyl)-methanol

To a solution of tert-butyl-(3,5-diethoxy-4-fluoro-benzyloxy)-dimethyl-silane (1.20 g, 3.65 mmol, 1.0 equiv) in methanol (8 mL) was added Dowex 50W-X8 (0.33 g, cation exchange resin) and the reaction mixture stirred under Ar at rt for 22 h. The resin was removed by filtration and the reaction mixture concentrated by evaporation under reduced pressure yielding the title compound in quantitative yield (0.78 g). $^1$H NMR (400 MHz, $CDCl_3$): δ 1.34 (t, J=7.0 Hz, 6H), 1.57 (t, J=5.4 Hz, 1H), 4.01 (q, J=7.0 Hz, 4H), 4.51 (d, J=5.4 Hz, 2H), 6.51 (d, J=6.8 Hz, 2H). MS (EI): 214.2 [M]$^+$.

Step 7

To a solution of (3,5-diethoxy-4-fluoro-phenyl)-methanol (2.30 g, 10.7 mmol, 1.0 equiv) in 1,2-dichloroethane (50 mL) was added activated $MnO_2$ (2.89 g, 33.3 mmol, 3.1 equiv). The reaction mixture was stirred for 21 h at 50° C. and then filtered through Hyflo Super Cel providing after evaporation of the solvent under reduced pressure 1.90 g (83%) of the title compound. $^1$H NMR (400 MHz, CDCl$_3$): δ 1.38 (t, J=7.0 Hz, 6H), 4.09 (q, J=7.0 Hz, 4H), 7.04 (d, J=7.2 Hz, 2H), 9.75 (s, 1H). MS (EI): 212.1 [M]$^+$.

Intermediate 22

2,6-Diethoxy-4-formyl-benzoic acid ethyl ester [CAS RN 55687-55-3]

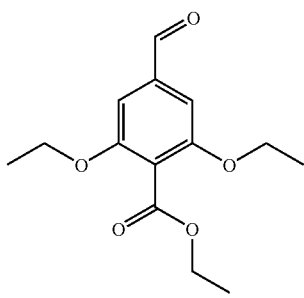

The title compound was prepared as described in DE 243 59 34 (Hoffmann-La Roche A G).

Intermediate 23

4-Amino-3,5-diethoxy-benzaldehyde

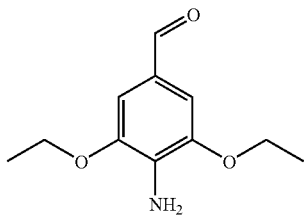

Step 1

(4-Amino-3,5-diethoxy-phenyl)-methanol

To a solution of 4-amino-3,5-diethoxy-benzoic acid ethyl ester (2.8 g, 11.05 mmol, 1.0 equiv; prepared as described in I. Kompis, A. Wick Helv. Chim. Acta 1977, 60, 3025-3034) in dichloromethane (50 mL) at 0° C. under Ar was slowly added diisobutylaluminium hydride (27.6 mL, 27.64 mmol, 2.5 equiv, 1 M solution in dichloromethane) over a time period of 15 min, the cooling bath removed on completion of addition. After 18 h, the excess hydride was quenched by cautious addition of a sat. solution of potassium sodium tartrate (10 mL). The solidified mixture was extracted with dichloromethane (5×200 mL) and THF (2×150 mL), the combined organic phases washed with water (3×100 mL), dried over MgSO$_4$, concentrated by evaporation under reduced pressure and the crude material purified with column chromatography on silica eluting with a gradient of heptane/ethyl acetate (4:1→1:1) providing 1.10 g (47%) of the title compound. $^1$H NMR (300 MHz, CDCl$_3$): δ 1.42 (t, J=7.0 Hz, 3H), 3.82 (br s, 2H), 4.05 (q, J=7.0 Hz, 2H), 4.54 (s, 2H), 6.50 (s, 2H). $^{13}$C NMR (75 MHz, CDCl$_3$): δ 15.03, 64.21, 66.00, 104.51, 125.44, 129.89, 146.71. MS (ISP): 211.9 [M+H]$^+$.

Step 2

To a solution of (4-amino-3,5-diethoxy-phenyl)-methanol (0.79 g, 3.74 mmol, 1.0 equiv) in DMF (20 mL) was added activated MnO$_2$ (1.63 g, 18.70 mmol, 5.0 equiv). The reaction mixture was stirred for 24 h at rt, filtered through Hyflo Super Cel, the filtrate extracted with ethyl acetate (3×50 mL) and the combined organic phases dried over MgSO$_4$ providing after evaporation of the solvent under reduced pressure 0.69 g (88%) of the title compound. $^1$H NMR (300 MHz, DMSO): δ 1.46 (t, J=7.0 Hz, 3H), 4.15 (q, J=7.0 Hz, 2H), 4.50 (br s, 2H), 7.04 (s, 2H), 9.70 (s, 1H). MS (ISP): 210.0 [M+H]$^+$.

Intermediate 24

4-Acetimido-3,5-diethoxy-benzaldehyde

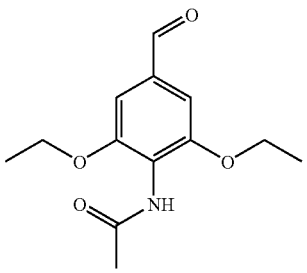

To a solution of 4-acetylamino-3,5-diethoxy-benzoic acid ethyl ester (1.0 g, 3.56 mmol, 1.0 equiv; [CAS RN 142955-43-9] prepared as described in EP 488 861 A1, Rhone Poulenc Chimie) in anhydrous THF (40 mL) was added lithium aluminium hydride (0.283 g, 7.47 mmol, 2.1 equiv) and the reaction mixture stirred at rt for 2 h. The crude reaction mixture was filtered over Hyflo Super Cel, the filtrate extracted with ethyl acetate (3×50 mL) and the combined organic phases dried over MgSO$_4$ providing 0.58 g (64%) of the benzyl alcohol. The crude reaction product (0.39 g, 1.54 mmol, 1.0 equiv) was dissolved in THF (20 mL) and activated MnO$_2$ (1.34 g, 15.40 mmol, 10.0 equiv) was added. After stirring at 60° C. for 2 h, the reaction mixture was filtered over Hyflo Super Cel and the solvent removed by evaporation under reduced pressure providing 0.35 g (90%) of the title compound. MS (ISP): 252.1 [M+H]$^+$.

Intermediate 25

3-Amino-5-ethoxy-4-iodo-benzaldehyde

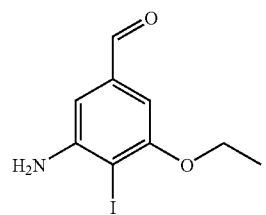

Step 1

3-Amino-5-hydroxy-4-iodo-benzoic acid

To a solution of 3-amino-5-hydroxy-benzoic acid (0.33 g, 2.16 mmol, 1.0 equiv; [CAS RN 76045-71-1]) in methanol (18 mL) at 0° C. was added within 10 min N-iodo succinimide (0.58 g, 2.59 mmol, 1.2 equiv), dissolved in methanol (3 mL). After stirring for 15 min, the reaction mixture was poured on ice and partly decolorized by addition of a 5% solution of sodium thiosulfate. The solution was extracted with ethyl acetate (3×50 mL), the combined organic phases dried over $MgSO_4$, concentrated by evaporation under reduced pressure and the crude material purified with column chromatography on silica eluting with ethyl acetate/methanol (9:1) providing 0.21 g (35%) of the title compound. $^1$H NMR (300 MHz, DMSO): δ 5.25 (br s, 2H), 6.61 (d, J=1.9 Hz, 1H), 6.78 (d, J=1.9 Hz, 1H), 10.16 (br s, 1H), 12.58 (br s, 1H). MS (ISP): 280.0 [M+H]$^+$.

Step 2

3-Amino-5-hydroxy-4-iodo-benzoic acid methyl ester

To a solution of 3-amino-5-hydroxy-4-iodo-benzoic acid (0.20 g, 0.72 mmol, 1.0 equiv) in methanol (5 mL) was added conc. sulfuric acid (0.20 mL, 0.035 g, 0.36 mmol, 0.5 equiv) and the reaction mixture heated to reflux. After 2 h, the reaction mixture was poured on ice, the pH adjusted to 9 by addition of a sat. solution of sodium hydrogencarbonate and extracted with ethyl acetate (2×50 mL). The combined organic phases were dried over $MgSO_4$, concentrated by evaporation under reduced pressure and the crude material purified with column chromatography on silica eluting with hexane/ethyl acetate (1:1) providing 0.07 g (33%) of the title compound. $^1$H NMR (250 MHz, DMSO): δ 3.78 (s, 3H), 5.45 (br s, 2H), 6.68 (s, 1H), 6.85 (s, 1H), 10.32 (br s, 1H). MS (EI): 293.0 [M]$^+$.

Step 3

3-Amino-5-ethoxy-4-iodo-benzoic acid methyl ester

To a solution of 3-amino-5-hydroxy-4-iodo-benzoic acid methyl ester (0.25 g, 0.85 mmol, 1.0 equiv) in DMF (3 mL) and ethyl iodide (0.10 mL, 0.146 g, 0.94 mmol, 1.1 equiv) at 0° C. was added sodium tert-butoxide (0.11 g, 0.94 mmol, 1.1 equiv) in small portions over a time period of 10 min. After stirring for 1 h, the cooling bath was removed and the the reaction mixture stirred at rt for an additional 18 h. The solution was concentrated by evaporation under reduced pressure and extracted with ethyl acetate (3×50 mL). The combined organic phases were dried over $MgSO_4$, concentrated by evaporation under reduced pressure and the crude material purified with column chromatography on silica eluting with hexane/ethyl acetate (2:1) yielding 0.19 g (69%) of the title compound. $^1$H NMR (250 MHz, CDCl$_3$): δ 1.49 (t, J=7.0 Hz, 3H), 3.89 (s, 3H), 4.11 (q, J=7.0 Hz, 2H), 4.33 (br s, 2H), 6.82 (d, J=2.7 Hz, 1H), 7.07 (d, J=2.7 Hz, 1H). MS (EI): 321.0 [M]$^+$.

Step 4

(3-Amino-5-ethoxy-4-iodo-phenyl)-methanol

To a solution of 3-amino-5-ethoxy-4-iodo-benzoic acid methyl ester (0.18 g, 0.56 mmol, 1.0 equiv) in THF (5 mL) at 0° C. under Ar was slowly added diisobutylaluminium hydride (2.8 mL, 2.80 mmol, 5.0 equiv, 1 M solution in THF) over a time period of 30 min, the cooling bath removed on completion of addition and the reaction allowed to reach rt. After 2 h, the excess hydride was quenched by cautious addition of a sat. solution of potassium sodium tartrate (50 mL). The solidified mixture was extracted with hot THF, the combined organic phases concentrated by evaporation under reduced pressure and the crude material purified with column chromatography on silica eluting with hexane/ethyl acetate (2:1) providing 0.056 g (34%) of the title compound. $^1$H NMR (250 MHz, CDCl$_3$): δ 1.47 (t, J=7.0 Hz, 3H), 4.08 (q, J=7.0 Hz, 2H), 4.23 (br s, 2H), 4.58 (d, J=6.0 Hz, 2H), 6.23 (s, 1H), 6.42 (s, 1H). MS (EI): 293.0 [M]$^+$.

Step 5

To a solution of (3-amino-5-ethoxy-4-iodo-phenyl)-methanol (4.9 g, 16.72 mmol, 1.0 equiv) in dichloromethane (100 mL) was added activated $MnO_2$ (7.27 g, 83.59 mmol, 5.0 equiv) and the reaction mixture heated to reflux for 3 h. Filtration through Hyflo Super Cel, concentration by evaporation under reduced pressure and purification with column chromatography on silica eluting with hexane/ethyl acetate (3:1) yielded 3.14 g (60%) of the title compound. $^1$H NMR (300 MHz, DMSO): δ 1.37 (t, J=7.0 Hz, 3H), 4.15 (q, J=7.0 Hz, 2H), 4.49 (d, J=5.6 Hz, 2H), 5.21 (t, J=5.6 Hz, 1H), 6.82 (s, 1H), 6.85 (s, 1H), 11.64 (br s, 1H). $^{13}$C NMR (75 MHz, DMSO): δ 14.61, 62.89, 64.26, 100.74, 106.46, 117.80, 137.50, 142.74, 144.05, 154.54. MS (ISP): 291.9 [M+H]$^+$.

Intermediate 26

3-Acetimido-5-ethoxy-4-iodo-benzaldehyde

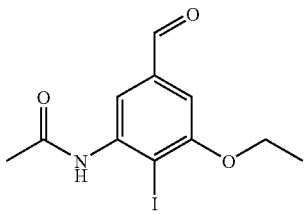

To a solution of 3-amino-5-ethoxy-4-iodo-benzaldehyde (0.27 g, 0.93 mmol, 1.0 equiv; intermediate 25) and acetyl chloride (0.138 mL, 0.153 g, 1.95 mmol, 2.1 equiv) in anhydrous DMF (5 mL) was added diisopropylethylamine (0.48 mL, 0.36 g, 2.78 mmol, 3.0 equiv) and the mixture stirred at 50° C. for 48 h. Removal of the solvent under reduced pressure and purification of the crude reaction mixture with column chromatography on silica eluting with a gradient of heptane/ethyl acetate (4:1→1:1) yielded 0.11 g (35%) of the title compound. $^1$H NMR (300 MHz, CDCl$_3$): δ 1.51 (t, J=7.0 Hz, 3H), 2.29 (s, 3H), 4.19 (q, J=7.0 Hz, 2H), 7.06 (s, 1H), 7.76 (br s, 1H), 8.42 (s, 1H), 9.96 (s, 1H). MS (ISP): 334.0 [M+H]$^+$.

Intermediate 27

4-Ethoxy-1H-indole-6-carbaldehyde [CAS RN 372099-88-2]

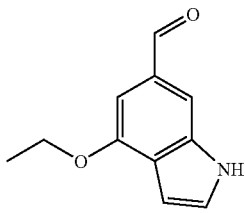

The title compound was prepared according to WO 01/083 474 A1 (Hoffmann-La Roche AG).

Intermediate 28

Ethoxy-6-methoxy-pyridine-3-carbaldehyde

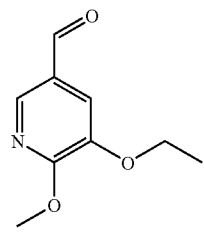

Step 1

3-Ethoxy-pyridin-2-ol

To a solution of 2,3-dihydroxypyridine (5.0 g, 45.0 mmol, 1.0 equiv) and sodium tert-butoxide (4.33 g, 45.0 mmol, 1.0 equiv) in methanol (25 mL) was added ethyl iodide (5.21 mL, 7.72 g, 49.5 mmol, 1.1 equiv) and the reaction mixture heated to 100° C. under microwave irradiation for 20 min. The solvent was removed and the reaction product dissolved in dichloromethane (50 mL), the obtained suspension filtered and the organic phase concentrated by evaporation under reduced pressure. The crude material was purified by column chromatography on silica eluting with dichloromethane/methanol (9:1) yielding 3.0 g (41%) of the title compound. $^1$H NMR (300 MHz, CDCl$_3$): δ 1.50 (t, J=7.0 Hz, 3H), 4.05 (q, J=7.0 Hz, 2H), 6.20 (t, J=7.1 Hz, 1H), 6.76 (dd, J=7.4 Hz, J=1.3 Hz, 1H), 7.05 (dd, J=6.5 Hz, J=1.3 Hz, 1H), 13.36 (br s, 1H).

Step 2

2-Chloro-3-ethoxy-pyridine

A mixture of 3-ethoxy-pyridin-2-ol (4.0 g, 28.8 mmol, 1.0 equiv), N,N-diethylaniline (4.61 mL, 4.29 g, 28.8 mmol, 1.0 equiv) and phosphorus oxychloride (2.62 mL, 4.41 g, 28.8 mmol, 1.0 equiv) was heated to 150° C. under microwave irradiation for 20 min. The crude reaction mixture was poured into water (100 mL), the solution adjusted to pH 7 and extracted with dichloromethane (3×100 mL). The combined organic phases were dried over MgSO$_4$, the solvent removed by evaporation under reduced pressure and the crude material purified with column chromatography on silica eluting with hexane/ethyl acetate (4:1) providing 3.2 g (71%) of the title compound. $^1$H NMR (300 MHz, CDCl$_3$): δ 1.50 (t, J=7.0 Hz, 3H), 4.12 (q, J=7.0 Hz, 2H), 7.18 (d, J=3.2 Hz, 2H), 7.98 (t, J=3.2 Hz, 1H). MS (ISP): 157.7 [M+H]$^+$.

Step 3

3-Ethoxy-2-methoxy-pyridine

A solution of 2-chloro-3-ethoxy-pyridine (3.0 g, 19.0 mmol, 1.0 equiv) and sodium methoxide (8.8 mL, 47.5 mmol, 2.5 equiv, 5.4 M solution in methanol) was heated to 100° C. under microwave irradiation for 20 min. The crude reaction mixture was poured into water (100 mL) and extracted with dichloromethane (3×100 mL). The combined organic phases were dried over MgSO$_4$ and the solvent removed by evaporation under reduced pressure to yield 2.75 g (95%) of the title compound. $^1$H NMR (300 MHz, CDCl$_3$): δ 1.40 (t, J=7.0 Hz, 3H), 3.94 (s, 3H), 4.02 (q, J=7.0 Hz, 2H), 6.75 (dd, J=7.8 Hz, J=5.0 Hz, 1H), 6.96 (dd, J=7.8 Hz, J=1.5 Hz, 1H), 7.65 (dd, J=5.0 Hz, 1=1.5 Hz, 1H). $^{13}$C NMR (75 MHz, CDCl$_3$): δ 13.62, 52.53, 63.25, 115.69, 117.53, 136.13, 142.45, 153.84. MS (ISP): 153.8 [M+H]$^+$.

Step 4

5-Bromo-3-ethoxy-2-methoxy-pyridine

To a stirred mixture of 3-ethoxy-2-methoxy-pyridine (2.7 g, 17.6 mmol, 1.0 equiv) and sodium acetate (1.74 g, 21.2 mmol, 1.2 equiv) in acetic acid (50 mL) at 10° C. was slowly added a solution of bromine (1.09 mL, 3.38 g, 21.2 mmol, 1.2 equiv) in acetic acid (10 mL). After the addition was completed the reaction mixture was stirred for 1 h at rt. The reaction mixture was poured on ice, neutralized with NaOH and the solution extracted with diethylether (3×50 mL). The combined organic phases were dried over MgSO$_4$ and the solvent removed by evaporation under reduced pressure yielding 3.86 g (94%) of a mixture of 5-bromo-3-ethoxy-2-methoxy-pyridine and 6-bromo-3-ethoxy-2-methoxy-pyridine in the ratio 3:2 as indicated by $^1$H NMR, which was used directly in the next reaction step. $^1$H NMR (300 MHz, CDCl$_3$): δ 1.39 (t, J=7.0 Hz, 3H), 3.91 (s, 3H), 3.98 (q, J=7.0 Hz, 2H), 7.05 (d, J=1.9 Hz, 1H), 7.69 (d, J=1.9 Hz, 1H).

Step 5

To a 3:2 mixture of 5-bromo-3-ethoxy-2-methoxy-pyridine and 6-bromo-3-ethoxy-2-methoxy-pyridine (1.0 g, 4.31 mmol, 1.0 equiv) in anhydrous THF (20 mL) was added at −78° C. under Ar a solution of n-BuLi (3.23 mL, 5.17 mmol, 1.2 equiv, 1.6 M solution in hexane). After stirring for 1 h, anhydrous DMF (0.7 mL, 9.05 mmol, 2.1 equiv) was added and the reaction mixture stirred for an additional 30 min. A sat. solution of ammonium chloride (20 mL) was added and the solution extracted with ethyl acetate (3×50 mL). The combined organic phases were dried over MgSO$_4$, the solvent removed by evaporation under reduced pressure and the crude material purified by twice recrystallization from isopropanol yielding 0.35 g (75%) of the title compound. $^1$H NMR (300 MHz, CDCl$_3$): δ 1.50 (t, J=7.0 Hz, 3H), 4.11 (s, 3H), 4.15 (q, J=7.0 Hz, 2H), 7.46 (d, J=1.9 Hz, 1H), 8.19 (d, J=1.9 Hz, 1H), 9.93 (s, 1H). $^{13}$C NMR (75 MHz, CDCl$_3$): δ 14.44, 54.67, 64.59, 113.72, 127.59, 144.29, 144.31, 158.80, 189.66. MS (ISP): 181.8 [M+H]$^+$.

Intermediate 29

3-Ethylamino-4-methoxy-benzaldehyde

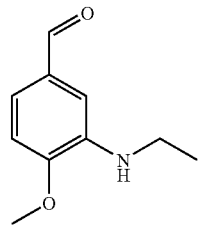

Through a solution of 2-(3-bromo-4-methoxy-phenyl)-[1,3]dioxolane (1.2 g, 4.63 mmol, 1.0 equiv; prepared as described in WO 01/74775 A1, Sanofi-Synthelabo) in toluene (6 mL) was bubbled ethylamine for 10 min. To this solution was added sodium tert-butoxide (0.67 g, 6.95 mmol, 1.5 equiv), (±)-BINAP (0.029 g, 0.046 mmol, 0.01 equiv) and $Pd_2(dba)_3$ (Tris(dibenzylideneacetone)dipailadium, 0.021 g, 0.023 mmol, 0.005 equiv) and the solution heated to 110° C. under microwave irradiation for 20 min. A few drops of a solution of 37% HCl were added and the reaction mixture heated again to 100° C. under microwave irradiation for 5 min. Evaporation of the solvent and purification of the crude reaction product by column chromatography on silica eluting with hexane/ethyl acetate (7:3) provided 0.52 g (63%) of the title compound. $^1$H NMR (300 MHz, $CDCl_3$): δ 1.24 (t, J=7.1 Hz, 3H), 3.16 (q, J=7.1 Hz, 2H), 3.86 (s, 3H), 4.17 (br s, 1H), 6.78 (d, J=8.1 Hz, 1H), 7.01 (d, J=1.9 Hz, 1H), 7.13 (dd, J=8.1 Hz, J=1.9 Hz, 1H). MS (ISP): 179.9 $[M+H]^+$.

Intermediate 30

3,5-Diethoxy-benzaldehyde [CAS RN 120355-79-5]

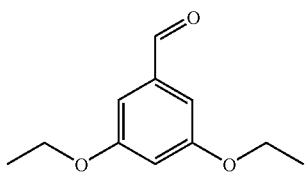

The title compound was prepared analogously to intermediate 2 (4-methoxy-3-propoxy-benzaldehyde) by reaction of 3,5-dihydroxybenzaldehyde with ethyl iodide in DMF using $K_2CO_3$ as base.

Intermediate 31

3-Ethoxy-4,5-dihydroxy-benzaldehyde [CAS RN 62040-18-0]

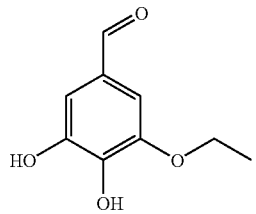

The title compound was prepared analogously to intermediate 2 (4-methoxy-3-propoxy-benzaldehyde) by reaction of 3,4,5-trihydroxybenzaldehyde with ethyl iodide in DMF using $K_2CO_3$ as base. MS (ISN): 181.1 $[M-H]^-$.

Intermediate 32

Methanesulfonic acid 2-ethoxy-4-formyl-phenyl ester

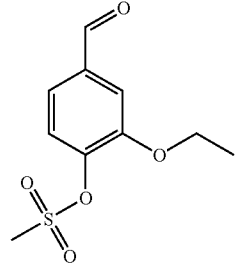

To a solution of 3-ethoxy-4-hydroxybenzaldehyde (3.0 g, 18.1 mmol, 1.0 equiv) and N,N-dimethylaminopyridine (2.87 g, 23.5 mmol, 1.3 equiv) in dichloromethane (10 mL) under Ar at 0° C. was added methanesulfonyl chloride (1.68 mL, 2.48 g, 21.7 mmol, 1.2 equiv). After the reaction mixture was stirred for 1 h, water (100 mL) was added, the solution extracted with dichloro-methane (3×50 mL) and the combined organic phases dried over $MgSO_4$. Removal of the solvent by evaporation under reduced pressure provided the title compound in quantitative yield (4.8 g). $^1$H NMR (300 MHz, $CDCl_3$): δ 1.42 (t, J=7.0 Hz, 3H), 3.19 (s, 3H), 4.14 (q, J=7.0 Hz, 2H), 7.41 (s, 2H), 7.45 (s, 1H), 9.89 (s, 1H). $^{13}$C NMR (75 MHz, $CDCl_3$): δ 14.53, 38.94, 64.99, 112.20, 124.38, 125.17, 136.01, 142.92, 151.63, 190.65. MS (ISP): 245.2 $[M+H]^+$.

Intermediate 33

4,5-Diethoxy-2-hydroxy-benzaldehyde [CAS RN 100059-45-8]

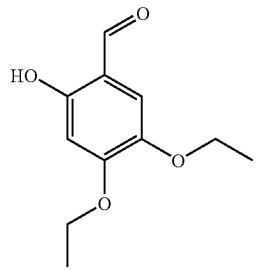

The title compound was prepared analogously to intermediate 2 (4-methoxy-3-propoxy-benzaldehyde) by reaction of 2,4,5-trihydroxybenzaldehyde with ethyl iodide in DMF using $K_2CO_3$ as base. MS (ISP): 210.9 $[M+H]^+$.

Intermediate 34

3,4-Diisopropoxy-benzaldehyde [CAS RN 64000-54-0]

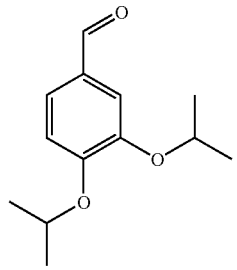

The title compound was prepared analogously to intermediate 2 (4-methoxy-3-propoxy-benzaldehyde) by reaction of 3,4-dihydroxybenzaldehyde with 2-bromopropane in DMF using K₂CO₃ as base.

Intermediate 35

4-Methoxy-3-(2,2,2-trifluoro-ethoxy)-benzaldehyde
[CAS RN 76588-84-6]

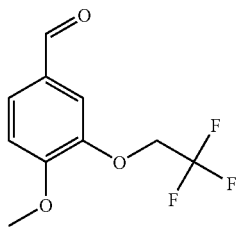

The title compound was prepared according to EP 0 251 294 B1 (Shionogi & Co.).

Intermediate 36

(±)-3-Ethanesulfinyl-5-ethoxy-benzaldehyde

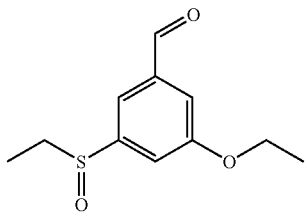

Step 1

2-(3,5-Dibromo-phenyl)-[1,3]dioxolane

A suspension of 3,5-dibromo-benzaldehyde (20.0 g, 75.8 mmol, 1.0 equiv; [CAS RN 56990-02-4]), ethane-1,2-diol (12.7 mL, 14.1 g, 227.3 mmol, 3.0 equiv) and p-toluene sulfonic acid monohydrate (0.29 g, 1.52 mmol, 0.02 equiv) in toluene (50 mL) was heated to reflux under Dean-Stark conditions for 1 h. The reaction mixture was extracted with ethyl acetate (3×200 mL), the combined organic phases washed with a sat. solution of sodium carbonate (4×50 mL) and dried over MgSO₄. Removal of the solvent by evaporation under reduced pressure yielded 23.3 g (100%) of the title compound. $^1$H NMR (300 MHz, CDCl₃): δ 4.00-4.12 (m, 4H), 5.76 (s, 1H), 7.55-7.56 (m, 2H), 7.65-7.66 (m, 1H). MS (EI): 306.8 [M]⁺.

Step 2

3-Bromo-5-[1,3]dioxolan-2-yl-phenol

To a solution of 2-(3,5-dibromo-phenyl)-[1,3]dioxolane (20.25 g, 65.75 mmol, 1.0 equiv) in anhydrous THF (200 mL) was added n-BuLi (45.2 mL, 72.33 mmol, 1.1 equiv, 1.6 M solution in hexane) at −78° C. under Ar. After stirring the reaction mixture for 30 min, trimethyl borate (7.33 mL, 6.83 g, 65.75 mmol, 1.0 equiv) was added rapidly and the reaction allowed to come to 0° C. over a time period of 4 h. A solution of conc. acetic acid (5.64 mL, 5.92 g, 98.63 mmol, 1.5 equiv) was slowly added followed by addition of a solution of 35% hydrogen peroxide in water (6.3 mL, 7.03 g, 72.33 mmol, 1.1 equiv) and the reaction mixture kept at 0° C. for 30 min. After stirring at rt for an additional 4 h, the reaction was extracted with ethyl actetate (3×200 mL), the combined organic phases washed with water, dried over MgSO₄ and concentrated by evaporation under reduced pressure. The title compound was obtained in quantitative yield (16.1 g). MS (EI): 245.0 [M]⁺.

Step 3

2-(3-Bromo-5-ethoxy-phenyl)-[1,3]dioxolane

To a solution of 3-bromo-5-[1,3]dioxolan-2-yl-phenol (0.53 g, 2.16 mmol, 1.0 equiv) in DMF (2 mL) was added K₂CO₃ (0.33 g, 2.38 mmol, 1.1 equiv) and ethyl iodide (0.19 mL, 0.37 g, 2.38 mmol, 1.1 equiv) and the reaction mixture stirred under Ar at rt for 18 h. The K₂CO₃ was removed by filtration, the filtrate extracted with cyclohexane (3×50 mL), the combined organic phases washed with water (2×50 ml) and dried over MgSO₄. The solvent was removed by evaporation under reduced pressure and the crude material purified with column chromatography on silica eluting with hexane/ethyl acetate (6:1) providing 0.42 g (72%) of the title compound. $^1$H NMR (300 MHz, CDCl₃): δ 1.40 (t, J=7.0 Hz, 3H), 4.01-4.10 (m, 6H), 5.75 (s, 1H), 6.93-6.94 (m, 1H), 7.02-7.04 (m, 1H), 7.19-7.20 (m, 1H). MS (EI): 273.0 [M]⁺.

Step 4

To a solution of ethyl mercaptane (0.91 g, 14.65 mmol, 2.0 equiv) in DMF (50 mL) was added sodium hydride (0.64 g, 14.65 mmol, 2.0 equiv; 55% free-flowing powder moistened with oil) and the reaction mixture stirred at rt under Ar for 15 min. To the reaction mixture was added 2-(3-bromo-5-ethoxy-phenyl)-[1,3]dioxolane (2.0 g, 7.32 mmol, 1.0 equiv), stirred at rt for 30 min and then heated to 120° C. under microwave irradiation for 30 min. The reaction mixture was concentrated by evaporation under reduced pressure and the crude material purified with column chromatography on silica eluting with heptane/ethyl acetate (1:1) providing 1.36 g (73%) of 2-(3-ethoxy-5-ethylsulfanyl-phenyl)-[1,3]dioxolane. The product (1.36 g, 5.35 mmol, 1.0 equiv) was dissolved in conc. acetic acid (20 mL) and a solution of 35% hydrogen peroxide in water (0.70 mL, 0.78 g, 8.02 mmol, 1.5 equiv) was added. After stirring the solution for 3 h at rt the reaction mixture was neutralized by addition of a 1 M solution of NaOH, extracted with ethyl acetate (3×50 mL) and the combined organic phases dried over MgSO₄. The organic solvent was removed by evaporation under reduced pressure and the crude material purified with column chromatography on silica eluting with heptane/ethyl acetate (1:1+1% methanol) providing 0.55 g (46%) of the title compound. $^1$H NMR (300 MHz, CDCl₃): δ 1.23 (t, J=7.4 Hz, 3H), 1.47 (t, J=7.0 Hz, 3H), 2.82 (h, J=7.4 Hz, 1H), 3.02 (h, J=7.4 Hz, 1H), 4.18 (q, J=7.0 Hz, 2H), 7.44-7.46 (m, 1H), 7.48-7.49 (m, 1H), 7.65-7.66 (m, 1H), 10.03 (s, 1H). $^{13}$C NMR (75 MHz, CDCl₃): δ 5.61, 14.43, 50.00, 64.33, 115.71, 116.46, 117.24, 138.21, 146.48, 160.15, 190.66. MS (ISP): 227.1 [M+H]⁺.

Intermediate 37

3-Ethanesulfonyl-5-ethoxy-benzaldehyde

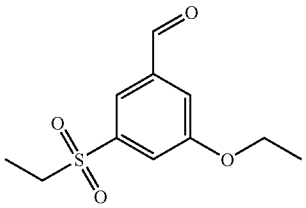

To a solution of (±)-3-ethanesulfinyl-5-ethoxy-benzaldehyde (0.39 g, 1.72 mmol, 1.0 equiv) in conc. acetic acid (10 mL) was added a solution of 35% hydrogen peroxide in water (0.60 mL, 0.67 g, 6.89 mmol, 4.0 equiv). After stirring the reaction mixture for 18 h at rt, the pH was adjusted to 10 by addition of a 1 M solution of NaOH, extracted with ethyl acetate (3×50 mL) and the combined organic phases dried over MgSO$_4$. The organic solvent was removed by evaporation under reduced pressure and the crude material purified with column chromatography on silica eluting with heptane/ethyl acetate (1:1) providing 0.09 g (22%) of the title compound. $^1$H NMR (300 MHz, CDCl$_3$): δ 1.31 (t, J=7.4 Hz, 3H), 1.48 (t, J=7.0 Hz, 3H), 3.17 (q, J=7.4 Hz, 2H), 4.17 (q, J=7.0 Hz, 2H), 7.63-7.66 (m, 2H), 7.94-7.95 (m, 1H), 10.04 (s, 1H). $^{13}$C NMR (75 MHz, CDCl$_3$): δ 11.46, 18.59, 54.59, 68.89, 122.74, 123.94, 125.68, 142.60, 145.26, 164.29, 194.24. MS (ISP): 243.3 [M+H]$^+$.

Intermediate 38

3-Ethoxy-5-isobutoxy-benzaldehyde

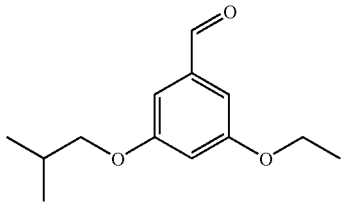

Step 1

(3-Ethoxy-5-isobutoxy-phenyl)-methanol

To a solution of 3-ethoxy-5-hydroxymethyl-phenol (0.3 g, 1.78 mmol, 1.0 equiv; prepared as described for intermediate 41 [3-ethoxy-5-(3-hydroxy-2-2-dimethylpropoxy)-benzaldehyde]) in DMF (2 mL) was added cesium carbonate (2.32 g, 7.14 mmol, 4.0 equiv), potassium iodide (0.59 g, 3.57 mmol, 2.0 equiv) and 1-bromo-2-methyl-propane (0.58 mL, 0.73 g, 5.35 mmol, 3.0 equiv) and the reaction mixture stirred under Ar at 100° C. for 24 h. The reaction mixture was filtered, the solid material washed with DMF and the organic filtrate evaporated to dryness under reduced pressure. The crude reaction mixture was suspended in water (20 mL), extracted with dichloromethane (3×50 mL), the combined organic phases washed with a sat. solution of sodium chloride (1×20 ml) and dried over Na$_2$SO$_4$ providing 0.30 g (75%) of the title compound in sufficient purity for the next reaction step. $^1$H NMR (300 MHz, CDCl$_3$): δ 1.01 (d, J=6.7 Hz, 6H), 1.40 (t, J=7.0 Hz, 3H), 2.07 (h, J=6.7 Hz, 1H), 3.70 (d, J=6.7 Hz, 2H), 4.02 (q, J=7.0 Hz, 2H), 4.61 (br s, 2H), 6.37-6.39 (m, 1H), 6.49-6.51 (m, 2H). $^{13}$C NMR (75 MHz, CDCl$_3$): δ 14.84, 19.26, 28.31, 63.56, 65.49, 74.62, 100.76, 105.14, 105.32, 143.29, 160.41, 160.78. MS (ISP): 225.1 [M+H]$^+$.

Step 2

To a solution of (3-ethoxy-5-isobutoxy-phenyl)-methanol (0.28 g, 1.25 mmol, 1.0 equiv) in DMF (20 mL) was added activated MnO$_2$ (1.09 g, 12.48 mmol, 10.0 equiv). The reaction mixture was heated to 60° C. for 2 h, filtered through Hyflo Super Cel and concentrated by evaporation under reduced pressure yielding 0.28 g (99% yield) of the title compound. MS (ISP): 223.0 [M+H]$^+$.

Intermediate 39

3,5-Diethoxy-2-fluoro-benzaldehyde [CAS RN 277324-21-7]

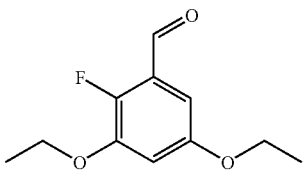

The title compound was prepared as described in WO 00/035 858 A1 (Hoffmann-La Roche AG).

Intermediate 40

2-Chloro-3,5-diethoxy-benzaldehyde

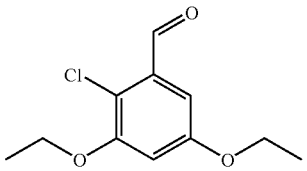

The title compound was prepared analogously to intermediate 2 (4-methoxy-3-propoxy-benzaldehyde) by reaction of 2-chloro-3,5-dihydroxy benzaldehyde with iodoethane in DMF using K$_2$CO$_3$ as base. MS (ISP): 229.3 [M+H]$^+$.

Intermediate 41

3-Ethoxy-5-(3-hydroxy-2-2-dimethylpropoxy)-benzaldehyde

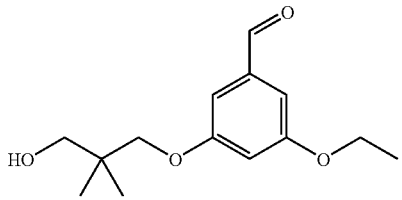

Step 1

3-Ethoxy-5-hydroxymethyl-phenol

To a solution of 5-hydroxymethyl-benzene-1,3-diol (0.5 g, 3.57 mmol, 1.0 equiv) in DMF (5 mL) was added K$_2$CO$_3$ (0.99 g, 7.14 mmol, 2.0 equiv) and ethyl iodide (0.29 mL, 0.43 g, 3.93 mmol, 1.1 equiv) and the reaction mixture stirred under Ar at 60° C. for 4 h. The K$_2$CO$_3$ was removed by filtration, the filtrate extracted with ethyl acetate (3×50 mL), the combined organic phases washed with a sat. solution of sodium chloride (1×50 ml) and dried over Na$_2$SO$_4$. The solvent was removed by evaporation under reduced pressure and the crude material purified with column chromatography on silica eluting with a gradient of hexane/ethyl acetate (4:1→2:1) providing 0.25 g (42%) of the title compound. $^1$H NMR (250 MHz, CDCl$_3$): δ 1.40 (t, J=7.0 Hz, 3H), 4.02 (q, J=7.0 Hz, 2H), 4.61 (d, J=5.6 Hz, 2H), 4.91 (br s, 1H), 6.29-6.31 (m, 1H), 6.43 (br s, 1H), 6.49 (br s, 1H). MS (EI): 168.0 [M]$^+$.

Step 2

3-(3-Ethoxy-5-hydroxymethyl-phenoxy)-2,2-dimethyl-propan-1-ol

To a solution of 3-ethoxy-5-hydroxymethyl-phenol (0.3 g, 1.78 mmol, 1.0 equiv) in DMF (2 mL) was added cesium carbonate (2.32 g, 7.14 mmol, 4.0 equiv), potassium iodide (0.59 g, 3.57 mmol, 2.0 equiv) and 3-bromo-2,2-dimethyl-propan-1-ol (0.66 mL, 0.89 g, 5.35 mmol, 3.0 equiv) and the reaction mixture stirred under Ar at 100° C. for 24 h. The reaction mixture was filtered, the solid material washed with DMF and the organic filtrate evaporated to dryness under reduced pressure. The crude reaction mixture was suspended in water (20 mL), extracted with dichloromethane (3×50 mL), the combined organic phases washed with a sat. solution of sodium chloride (1×20 ml) and dried over Na$_2$SO$_4$ providing 0.15 g (33%) of the title compound in sufficient purity for the next reaction step. MS (ISP): 255.2 [M+H]$^+$.

Step 3

To a solution of 3-(3-ethoxy-5-hydroxymethyl-phenoxy)-2,2-dimethyl-propan-1-ol (0.15 g, 0.59 mmol, 1.0 equiv) in DMF (10 mL) was added activated MnO$_2$ (0.51 g, 5.90 mmol, 10.0 equiv). The reaction mixture was heated to 60° C. for 2 h, filtered through Hyflo Super Cel and concentrated by evaporation under reduced pressure yielding 0.14 g (95% yield) of the title compound. MS (ISP): 253.1 [M+H]$^+$.

Intermediate 42

3,5-Diethoxy-4-methylsulfanyl-benzaldehyde

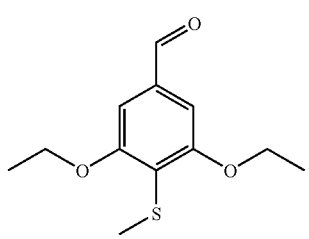

To a suspension of sodium hydride (2.62 g, 60.0 mmol, 2.0 equiv; 55% free-flowing powder moistened with oil) in DMF (50 mL) under Ar was added carefully methanethiol (2.88 g, 60.0 mmol, 2.0 equiv). After 15 min, a solution of 4-bromo-3,5-diethoxy-benzaldehyde (8.2 g, 30.0 mmol, 1.0 equiv; prepared according to S. P. Dudek, H. D. Sikes, C. E. D. Chidsey *J. Am Chem. Soc.* 2001, 123, 8033-8038) in DMF (30 mL) was added, and the reaction mixture stirred overnight. The mixture was acidified to pH 2 by addition of a solution of 1 M HCl and extracted with ethyl acetate (3×100 mL). The combined organic phases were dried over MgSO$_4$, the solvent removed by evaporation under reduced pressure and the crude material purified with column chromatography on silica eluting with heptane/ethyl acetate (1:1) providing 6.9 g (96%) of the title compound. $^1$H NMR (300 MHz, CDCl$_3$): δ 1.50 (t, J=7.0 Hz, 6H), 2.50 (s, 3H), 4.18 (q, J=7.0 Hz, 4H), 7.02 (s, 2H), 9.88 (s, 1H). $^{13}$C NMR (75 MHz, CDCl$_3$): δ 14.66, 17.50, 64.88, 105.71, 122.00, 135.90, 159.54, 191.31. MS (ISP): 240.9 [M+H]$^+$.

Intermediate 43

(±)-3,5-Diethoxy-4-methanesulfinyl-benzaldehyde

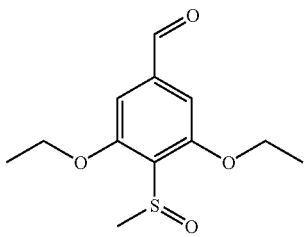

To a solution of 3,5-diethoxy-4-methylsulfanyl-benzaldehyde (0.28 g, 1.16 mmol, 1.0 equiv) in conc. acetic acid (5 mL) was added a solution of 35% hydrogen peroxide in water (0.13 mL, 0.15 g, 1.50 mmol, 1.3 equiv). After stirring the solution for 2 h at rt the reaction mixture was extracted with ethyl acetate (3×50 mL) and the combined organic phases dried over MgSO$_4$. The organic solvent was removed by evaporation under reduced pressure and the crude material purified with column chromatography on silica eluting with ethyl acetate (1% methanol) providing 0.25 g (84%) of the title compound. $^1$H NMR (300 MHz, CDCl$_3$): δ 1.50 (t, J=7.0 Hz, 6H), 3.11 (s, 3H), 4.15-4.26 (m, 4H), 7.07 (s, 2H), 9.93 (s, 1H). $^{13}$C NMR (75 MHz, CDCl$_3$): δ 14.50, 37.62, 65.34, 106.10, 125.13, 139.95, 159.53, 191.07. MS (ISP): 257.1 [M+H]$^+$.

Intermediate 44

3,5-Diethoxy-4-methysufonyl-benzaldehyde

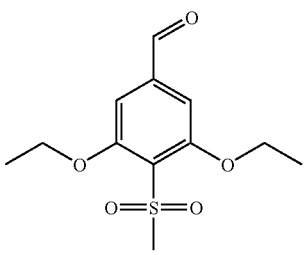

To a solution of (±)-3,5-diethoxy-4-methanesulfinyl-benzaldehyde (0.60 g, 2.34 mmol, 1.0 equiv) in conc. acetic acid (10 mL) was added a solution of 35% hydrogen peroxide in water (0.41 mL, 0.46 g, 4.68 mmol, 2.0 equiv) and the solution stirred for 2 h at 40° C. Periodically, every 2 hours another 2.0 equivalents of hydrogen peroxide were added to the reaction mixture to drive the reaction to completion. After 6 h the reaction mixture was extracted with ethyl acetate (3×50 mL) and the combined organic phases dried over MgSO₄. The organic solvent was removed by evaporation under reduced pressure and the crude material purified with column chromatography on silica eluting with heptane/ethyl acetate (1:1) providing 0.27 g (42%) of the title compound. ¹H NMR (300 MHz, CDCl₃): δ 1.51 (t, J=7.0 Hz, 6H), 3.34 (s, 3H), 4.24 (q, J=7.0 Hz, 4H), 7.10 (s, 2H), 9.95 (s, 1H). ¹³C NMR (75 MHz, CDCl₃): δ 814.39, 46.59, 66.02, 106.62, 123.29, 140.08, 158.91, 190.95. MS (ISP): 273.0 [M+H]⁺.

Intermediate 45

4-Ethoxy-2-oxo-2,3-dihydro-benzooxazole-6-carbaldehyde

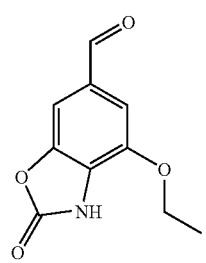

Step 1

4-Ethoxy-6-hydroxymethyl-3H-benzooxazol-2-one

To a solution of 4-ethoxy-2-oxo-2,3-dihydro-benzooxazole-6-carboxylic acid ethyl ester (1.1 g, 4.38 mmol, 1.0 equiv; prepared as described in I. Kompis, A. Wick *Helv. Chim. Acta* 1977, 60, 3025-3034) in a mixture of dichloromethane (20 mL) and THF (10 mL) at −78° C. under Ar was slowly added diisobutylaluminium hydride (14.0 mL, 14.02 mmol, 3.2 equiv, 1 M solution in dichloromethane) over a time period of 15 min, the cooling bath removed on completion of addition and the reaction allowed to reach 0° C. After 1 h, the excess hydride was quenched by cautious addition of a sat. solution of potassium sodium tartrate (10 mL). The solidified mixture was extracted with hot THF, the combined organic phases concentrated by evaporation under reduced pressure and the crude material purified with column chromatography on silica eluting with hexane/ethyl acetate (1:2) providing 0.69 g (75%) of the title compound. ¹H NMR (300 MHz, DMSO): δ 1.37 (t, J=7.0 Hz, 3H), 4.15 (q, J=7.0 Hz, 2H), 4.49 (d, J=5.6 Hz, 2H), 5.21 (t, J=5.6 Hz, 1H), 6.82 (s, 1H), 6.85 (s, 1H), 11.64 (br s, 1H). ¹³C NMR (75 MHz, DMSO): δ 14.61, 62.89, 64.26, 100.74, 106.46, 117.80, 137.50, 142.74, 144.05, 154.54. MS (ISP): 209.8 [M+H]⁺.

Step 2

To a solution of 4-ethoxy-6-hydroxymethyl-3H-benzooxazol-2-one (0.69 g, 3.30 mmol, 1.0 equiv) in a mixture of dichloromethane (40 mL) and ethanol (5 mL) was added activated MnO₂ (1.15 g, 13.2 mmol, 4.0 equiv). The reaction mixture was heated to 40° C. for 2 h, filtered through Hyflo Super Cel and concentrated by evaporation under reduced pressure. The residue was purified by flash column chromatography on silica eluting with heptane/ethyl acetate (1:1) to yield 0.53 g (78% yield) of the title compound. ¹H NMR (300 MHz, DMSO): δ 1.43 (t, J=7.0 Hz, 3H), 4.23 (q, J=7.0 Hz, 2H), 7.38 (s, 1H), 7.42 (s, 1H), 9.87 (s, 1H), 12.28 (br s, 1H). ¹³C NMR (75 MHz, DMSO): δ 14.41, 64.63, 104.07, 109.32, 125.20, 131.05, 143.13, 143.88, 154.21, 191.11. MS (ISP): 208.1 [M+H]⁺.

Intermediate 46

N-(2-Chloro-3-ethoxy-5-formyl-phenyl)-acetamide

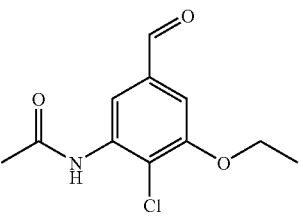

Step 1

3-Ethoxy-4-hydroxy-benzoic acid

A solution of silver nitrate (45.0 g, 265.0 mmol, 1.0 equiv) in water (230 mL) was treated with NaOH (10.6 g, 265 mmol, 1.0 equiv) and stirred for 20 min at rt. The formed precipitate was filtered off, washed with water (3×200 mL) and directly suspended in water (260 mL). To this suspension was added 3-ethoxy-4-hydroxy-benzaldehyde (20.0 g, 120.4 mmol, 0.45 equiv) and NaOH (26.5 g, 662.5 mmol, 2.5 equiv) the reaction mixture heated to reflux for 2 h. The reaction mixture was filtered, acidified to pH 2 by addition of sulfuric acid and the solution extracted with ethyl acetate (3×100 mL). The combined organic phases were dried over MgSO₄, the solvent removed by evaporation under reduced pressure and the crude material purified over a plug of silica eluting with dichloromethane/methanol/acetic acid (97:2:1) to give 5.8 g (27%) of the title compound. ¹H NMR (300 MHz, DMSO): δ 1.32 (t, J=7.0 Hz, 3H), 4.04 (q, J=7.0 Hz, 2H), 6.88 (d, J=8.0 Hz, 1H), 7.46 (s, 1H), 7.48 (d, J=8.0 Hz, 1H), 9.67 (br s, 1H), 12.42 (br s, 1H). ¹³C NMR (75 MHz, DMSO): δ 14.52, 63.93, 114.09, 115.11, 121.68, 123.49, 146.29, 151.32, 167.22. MS (ISN): 181.0 [M−H]⁻.

Step 2

3-Ethoxy-4-hydroxy-benzoic acid methyl ester

A solution of 3-ethoxy-4-hydroxy-benzoic acid (5.5 g, 30.19 mmol, 1.0 equiv) in methanol (300 mL) was saturated with anhydrous HCl gas and heated to reflux overnight. Evaporation of the solvent and purification of the crude reaction product over a short plug of silica eluting with dichloromethane yielded 5.4 g (91%) of the title compound. ¹H NMR (300 MHz, CDCl₃): δ 1.37 (t, J=7.0 Hz, 3H), 3.80 (s, 3H), 4.08 (q, J=7.0 Hz, 2H), 6.11 (s, 1H), 6.86 (d, J=8.3 Hz, 1H), 7.45 (d, J=1.9 Hz, 1H), 7.54 (dd, J=8.3 Hz, J=1.9 Hz, 1H). ¹³C NMR (75 MHz, CDCl₃): δ 14.69, 51.85, 64.74, 112.67, 114.05, 122.21, 124.05, 145.46, 150.20, 166.88. MS (ISN): 195.0 [M−H]⁻.

Step 3

3-Ethoxy-4-hydroxy-5-nitro-benzoic acid methyl ester

To a solution of 3-ethoxy-4-hydroxy-benzoic acid methyl ester (5.3 g, 27.0 mmol, 1.0 equiv) in diethyl ether (60 mL) was added dropwise nitric acid 65% (3.71 mL, 5.24 g, 54.0 mmol, 2.0 equiv) over a period of 30 min. After the addition was completed the reaction mixture was stirred for 4 h at rt. The reaction product precipitated out of solution, was filtered off, washed with cold diethyl ether (3×20 mL) and dried yielding 4.61 g (%) of the title compound. $^1$H NMR (300 MHz, CDCl$_3$): δ 1.53 (t, J=7.0 Hz, 3H), 3.94 (s, 3H), 4.21 (q, J=7.0 Hz, 2H), 7.75 (d, J=1.8 Hz, 1H), 8.42 (d, J=1.8 Hz, 1H), 11.01 (s, 1H). $^{13}$C NMR (75 MHz, CDCl$_3$): δ 14.56, 52.59, 65.77, 118.37, 118.54, 121.36, 133.59, 149.44, 149.83, 165.09. MS (ISN): 240.1 [M−H]$^-$.

Step 4

4-Chloro-3-ethoxy-5-nitro-benzoic acid methyl ester

To a solution of 3-ethoxy-4-hydroxy-5-nitro-benzoic acid methyl ester (2.0 g, 8.29 mmol, 1.0 equiv) in anhydrous DMF (100 mL) at −25° C. under Ar was added slowly oxalyl chloride (1.40 mL, 2.11 g, 16.58 mmol, 2.0 equiv) over a period of 30 min. After the addition was completed the reaction mixture was heated to 80° C. for 3 h. The reaction mixture was poured on ice, the yellow precipitate washed with cold dichloromethane (3×20 mL), filtered and dried providing 1.97 g (86%) of the title compound. $^1$H NMR (300 MHz, CDCl$_3$): δ 1.53 (t, J=7.0 Hz, 3H), 3.96 (s, 3H), 4.24 (q, J=7.0 Hz, 2H), 7.74 (d, J=1.8 Hz, 1H), 8.00 (d, J=1.8 Hz, 1H). $^{13}$C NMR (75 MHz, CDCl$_3$): δ 14.47, 52.91, 66.17, 115.93, 117.25, 120.95, 129.82, 149.61, 156.03, 164.56. MS (ISP): 276.9 [M+NH$_4$]$^+$.

Step 5

3-Amino-4-chloro-5-ethoxy-benzoic acid methyl ester

To a solution of 4-chloro-3-ethoxy-5-nitro-benzoic acid methyl ester (1.0 g, 3.85 mmol, 1.0 equiv) in methanol (20 mL) was added dropwise under stirring at 0° C. a solution of tin chloride (2.92 g, 15.41 mmol, 4.0 equiv) in 37% HCl (7.5 mL). After the addition was completed the cooling bath was removed and the reaction mixture stirred at rt for 18 h. The solution was concentrated by evaporation under reduced pressure and the solution extracted with ethyl acetate (3×100 mL). The combined organic phases were dried over MgSO$_4$, the solvent removed by evaporation under reduced pressure and the crude material purified by recrystallization from dichloromethane yielding 0.88 g (100%) of the title compound. $^1$H NMR (300 MHz, DMSO): δ 1.28 (t, J=7.0 Hz, 3H), 3.75 (s, 3H), 4.01 (q, J=7.0 Hz, 2H), 5.57 (br s, 2H), 6.71 (d, J=1.7 Hz, 1H), 7.03 (d, J=1.7 Hz, 1H). $^{13}$C NMR (75 MHz, DMSO): δ 14.51, 52.09, 64.31, 100.87, 108.93, 110.33, 128.52, 145.93, 154.51, 166.10. MS (ISP): 230.0 [M+H]$^+$.

Step 6

3-Acetylamino-4-chloro-5-ethoxy-benzoic acid methyl ester

To a solution of 3-acetylamino-4-chloro-5-ethoxy-benzoic acid methyl ester (3.5 g, 15.24 mmol, 1.0 equiv) and diisopropylethylamine (3.74 mL, 4.14 g, 32.00 mmol, 2.1 equiv) in anhydrous DMF (20 mL) was added acetyl chloride (1.19 mL, 1.32 g, 16.76 mmol, 1.1 equiv) and the reaction mixture stirred at rt for 18 h. To the crude reaction mixture was added a conc. solution of sodium chloride (100 mL), the solution extracted with ethyl acetate (3×100 mL) and the combined organic phases dried over MgSO$_4$. Purification of the crude material with column chromatography on silica eluting with heptane/ethyl acetate (4:1→2:1) yielded 2.4 g (58%) of the title compound. $^1$H NMR (300 MHz, CDCl$_3$): δ 1.48 (t, J=7.0 Hz, 3H), 2.26 (s, 3H), 3.91 (s, 3H), 4.18 (q, J=7.0 Hz, 2H), 7.37 (d, J=1.5 Hz, 1H), 7.67 (d, J=1.5 Hz, 1H), 8.63 (br s, 1H). MS (ISP): 272.0 [M+H]$^+$.

Step 7

To a solution of 3-amino-4-chloro-5-ethoxy-benzoic acid methyl ester (1.8 g, 6.63 mmol, 1.0 equiv) in anhydrous THF (50 mL) was added lithium aluminium hydride (0.50 g, 13.25 mmol, 2.0 equiv) and the reaction mixture stirred at rt for 4 h. The crude reaction mixture was filtered, the filtrate extracted with diethyl ether (3×50 mL) and the combined organic phases dried over MgSO$_4$ providing 1.58 g (100%) of the benzyl alcohol. The crude reaction product (0.13 g, 0.53 mmol, 1.0 equiv) was dissolved in THF (20 mL) and activated MnO$_2$ (0.46 g, 5.34 mmol, 10.0 equiv) was added. After stirring at rt for 1 h, the reaction mixture was filtered and the solvent removed by evaporation under reduced pressure. A conc. solution of sodium chloride (100 mL) was added, the mixture extracted with ethyl acetate (3×100 mL) and the combined organic phases dried over MgSO$_4$. Purification of the crude material with column chromatography on silica eluting with heptane/ethyl acetate (2:1) provided 0.058 g (45%) of the title compound. $^1$H NMR (300 MHz, CDCl$_3$): δ 1.49 (t, J=7.0 Hz, 3H), 2.29 (s, 3H), 4.19 (q, J=7.0 Hz, 2H), 7.22 (d, J=1.6 Hz, 1H), 7.78 (br s, 1H), 8.56 (br s, 1H), 9.94 (br s, 1H). MS (ISP): 242.1 [M+H]$^+$.

Intermediate 47

3-Ethoxy-4-iodo-5-methoxymethoxy-benzaldehyde [CAS RN 338451-02-8]

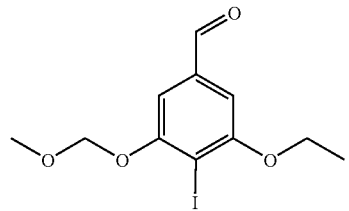

The title compound was prepared as described in WO 01/032 633 A1 (Hoffmann-La Roche AG).

Intermediate 48

4-Chloro-3-(1,1-dioxo-1λ$^6$-thiomorpholin-4-yl)-5-ethoxy-benzaldehyde

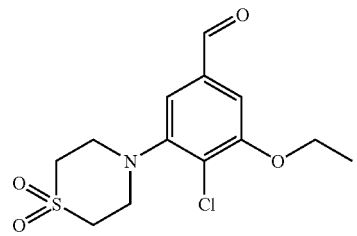

Step 1

4-Chloro-3-(1,1-dioxo-1λ⁶-thiomorpholin-4-yl)-5-ethoxy-benzoic acid

A mixture of 3-amino-4-chloro-5-ethoxy-benzoic acid methyl ester (1.0 g, 4.35 mmol, 1.0 equiv) and divinylsulfone (0.44 mL, 0.51 g, 4.35 mmol, 1.0 equiv) in phosphoric acid 85% (25 mL) was heated to 140° C. overnight. The reaction mixture was poured into water (50 mL) and extracted with dichloromethane (3×50 mL). The combined organic phases were dried over MgSO$_4$, the solvent removed by evaporation under reduced pressure and the crude material purified with column chromatography on silica eluting with heptane/ethyl acetate (1:1+1% acetic acid) yielding 0.18 g (12%) of the title compound. $^1$H NMR (300 MHz, CDCl$_3$): δ 1.51 (t, J=7.0 Hz, 3H), 3.25-3.29 (m, 4H), 3.57-3.60 (m, 4H), 4.19 (q, J=7.0 Hz, 2H), 7.44 (d, J=1.7 Hz, 1H), 7.47 (d, J=1.7 Hz, 1H). MS (ISN): 332.1 [M−H]⁻.

Step 2

[4-Chloro-3-(1,1-dioxo-1λ⁶-thiomorpholin-4-yl)-5-ethoxy-phenyl]-methanol

To a solution of 4-chloro-3-(1,1-dioxo-1λ⁶-thiomorpholin-4-yl)-5-ethoxy-benzoic acid (0.17 g, 0.51 mmol, 1.0 equiv) was added borane (1.02 mL, 1.02 mmol, 2.0 equiv; 1 M solution in THF) and the reaction mixture stirred at rt overnight. The reaction was quenched by addition of a few drops of methanol, ethyl acetate was added (50 mL) and the organic phase washed with a 1 M solution of NaOH (3×20 mL). The organic phase was dried over MgSO$_4$, the solvent removed by evaporation under reduced pressure and the crude material used in the next step without further purification. Yield: 0.089 g (58%). $^1$H NMR (300 MHz, CDCl$_3$): δ 1.39 (t, J=7.0 Hz, 3H), 3.13-3.16 (m, 4H), 3.42-3.45 (m, 4H), 4.04 (q, J=7.0 Hz, 2H), 4.56 (s, 2H), 6.64 (br s, 1H), 6.67 (br s, 1H).

Step 3

To a solution of [4-chloro-3-(1,1-dioxo-1λ⁶-thiomorpholin-4-yl)-5-ethoxy-phenyl]-methanol (0.089 g, 0.28 mmol, 1.0 equiv) in THF (20 mL) was added activated MnO$_2$ (0.242 g, 2.78 mmol, 10.0 equiv). After stirring at rt for 4 h, the reaction mixture was filtered and the solvent removed by evaporation under reduced pressure providing 0.084 g (95%) of the title compound in sufficient quality for the reductive alkylation step. MS (ISP): 318.0 [M+H]⁺.

Intermediate 49

4-Methoxy-3-(2-methoxy-ethoxy)-benzaldehyde [CAS RN 116168-89-9]

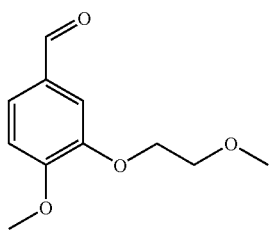

The title compound was prepared as described in D. H. Boschelli, D. Powell, J. M. Golas, F. Boschelli *Bioorg. Med. Chem. Lett.* 2003, 13, 2977-2980.

Intermediate 50

3-Ethoxy-4-hydroxy-5-nitro benzaldehyde [CAS RN 178686-24-3]

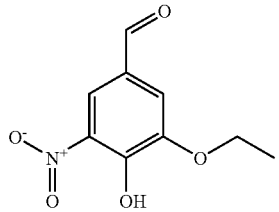

The title compound was prepared as described in WO 96/09274 A1 (Orion Corporation).

Intermediate 51

3-Ethoxy-4-methoxy-5-nitro benzaldehyde

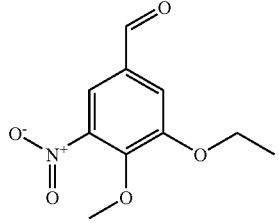

To a solution of 3-ethoxy-4-methoxybenzaldehyde (6.0 g, 33.3 mmol, 1.0 equiv) in diethyl ether (50 mL) was added dropwise nitric acid 65% (4.12 mL, 5.81 g, 59.9 mmol, 1.8 equiv) over a period of 30 min at rt. After the addition was completed the reaction mixture was heated to reflux for 4 h. The reaction product precipitated out of solution, was filtered off, washed with cold diethyl ether (3×20 mL) and dried yielding 5.85 g (78%) of the title compound. $^1$H NMR (300 MHz, CDCl$_3$): δ 1.53 (t, J=7.0 Hz, 3H), 4.04 (s, 3H), 4.26 (q, J=7.0 Hz, 2H), 7.37 (s, 1H), 7.61 (s, 1H), 10.40 (s, 1H). $^{13}$C NMR (75 MHz, CDCl$_3$): δ 14.34, 56.68, 65.35, 107.31, 110.48, 125.52, 143.56, 152.54, 152.70, 187.60. MS (ISP): 225.9 [M+H]⁺.

Intermediate 52

5-Methoxy-1H-indole-2-carbaldehyde [CAS RN 21778-81-4]

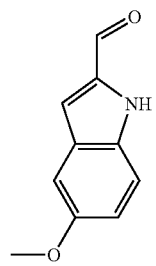

The title compound was prepared as described in P. Léon, C. Garbay-Jaureguiberry, M. C. Barsi, J. B. Le Pecq, B. P. Roques *J. Med. Chem.* 1987, 30, 2074-2080.

Examples 2 to 36

According to the procedure described for the synthesis of example 1/step 3 further benzothiazole derivatives have been synthesized from benzothiazol-2-yl-piperidin-4-yl-amine (intermediate A), (6-chloro-benzothiazol-2-yl)-piperidin-4-yl-amine dihydrobromide (intermediate B) and piperidin-4-yl-thiazolo[5,4-b]pyridin-2-yl-amine dihydrobromide (intermediate C) and the respective benzaldehyde as indicated in Table 1. The deproteced piperidines were used either as the free amine or the corresponding dihydrobromide salt. The results are compiled in Table 1 and comprise example 2 to example 36.

TABLE 1

| No | MW | Name | Starting materials | ISP [M + H]+ found |
|---|---|---|---|---|
| 2 | 433.57 | benzothiazol-2-yl-[1-(1,4-dimethoxy-naphthalen-2-ylmethyl)-piperidin-4-yl]-amine | benzothiazol-2-yl-piperidin-4-yl-amine (intermediate A) and 1,4-dimethoxy-naphthalene-2-carbaldehyde (intermediate 1) | 434.4 |
| 3 | 369.49 | 4-[4-(benzothiazol-2-ylamino)-piperidin-1-ylmethyl]-2-methoxy-phenol | benzothiazol-2-yl-piperidin-4-yl-amine (intermediate A) and 4-hydroxy-3-methoxy-benzaldehyde (commercially available) | 370.2 |
| 4 | 383.51 | benzothiazol-2-yl-[1-(3,4-dimethoxy-benzyl)-piperidin-4-yl]-amine | benzothiazol-2-yl-piperidin-4-yl-amine (intermediate A) and 3,4-dimethoxy-benzaldehyde (commercially available) | 384.2 |
| 5 | 383.51 | 4-[4-(benzothiazol-2-ylamino)-piperidin-1-ylmethyl]-2-ethoxy-phenol | benzothiazol-2-yl-piperidin-4-yl-amine (intermediate A) and 3-ethoxy-4-hydroxy-benzaldehyde (commercially available) | 384.2 |
| 6 | 397.54 | benzothiazol-2-yl-[1-(3-ethoxy-4-methoxy-benzyl)-piperidin-4-yl]-amine | benzothiazol-2-yl-piperidin-4-yl-amine (intermediate A) and 3-ethoxy-4-methoxy-benzaldehyde (commercially available) | 398.3 |
| 7 | 425.59 | benzothiazol-2-yl-[1-(3-ethoxy-4-isopropoxy-benzyl)-piperidin-4-yl]-amine | benzothiazol-2-yl-piperidin-4-yl-amine (intermediate A) and 3-ethoxy-4-isopropoxy-benzaldehyde (commercially available) | 426.2 |
| 8 | 411.57 | benzothiazol-2-yl-[1-(4-methoxy-3-propoxy-benzyl)-piperidin-4-yl]-amine | benzothiazol-2-yl-piperidin-4-yl-amine (intermediate A) and 4-ethoxy-3-propoxy-benzaldehyde (intermediate 2) | 412.2 |
| 9 | 415.53 | benzothiazol-2-yl-{1-[3-(2-fluoro-ethoxy)-4-methoxy-benzyl]-piperidin-4-yl}-amine | benzothiazol-2-yl-piperidin-4-yl-amine (intermediate A) and 3-(2-fluoro-ethoxy)-4-methoxy-benzaldehyde (intermediate 3) | 416.2 |
| 10 | 383.51 | benzothiazol-2-yl-[1-(3,5-dimethoxy-benzyl)-piperidin-4-yl]-amine | benzothiazol-2-yl-piperidin-4-yl-amine (intermediate A) and 3,5-dimethoxy-benzaldehyde (commercially available) | 384.2 |
| 11 | 383.51 | benzothiazol-2-yl-[1-(2,4-dimethoxy-benzyl)-piperidin-4-yl]-amine | benzothiazol-2-yl-piperidin-4-yl-amine (intermediate A) and 2,4-dimethoxy-benzaldehyde (commercially available) | 384.2 |
| 12 | 369.49 | 2-[4-(benzothiazol-2-ylamino)-piperidin-1-ylmethyl]-6-methoxy-phenol | benzothiazol-2-yl-piperidin-4-yl-amine (intermediate A) and 2-hydroxy-3-methoxy-benzaldehyde (commercially available) | 370.2 |
| 13 | 413.54 | benzothiazol-2-yl-[1-(3,4,5-trimethoxy-benzyl)-piperidin-4-yl]-amine | benzothiazol-2-yl-piperidin-4-yl-amine (intermediate A) and 3,4,5-trimethoxy-benzaldehyde (commercially available) | 414.2 |
| 14 | 489.64 | benzothiazol-2-yl-[1-(2-benzyloxy-4,5-dimethoxy-benzyl)-piperidin-4-yl]-amine | benzothiazol-2-yl-piperidin-4-yl-amine (intermediate A) and 2-benzyloxy-4,5-dimethoxy-benzaldehyde (commercially available) | 490.2 |
| 15 | 476.64 | benzothiazol-2-yl-[1-(3,5-diethoxy-4-pyrrol-1-yl-benzyl)-piperidin-4-yl]-amine | benzothiazol-2-yl-piperidin-4-yl-amine (intermediate A) and 3,5-diethoxy-4-pyrrol-1-yl-benzaldehyde (intermediate 4) | 477.2 |
| 16 | 376.53 | benzothiazol-2-yl-[1-(1-methyl-1H-indole-3- | benzothiazol-2-yl-piperidin-4-yl-amine (intermediate A) and | 396.2 |

TABLE 1-continued

| No | MW | Name | Starting materials | ISP [M + H]+ found |
|---|---|---|---|---|
|  |  | ylmethyl)-piperidin-4-yl]-amine | 1-methyl-1H-indole-3-carbaldehyde (commercially available) |  |
| 17 | 462.62 | 3-[4-(benzothiazol-2-ylamino)-piperidin-1-ylmethyl]-indole-1-carboxylic acid tert-butyl ester | benzothiazol-2-yl-piperidin-4-yl-amine (intermediate A) and 3-formyl-indole-1-carboxylic acid tert-butyl ester (commercially available) | 463.2 |
| 18 | 389.53 | benzothiazol-2-yl-[1-(2-phenyl-3H-imidazol-4-ylmethyl)-piperidin-4-yl]-amine | benzothiazol-2-yl-piperidin-4-yl-amine (intermediate A) and 2-phenyl-3H-imidazole-4-carbaldehyde (commercially available) | 390.3 |
| 19 | 468.02 | (6-chloro-benzothiazol-2-yl)-[1-(1,4-dimethoxy-naphthalen-2-ylmethyl)-piperidin-4-yl]-amine | (6-chloro-benzothiazol-2-yl)-piperidin-4-yl-amine dihydrobromide (intermediate B) and 1,4-dimethoxy-naphthalene-2-carbaldehyde (intermediate 1) | 467.5 |
| 20 | 417.96 | (6-chloro-benzothiazol-2-yl)-[1-(3,4-dimethoxy-benzyl)-piperidin-4-yl]-amine | (6-chloro-benzothiazol-2-yl)-piperidin-4-yl-amine dihydrobromide (intermediate B) and 3,4-dimethoxy-benzaldehyde (commercially available) | 417.5 |
| 21 | 415.99 | (6-chloro-benzothiazol-2-yl)-[1-(3-ethoxy-4-methyl-benzyl)-piperidin-4-yl]-amine | (6-chloro-benzothiazol-2-yl)-piperidin-4-yl-amine dihydrobromide (intermediate B) and 3-ethoxy-4-methyl-benzaldehyde (intermediate 5) | 415.5 |
| 22 | 436.41 | (6-chloro-benzothiazol-2-yl)-[1-(4-chloro-3-ethoxy-benzyl)-piperidin-4-yl]-amine | (6-chloro-benzothiazol-2-yl)-piperidin-4-yl-amine dihydrobromide (intermediate B) and 4-chloro-3-ethoxy-benzaldehyde (intermediate 6) | 438.2 |
| 23 | 417.96 | 4-[4-(6-chloro-benzothiazol-2-ylamino)-piperidin-1-ylmethyl]-2-ethoxy-phenol | (6-chloro-benzothiazol-2-yl)-piperidin-4-yl-amine dihydrobromide (intermediate B) and 3-ethoxy-4-hydroxy-benzaldehyde (commercially available) | 419.5 |
| 24 | 431.99 | (6-chloro-benzothiazol-2-yl)-[1-(3-ethoxy-4-methoxy-benzyl)-piperidin-4-yl]-amine | (6-chloro-benzothiazol-2-yl)-piperidin-4-yl-amine dihydrobromide (intermediate B) and 3-ethoxy-4-methoxy-benzaldehyde (commercially available) | 433.5 |
| 25 | 449.98 | (6-chloro-benzothiazol-2-yl)-{1-[3-(2-fluoro-ethoxy)-4-methoxy-benzyl]-piperidin-4-yl}-amine | (6-chloro-benzothiazol-2-yl)-piperidin-4-yl-amine dihydrobromide (intermediate B) and 3-(2-fluoro-ethoxy)-4-methoxy-benzaldehyde (intermediate 3) | 451.5 |
| 26 | 435.95 | 4-[4-(6-chloro-benzothiazol-2-ylamino)-piperidin-1-ylmethyl]-2-ethoxy-5-fluoro-phenol | (6-chloro-benzothiazol-2-yl)-piperidin-4-yl-amine dihydrobromide (intermediate B) and 5-ethoxy-2-fluoro-4-hydroxy-benzaldehyde (intermediate 7) | 437.5 |
| 27 | 423.97 | (6-chloro-benzothiazol-2-yl)-[1-(2-phenyl-1H-imidazol-4-ylmethyl)-piperidin-4-yl]-amine | (6-chloro-benzothiazol-2-yl)-piperidin-4-yl-amine dihydrobromide (intermediate B) and 2-phenyl-3H-imidazole-4-carbaldehyde (commercially available) | 425.5 |
| 28 | 418.56 | [1-(2-ethoxy-naphthalen-1-ylmethyl)-piperidin-4-yl]-thiazolo[5,4-b]pyridin-2-yl-amine | piperidin-4-yl-thiazolo[5,4-b]pyridin-2-yl-amine dihydrobromide (intermediate C) and 2-ethoxy-naphthalene-1-carbaldehyde (commercially available) | 419.3 |
| 29 | 434.56 | [1-(1,4-dimethoxy-naphthalen-2-ylmethyl)-piperidin-4-yl]-thiazolo[5,4-b]pyridin-2- | piperidin-4-yl-thiazolo[5,4-b]pyridin-2-yl-amine dihydrobromide (intermediate C) and 1,4-dimethoxy- | 435.3 |

TABLE 1-continued

| No | MW | Name | Starting materials | ISP [M + H]+ found |
|---|---|---|---|---|
|  |  | yl-amine | naphthalene-2-carbaldehyde (intermediate 1) |  |
| 30 | 402.95 | [1-(4-chloro-3-ethoxy-benzyl)-piperidin-4-yl]-thiazolo[5,4-b]pyridin-2-yl-amine | piperidin-4-yl-thiazolo[5,4-b]pyridin-2-yl-amine dihydrobromide (intermediate C) and 4-chloro-3-ethoxy-benzaldehyde (intermediate 6) | 403.2 |
| 31 | 398.53 | [1-(3-ethoxy-4-methoxy-benzyl)-piperidin-4-yl]-thiazolo[5,4-b]pyridin-2-yl-amine | piperidin-4-yl-thiazolo[5,4-b]pyridin-2-yl-amine dihydrobromide (intermediate C) and 3-ethoxy-4-methoxy-benzaldehyde (commercially available) | 399.2 |
| 32 | 412.56 | [1-(4-methoxy-3-propoxy-benzyl)-piperidin-4-yl]-thiazolo[5,4-b]pyridin-2-yl-amine | piperidin-4-yl-thiazolo[5,4-b]pyridin-2-yl-amine dihydrobromide (intermediate C) and 4-ethoxy-3-propoxy-benzaldehyde (intermediate 2) | 413.3 |
| 33 | 416.52 | {1-[3-(2-fluoro-ethoxy)-4-methoxy-benzyl]-piperidin-4-yl}-thiazolo[5,4-b]pyridin-2-yl-amine | piperidin-4-yl-thiazolo[5,4-b]pyridin-2-yl-amine dihydrobromide (intermediate C) and 3-(2-fluoro-ethoxy)-4-methoxy-benzaldehyde (intermediate 3) | 417.2 |
| 34 | 426.58 | [1-(3-isobutoxy-4-methoxy-benzyl)-piperidin-4-yl]-thiazolo[5,4-b]pyridin-2-yl-amine | piperidin-4-yl-thiazolo[5,4-b]pyridin-2-yl-amine dihydrobromide (intermediate C) and 3-isobutoxy-4-methoxy-benzaldehyde (intermediate 8) | 427.3 |
| 35 | 442.58 | 2-{2-isopropoxy-5-[4-(thiazolo[5,4-b]pyridin-2-ylamino)-piperidin-1-ylmethyl]-phenoxy}-ethanol | piperidin-4-yl-thiazolo[5,4-b]pyridin-2-yl-amine dihydrobromide (intermediate C) and 3-(2-hydroxy-ethoxy)-4-isopropoxy-benzaldehyde (intermediate 9) | 443.3 |
| 36 | 384.50 | [1-(2,5-dimethoxy-benzyl)-piperidin-4-yl]-thiazolo[5,4-b]pyridin-2-yl-amine | piperidin-4-yl-thiazolo[5,4-b]pyridin-2-yl-amine dihydrobromide (intermediate C) and 2,5-dimethoxy-benzaldehyde (commercially available) | 385.2 |

Example 37

Benzooxazol-2-yl-[1-(2-ethoxy-naphthalen-1-ylmethyl)-piperidin-4-yl]-amine

Step 1:

4-(Benzooxazol-2-ylamino)-piperidine-1-carboxylic acid ethyl ester

A mixture of 2-chloro-benzooxazole (8.00 g, 52.1 mmol, 1.0 equiv) and ethyl 4-amino-1-piperidine carboxylate (10.78 g, 62.5 mmol, 1.2 equiv) in anhydrous DMF (50 mL) was stirred at rt. A precipitate formed over night which was filtered off, the volume of the filtrate reduced and the residue taken up in ethyl acetate (10 mL). Precipitation of this solution from hexane provided an additional batch of the title compound as a white solid. Combined yield: 6.8 g (45%). $^1$H NMR (400 MHz, CDCl$_3$): δ 1.27 (t, J=7.2 Hz, 3H), 1.48-1.52 (m, 2H), 2.14-2.18 (m, 2H), 3.09 (br t, 2H), 3.81-3.95 (m, 1H), 4.12-4.18 (m, 2H), 4.15 (q, J=7.2 Hz, 2H), 5.64 (br d, J=7.8 Hz, 1H), 7.04 (t, J=7.8 Hz, 1H), 7.17 (t, J=7.6 Hz, 1H), 7.25 (d, J=7.8 Hz, 1H), 7.36 (d, J=7.6 Hz, 1H). $^{13}$C NMR (100 MHz, CDCl$_3$): δ 14.93, 32.53, 42.85, 50.66, 61.72, 109.00, 116.62, 121.24, 124.24, 143.10, 148.66, 155.72, 161.32. MS (ISP): 290.0 [M+H]+.

Step 2:

Benzooxazol-2-yl-piperidin-4-yl-amine dihydrobromide (Intermediate D)

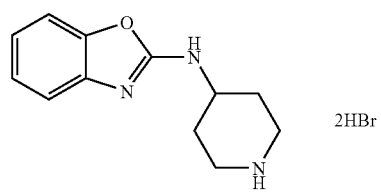

According to the procedure described for the synthesis of example 1/step 2 (benzothiazol-2-yl-piperidin-4-yl-amine) the title compound was synthesized from 4-(benzooxazol-2-ylamino)-piperidine-1-carboxylic acid ethyl ester using identical conditions. The product was used in the consecutive step without further purification assuming 100% conversion and formation of the dihydrobromide salt. MS (ESI): 218.3 [M+H]+.

Step 3:

According to the procedure described for the synthesis of example 1/step 3 (benzothiazol-2-yl-[1-(2-ethoxy-naphthalen-1-ylmethyl)-piperidin-4-yl]-amine) the title compound was synthesized from benzooxazol-2-yl-piperidin-4-yl-amine dihydrobromide and 2-ethoxy-naphthalene-1-carbaldehyde using identical conditions. Isolated yield after purification by preparative HPLC: 20.8 mg (52%). MS (ESI): 402.1 [M+H]+.

Synthesis of Benzooxazole Intermediates E and F to be Used in Table 2

Intermediate E (5-Chloro-benzooxazol-2-yl)-piperidin-4-yl-amine dihydrobromide

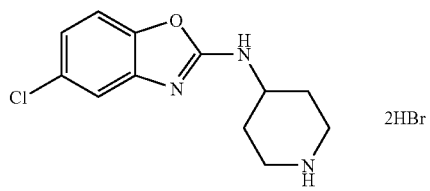

Step 1:

4-(5-Chloro-benzooxazol-2-ylamino)-piperidine-1-carboxylic acid ethyl ester

A mixture of 5-chloro-benzooxazole-2-thiol (4.00 g, 21.5 mmol, 1.0 equiv; commercially available from Aldrich) and ethyl 4-amino-1-piperidine carboxylate (4.9 g, 28.0 mmol, 1.3 equiv) in anhydrous DMAc (5 mL) was heated to 200° C. under microwave irradiation for 20 min. To the crude reaction mixture was added a conc. solution of sodium chloride (100 mL), the solution extracted with ethyl acetate (3×100 mL) and the combined organic phases dried over MgSO4. Purification of the crude material with column chromatography on silica eluting with hexane/ethyl acetate (2:1→1:1) yielded 2.7 g (39%) of the title compound. 1H NMR (400 MHz, DMSO): δ 1.19 (t, J=7.1 Hz, 3H), 1.39-1.45 (m, 2H), 1.93-1.97 (m, 2H), 2.98 (br s, 2H), 3.77-3.78 (m, 1H), 3.91-3.95 (m, 2H), 4.04 (q, J=7.1 Hz, 2H), 7.00 (dd, J=8.4 Hz, J=2.1 Hz, 1H), 7.29 (d, J=2.1 Hz, 1H), 7.36 (d, J=8.4 Hz, 1H), 8.19 (d, J=7.6 Hz, 1H). 13C NMR (100 MHz, DMSO): δ 14.53, 31.11, 42.07, 49.60, 60.63, 109.45, 115.10, 119.65, 127.78, 144.86, 146.71, 154.56, 162.50. MS (ISP): 324.1 [M+H]+.

Step 2:

According to the procedure described for the synthesis of example 1/step 2 (benzothiazol-2-yl-piperidin-4-yl-amine) the title compound was synthesized from 4-(5-chloro-benzooxazol-2-ylamino)-piperidine-1-carboxylic acid ethyl ester using identical conditions. The product was used in the consecutive step without further purification assuming 100% conversion and formation of the dihydrobromide salt. MS (ISP): 251.9 [M+H]+.

Intermediate F (6-Chloro-benzooxazol-2-yl)-piperidin-4-yl-amine dihydrobromide

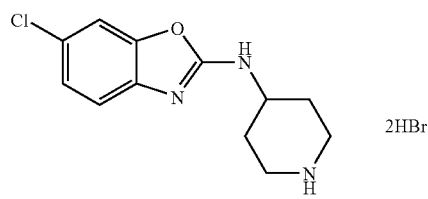

Step 1:

4-(6-Chloro-benzooxazol-2-ylamino)-piperidine-1-carboxylic acid ethyl ester

According to the procedure described for the synthesis of intermediate E/step 1 (4-(5-chloro-benzooxazol-2-ylamino)-piperidine-1-carboxylic acid ethyl ester) the title compound was synthesized from 6-chloro-benzooxazole-2-thiol (commercially available) and purified using identical conditions. Yield: 54%. 1H NMR (300 MHz, DMSO): δ 1.18 (t, J=7.1 Hz, 3H), 1.38-1.43 (m, 2H), 1.91-1.99 (m, 2H), 2.91-2.98 (m, 2H), 3.74-3.79 (m, 1H), 3.90-3.94 (m, 2H), 4.04 (q, J=7.1 Hz, 2H), 7.15 (dd, J=8.3 Hz, J=2.0 Hz, 1H), 7.23 (d, J=8.3 Hz, 1H), 7.52 (d, J=2.0 Hz, 1H), 8.13 (d, J=7.5 Hz, 1H). 13C NMR (75 MHz, DMSO): δ 13.27, 29.81, 40.80, 48.34, 59.35, 107.89, 114.73, 122.35, 122.64, 141.09, 146.94, 153.31, 160.70. MS (ISP): 324.0 [M+H]+.

Step 2:

According to the procedure described for the synthesis of example 1/step 2 (benzothiazol-2-yl-piperidin-4-yl-amine) the title compound was synthesized from 4-(6-chloro-benzooxazol-2-ylamino)-piperidine-1-carboxylic acid ethyl ester using identical conditions. The product was used in the consecutive step without further purification assuming 100% conversion and formation of the dihydrobromide salt. MS (ESI): 252.3 [M+H]+.

Examples 38 to 94

According to the procedure described for the synthesis of example 37/step 3 further benzooxazole-derivatives have been synthesized from benzooxazol-2-yl-piperidin-4-yl-amine dihydrobromide (intermediate D), (5-chloro-benzooxazol-2-yl)-piperidin-4-yl-amine dihydrobromide (intermediate E) and (6-chloro-benzooxazol-2-yl)-piperidin-4-yl-amine dihydrobromide (intermediate F) and the respective benzaldehyde as indicated in Table 2. The deproteced piperidines were used either as the free amine or the corresponding hydrobromide salt. The results are compiled in Table 2 and comprise example 38 to example 94.

TABLE 2

| No | MW | Name | Starting materials | ISP [M + H]+ found |
|---|---|---|---|---|
| 38 | 417.51 | benzooxazol-2-yl-[1-(1,4-dimethoxy-naphthalen-2-ylmethyl)-piperidin-4-yl]-amine | benzooxazol-2-yl-piperidin-4-yl-amine dihydrobromide (intermediate D) and 1,4-dimethoxy-naphthalene-2-carbaldehyde (intermediate 1) | 418.2 |
| 39 | 367.45 | benzooxazol-2-yl-[1-(3,4-dimethoxy-benzyl)-piperidin-4-yl]-amine | benzooxazol-2-yl-piperidin-4-yl-amine dihydrobromide (intermediate D) and 3,4-dimethoxy-benzaldehyde (commercially available) | 368.1 |
| 40 | 365.47 | benzooxazol-2-yl-[1-(3-ethoxy-4-methyl-benzyl)-piperidin-4-yl]-amine | benzooxazol-2-yl-piperidin-4-yl-amine dihydrobromide (intermediate D) and 3-ethoxy-4-methyl-benzaldehyde (intermediate 5) | 366.2 |
| 41 | 385.89 | benzooxazol-2-yl-[1-(4-chloro-3-ethoxy-benzyl)-piperidin-4-yl]-amine | benzooxazol-2-yl-piperidin-4-yl-amine dihydrobromide (intermediate D) and 4-chloro-3-ethoxy-benzaldehyde (intermediate 6) | 386.3 |
| 42 | 369.44 | benzooxazol-2-yl-[1-(3-ethoxy-4-fluoro-benzyl)-piperidin-4-yl]-amine | benzooxazol-2-yl-piperidin-4-yl-amine dihydrobromide (intermediate D) and 3-ethoxy-4-fluoro-benzaldehyde (intermediate 10) | 370.2 |
| 43 | 419.45 | benzooxazol-2-yl-[1-(3-ethoxy-4-trifluoromethyl-benzyl)-piperidin-4-yl]-amine | benzooxazol-2-yl-piperidin-4-yl-amine dihydrobromide (intermediate D) and 3-ethoxy-4-trifluoromethyl-benzaldehyde (intermediate 11) | 420.4 |
| 44 | 367.45 | 4-[4-(benzooxazol-2-ylamino)-piperidin-1-ylmethyl]-2-ethoxy-phenol | benzooxazol-2-yl-piperidin-4-yl-amine dihydrobromide (intermediate D) and 3-ethoxy-4-hydroxy-benzaldehyde (commercially available) | 368.1 |
| 45 | 381.47 | benzooxazol-2-yl-[1-(3-ethoxy-4-methoxy-benzyl)-piperidin-4-yl]-amine | benzooxazol-2-yl-piperidin-4-yl-amine dihydrobromide (intermediate D) and 3-ethoxy-4-methoxy-benzaldehyde (commercially available) | 382.1 |
| 46 | 395.50 | benzooxazol-2-yl-[1-(3,4-diethoxy-benzyl)-piperidin-4-yl]-amine | benzooxazol-2-yl-piperidin-4-yl-amine dihydrobromide (intermediate D) and 3,4-diethoxy-benzaldehyde (commercially available) | 396.3 |
| 47 | 409.53 | benzooxazol-2-yl-[1-(3-ethoxy-4-isopropoxy-benzyl)-piperidin-4-yl]-amine | benzooxazol-2-yl-piperidin-4-yl-amine dihydrobromide (intermediate D) and 3-ethoxy-4-isopropoxy-benzaldehyde (commercially available) | 410.2 |
| 48 | 407.51 | benzooxazol-2-yl-[1-(4-cyclopropoxy-3-ethoxy-benzyl)-piperidin-4-yl]-amine | benzooxazol-2-yl-piperidin-4-yl-amine dihydrobromide (intermediate D) and 4-cyclopropoxy-3-ethoxy-benzaldehyde (intermediate 12) | 408.2 |
| 49 | 437.58 | benzooxazol-2-yl-{1-[3-ethoxy-4-(1-ethyl-propoxy)-benzyl]-piperidin-4-yl}-amine | benzooxazol-2-yl-piperidin-4-yl-amine dihydrobromide (intermediate D) and 3-ethoxy-4-(1-ethyl-propoxy)-benzaldehyde (intermediate 13) | 438.3 |
| 50 | 435.57 | benzooxazol-2-yl-{1-[3-ethoxy-4-(3-methyl-but-2-enyloxy)-benzyl]-piperidin-4-yl}-amine | benzooxazol-2-yl-piperidin-4-yl-amine dihydrobromide (intermediate D) and 3-ethoxy-4-(3-methyl-but-2-enyloxy)-benzaldehyde (intermediate 14) | 436.3 |
| 51 | 421.54 | benzooxazol-2-yl-[1-(3-cyclopentyloxy-4-methoxy-benzyl)-piperidin-4-yl]-amine | benzooxazol-2-yl-piperidin-4-yl-amine dihydrobromide (intermediate D) and 3-cyclopentyloxy-4-methoxy-benzaldehyde (commercially available) | 422.6 |
| 52 | 393.48 | [1-(3-allyloxy-4-methoxy-benzyl)-piperidin-4-yl]- | benzooxazol-2-yl-piperidin-4-yl-amine dihydrobromide (intermediate D) and 3- | 394.2 |

TABLE 2-continued

| No | MW | Name | Starting materials | ISP [M + H]+ found |
|---|---|---|---|---|
| | | benzooxazol-2-yl-amine | allyloxy-4-methoxy-benzaldehyde (intermediate 15) | |
| 53 | 395.50 | benzooxazol-2-yl-[1-(4-methoxy-3-propoxy-benzyl)-piperidin-4-yl]-amine | benzooxazol-2-yl-piperidin-4-yl-amine dihydrobromide (intermediate D) and 4-ethoxy-3-propoxy-benzaldehyde (intermediate 2) | 396.2 |
| 54 | 399.46 | benzooxazol-2-yl-{1-[3-(2-fluoro-ethoxy)-4-methoxy-benzyl]-piperidin-4-yl}-amine | benzooxazol-2-yl-piperidin-4-yl-amine dihydrobromide (intermediate D) and 3-(2-fluoro-ethoxy)-4-methoxy-benzaldehyde (intermediate 3) | 400.0 |
| 55 | 409.53 | benzooxazol-2-yl-[1-(3-butoxy-4-methoxy-benzyl)-piperidin-4-yl]-amine | benzooxazol-2-yl-piperidin-4-yl-amine dihydrobromide (intermediate D) and 3-butoxy-4-methoxy-benzaldehyde (intermediate 16) | 410.2 |
| 56 | 409.53 | benzooxazol-2-yl-[1-(3-isobutoxy-4-methoxy-benzyl)-piperidin-4-yl]-amine | benzooxazol-2-yl-piperidin-4-yl-amine dihydrobromide (intermediate D) and 3-isobutoxy-4-methoxy-benzaldehyde (intermediate 8) | 410.2 |
| 57 | 385.44 | 4-[4-(benzooxazol-2-ylamino)-piperidin-1-ylmethyl]-2-ethoxy-5-fluoro-phenol | benzooxazol-2-yl-piperidin-4-yl-amine dihydrobromide (intermediate D) and 5-ethoxy-2-fluoro-4-hydroxy-benzaldehyde (intermediate 7) | 386.2 |
| 58 | 429.49 | 2-{4-[4-(benzooxazol-2-ylamino)-piperidin-1-ylmethyl]-2-ethoxy-5-fluoro-phenoxy}-ethanol | benzooxazol-2-yl-piperidin-4-yl-amine dihydrobromide (intermediate D) and 5-ethoxy-2-fluoro-4-(2-hydroxy-ethoxy)-benzaldehyde (intermediate 17) | 430.2 |
| 59 | 397.47 | benzooxazol-2-yl-[1-(3,4,5-trimethoxy-benzyl)-piperidin-4-yl]-amine | benzooxazol-2-yl-piperidin-4-yl-amine dihydrobromide (intermediate D) and 3,4-trimethoxy-benzaldehyde (commercially available) | 398.1 |
| 60 | 397.47 | benzooxazol-2-yl-[1-(2,4,5-trimethoxy-benzyl)-piperidin-4-yl]-amine | benzooxazol-2-yl-piperidin-4-yl-amine dihydrobromide (intermediate D) and 2,4,5-trimethoxy-benzaldehyde (commercially available) | 398.1 |
| 61 | 473.57 | benzooxazol-2-yl-[1-(2-benzyloxy-4,5-dimethoxy-benzyl)-piperidin-4-yl]-amine | benzooxazol-2-yl-piperidin-4-yl-amine dihydrobromide (intermediate D) and 2-benzyloxy-4,5-dimethoxy-benzaldehyde (commercially available) | 474.2 |
| 62 | 397.47 | benzooxazol-2-yl-[1-(2,3,4-trimethoxy-benzyl)-piperidin-4-yl]-amine | benzooxazol-2-yl-piperidin-4-yl-amine dihydrobromide (intermediate D) and 2,3,4-trimethoxy-benzaldehyde (commercially available) | 398.1 |
| 63 | 433.55 | benzooxazol-2-yl-[1-(8-ethoxy-2,2-dimethyl-2H-chromen-6-ylmethyl)-piperidin-4-yl]-amine | benzooxazol-2-yl-piperidin-4-yl-amine dihydrobromide (intermediate D) and 8-ethoxy-2,2-dimethyl-2H-chromene-6-carbaldehyde (intermediate 18) | 434.2 |
| 64 | 449.47 | benzooxazol-2-yl-{1-[3-ethoxy-5-(2,2,2-trifluoro-ethoxy)-benzyl]-piperidin-4-yl}-amine | benzooxazol-2-yl-piperidin-4-yl-amine dihydrobromide (intermediate D) and 3-ethoxy-5-(2,2,2-trifluoro-ethoxy)-benzaldehyde (intermediate 19) | 450.6 |
| 65 | 451.56 | benzooxazol-2-yl-{1-[3-ethoxy-5-(tetrahydro-pyran-4-yloxy)-benzyl]-piperidin-4-yl}-amine | benzooxazol-2-yl-piperidin-4-yl-amine dihydrobromide (intermediate D) and 3-ethoxy-5-(tetrahydro-pyran-4-yloxy)-benzaldehyde (intermediate 20) | 452.2 |
| 66 | 413.49 | benzooxazol-2-yl-[1-(3,5-diethoxy-4-fluoro-benzyl)-piperidin-4-yl]-amine | benzooxazol-2-yl-piperidin-4-yl-amine dihydrobromide (intermediate D) and 3,5-diethoxy-4-fluoro-benzaldehyde (intermediate 21) | 414.2 |

TABLE 2-continued

| No | MW | Name | Starting materials | ISP [M + H]+ found |
|---|---|---|---|---|
| 67 | 467.56 | 4-[4-(benzooxazol-2-ylamino)-piperidin-1-ylmethyl]-2,6-diethoxy-benzoic acid ethyl ester | benzooxazol-2-yl-piperidin-4-yl-amine dihydrobromide (intermediate D) and 2,6-diethoxy-4-formyl-benzoic acid ethyl ester (intermediate 22) | 468.20 |
| 68 | 410.52 | [1-(4-amino-3,5-diethoxy-benzyl)-piperidin-4-yl]-benzooxazol-2-yl-amine | benzooxazol-2-yl-piperidin-4-yl-amine dihydrobromide (intermediate D) and 4-amino-3,5-diethoxy-benzaldehyde (intermediate 23) | 411.20 |
| 69 | 452.55 | N-{4-[4-(benzooxazol-2-ylamino)-piperidin-1-ylmethyl]-2,6-diethoxy-phenyl}-acetamide | benzooxazol-2-yl-piperidin-4-yl-amine dihydrobromide (intermediate D) and N-(2,6-diethoxy-4-formyl-phenyl)-acetamide (intermediate 24) | 453.1 |
| 70 | 492.36 | [1-(3-amino-5-ethoxy-4-iodo-benzyl)-piperidin-4-yl]-benzooxazol-2-yl-amine | benzooxazol-2-yl-piperidin-4-yl-amine dihydrobromide (intermediate D) and 3-amino-5-ethoxy-4-iodo-benzaldehyde (intermediate 25) | 493.10 |
| 71 | 534.39 | N-{5-[4-(benzooxazol-2-ylamino)-piperidin-1-ylmethyl]-3-ethoxy-2-iodo-phenyl}-acetamide | benzooxazol-2-yl-piperidin-4-yl-amine dihydrobromide (intermediate D) and N-(3-ethoxy-5-formyl-2-iodo-phenyl)-acetamide (intermediate 26) | 533.40 |
| 72 | 390.48 | benzooxazol-2-yl-[1-(4-ethoxy-1H-indol-6-ylmethyl)-piperidin-4-yl]-amine | benzooxazol-2-yl-piperidin-4-yl-amine dihydrobromide (intermediate D) and 4-ethoxy-1H-indole-6-carbaldehyde (intermediate 27) | 391.50 |
| 73 | 382.46 | benzooxazol-2-yl-[1-(5-ethoxy-6-methoxy-pyridin-3-ylmethyl)-piperidin-4-yl]-amine | benzooxazol-2-yl-piperidin-4-yl-amine dihydrobromide (intermediate D) and 5-ethoxy-6-methoxy-pyridine-3-carbaldehyde (intermediate 28) | 383.40 |
| 74 | 380.49 | benzooxazol-2-yl-[1-(3-ethylamino-4-methoxy-benzyl)-piperidin-4-yl]-amine | benzooxazol-2-yl-piperidin-4-yl-amine dihydrobromide (intermediate D) and 3-ethylamino-4-methoxy-benzaldehyde (intermediate 29) | 381.1 |
| 75 | 373.46 | benzooxazol-2-yl-[1-(2-phenyl-3H-imidazol-4-ylmethyl)-piperidin-4-yl]-amine | benzooxazol-2-yl-piperidin-4-yl-amine dihydrobromide (intermediate D) and 2-phenyl-3H-imidazole-4-carbaldehyde (commercially available) | 374.1 |
| 76 | 399.92 | (5-chloro-benzooxazol-2-yl)-[1-(3-ethoxy-4-methyl-benzyl)-piperidin-4-yl]-amine | (5-chloro-benzooxazol-2-yl)-piperidin-4-yl-amine dihydrobromide (intermediate E) and 3-ethoxy-4-methyl-benzaldehyde (intermediate 5) | 402.3 |
| 77 | 420.34 | (5-chloro-benzooxazol-2-yl)-[1-(4-chloro-3-ethoxy-benzyl)-piperidin-4-yl]-amine | (5-chloro-benzooxazol-2-yl)-piperidin-4-yl-amine dihydrobromide (intermediate E) and 4-chloro-3-ethoxy-benzaldehyde (intermediate 6) | 422.3 |
| 78 | 401.89 | 4-[4-(5-chloro-benzooxazol-2-ylamino)-piperidin-1-ylmethyl]-2-ethoxy-phenol | (5-chloro-benzooxazol-2-yl)-piperidin-4-yl-amine dihydrobromide (intermediate E) and 3-ethoxy-4-hydroxy-benzaldehyde (commercially available) | 402.3 |
| 79 | 415.92 | (5-chloro-benzooxazol-2-yl)-[1-(3-ethoxy-4-methoxy-benzyl)-piperidin-4-yl]-amine | (5-chloro-benzooxazol-2-yl)-piperidin-4-yl-amine dihydrobromide (intermediate E) and 3-ethoxy-4-methoxy-benzaldehyde (commercially available) | 416.4 |
| 80 | 429.95 | (5-chloro-benzooxazol-2-yl)-[1-(4-methoxy-3-propoxy-benzyl)-piperidin-4-yl]-amine | (5-chloro-benzooxazol-2-yl)-piperidin-4-yl-amine dihydrobromide (intermediate E) and 4-ethoxy-3-propoxy-benzaldehyde (intermediate 2) | 430.4 |
| 81 | 433.91 | (5-chloro-benzooxazol-2-yl)-{1-[3-(2-fluoro- | (5-chloro-benzooxazol-2-yl)-piperidin-4-yl-amine | 434.4 |

TABLE 2-continued

| No | MW | Name | Starting materials | ISP [M + H]+ found |
|----|-----|------|-------------------|--------------------|
|  |  | ethoxy)-4-methoxy-benzyl]-piperidin-4-yl}-amine | dihydrobromide (intermediate E) and 3-(2-fluoro-ethoxy)-4-methoxy-benzaldehyde (intermediate 3) |  |
| 82 | 429.95 | (5-chloro-benzooxazol-2-yl)-[1-(3,5-diethoxy-benzyl)-piperidin-4-yl]-amine | (5-chloro-benzooxazol-2-yl)-piperidin-4-yl-amine dihydrobromide (intermediate E) and 3,5-diethoxy-benzaldehyde (intermediate 30) | 430.4 |
| 83 | 447.94 | (5-chloro-benzooxazol-2-yl)-[1-(3,5-diethoxy-4-fluoro-benzyl)-piperidin-4-yl]-amine | (5-chloro-benzooxazol-2-yl)-piperidin-4-yl-amine dihydrobromide (intermediate E) and 3,5-diethoxy-4-fluoro-benzaldehyde (intermediate 21) | 448.4 |
| 84 | 495.02 | (5-chloro-benzooxazol-2-yl)-[1-(3,5-diethoxy-4-pyrrol-1-yl-benzyl)-piperidin-4-yl]-amine | (5-chloro-benzooxazol-2-yl)-piperidin-4-yl-amine dihydrobromide (intermediate E) and 3,5-diethoxy-4-pyrrol-1-yl-benzaldehyde (intermediate 4) | 497.4 |
| 85 | 401.89 | (6-chloro-benzooxazol-2-yl)-[1-(3,4-dimethoxy-benzyl)-piperidin-4-yl]-amine | (6-chloro-benzooxazol-2-yl)-piperidin-4-yl-amine dihydrobromide (intermediate F) and 3,4-dimethoxy-benzaldehyde (commercially available) | 402.2 |
| 86 | 399.92 | (6-chloro-benzooxazol-2-yl)-[1-(3-ethoxy-4-methyl-benzyl)-piperidin-4-yl]-amine | (6-chloro-benzooxazol-2-yl)-piperidin-4-yl-amine dihydrobromide (intermediate F) and 3-ethoxy-4-methyl-benzaldehyde (intermediate 5) | 402.2 |
| 87 | 420.34 | (6-chloro-benzooxazol-2-yl)-[1-(4-chloro-3-ethoxy-benzyl)-piperidin-4-yl]-amine | (6-chloro-benzooxazol-2-yl)-piperidin-4-yl-amine dihydrobromide (intermediate F) and 4-chloro-3-ethoxy-benzaldehyde (intermediate 6) | 422.2 |
| 88 | 401.89 | 4-[4-(6-chloro-benzooxazol-2-ylamino)-piperidin-1-ylmethyl]-2-ethoxy-phenol | (6-chloro-benzooxazol-2-yl)-piperidin-4-yl-amine dihydrobromide (intermediate F) and 3-ethoxy-4-hydroxy-benzaldehyde (commercially available) | 402.2 |
| 89 | 429.95 | (6-chloro-benzooxazol-2-yl)-[1-(4-methoxy-3-propoxy-benzyl)-piperidin-4-yl]-amine | (6-chloro-benzooxazol-2-yl)-piperidin-4-yl-amine dihydrobromide (intermediate F) and 4-ethoxy-3-propoxy-benzaldehyde (intermediate 2) | 430.3 |
| 90 | 433.91 | (6-chloro-benzooxazol-2-yl)-{1-[3-(2-fluoro-ethoxy)-4-methoxy-benzyl]-piperidin-4-yl}-amine | (6-chloro-benzooxazol-2-yl)-piperidin-4-yl-amine dihydrobromide (intermediate F) and 3-(2-fluoro-ethoxy)-4-methoxy-benzaldehyde (intermediate 3) | 434.2 |
| 91 | 443.97 | (6-chloro-benzooxazol-2-yl)-[1-(3-isobutoxy-4-methoxy-benzyl)-piperidin-4-yl]-amine | (6-chloro-benzooxazol-2-yl)-piperidin-4-yl-amine dihydrobromide (intermediate F) and 3-isobutoxy-4-methoxy-benzaldehyde (intermediate 8) | 444.3 |
| 92 | 429.95 | (6-chloro-benzooxazol-2-yl)-[1-(3,5-diethoxy-benzyl)-piperidin-4-yl]-amine | (6-chloro-benzooxazol-2-yl)-piperidin-4-yl-amine dihydrobromide (intermediate F) and 3,5-diethoxy-benzaldehyde (intermediate 30) | 432.2 |
| 93 | 447.94 | (6-chloro-benzooxazol-2-yl)-[1-(3,5-diethoxy-4-fluoro-benzyl)-piperidin-4-yl]-amine | (6-chloro-benzooxazol-2-yl)-piperidin-4-yl-amine dihydrobromide (intermediate F) and 3,5-diethoxy-4-fluoro-benzaldehyde (intermediate 21) | 448.30 |
| 94 | 495.02 | (6-chloro-benzooxazol-2-yl)-[1-(3,5-diethoxy-4-pyrrol-1-yl-benzyl)-piperidin-4-yl]-amine | (6-chloro-benzooxazol-2-yl)-piperidin-4-yl-amine dihydrobromide (intermediate F) and 3,5-diethoxy-4-pyrrol-1-yl-benzaldehyde (intermediate 4) | 497.3 |

Example 95

2-[1-(3-Ethoxy-4-methyl-benzyl)-piperidin-4-ylamino]-benzooxazole-5-sulfonic acid amide Step 1:

2-Mercapto-benzooxazole-5-sulfonic acid amide

To a solution of 3-amino-4-hydroxy-benzenesulfonamide (5.00 g, 26.6 mmol, 1.0 equiv) in anhydrous THF (250 mL) was added slowly thiophosgene (3.67 g, 2.43 mL, 31.9 mmol, 1.2 equiv) via syringe pump over a time period of 1 h. After stirring for 4 h at rt, excess thiophosgene was quenched by addition of a conc. solution of ammonium chloride (100 mL) and the majority of solvent removed by evaporation under reduced pressure. The residue was extracted with ethyl acetate (3×100 mL) and the combined organic phases dried over $MgSO_4$ yielding 6.1 g (92%) of crude product, which was used in the subsequent reaction step without further purification. $^1$H NMR (300 MHz, DMSO): δ 7.51 (br s, 2H), 7.68 (s, 1H), 7.70 (d, J=7.7 Hz, 1H), 7.78 (d, J=7.7 Hz, 1H), 14.21 (br s, 1H). $^{13}$C NMR (75 MHz, DMSO): δ 106.29, 108.47, 120.06, 129.91, 139.54, 148.16, 179.38. MS (ISP): 230.9 $[M+H]^+$.

Step 2:

2-Methylsulfanyl-benzooxazole-5-sulfonic acid amide

To a solution of 2-mercapto-benzooxazole-5-sulfonic acid amide (17.0 g, 73.8 mmol, 1.0 equiv) in anhydrous DMF (200 mL) was added anhydrous $K_2CO_3$ (51.0 g, 369.1 mmol, 5.0 equiv) and methyl iodide (16.1 mL, 36.7 g, 258.4 mmol, 3.5 equiv). After stirring for 3 h at rt, the $K_2CO_3$ was removed by filtration and the reaction mixture concentrated by evaporation under reduced pressure. The residue was washed with ethyl acetate (50 mL) give 17.4 g (97%) of the title compound. $^1$H NMR (300 MHz, DMSO): δ 2.80 (s, 3H), 7.47 (br s, 2H), 7.83 (s, 2H), 8.07 (s, 1H). $^{13}$C NMR (75 MHz, DMSO): δ 4.28, 110.47, 115.71, 122.04, 140.99, 141.37, 152.92, 167.84. MS (ISP): 244.9 $[M+H]^+$.

Step 3:

4-(5-Sulfamoyl-benzooxazol-2-ylamino)-piperidine-1-carboxylic acid ethyl ester A mixture of 2-methylsulfanyl-benzooxazole-5-sulfonic acid amide (5.00 g, 20.5 mmol, 1.0 equiv) and ethyl 4-amino-1-piperidine carboxylate (3.53 g, 20.5 mmol, 1.0 equiv) in anhydrous acetonitrile (25 mL) was heated to 190° C. under microwave irradiation for 1 h. The crude reaction mixture was concentrated by evaporation under reduced pressure, the organic phase filtered over silica with ethyl acetate and purified by preparative HPLC on reversed phase eluting with a gradient of acetonitrile/water to afford 1.72 g (23%) of the title compound. $^1$H NMR (300 MHz, DMSO): δ 1.19 (t, J=7.1 Hz, 3H), 1.37-1.49 (m, 2H), 1.94-1.99 (m, 2H), 2.94-3.02 (m, 2H), 3.80-3.83 (m, 1H), 3.91-3.95 (m, 2H), 4.04 (q, J=7.1 Hz, 2H), 7.26 (br s, 2H), 7.49 (d, J=0.9 Hz, 2H), 7.63 (d, J=0.8 Hz, 1H), 8.28 (d, J=7.6 Hz, 1H). $^{13}$C NMR (75 MHz, DMSO): δ 14.56, 31.10, 42.05, 49.60, 60.65, 108.39, 112.71, 118.35, 140.08, 143.52, 149.76, 154.59, 162.67. MS (ISP): 368.9 $[M+H]^+$.

Step 4:

2-(Piperidin-4-ylamino)-benzooxazole-5-sulfonic acid amide dihydrobromide (Intermediate G)

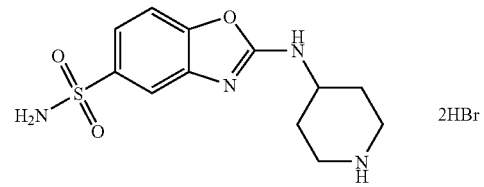

According to the procedure described for the synthesis of intermediate C/step 2 (piperidin-4-yl-thiazolo[5,4-b]pyridin-2-yl-amine dihydrobromide) the title compound was synthesized from 4-(5-sulfamoyl-benzooxazol-2-ylamino)-piperidine-1-carboxylic acid ethyl ester using identical conditions. The product was used in the consecutive step without further purification assuming quantitative deprotection and formation of the dihydrobromide salt. MS (ISP): 297.0 $[M+H]^+$.

Step 5:

According to the procedure described for the synthesis of example 1/step 3 (benzothiazol-2-yl-[1-(2-ethoxy-naphthalen-1-ylmethyl)-piperidin-4-yl]-amine) the title compound was synthesized from 2-(piperidin-4-ylamino)-benzooxazole-5-sulfonic acid amide dihydrobromide and 3-ethoxy-4-methyl-benzaldehyde using identical conditions. Isolated yield after purification by preparative HPLC: 3.1 mg (7%). MS (ISP): 443.6 $[M+H]^+$.

Synthesis of Benzooxazole and Oxazolopyridine Intermediates H to N to be Used in Table 3

Intermediate H

2-(Piperidin-4-ylamino)-benzooxazole-5-sulfonic acid dimethylamide dihydrobromide

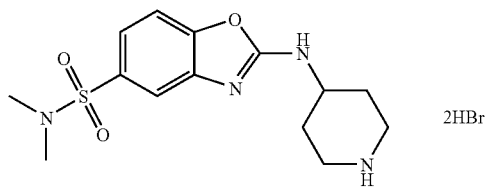

Step 1:

2-Methylsulfanyl-benzooxazole-5-sulfonic acid dimethylamide

To a solution of 2-methylsulfanyl-benzooxazole-5-sulfonic acid amide (0.43 g, 1.76 mmol, 1.0 equiv) in anhydrous DMF (20 mL) was added slowly sodium hydride (0.23 g, 5.28 mmol, 3.0 equiv; 55% free-flowing powder moistened with oil). After hydrogen evolution ceased, methyl iodide (0.27 mL, 0.63 g, 4.40 mmol, 2.5 equiv) was added and the reaction mixture stirred at rt over night. The solution was concentrated by evaporation under reduced pressure and the crude reaction product purified with column chromatography on silica eluting with hexane/ethyl acetate (1:1) to give 0.38 g (80%) of the title compound. ¹H NMR (300 MHz, DMSO): δ 2.62 (s, 6H), 2.81 (s, 3H), 7.71 (dd, J=8.5 Hz, J=1.7 Hz, 1H), 7.91 (d, J=8.5 Hz, 1H), 7.99 (d, J=1.7 Hz, 1H). ¹³C NMR (75 MHz, DMSO): δ 14.33, 37.58, 110.94, 117.54, 123.86, 131.51, 141.82, 153.77, 168.21. MS (ISP): 272.8 [M+H]⁺.

Step 2:

4-(5-Dimethylsulfamoyl-benzooxazol-2-ylamino)-piperidine-1-carboxylic acid ethyl ester A mixture of 2-methylsulfanyl-benzooxazole-5-sulfonic acid dimethylamide (1.43 g, 5.25 mmol, 1.0 equiv) and ethyl 4-amino-1-piperidine carboxylate (1.36 g, 7.88 mmol, 1.5 equiv) in anhydrous DMAc (7.5 mL) was heated to 100° C. for 48 h. The solution was concentrated by evaporation under reduced pressure and the crude reaction product purified with column chromatography on silica eluting with ethyl acetate/hexane (2:1) to give 1.40 g (67%) of the title compound. ¹H NMR (300 MHz, DMSO): δ 1.19 (t, J=7.1 Hz, 3H), 1.37-1.49 (m, 2H), 1.94-1.99 (m, 2H), 2.59 (s, 6H), 2.94-3.02 (m, 2H), 3.80-3.83 (m, 1H), 3.91-3.95 (m, 2H), 4.04 (q, J=7.1 Hz, 2H), 7.39 (dd, J=8.2 Hz, J=1.8 Hz, 1H), 7.53 (d, J=1.8 Hz, 1H), 7.59 (d, J=8.2 Hz, 1H), 8.39 (d, J=7.6 Hz, 1H). ¹³C NMR (75 MHz, DMSO): δ 14.56, 31.07, 37.62, 42.05, 49.70, 60.65, 108.88, 114.22, 120.40, 130.37, 143.98, 150.67, 154.59, 162.76. MS (ISP): 397.0 [M+H]⁺.

Step 3:

According to the procedure described for the synthesis of intermediate C/step 2 (piperidin-4-yl-thiazolo[5,4-b]pyridin-2-yl-amine dihydrobromide) the title compound was synthesized from 4-(5-dimethylsulfamoyl-benzooxazol-2-ylamino)-piperidine-1-carboxylic acid ethyl ester using identical conditions. The product was used in the consecutive step without further purification assuming quantitative deprotection and formation of the dihydrobromide salt. MS (ESI): 325.4 [M+H]⁺.

Intermediate I

5-Chloro-2-(piperidin-4-ylamino)-benzooxazole-6-sulfonic acid amide dihydrobromide

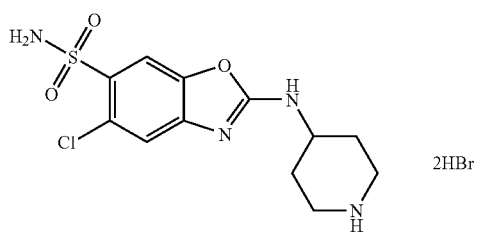

2HBr

Step 1:

5-Chloro-2-mercapto-benzooxazole-6-sulfonic acid amide

According to the procedure described for the synthesis of example 95/step 1 (2-mercapto-benzooxazole-5-sulfonic acid amide) the title compound was synthesized from 4-amino-2-chloro-5-hydroxy-benzenesulfonamide using identical conditions in 99% yield. ¹H NMR (300 MHz, DMSO): δ 7.48 (br s, 1H), 7.69 (br s, 2H), 8.02 (br s, 1H), 13.7 (br s, 1H). MS (ISP): 264.7 [M+H]⁺.

Step 2:

5-Chloro-2-methylsulfanyl-benzooxazole-6-sulfonic acid amide

According to the procedure described for the synthesis of example 95/step 2 (2-mercapto-benzooxazole-5-sulfonic acid amide) the title compound was synthesized from 5-chloro-2-mercapto-benzooxazole-6-sulfonic acid amide using identical conditions in 82% yield. ¹H NMR (300 MHz, DMSO): δ 2.80 (s, 3H), 7.67 (br s, 2H), 7.96 (s, 1H), 8.21 (s, 1H). ¹³C NMR (75 MHz, DMSO): δ 12.84, 109.20, 118.87, 125.13, 135.17, 143.17, 147.72, 168.83. MS (ISP): 278.8 [M+H]⁺.

Step 3:

4-(5-Chloro-6-sulfamoyl-benzooxazol-2-ylamino)-piperidine-1-carboxylic acid ethyl ester According to the procedure described for the synthesis of intermediate H/step 2 (4-(5-dimethylsulfamoyl-benzooxazol-2-ylamino)-piperidine-1-carboxylic acid ethyl ester) the title compound was synthesized from 5-chloro-2-methylsulfanyl-benzooxazole-6-sulfonic acid amide using identical conditions. Purification of the crude reaction mixture with column chromatography on silica eluting with dichloromethane/methanol (4:1) afforded the title compound in 46% yield. ¹H NMR (300 MHz, CDCl₃): δ 1.19 (t, J=7.1 Hz, 3H), 1.37-1.49 (m, 2H), 1.94-1.99 (m, 2H), 2.94-3.02 (m, 2H), 3.80-3.83 (m, 1H), 3.91-3.95 (m, 2H), 4.04 (q, J=7.1 Hz, 2H), 7.46 (br s, 3H), 7.88 (s, 1H), 8.61 (d, J=7.4 Hz, 1H). ¹³C NMR (75 MHz, DMSO): δ 13.45, 29.91, 40.92, 48.71, 59.55, 107.81, 116.01, 125.06, 131.47, 144.66, 146.47, 153.48, 162.94. MS (ISP): 405.1 [M+H]⁺.

Step 4:

According to the procedure described for the synthesis of intermediate C/step 2 (piperidin-4-yl-thiazolo[5,4-b]pyridin-2-yl-amine dihydrobromide) the title compound was synthesized from 4-(5-chloro-6-sulfamoyl-benzooxazol-2-ylamino)-piperidine-1-carboxylic acid ethyl ester using identical conditions. The product was used in the consecutive step without further purification assuming quantitative deprotection and formation of the dihydrobromide salt. MS (ISP): 331.0 [M+H]⁺.

Intermediate I (5-Ethanesulfonyl-benzooxazol-2-yl)-piperidin-4-yl-amine dihydrobromide

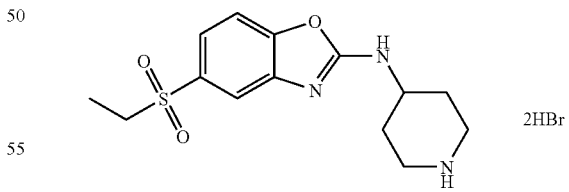

2HBr

Step 1:

5-Ethanesulfonyl-benzooxazole-2-thiol

To a solution of 1-amino-5-ethylsulfonyl-2-hydroxybenzene (20.13 g, 100.0 mmol, 1.0 equiv) in ethanol (200 mL) were added carbon disulfide (190.0 g, 150 mL, 2494 mmol, 25.0 equiv) and potassium hydroxide (6.73 g, 120 mmol, 1.2 equiv) and the reaction mixture heated to reflux over night. The solvent was evaporated, the residue treated with 1 M hydrochloric acid, extracted with ethyl acetate (3×150 mL) and the combined organic fractions dried over MgSO₄. Evaporation of the organic solvent gave the crude product which was recrystallized from ethyl acetate to yield the title compound as yellowish solid. MS (ISN): 242.4 [M–H]⁻.

Step 2:

5-Chloro-2-methylsulfanyl-benzooxazole-6-sulfonic acid amide

According to the procedure described for the synthesis of example 95/step 2 (2-mercapto-benzooxazole-5-sulfonic acid amide) the title compound was synthesized from 5-ethanesulfonyl-benzooxazole-2-thiol using identical conditions in 95% yield. $^1$H NMR (300 MHz, CDCl₃): δ 1.28 (t, J=7.4 Hz, 3H), 2.80 (s, 3H), 3.15 (q, J=7.4 Hz, 2H), 7.59 (d, J=8.5 Hz, 1H), 7.83 (dd, J=8.5 Hz, J=1.8 Hz, 1H), 8.15 (d, J=1.8 Hz, 1H). $^{13}$C NMR (75 MHz, CDCl₃): δ 5.24, 12.33, 48.72, 108.16, 116.80, 121.93, 132.83, 140.36, 152.69, 166.71. MS (ISP): 257.9 [M+H]⁺.

Step 3:

4-(5-Ethanesulfonyl-benzooxazol-2-ylamino)-piperidine-1-carboxylic acid ethyl ester According to the procedure described for the synthesis of intermediate H/step 2 (4-(5-dimethylsulfamoyl-benzooxazol-2-ylamino)-piperidine-1-carboxylic acid ethyl ester) the title compound was synthesized from 5-chloro-2-methylsulfanyl-benzooxazole-6-sulfonic acid amide using identical conditions. Purification of the crude reaction mixture with column chromatography on silica eluting with ethyl acetate/hexane (2:1→10:1) afforded the title compound in 93% yield. $^1$H NMR (300 MHz, DMSO): δ 1.09 (t, J1=7.4 Hz, 3H), 1.19 (t, J=7.1 Hz, 3H), 1.41-1.45 (m, 2H), 1.94-2.00 (m, 2H), 2.98-3.06 (m, 2H), 3.27 (q, J=7.4 Hz, 2H), 3.88-3.98 (m, 3H), 4.04 (q, J=7.1 Hz, 2H), 7.52 (dd, J=8.3 Hz, J=1.8 Hz, 1H), 7.61 (d, J=8.3 Hz, 1H), 7.67 (d, J=1.8 Hz, 1H). $^{13}$C NMR (75 MHz, DMSO): δ 6.98, 14.31, 30.36, 41.79, 49.30, 49.44, 60.41, 108.72, 114.25, 120.42, 133.88, 143.81, 150.90, 154.35, 162.61. MS (ISP): 382.1 [M+H]⁺.

Step 4:

According to the procedure described for the synthesis of intermediate C/step 2 (piperidin-4-yl-thiazolo[5,4-b]pyridin-2-yl-amine dihydrobromide) the title compound was synthesized from 4-(5-ethanesulfonyl-benzooxazol-2-ylamino)-piperidine-1-carboxylic acid ethyl ester using identical conditions. The product was used in the consecutive step without further purification assuming quantitative deprotection and formation of the dihydrobromide salt. MS (ISP): 382.1 [M+H]⁺.

Intermediate K

Piperidin-4-yl-(5-trifluoromethoxy-benzooxazol-2-yl)-amine dihydrobromide

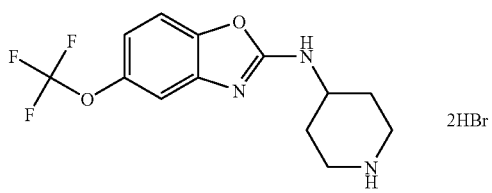

Step 1:

5-Trifluoromethoxy-benzooxazole-2-thiol

According to the procedure described for the synthesis of example 95/step 1 (2-mercapto-benzooxazole-5-sulfonic acid amide) the title compound was synthesized from 2-amino-4-trifluoromethoxy-phenol using identical conditions in 58% yield. $^1$H NMR (300 MHz, DMSO): δ 7.27 (br d, J=7.6 Hz, 2H), 7.64 (dd, J=8.5 Hz, J=1.7 Hz, 1H), 14.2 (br s, 1H). $^{13}$C NMR (75 MHz, DMSO): δ 104.40, 111.19, 116.92, 120.37 (q, J=254.3 Hz), 132.65, 145.55, 147.03, 181.59. $^{19}$F NMR (282 MHz, DMSO): □ –57.50. MS (ISN): 234.1 [M–H]⁻.

Step 2:

2-Methylsulfanyl-5-trifluoromethoxy-benzooxazole

According to the procedure described for the synthesis of example 95/step 2 (2-mercapto-benzooxazole-5-sulfonic acid amide) the title compound was synthesized from 5-trifluoromethoxy-benzooxazole-2-thiol using identical conditions in 69% yield. $^1$H NMR (300 MHz, DMSO): δ 2.78 (s, 3H), 7.33 (br dd, J=8.8 Hz, J=1.5 Hz, 1H), 7.71 (br d, J=1.3 Hz, 1H), 7.77 (d, J=8.8 Hz, 1H). $^{13}$C NMR (75 MHz, DMSO): δ 14.22, 110.97, 111.36, 117.32, 120.12 (q, J=254.3 Hz), 142.28, 145.10, 149.97, 167.93. $^{19}$F NMR (282 MHz, DMSO): δ –57.23. MS (ISP): 249.9 [M+H]⁺.

Step 3:

4-(5-Trifluoromethoxy-benzooxazol-2-ylamino)-piperidine-1-carboxylic acid ethyl ester According to the procedure described for the synthesis of example 95/step 3 (4-(5-sulfamoyl-benzooxazol-2-ylamino)-piperidine-1-carboxylic acid ethyl ester) the title compound was synthesized from 2-methylsulfanyl-5-trifluoromethoxy-benzooxazole under microwave irradiation at 220° C. in DMAc for 30 min. Purification of the crude reaction mixture with column chromatography on silica eluting with ethyl acetate/hexane (1:1) afforded the title compound in 26% yield. $^1$H NMR (300 MHz, DMSO): δ 1.19 (t, J=7.1 Hz, 3H), 1.36-1.48 (m, 2H), 1.93-1.97 (m, 2H), 2.92-3.03 (m, 2H), 3.75-3.84 (m, 1H), 3.92-3.95 (m, 2H), 4.04 (q, J=7.1 Hz, 2H), 6.95 (br d, J=8.6 Hz, 1H), 7.24 (br s, 1H), 7.43 (d, J=8.6 Hz, 1H), 8.25 (d, J=7.6 Hz, 1H). $^{13}$C NMR (75 MHz, DMSO): δ 14.55, 31.08, 42.07, 49.63, 60.64, 108.58, 108.91, 112.82, 117.78 (q, J=254.3 Hz), 144.53, 144.80, 146.54, 154.59, 162.95. $^{19}$F NMR (282 MHz, DMSO): δ –57.05. MS (ISP): 374.0 [M+H]⁺.

Step 4:

According to the procedure described for the synthesis of intermediate C/step 2 (piperidin-4-yl-thiazolo[5,4-b]pyridin-2-yl-amine dihydrobromide) the title compound was synthesized from 4-(5-trifluoromethoxy-benzooxazol-2-ylamino)-piperidine-1-carboxylic acid ethyl ester using identical conditions. The product was used in the consecutive step without further purification assuming quantitative deprotection and formation of the dihydrobromide salt. MS (ESI): 302.2 [M+H]⁺.

Intermediate L (5-Nitro-benzooxazol-2-yl)-piperidin-4-yl-amine dihydrobromide

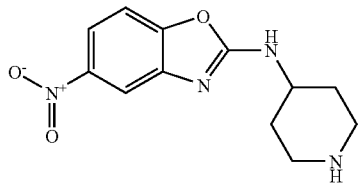

Step 1:

5-Nitro-benzooxazole-2-thiol

According to the procedure described for the synthesis of example 95/step 1 (2-mercapto-benzooxazole-5-sulfonic acid amide) the title compound was synthesized from 2-amino-4-nitro-phenol using identical conditions in 90% yield. $^1$H NMR (300 MHz, DMSO): δ 7.73 (d, J=8.6 Hz, 1H), 7.98 (d, J=2.3 Hz, 1H), 8.18 (dd, J=8.6 Hz, J=2.3 Hz, 1H), 13.8 (br s, 1H). $^{13}$C NMR (75 MHz, DMSO): δ 105.93, 110.23, 119.94, 132.62, 144.62, 152.05, 180.97. MS (ISN): 195.1 [M−H]$^-$.

Step 2:

2-Methylsulfanyl-5-nitro-benzooxazole

According to the procedure described for the synthesis of example 95/step 2 (2-mercapto-benzooxazole-5-sulfonic acid amide) the title compound was synthesized from 5-nitro-benzooxazole-2-thiol using identical conditions in 82% yield. $^1$H NMR (300 MHz, DMSO): δ 2.81 (s, 3H), 7.90 (d, J=8.9 Hz, 1H), 8.25 (dd, J=8.9 Hz, J=2.3 Hz, 1H), 8.48 (d, J=2.3 Hz, 1H). $^{13}$C NMR (75 MHz, DMSO): δ 13.35, 109.77, 112.73, 119.22, 140.84, 143.88, 154.03, 168.32. MS (ISP): 210.8 [M+H]$^+$.

Step 3:

4-(5-Nitro-benzooxazol-2-ylamino)-piperidine-1-carboxylic acid ethyl ester

According to the procedure described for the synthesis of intermediate H/step 2 (4-(5-dimethylsulfamoyl-benzooxazol-2-ylamino)-piperidine-1-carboxylic acid ethyl ester) the title compound was synthesized from 2-methylsulfanyl-5-nitro-benzooxazole using identical conditions. Purification of the crude reaction mixture with column chromatography on silica eluting with ethyl acetate/hexane (1:1→2:1) afforded the title compound in 86% yield. $^1$H NMR (300 MHz, DMSO): δ 1.19 (t, J=7.1 Hz, 3H), 1.37-1.49 (m, 2H), 1.95-2.00 (m, 2H), 2.97-3.05 (m, 2H), 3.77-3.85 (m, 1H), 3.91-3.96 (m, 2H), 4.04 (q, J=7.1 Hz, 2H), 7.59 (d, J=8.7 Hz, 1H), 7.96 (dd, J=8.7 Hz, J=2.3 Hz, 1H), 8.03 (d, J=2.3 Hz, 1H), 8.52 (d, J=7.6 Hz, 1H). $^{13}$C NMR (75 MHz, DMSO): δ 14.55, 31.02, 42.03, 49.76, 60.66, 108.70, 110.15, 116.82, 144.20, 144.47, 152.24, 154.59, 163.33. MS (ISP): 335.1 [M+H]$^+$.

Step 4:

According to the procedure described for the synthesis of intermediate C/step 2 (piperidin-4-yl-thiazolo[5,4-b]pyridin-2-yl-amine dihydrobromide) the title compound was synthesized from 4-(5-nitro-benzooxazol-2-ylamino)-piperidine-1-carboxylic acid ethyl ester using identical conditions. The product was used in the consecutive step without further purification assuming quantitative deprotection and formation of the dihydrobromide salt. MS (ISP): 263.0 [M+H]$^+$.

Intermediate M

N$^2$-Piperidin-4-yl-benzooxazole-2,5-diamine dihydrobromide

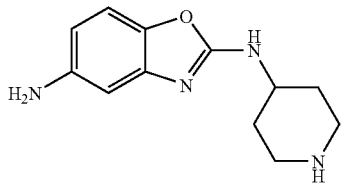

Step 1:

4-(5-Amino-benzooxazol-2-ylamino)-piperidine-1-carboxylic acid ethyl ester

To a solution of 4-(5-nitro-benzooxazol-2-ylamino)-piperidine-1-carboxylic acid ethyl ester (2.0 g, 5.98 mmol, 1.0 equiv; intermediate L/step 3 (4-(5-nitro-benzooxazol-2-ylamino)-piperidine-1-carboxylic acid ethyl ester)) in ethanol (90 mL) was added palladium on activated charcoal 10% (0.2 g, 0.19 mmol, 0.03 equiv) and the reaction vessel filled with hydrogen (3.5 bar). After stirring at 40° C. for 18 h, the reaction mixture was filtered over celite, concentrated under reduced pressure and the residue purified with column chromatography on silica eluting with ethyl acetate/hexane (2:1) containing 5% methanol to yield 1.8 g (99%) of the title compound. $^1$H NMR (300 MHz, CDCl$_3$): δ 1.25 (t, J=7.1 Hz, 3H), 1.44-1.54 (m, 2H), 2.07-2.10 (m, 2H), 2.92-3.01 (m, 2H), 3.72 (br s, 1H), 3.88 (br s, 1H), 4.10 (br s, 1H), 4.14 (q, J=7.1 Hz, 2H), 6.33 (dd, J=8.4 Hz, J=2.2 Hz, 1H), 6.61 (br d, J=4.6 Hz, 1H), 6.67 (d, J=2.2 Hz, 1H), 6.97 (d, J=8.4 Hz, 1H). $^{13}$C NMR (75 MHz, CDCl$_3$): δ 14.61, 32.13, 42.29, 50.18, 61.37, 102.92, 107.98, 108.53, 142.04, 143.49, 143.80, 155.46, 162.14. MS (ISP): 305.4 [M+H]$^+$.

Step 2:

According to the procedure described for the synthesis of intermediate C/step 2 (piperidin-4-yl-thiazolo[5,4-b]pyridin-2-yl-amine dihydrobromide) the title compound was synthesized from 4-(5-amino-benzooxazol-2-ylamino)-piperidine-1-carboxylic acid ethyl ester using identical conditions. The product was used in the consecutive step without further purification assuming quantitative deprotection and formation of the dihydrobromide salt. MS (ESI): 233.2 [M+H]$^+$.

Intermediate N

Oxazolo[4,5-b]pyridin-2-yl-piperidin-4-yl-amine dihydrobromide

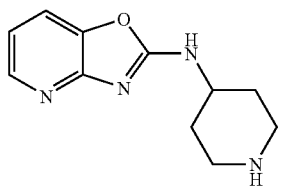

Step 1:

Oxazolo[4,5-b]pyridine-2-thiol

According to the procedure described for the synthesis of example 95/step 1 (2-mercapto-benzooxazole-5-sulfonic acid amide) the title compound was synthesized from 2-amino-pyridin-3-ol using identical conditions in 30% yield. ¹H NMR (300 MHz, DMSO): δ 7.28 (dd, J=8.1 Hz, J=5.2 Hz, 1H), 7.88 (dd, J=8.1 Hz, J=1.3 Hz, 1H), 8.24 (dd, J=5.2 Hz, J=1.3 Hz, 1H), 14.5 (br s, 1H). ¹³C NMR (75 MHz, DMSO): δ 117.00, 119.09, 141.62, 144.16, 147.01, 181.40. MS (ESI): 167.1 [M+H]⁺.

Step 2:

2-Methylsulfanyl-oxazolo[4,5-b]pyridine

According to the procedure described for the synthesis of example 95/step 2 (2-mercapto-benzooxazole-5-sulfonic acid amide) the title compound was synthesized from oxazolo[4,5-b]pyridine-2-thiol using identical conditions in 79% yield. ¹H NMR (300 MHz, DMSO): δ 2.81 (s, 3H), 7.35 (dd, J=8.1 Hz, J=5.0 Hz, 1H), 8.08 (dd, J=8.1 Hz, J=1.4 Hz, 1H), 8.43 (dd, J=5.0 Hz, J=1.4 Hz, 1H). ¹³CNMR (75 MHz, DMSO): δ 11.99, 115.60, 117.12, 141.22, 143.40, 152.78, 166.75. MS (ISP): 167.1 [M+H]⁺.

Step 3:

4-(Oxazolo[4,5-b]pyridin-2-ylamino)-piperidine-1-carboxylic acid ethyl ester According to the procedure described for the synthesis of intermediate H/step 2 (4-(5-dimethylsulfamoyl-benzooxazol-2-ylamino)-piperidine-1-carboxylic acid ethyl ester) the title compound was synthesized from 2-methylsulfanyl-oxazolo[4,5-b]pyridine using identical conditions. Purification of the crude reaction mixture with column chromatography on silica eluting with ethyl acetate/hexane (2:1) containing 5% methanol afforded the title compound in 24% yield. ¹H NMR (300 MHz, CDCl₃): δ 1.27 (t, J=7.1 Hz, 3H), 1.63-1.74 (m, 2H), 1.89-1.95 (m, 2H), 2.95-3.05 (m, 2H), 3.76-3.86 (m, 1H), 4.00 (br s, 2H), 4.14 (q, J=7.1 Hz, 2H), 6.92 (dd, J=7.8 Hz, J=5.2 Hz, 1H), 7.42 (dd, J=7.8 Hz, J=1.0 Hz, 1H), 7.88 (br s, 1H), 8.20 (dd, J=5.2 Hz, J=1.0 Hz, 1H). ¹³C NMR (75 MHz, CDCl₃): δ 14.55, 31.51, 42.48, 50.44, 61.25, 114.75, 115.53, 140.94, 143.72, 155.40, 157.97, 163.53. MS (ISP): 291.0 [M+H]⁺.

Step 4:

According to the procedure described for the synthesis of intermediate C/step 2 (piperidin-4-yl-thiazolo[5,4-b]pyridin-2-yl-amine dihydrobromide) the title compound was synthesized from 4-(oxazolo[4,5-b]pyridin-2-ylamino)-piperidine-1-carboxylic acid ethyl ester using identical conditions. The product was used in the consecutive step without further purification assuming quantitative deprotection and formation of the dihydrobromide salt. MS (ESI): 219.3 [M+H]⁺.

Examples 96 to 240

According to the procedure described for the synthesis of example 95/step 5 further benzooxazole derivatives have been synthesized from 2-(piperidin-4-ylamino)-benzooxazole-5-sulfonic acid amide dihydrobromide (intermediate G), 2-(piperidin-4-ylamino)-benzooxazole-5-sulfonic acid dimethylamide dihydrobromide (intermediate H), 5-chloro-2-(piperidin-4-ylamino)-benzooxazole-6-sulfonic acid amide dihydrobromide (intermediate I), (5-ethanesulfonyl-benzooxazol-2-yl)-piperidin-4-yl-amine dihydrobromide (intermediate J), piperidin-4-yl-(5-trifluoromethoxy-benzooxazol-2-yl)-amine dihydrobromide (intermediate K), (5-nitro-benzooxazol-2-yl)-piperidin-4-yl-amine dihydrobromide (intermediate L), N²-piperidin-4-yl-benzooxazole-2,5-diamine dihydrobromide (intermediate M) and oxazolo[4,5-b]pyridin-2-yl-piperidin-4-yl-amine dihydrobromide (intermediate N) and the respective benzaldehyde as indicated in Table 3. The results are compiled in Table 3 and comprise example 96 to example 240.

TABLE 3

| No | MW | Name | Starting materials | ISP [M + H]⁺ or [M − H]⁻ found |
|---|---|---|---|---|
| 96 | 464.97 | 2-[1-(4-chloro-3-ethoxy-bezyl)-piperidin-4-ylamino]-benzooxazole-5-sulfonic acid amide | 2-(piperidin-4-ylamino)-benzooxazole-5-sulfonic acid amide dihydrobromide (intermediate G) and 4-chloro-3-ethoxy-benzaldehyde (intermediate 6) | 463.5 |
| 97 | 448.52 | 2-[1-(3-ethoxy-4-fluoro-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3-ethoxy-4-fluoro-benzaldehyde (intermediate 10) | 449.5 |
| 98 | 498.52 | 2-[1-(3-ethoxy-4-trifluoromethyl-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3-ethoxy-4-trifluoromethyl-benzaldehyde (intermediate 11) | 497.5 |
| 99 | 446.53 | 2-[1-(3-ethoxy-4-hydroxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3-ethoxy-4-hydroxy-benzaldehyde (commercially available) | 445.5 |
| 100 | 462.52 | 2-[1-(3-ethoxy-4,5-dihydroxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3-ethoxy-4,5-dihydroxy-benzaldehyde (intermediate 31) | 463.5 |

TABLE 3-continued

| No | MW | Name | Starting materials | ISP [M + H]+ or [M − H]− found |
|---|---|---|---|---|
| 101 | 460.55 | 2-[1-(3-ethoxy-4-methoxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3-ethoxy-4-methoxy-benzaldehyde (commercially available) | 461.1 |
| 102 | 524.62 | methanesulfonic acid 2-ethoxy-4-[4-(5-sulfamoyl-benzooxazol-2-ylamino)-piperidin-1-ylmethyl]-phenyl ester | 2-(piperidin-4-ylamino)-benzooxazole-5-sulfonic acid amide dihydrobromide (intermediate G) and methanesulfonic acid 2-ethoxy-4-formyl-phenyl ester (intermediate 32) | 523.5 |
| 103 | 474.58 | 2-[1-(3,4-diethoxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3,4-diethoxy-benzaldehyde (commercially available) | 475.6 |
| 104 | 490.58 | 2-[1-(4,5-diethoxy-2-hydroxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 4,5-diethoxy-2-hydroxy-benzaldehyde (intermediate 33) | 491.6 |
| 105 | 488.61 | 2-[1-(3-ethoxy-4-isopropoxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3-ethoxy-4-isopropoxy-benzaldehyde (commercially available) | 489.6 |
| 106 | 504.61 | 2-{1-[3-(2-hydroxy-ethoxy)-4-isopropoxy-benzyl]-piperidin-4-ylamino}-benzooxazole-5-sulfonic acid amide | 2-(piperidin-4-ylamino)-benzooxazole-5-sulfonic acid amide dihydrobromide (intermediate G) and 3-(2-hydroxy-ethoxy)-4-isopropoxy-benzaldehyde (intermediate 9) | 505.6 |
| 107 | 516.66 | 2-{1-[3-ethoxy-4-(1-ethyl-propoxy)-benzyl]-piperidin-4-ylamino}-benzooxazole-5-sulfonic acid amide | 2-(piperidin-4-ylamino)-benzooxazole-5-sulfonic acid amide dihydrobromide (intermediate G) and 3-ethoxy-4-(1-ethyl-propoxy)-benzaldehyde (intermediate 13) | 515.7 |
| 108 | 514.64 | 2-{1-[3-ethoxy-4-(3-methyl-but-2-enyloxy)-benzyl]-piperidin-4-ylamino}-benzooxazole-5-sulfonic acid amide | 2-(piperidin-4-ylamino)-benzooxazole-5-sulfonic acid amide dihydrobromide (intermediate G) and 3-ethoxy-4-(3-methyl-but-2-enyloxy)-benzaldehyde (intermediate 14) | 515.6 |
| 109 | 502.63 | 2-[1-(3,4-diisopropoxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3,4-diisopropoxy-benzaldehyde (intermediate 34) | 503.6 |
| 110 | 474.58 | 2-[1-(4-methoxy-3-propoxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 4-ethoxy-3-propoxy-benzaldehyde (intermediate 2) | 475.6 |
| 111 | 478.54 | 2-{1-[3-(2-fluoro-ethoxy)-4-methoxy-benzyl]-piperidin-4-ylamino}-benzooxazole-5-sulfonic acid amide | 2-(piperidin-4-ylamino)-benzooxazole-5-sulfonic acid amide dihydrobromide (intermediate G) and 3-(2-fluoro-ethoxy)-4-methoxy-benzaldehyde (intermediate 3) | 479.5 |
| 112 | 514.52 | 2-{1-[4-methoxy-3-(2,2,2-trifluoro-ethoxy)-benzyl]-piperidin-4-ylamino}-benzooxazole- | 2-(piperidin-4-ylamino)-benzooxazole-5-sulfonic acid amide dihydrobromide (intermediate G) and 4- | 513.6 |

TABLE 3-continued

| No | MW | Name | Starting materials | ISP [M + H]+ or [M − H]− found |
|---|---|---|---|---|
| | | 5-sulfonic acid amide | methoxy-3-(2,2,2-trifluoro-ethoxy)-benzaldehyde (intermediate 35) | |
| 113 | 488.61 | 2-[1-(3-isobutoxy-4-methoxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3-isobutoxy-4-methoxy-benzaldehyde (intermediate 8) | 487.6 |
| 114 | 464.52 | 2-[1-(5-ethoxy-2-fluoro-4-hydroxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 5-ethoxy-2-fluoro-4-hydroxy-benzaldehyde (intermediate 7) | 463.6 |
| 115 | 506.64 | (±)-2-[1-(3-ethanesulfinyl-5-ethoxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and (±)-3-ethanesulfinyl-5-ethoxy-benzaldehyde (intermediate 36) | 507.5 |
| 116 | 464.52 | 2-[1-(3-ethanesulfonyl-5-ethoxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3-ethanesulfonyl-5-ethoxy-benzaldehyde (intermediate 37) | 523.5 |
| 117 | 474.58 | 2-[1-(3,5-diethoxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3,5-diethoxy-benzaldehyde (intermediate 30) | [M −H]− 473.6 |
| 118 | 502.64 | 2-[1-(3-ethoxy-5-isobutoxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3-ethoxy-5-isobutoxy-benzaldehyde (intermediate 38) | 503.6 |
| 119 | 492.57 | 2-[1-(3,5-diethoxy-2-fluoro-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3,5-diethoxy-2-fluoro-benzaldehyde (intermediate 39) | 493.6 |
| 120 | 509.02 | 2-[1-(2-chloro-3,5-diethoxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 2-chloro-3,5-diethoxy-benzaldehyde (intermediate 40) | 509.5 |
| 121 | 530.64 | 2-{1-[3-ethoxy-5-(tetrahydro-pyran-4-yloxy)-benzyl]-piperidin-4-ylamino}-benzooxazole-5-sulfonic acid amide | 2-(piperidin-4-ylamino)-benzooxazole-5-sulfonic acid amide dihydrobromide (intermediate G) and 3-ethoxy-5-(tetrahydro-pyran-4-yloxy)-benzaldehyde (intermediate 20) | 531.6 |
| 122 | 532.66 | 2-{1-[3-ethoxy-5-(3-hydroxy-2,2-dimethyl-propoxy)-benzyl]-piperidin-4-ylamino}-benzooxazole-5-sulfonic acid amide | 2-(piperidin-4-ylamino)-benzooxazole-5-sulfonic acid amide dihydrobromide (intermediate G) and 3-ethoxy-5-(3-hydroxy-2,2-dimethyl-propoxy)-benzaldehyde (intermediate 41) | 533.6 |
| 123 | 492.57 | 2-[1-(3,5-diethoxy-4-fluoro-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3,5-diethoxy-4-fluoro-benzaldehyde (intermediate 21) | 493.4 |
| 124 | 520.67 | 2-[1-(3,5-diethoxy-4-methylsulfanyl-benzyl)-piperidin-4-ylamino]-benzooxazole-5-sulfonic | 2-(piperidin-4-ylamino)-benzooxazole-5-sulfonic acid amide dihydrobromide (intermediate G) and 3,5- | 521.5 |

TABLE 3-continued

| No | MW | Name | Starting materials | ISP [M + H]+ or [M − H]− found |
|---|---|---|---|---|
| | | acid amide | diethoxy-4-methylsulfanyl-benzaldehyde (intermediate 42) | |
| 125 | 536.67 | (±)-2-[1-(3,5-diethoxy-4-methanesulfinyl-benzyl)-piperidin-4-ylamino]-benzooxazole-5-sulfonic acid amide | 2-(piperidin-4-ylamino)-benzooxazole-5-sulfonic acid amide dihydrobromide (intermediate G) and (±)-3,5-diethoxy-4-methanesulfinyl-benzaldehyde (intermediate 43) | [M −H]− 535.6 |
| 126 | 552.70 | 2-[1-(3,5-diethoxy-4-methanesulfonyl-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3,5-diethoxy-4-methanesulfonyl-benzaldehyde (intermediate 44) | 552.6 |
| 127 | 489.59 | 2-[1-(4-amino-3,5-diethoxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 4-amino-3,5-diethoxy-benzaldehyde (intermediate 23) | 488.6 |
| 128 | 531.64 | N-{2,6-diethoxy-4-[4-(5-sulfamoyl-benzooxazol-2-ylamino)-piperidin-1-ylmethyl]-phenyl}-acetamide | 2-(piperidin-4-ylamino)-benzooxazole-5-sulfonic acid amide dihydrobromide (intermediate G) and N-(2,6-diethoxy-4-formyl-phenyl)-acetamide (intermediate 24) | 532.5 |
| 129 | 539.65 | 2-[1-(3,5-diethoxy-4-pyrrol-1-yl-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3,5-diethoxy-4-pyrrol-1-yl-benzaldehyde (intermediate 4) | 540.6 |
| 130 | 512.63 | 2-[1-(8-ethoxy-2,2-dimethyl-2H-chromen-6-ylmethyl)-piperidin-4-ylamino]-benzooxazole-5-sulfonic acid amide | 2-(piperidin-4-ylamino)-benzooxazole-5-sulfonic acid amide dihydrobromide (intermediate G) and 8-ethoxy-2,2-dimethyl-2H-chromene-6-carbaldehyde (intermediate 18) | [M −H]− 511.6 |
| 131 | 487.53 | 2-[1-(4-ethoxy-2-oxo-2,3-dihydro-benzooxazol-6-ylmethyl)-piperidin-4-ylamino]-benzooxazole-5-sulfonic acid amide | 2-(piperidin-4-ylamino)-benzooxazole-5-sulfonic acid amide dihydrobromide (intermediate G) and 4-ethoxy-2-oxo-2,3-dihydro-benzooxazole-6-carbaldehyde(intermediate 45) | 488.5 |
| 132 | 522.02 | N-{2-chloro-3-ethoxy-5-[4-(5-sulfamoyl-benzooxazol-2-ylamino)-piperidin-1-ylmethyl]-phenyl}-acetamide | 2-(piperidin-4-ylamino)-benzooxazole-5-sulfonic acid amide dihydrobromide (intermediate G) and N-(2-chloro-3-ethoxy-5-formyl-phenyl)-acetamide (intermediate 46) | 522.6 |
| 133 | 613.47 | N-{3-ethoxy-2-iodo-5-[4-(5-sulfamoyl-benzooxazol-2-ylamino)-piperidin-1-ylmethyl]-phenyl}-acetamide | 2-(piperidin-4-ylamino)-benzooxazole-5-sulfonic acid amide dihydrobromide (intermediate G) and N-(3-ethoxy-5-formyl-2-iodo-phenyl)-acetamide (intermediate 26) | 612.5 |
| 134 | 616.50 | 2-[1-(3-ethoxy-4-iodo-5-methoxymethoxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3-ethoxy-4-iodo-5-methoxymethoxy-benzaldehyde (intermediate 47) | 617.5 |
| 135 | 598.14 | 2-{1-[4-chloro-3-(1,1-dioxo-1λ6-thiomorpholin-4-yl)-5-ethoxy-benzyl]-piperidin-4-ylamino}-benzooxazole-5-sulfonic acid amide | 2-(piperidin-4-ylamino)-benzooxazole-5-sulfonic acid amide dihydrobromide (intermediate G) and 4-chloro-3-(1,1-dioxo-1λ6-thiomorpholin-4-yl)-5-ethoxy-benzaldehyde (intermediate 48) | 598.5 |

TABLE 3-continued

| No | MW | Name | Starting materials | ISP [M + H]+ or [M − H]− found |
|---|---|---|---|---|
| 136 | 469.57 | 2-[1-(4-ethoxy-1H-indol-6-ylmethyl)-piperidin-4-ylamino]-benzooxazole-5-sulfonic acid amide | 2-(piperidin-4-ylamino)-benzooxazole-5-sulfonic acid amide dihydrobromide (intermediate G) and 4-ethoxy-1H-indole-6-carbaldehyde (intermediate 27) | 470.5 |
| 137 | 459.57 | 2-[1-(3-ethylamino-4-methoxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3-ethylamino-4-methoxy-benzaldehyde (intermediate 29) | 460.5 |
| 138 | 474.58 | 2-[1-(3,4-dimethoxy-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 3,4-dimethoxy-benzaldehyde (commercially available) | 473.5 |
| 139 | 472.61 | 2-[1-(3-ethoxy-4-methyl-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 3-ethoxy-4-methyl-benzaldehyde (intermediate 5) | 471.5 |
| 140 | 493.03 | 2-[1-(4-chloro-3-ethoxy-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 4-chloro-3-ethoxy-benzaldehyde (intermediate 6) | 491.5 |
| 141 | 476.57 | 2-[1-(3-ethoxy-4-fluoro-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 3-ethoxy-4-fluoro-benzaldehyde (intermediate 10) | 475.5 |
| 142 | 526.58 | 2-[1-(3-ethoxy-4-trifluoromethyl-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 3-ethoxy-4-trifluoromethyl-benzaldehyde (intermediate 11) | 525.4 |
| 143 | 474.58 | 2-[1-(3-ethoxy-4-hydroxy-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 3-ethoxy-4-hydroxy-benzaldehyde (commercially available) | 473.5 |
| 144 | 488.61 | 2-[1-(3-ethoxy-4-methoxy-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 3-ethoxy-4-methoxy-benzaldehyde (commercially available) | 489.5 |
| 145 | 552.67 | methanesulfonic acid 4-[4-(5-dimethylsulfamoyl-benzooxazol-2-ylamino)-piperidin-1-ylmethyl]-2-ethoxy-phenyl ester | 2-(piperidin-4-ylamino)-benzooxazole-5-sulfonic acid dimethylamide dihydrobromide (intermediate H) and methanesulfonic acid 2-ethoxy-4-formyl-phenyl ester (intermediate 32) | 553.5 |
| 146 | 516.66 | 2-[1-(3-ethoxy-4-isopropoxy-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 3-ethoxy-4-isopropoxy-benzaldehyde (commercially available) | 517.5 |

TABLE 3-continued

| No | MW | Name | Starting materials | ISP [M + H]+ or [M − H]− found |
|---|---|---|---|---|
| 147 | 502.63 | 2-[1-(4-methoxy-3-propoxy-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 4-ethoxy-3-propoxy-benzaldehyde (intermediate 2) | 501.5 |
| 148 | 506.60 | 2-{1-[3-(2-fluoro-ethoxy)-4-methoxy-benzyl]-piperidin-4-ylamino}-benzooxazole-5-sulfonic acid dimethylamide | 2-(piperidin-4-ylamino)-benzooxazole-5-sulfonic acid dimethylamide dihydrobromide (intermediate H) and 3-(2-fluoro-ethoxy)-4-methoxy-benzaldehyde (intermediate 3) | 507.4 |
| 149 | 542.58 | 2-{1-[4-methoxy-3-(2,2,2-trifluoro-ethoxy)-benzyl]-piperidin-4-ylamino}-benzooxazole-5-sulfonic acid dimethylamide | 2-(piperidin-4-ylamino)-benzooxazole-5-sulfonic acid dimethylamide dihydrobromide (intermediate H) and 4-methoxy-3-(2,2,2-trifluoro-ethoxy)-benzaldehyde (intermediate 35) | 541.5 |
| 150 | 516.66 | 2-[1-(3-isobutoxy-4-methoxy-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 3-isobutoxy-4-methoxy-benzaldehyde (intermediate 8) | 515.6 |
| 151 | 518.63 | 2-{1-[4-methoxy-3-(2-methoxy-ethoxy)-benzyl]-piperidin-4-ylamino}-benzooxazole-5-sulfonic acid dimethylamide | 2-(piperidin-4-ylamino)-benzooxazole-5-sulfonic acid dimethylamide dihydrobromide (intermediate H) and 4-methoxy-3-(2-methoxy-ethoxy)-benzaldehyde (intermediate 49) | 517.5 |
| 152 | 492.57 | 2-[1-(5-ethoxy-2-fluoro-4-hydroxy-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 5-ethoxy-2-fluoro-4-hydroxy-benzaldehyde (intermediate 7) | 491.4 |
| 153 | 504.61 | 2-[1-(2,4,5-trimethoxy-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 2,4,5-trimethoxy-benzaldehyde (commercially available) | 505.4 |
| 154 | 580.70 | 2-[1-(2-benzyloxy-4,5-dimethoxy-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 2-benzyloxy-4,5-dimethoxy-benzaldehyde (commercially available) | 581.5 |
| 155 | 502.63 | 2-[1-(3,5-diethoxy-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 3,5-diethoxy-benzaldehyde (intermediate 30) | 501.5 |
| 156 | 558.70 | 2-{1-[3-ethoxy-5-(tetrahydro-pyran-4-yloxy)-benzyl]-piperidin-4-ylamino}-benzooxazole-5-sulfonic acid dimethylamide | 2-(piperidin-4-ylamino)-benzooxazole-5-sulfonic acid dimethylamide dihydrobromide (intermediate H) and 3-ethoxy-5-(tetrahydro-pyran-4-yloxy)-benzaldehyde (intermediate 20) | 559.5 |
| 157 | 520.62 | 2-[1-(3,5-diethoxy-4-fluoro-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 3,5-diethoxy-4-fluoro-benzaldehyde (intermediate 21) | 519.6 |

TABLE 3-continued

| No | MW | Name | Starting materials | ISP [M + H]+ or [M – H]− found |
|---|---|---|---|---|
| 158 | 517.65 | 2-[1-(4-amino-3,5-diethoxy-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 4-amino-3,5-diethoxy-benzaldehyde (intermediate 23) | 518.6 |
| 159 | 559.68 | N-{4-[4-(5-dimethylsulfamoyl-benzooxazol-2-ylamino)-piperidin-1-ylmethyl]-2,6-diethoxy-phenyl}-acetamide | 2-(piperidin-4-ylamino)-benzooxazole-5-sulfonic acid dimethylamide dihydrobromide (intermediate H) and N-(2,6-diethoxy-4-formyl-phenyl)-acetamide (intermediate 24) | 560.6 |
| 160 | 567.71 | 2-[1-(3,5-diethoxy-4-pyrrol-1-yl-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 3,5-diethoxy-4-pyrrol-1-yl-benzaldehyde (intermediate 4) | 566.6 |
| 161 | 599.49 | 2-[1-(3-amino-5-ethoxy-4-iodo-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 3-amino-5-ethoxy-4-iodo-benzaldehyde (intermediate 25) | 600.3 |
| 162 | 641.52 | N-{5-[4-(5-dimethylsulfamoyl-benzooxazol-2-ylamino)-piperidin-1-ylmethyl]-3-ethoxy-2-iodo-phenyl}-acetamide | 2-(piperidin-4-ylamino)-benzooxazole-5-sulfonic acid dimethylamide dihydrobromide (intermediate H) and N-(3-ethoxy-5-formyl-2-iodo-phenyl)-acetamide (intermediate 26) | 642.4 |
| 163 | 519.38 | 2-[1-(3-ethoxy-4-hydroxy-5-nitro-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 3-ethoxy-4-hydroxy-5-nitro-benzaldehyde (intermediate 50) | 520.4 |
| 164 | 533.60 | 2-[1-(3-ethoxy-4-methoxy-5-nitro-benzyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 3-ethoxy-4-methoxy-5-nitro-benzaldehyde (intermediate 51) | 534.4 |
| 165 | 515.59 | 2-[1-(4-ethoxy-2-oxo-2,3-dihydro-benzooxazol-6-ylmethyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 4-ethoxy-2-oxo-2,3-dihydro-benzooxazole-6-carbaldehyde (intermediate 45) | 516.6 |
| 166 | 497.62 | 2-[1-(4-ethoxy-1H-indol-6-ylmethyl)-piperidin-4-ylamino]-benzooxazole-5-sulfonic acid dimethylamide | 2-(piperidin-4-ylamino)-benzooxazole-5-sulfonic acid dimethylamide dihydrobromide (intermediate H) and 4-ethoxy-1H-indole-6-carbaldehyde (intermediate 27) | 496.6 |
| 167 | 479.00 | 5-chloro-2-[1-(3-ethoxy-4-methyl-benzyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 3-ethoxy-4-methyl-benzaldehyde (intermediate 5) | 479.4 |
| 168 | 499.42 | 5-chloro-2-[1-(4-chloro-3-ethoxy-benzyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 4-chloro-3-ethoxy-benzaldehyde (intermediate 6) | 499.3 |

TABLE 3-continued

| No | MW | Name | Starting materials | ISP [M + H]+ or [M − H]− found |
|---|---|---|---|---|
| 169 | 482.96 | 5-chloro-2-[1-(3-ethoxy-4-fluoro-benzyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 3-ethoxy-4-fluoro-benzaldehyde (intermediate 10) | 481.4 |
| 170 | 532.97 | 5-chloro-2-[1-(3-ethoxy-4-trifluoromethyl-benzyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 3-ethoxy-4-trifluoromethyl-benzaldehyde (intermediate 11) | 533.3 |
| 171 | 480.97 | 5-chloro-2-[1-(3-ethoxy-4-hydroxy-benzyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 3-ethoxy-4-hydroxy-benzaldehyde (commercially available) | 479.4 |
| 172 | 495.00 | 5-chloro-2-[1-(3-ethoxy-4-methoxy-benzyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 3-ethoxy-4-methoxy-benzaldehyde (commercially available) | 493.4 |
| 173 | 559.06 | methanesulfonic acid 4-[4-(5-chloro-6-sulfamoyl-benzooxazol-2-ylamino)-piperidin-1-ylmethyl]-2-ethoxy-phenyl ester | 5-chloro-2-(piperidin-4-ylamino)-benzooxazole-6-sulfonic acid amide dihydrobromide (intermediate I) and methanesulfonic acid 2-ethoxy-4-formyl-phenyl ester (intermediate 32) | 559.5 |
| 174 | 523.05 | 5-chloro-2-[1-(3-ethoxy-4-isopropoxy-benzyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 3-ethoxy-4-isopropoxy-benzaldehyde (commercially available) | 523.4 |
| 175 | 507.01 | 2-[1-(3-allyloxy-4-methoxy-benzyl)-piperidin-4-ylamino]-5-chloro-benzooxazole-6-sulfonic acid amide | 5-chloro-2-(piperidin-4-ylamino)-benzooxazole-6-sulfonic acid amide dihydrobromide (intermediate I) and 3-allyloxy-4-methoxy-benzaldehyde (intermediate 15) | 507.4 |
| 176 | 509.02 | 5-chloro-2-[1-(4-methoxy-3-propoxy-benzyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 4-ethoxy-3-propoxy-benzaldehyde (intermediate 2) | 507.4 |
| 177 | 512.99 | 5-chloro-2-{1-[3-(2-fluoro-ethoxy)-4-methoxy-benzyl]-piperidin-4-ylamino}-benzooxazole-6-sulfonic acid amide | 5-chloro-2-(piperidin-4-ylamino)-benzooxazole-6-sulfonic acid amide dihydrobromide (intermediate I) and 3-(2-fluoro-ethoxy)-4-methoxy-benzaldehyde (intermediate 3) | 511.4 |
| 178 | 498.96 | 5-chloro-2-[1-(5-ethoxy-2-fluoro-4-hydroxy-benzyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 5-ethoxy-2-fluoro-4-hydroxy-benzaldehyde (intermediate 7) | 497.4 |
| 179 | 509.02 | 5-chloro-2-[1-(3,5-diethoxy-benzyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 3,5-diethoxy-benzaldehyde (intermediate 30) | 509.4 |

TABLE 3-continued

| No | MW | Name | Starting materials | ISP [M + H]+ or [M − H]− found |
|---|---|---|---|---|
| 180 | 527.01 | 5-chloro-2-[1-(3,5-diethoxy-2-fluoro-benzyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 3,5-diethoxy-2-fluoro-benzaldehyde (intermediate 39) | 527.4 |
| 181 | 543.47 | 5-chloro-2-[1-(2-chloro-3,5-diethoxy-benzyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 2-chloro-3,5-diethoxy-benzaldehyde (intermediate 40) | 541.4 |
| 182 | 527.01 | 5-chloro-2-[1-(3,5-diethoxy-4-fluoro-benzyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 3,5-diethoxy-4-fluoro-benzaldehyde (intermediate 21) | 527.4 |
| 183 | 566.08 | N-{4-[4-(5-chloro-6-sulfamoyl-benzooxazol-2-ylamino)-piperidin-1-ylmethyl]-2,6-diethoxy-phenyl}-acetamide | 5-chloro-2-(piperidin-4-ylamino)-benzooxazole-6-sulfonic acid amide dihydrobromide (intermediate I) and N-(2,6-diethoxy-4-formyl-phenyl)-acetamide (intermediate 24) | 564.5 |
| 184 | 574.10 | 5-chloro-2-[1-(3,5-diethoxy-4-pyrrol-1-yl-benzyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 3,5-diethoxy-4-pyrrol-1-yl-benzaldehyde (intermediate 4) | 572.4 |
| 185 | 605.88 | 2-[1-(3-amino-5-ethoxy-4-iodo-benzyl)-piperidin-4-ylamino]-5-chloro-benzooxazole-6-sulfonic acid amide | 5-chloro-2-(piperidin-4-ylamino)-benzooxazole-6-sulfonic acid amide dihydrobromide (intermediate I) and 3-amino-5-ethoxy-4-iodo-benzaldehyde (intermediate 25) | 606.3 |
| 186 | 647.92 | N-{5-[4-(5-chloro-6-sulfamoyl-benzooxazol-2-ylamino)-piperidin-1-ylmethyl]-3-ethoxy-2-iodo-phenyl}-acetamide | 5-chloro-2-(piperidin-4-ylamino)-benzooxazole-6-sulfonic acid amide dihydrobromide (intermediate I) and N-(3-ethoxy-5-formyl-2-iodo-phenyl)-acetamide (intermediate 26) | 646.4 |
| 187 | 521.98 | 5-chloro-2-[1-(4-ethoxy-2-oxo-2,3-dihydro-benzooxazol-6-ylmethyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 4-ethoxy-2-oxo-2,3-dihydro-benzooxazole-6-carbaldehyde (intermediate 45) | 520.6 |
| 188 | 494.01 | 5-chloro-2-[1-(3-ethylamino-4-methoxy-benzyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 3-ethylamino-4-methoxy-benzaldehyde (intermediate 29) | 492.4 |
| 189 | 489.98 | 5-chloro-2-[1-(5-methoxy-1H-indol-2-ylmethyl)-piperidin-4-ylamino]-benzooxazole-6-sulfonic acid amide | 5-chloro-2-(piperidin-4-ylamino)-benzooxazole-6-sulfonic acid amide dihydrobromide (intermediate I) and 4-ethoxy-1H-indole-6-carbaldehyde (intermediate 52) | 488.4 |
| 190 | 443.57 | (5-ethanesulfonyl-benzooxazol-2-yl)-[1-(3-ethoxy-benzyl)-piperidin-4-yl]-amine | (5-ethanesulfonyl-benzooxazol-2-yl)-piperidin-4-yl-amine dihydrobromide (intermediate J) and 3-ethoxy-benzaldehyde (commercially available) | 442.5 |

TABLE 3-continued

| No | MW | Name | Starting materials | ISP [M + H]+ or [M − H]− found |
|---|---|---|---|---|
| 191 | 457.59 | (5-ethanesulfonyl-benzooxazol-2-yl)-[1-(3-ethoxy-4-methyl-benzyl)-piperidin-4-yl]-amine | (5-ethanesulfonyl-benzooxazol-2-yl)-piperidin-4-yl-amine dihydrobromide (intermediate J) and 3-ethoxy-4-methyl-benzaldehyde (intermediate 5) | 458.2 |
| 192 | 478.01 | [1-(4-chloro-3-ethoxy-benzyl)-piperidin-4-yl]-(5-ethanesulfonyl-benzooxazol-2-yl)-amine | (5-ethanesulfonyl-benzooxazol-2-yl)-piperidin-4-yl-amine dihydrobromide (intermediate J) and 4-chloro-3-ethoxy-benzaldehyde (intermediate 6) | 478.2 |
| 193 | 461.56 | (5-ethanesulfonyl-benzooxazol-2-yl)-[1-(3-ethoxy-4-fluoro-benzyl)-piperidin-4-yl]-amine | (5-ethanesulfonyl-benzooxazol-2-yl)-piperidin-4-yl-amine dihydrobromide (intermediate J) and 3-ethoxy-4-fluoro-benzaldehyde (intermediate 10) | 462.2 |
| 194 | 511.56 | (5-ethanesulfonyl-benzooxazol-2-yl)-[1-(3-ethoxy-4-trifluoromethyl-benzyl)-piperidin-4-yl]-amine | (5-ethanesulfonyl-benzooxazol-2-yl)-piperidin-4-yl-amine dihydrobromide (intermediate J) and 3-ethoxy-4-trifluoromethyl-benzaldehyde (intermediate 11) | 512.4 |
| 195 | 459.56 | 4-[4-(5-ethanesulfonyl-benzooxazol-2-ylamino)-piperidin-1-ylmethyl]-2-ethoxy-phenol | (5-ethanesulfonyl-benzooxazol-2-yl)-piperidin-4-yl-amine dihydrobromide (intermediate J) and 3-ethoxy-4-hydroxy-benzaldehyde (commercially available) | 460.2 |
| 196 | 473.59 | (5-ethanesulfonyl-benzooxazol-2-yl)-[1-(3-ethoxy-4-methoxy-benzyl)-piperidin-4-yl]-amine | (5-ethanesulfonyl-benzooxazol-2-yl)-piperidin-4-yl-amine dihydrobromide (intermediate J) and 3-ethoxy-4-methoxy-benzaldehyde (commercially available) | 474.2 |
| 197 | 501.64 | (5-ethanesulfonyl-benzooxazol-2-yl)-[1-(3-ethoxy-4-isopropoxy-benzyl)-piperidin-4-yl]-amine | (5-ethanesulfonyl-benzooxazol-2-yl)-piperidin-4-yl-amine dihydrobromide (intermediate J) and 3-ethoxy-4-isopropoxy-benzaldehyde (commercially available) | 502.3 |
| 198 | 487.62 | (5-ethanesulfonyl-benzooxazol-2-yl)-[1-(4-methoxy-3-propoxy-benzyl)-piperidin-4-yl]-amine | (5-ethanesulfonyl-benzooxazol-2-yl)-piperidin-4-yl-amine dihydrobromide (intermediate J) and 4-ethoxy-3-propoxy-benzaldehyde (intermediate 2) | 488.2 |
| 199 | 491.58 | (5-ethanesulfonyl-benzooxazol-2-yl)-{1-[3-(2-fluoro-ethoxy)-4-methoxy-benzyl]-piperidin-4-yl}-amine | (5-ethanesulfonyl-benzooxazol-2-yl)-piperidin-4-yl-amine dihydrobromide (intermediate J) and 3-(2-fluoro-ethoxy)-4-methoxy-benzaldehyde (intermediate 3) | 492.2 |
| 200 | 501.65 | (5-ethanesulfonyl-benzooxazol-2-yl)-[1-(3-isobutoxy-4-methoxy-benzyl)-piperidin-4-yl]-amine | (5-ethanesulfonyl-benzooxazol-2-yl)-piperidin-4-yl-amine dihydrobromide (intermediate J) and 3-isobutoxy-4-methoxy-benzaldehyde (intermediate 8) | 502.5 |
| 201 | 477.55 | 4-[4-(5-ethanesulfonyl-benzooxazol-2-ylamino)-piperidin-1-ylmethyl]-2-ethoxy-5-fluoro-phenol | (5-ethanesulfonyl-benzooxazol-2-yl)-piperidin-4-yl-amine dihydrobromide (intermediate J) and 5-ethoxy-2-fluoro-4-hydroxy-benzaldehyde (intermediate 7) | 478.2 |
| 202 | 487.62 | [1-(3,5-diethoxy-benzyl)-piperidin-4-yl]-(5-ethanesulfonyl-benzooxazol-2-yl)-amine | (5-ethanesulfonyl-benzooxazol-2-yl)-piperidin-4-yl-amine dihydrobromide (intermediate J) and 3,5-diethoxy-benzaldehyde (intermediate 30) | 488.3 |

TABLE 3-continued

| No | MW | Name | Starting materials | ISP [M + H]+ or [M − H]− found |
|---|---|---|---|---|
| 203 | 543.68 | (5-ethanesulfonyl-benzooxazol-2-yl)-{1-[3-ethoxy-5-(tetrahydro-pyran-4-yloxy)-benzyl]-piperidin-4-yl}-amine | (5-ethanesulfonyl-benzooxazol-2-yl)-piperidin-4-yl-amine dihydrobromide (intermediate J) and 3-ethoxy-5-(tetrahydro-pyran-4-yloxy)-benzaldehyde (intermediate 20) | 544.5 |
| 204 | 505.61 | [1-(3,5-diethoxy-2-fluoro-benzyl)-piperidin-4-yl]-(5-ethanesulfonyl-benzooxazol-2-yl)-amine | (5-ethanesulfonyl-benzooxazol-2-yl)-piperidin-4-yl-amine dihydrobromide (intermediate J) and 3,5-diethoxy-2-fluoro-benzaldehyde (intermediate 39) | 506.3 |
| 205 | 522.06 | [1-(2-chloro-3,5-diethoxy-benzyl)-piperidin-4-yl]-(5-ethanesulfonyl-benzooxazol-2-yl)-amine | (5-ethanesulfonyl-benzooxazol-2-yl)-piperidin-4-yl-amine dihydrobromide (intermediate J) and 2-chloro-3,5-diethoxy-benzaldehyde (intermediate 40) | 522.2 |
| 206 | 505.61 | [1-(3,5-diethoxy-4-fluoro-benzyl)-piperidin-4-yl]-(5-ethanesulfonyl-benzooxazol-2-yl)-amine | (5-ethanesulfonyl-benzooxazol-2-yl)-piperidin-4-yl-amine dihydrobromide (intermediate J) and 3,5-diethoxy-4-fluoro-benzaldehyde (intermediate 21) | 506.2 |
| 207 | 552.24 | [1-(3,5-diethoxy-4-pyrrol-1-yl-benzyl)-piperidin-4-yl]-(5-ethanesulfonyl-benzooxazol-2-yl)-amine | (5-ethanesulfonyl-benzooxazol-2-yl)-piperidin-4-yl-amine dihydrobromide (intermediate J) and 3,5-diethoxy-4-pyrrol-1-yl-benzaldehyde (intermediate 4) | 553.3 |
| 208 | 504.56 | 4-[4-(5-ethanesulfonyl-benzooxazol-2-ylamino)-piperidin-1-ylmethyl]-2-ethoxy-6-nitro-phenol | (5-ethanesulfonyl-benzooxazol-2-yl)-piperidin-4-yl-amine dihydrobromide (intermediate J) and 3-ethoxy-4-hydroxy-5-nitro-benzaldehyde (intermediate 50) | 505.5 |
| 209 | 518.59 | (5-ethanesulfonyl-benzooxazol-2-yl)-[1-(3-ethoxy-4-methoxy-5-nitro-benzyl)-piperidin-4-yl]-amine | (5-ethanesulfonyl-benzooxazol-2-yl)-piperidin-4-yl-amine dihydrobromide (intermediate J) and 3-ethoxy-4-methoxy-5-nitro-benzaldehyde (intermediate 51) | [M −H]− 517.6 |
| 210 | 584.47 | [1-(3-amino-5-ethoxy-4-iodo-benzyl)-piperidin-4-yl]-(5-ethanesulfonyl-benzooxazol-2-yl)-amine | (5-ethanesulfonyl-benzooxazol-2-yl)-piperidin-4-yl-amine dihydrobromide (intermediate J) and 3-amino-5-ethoxy-4-iodo-benzaldehyde (intermediate 25) | 585.3 |
| 211 | 474.58 | (5-ethanesulfonyl-benzooxazol-2-yl)-[1-(5-ethoxy-6-methoxy-pyridin-3-ylmethyl)-piperidin-4-yl]-amine | (5-ethanesulfonyl-benzooxazol-2-yl)-piperidin-4-yl-amine dihydrobromide (intermediate J) and 5-ethoxy-6-methoxy-pyridine-3-carbaldehyde (intermediate 28) | 475.5 |
| 212 | 472.61 | (5-ethanesulfonyl-benzooxazol-2-yl)-[1-(3-ethylamino-4-methoxy-benzyl)-piperidin-4-yl]-amine | (5-ethanesulfonyl-benzooxazol-2-yl)-piperidin-4-yl-amine dihydrobromide (intermediate J) and 3-ethylamino-4-methoxy-benzaldehyde (intermediate 29) | 473.3 |
| 213 | 468.58 | (5-ethanesulfonyl-benzooxazol-2-yl)-[1-(5-methoxy-1H-indol-2-ylmethyl)-piperidin-4-yl]-amine | (5-ethanesulfonyl-benzooxazol-2-yl)-piperidin-4-yl-amine dihydrobromide (intermediate J) and 4-ethoxy-1H-indole-6-carbaldehyde (intermediate 52) | 469.2 |
| 214 | 469.89 | [1-(4-chloro-3-ethoxy-benzyl)-piperidin-4-yl]-(5-trifluoromethoxy-benzooxazol-2-yl)-amine | piperidin-4-yl-(5-trifluoromethoxy-benzooxazol-2-yl)-amine dihydrobromide (intermediate K) and 4-chloro-3-ethoxy-benzaldehyde (intermediate 6) | 470.4 |

TABLE 3-continued

| No | MW | Name | Starting materials | ISP [M + H]+ or [M − H]− found |
|---|---|---|---|---|
| 215 | 465.47 | [1-(3-ethoxy-4-methoxy-benzyl)-piperidin-4-yl]-(5-trifluoromethoxy-benzooxazol-2-yl)-amine | piperidin-4-yl-(5-trifluoromethoxy-benzooxazol-2-yl)-amine dihydrobromide (intermediate K) and 3-ethoxy-4-methoxy-benzaldehyde (commercially available) | 466.5 |
| 216 | 497.49 | [1-(3,5-diethoxy-4-fluoro-benzyl)-piperidin-4-yl]-(5-trifluoromethoxy-benzooxazol-2-yl)-amine | piperidin-4-yl-(5-trifluoromethoxy-benzooxazol-2-yl)-amine dihydrobromide (intermediate K) and 3,5-diethoxy-4-fluoro-benzaldehyde (intermediate 21) | [M −H]− 496.5 |
| 217 | 410.47 | [1-(3-ethoxy-4-methyl-benzyl)-piperidin-4-yl]-(5-nitro-benzooxazol-2-yl)-amine | (5-nitro-benzooxazol-2-yl)-piperidin-4-yl-amine dihydrobromide (intermediate L) and 3-ethoxy-4-methyl-benzaldehyde (intermediate 5) | [M −H]− 409.4 |
| 218 | 430.89 | [1-(4-chloro-3-ethoxy-benzyl)-piperidin-4-yl]-(5-nitro-benzooxazol-2-yl)-amine | (5-nitro-benzooxazol-2-yl)-piperidin-4-yl-amine dihydrobromide (intermediate L) and 4-chloro-3-ethoxy-benzaldehyde (intermediate 6) | 431.4 |
| 219 | 414.44 | [1-(3-ethoxy-4-fluoro-benzyl)-piperidin-4-yl]-(5-nitro-benzooxazol-2-yl)-amine | (5-nitro-benzooxazol-2-yl)-piperidin-4-yl-amine dihydrobromide (intermediate L) and 3-ethoxy-4-fluoro-benzaldehyde (intermediate 10) | 415.4 |
| 220 | 412.44 | 2-ethoxy-4-[4-(5-nitro-benzooxazol-2-ylamino)-piperidin-1-ylmethyl]-phenol | (5-nitro-benzooxazol-2-yl)-piperidin-4-yl-amine dihydrobromide (intermediate L) and 3-ethoxy-4-hydroxy-benzaldehyde (commercially available) | 413.4 |
| 221 | 426.47 | [1-(3-ethoxy-4-methoxy-benzyl)-piperidin-4-yl]-(5-nitro-benzooxazol-2-yl)-amine | (5-nitro-benzooxazol-2-yl)-piperidin-4-yl-amine dihydrobromide (intermediate L) and 3-ethoxy-4-methoxy-benzaldehyde (commercially available) | 427.4 |
| 222 | 454.53 | [1-(3-ethoxy-4-isopropoxy-benzyl)-piperidin-4-yl]-(5-nitro-benzooxazol-2-yl)-amine | (5-nitro-benzooxazol-2-yl)-piperidin-4-yl-amine dihydrobromide (intermediate L) and 3-ethoxy-4-isopropoxy-benzaldehyde (commercially available) | 453.4 |
| 223 | 444.46 | {1-[3-(2-fluoro-ethoxy)-4-methoxy-benzyl]-piperidin-4-yl}-(5-nitro-benzooxazol-2-yl)-amine | (5-nitro-benzooxazol-2-yl)-piperidin-4-yl-amine dihydrobromide (intermediate L) and 3-(2-fluoro-ethoxy)-4-methoxy-benzaldehyde (intermediate 3) | 445.4 |
| 224 | 440.50 | [1-(4-methoxy-3-propoxy-benzyl)-piperidin-4-yl]-(5-nitro-benzooxazol-2-yl)-amine | (5-nitro-benzooxazol-2-yl)-piperidin-4-yl-amine dihydrobromide (intermediate L) and 4-ethoxy-3-propoxy-benzaldehyde (intermediate 2) | 441.4 |
| 225 | 430.44 | 2-ethoxy-5-fluoro-4-[4-(5-nitro-benzooxazol-2-ylamino)-piperidin-1-ylmethyl]-phenol | (5-nitro-benzooxazol-2-yl)-piperidin-4-yl-amine dihydrobromide (intermediate L) and 5-ethoxy-2-fluoro-4-hydroxy-benzaldehyde (intermediate 7) | 431.4 |
| 226 | 440.50 | [1-(3,5-diethoxy-benzyl)-piperidin-4-yl]-(5-nitro-benzooxazol-2-yl)-amine | (5-nitro-benzooxazol-2-yl)-piperidin-4-yl-amine dihydrobromide (intermediate L) and 3,5-diethoxy-benzaldehyde (intermediate 30) | 439.4 |
| 227 | 458.49 | [1-(3,5-diethoxy-4-fluoro-benzyl)-piperidin-4-yl]-(5-nitro-benzooxazol-2-yl)-amine | (5-nitro-benzooxazol-2-yl)-piperidin-4-yl-amine dihydrobromide (intermediate L) and 3,5-diethoxy-4-fluoro-benzaldehyde (intermediate 21) | 459.4 |

TABLE 3-continued

| No | MW | Name | Starting materials | ISP [M + H]+ or [M − H]− found |
|---|---|---|---|---|
| 228 | 505.57 | [1-(3,5-diethoxy-4-pyrrol-1-yl-benzyl)-piperidin-4-yl]-(5-nitro-benzooxazol-2-yl)-amine | (5-nitro-benzooxazol-2-yl)-piperidin-4-yl-amine dihydrobromide (intermediate L) and 3,5-diethoxy-4-pyrrol-1-yl-benzaldehyde (intermediate 4) | 506.4 |
| 229 | 421.46 | [1-(5-methoxy-1H-indol-2-ylmethyl)-piperidin-4-yl]-(5-nitro-benzooxazol-2-yl)-amine | (5-nitro-benzooxazol-2-yl)-piperidin-4-yl-amine dihydrobromide (intermediate L) and 4-ethoxy-1H-indole-6-carbaldehyde (intermediate 52) | 422.4 |
| 230 | 400.91 | $N^2$-[1-(4-chloro-3-ethoxy-benzyl)-piperidin-4-yl]-benzooxazole-2,5-diamine | $N^2$-piperidin-4-yl-benzooxazole-2,5-diamine dihydrobromide (intermediate M) and 4-chloro-3-ethoxy-benzaldehyde (intermediate 6) | 401.1 |
| 231 | 424.54 | $N^2$-[1-(3-ethoxy-4-isopropoxy-benzyl)-piperidin-4-yl]-benzooxazole-2,5-diamine | $N^2$-piperidin-4-yl-benzooxazole-2,5-diamine dihydrobromide (intermediate M) and 3-ethoxy-4-isopropoxy-benzaldehyde (commercially available) | 425.3 |
| 232 | 428.51 | $N^2$-[1-(3,5-diethoxy-4-fluoro-benzyl)-piperidin-4-yl]-benzooxazole-2,5-diamine | $N^2$-piperidin-4-yl-benzooxazole-2,5-diamine dihydrobromide (intermediate M) and 3,5-diethoxy-4-fluoro-benzaldehyde (intermediate 21) | 429.2 |
| 233 | 366.46 | [1-(3-ethoxy-4-methyl-benzyl)-piperidin-4-yl]-oxazolo[4,5-b]pyridin-2-yl-amine | oxazolo[4,5-b]pyridin-2-yl-piperidin-4-yl-amine dihydrobromide (intermediate N) and 3-ethoxy-4-methyl-benzaldehyde (intermediate 5) | 367.4 |
| 234 | 386.88 | [1-(4-chloro-3-ethoxy-benzyl)-piperidin-4-yl]-oxazolo[4,5-b]pyridin-2-yl-amine | oxazolo[4,5-b]pyridin-2-yl-piperidin-4-yl-amine dihydrobromide (intermediate N) and 4-chloro-3-ethoxy-benzaldehyde (intermediate 6) | 387.3 |
| 235 | 370.43 | [1-(3-ethoxy-4-fluoro-benzyl)-piperidin-4-yl]-oxazolo[4,5-b]pyridin-2-yl-amine | oxazolo[4,5-b]pyridin-2-yl-piperidin-4-yl-amine dihydrobromide (intermediate N) and 3-ethoxy-4-fluoro-benzaldehyde (intermediate 10) | 371.3 |
| 236 | 368.44 | 2-ethoxy-4-[4-(oxazolo[4,5-b]pyridin-2-ylamino)-piperidin-1-ylmethyl]-phenol | oxazolo[4,5-b]pyridin-2-yl-piperidin-4-yl-amine dihydrobromide (intermediate N) and 3-ethoxy-4-hydroxy-benzaldehyde (commercially available) | 369.4 |
| 237 | 382.46 | [1-(3-ethoxy-4-methoxy-benzyl)-piperidin-4-yl]-oxazolo[4,5-b]pyridin-2-yl-amine | oxazolo[4,5-b]pyridin-2-yl-piperidin-4-yl-amine dihydrobromide (intermediate N) and 3-ethoxy-4-methoxy-benzaldehyde (commercially available) | 383.4 |
| 238 | 396.49 | [1-(3,5-diethoxy-benzyl)-piperidin-4-yl]-oxazolo[4,5-b]pyridin-2-yl-amine | oxazolo[4,5-b]pyridin-2-yl-piperidin-4-yl-amine dihydrobromide (intermediate N) and 3,5-diethoxy-benzaldehyde (intermediate 30) | 397.4 |
| 239 | 414.48 | [1-(3,5-diethoxy-4-fluoro-benzyl)-piperidin-4-yl]-oxazolo[4,5-b]pyridin-2-yl-amine | oxazolo[4,5-b]pyridin-2-yl-piperidin-4-yl-amine dihydrobromide (intermediate N) and 3,5-diethoxy-4-fluoro-benzaldehyde (intermediate 21) | 415.4 |
| 240 | 461.56 | [1-(3,5-diethoxy-4-pyrrol-1-yl-benzyl)-piperidin-4-yl]-oxazolo[4,5-b]pyridin-2-yl-amine | oxazolo[4,5-b]pyridin-2-yl-piperidin-4-yl-amine dihydrobromide (intermediate N) and 3,5-diethoxy-4-pyrrol-1-yl-benzaldehyde (intermediate 4) | 462.4 |

Example 241

(5-Ethanesulfonyl-benzooxazol-2-yl)-[1-(5-ethoxy-4-methoxy-2-pyridin-4-yl-benzyl)-piperidin-4-yl]-amine Step 1:

2-Carbonyl-4-ethoxy 5-methoxy-phenylboronic acid

To a solution of 2-(2-bromo-5-ethoxy-4-methoxy-phenyl)-[1,3]dioxolane (3.03 g, 10.0 mmol, 1,0 equiv, prepared from 2-bromo-5-ethoxy-4-methoxy-benzaldehyde [CAS RN 56517-30-7] as described in F. R. Stermitz, J. P. Gillespie, L. G. Amoros, R. Romero, T. A. Stermitz, K. A. Larson, S. Earl, J. E. Ogg *J. Med. Chem.* 1975, 18, 708-713 and ethylene glycol under Dean-Stark conditions) in anhydrous THF (30 mL) was added n-BuLi (9.4 mL, 15.0 mmol, 1.5 equiv, 1.6 M solution in hexane) at −78° C. under Ar. After stirring the reaction for 30 min, trimethyl borate (3.46 mL, 3.22 g, 31.0 mmol, 3.1 equiv) was added rapidly and the reaction allowed to come to rt over a time period of 4 h. The pH of the reaction mixture was adjusted to 1 by addition of a solution of 1 M HCl and the solution stirred for an additional hour. The reaction was then extracted with dichloromethane (3×50 mL), the combined organic phases washed with water, dried over $Na_2SO_4$ and concentrated by evaporation under reduced pressure. The residue was crystallized from a mixture of ethyl acetate and heptane (1:1) affording 0.56 g (24%) of the title compound as a off-white powder. $^1$H NMR (300 MHz, $CDCl_3$): δ 1.53 (t, J=7.0 Hz, 3H), 4.03 (s, 3H), 4.22 (q, J=7.0 Hz, 2H), 7.38-7.39 (m, 1H), 7.79 (s, 1H), 9.75 (s, 1H).

Step 2:

[4-Ethoxy-2-[[4-[[5-(ethylsulfonyl)-2-benzooxazolyl]amino]-1-piperidinyl]methyl]-5-methoxyphenyl]-boronic acid

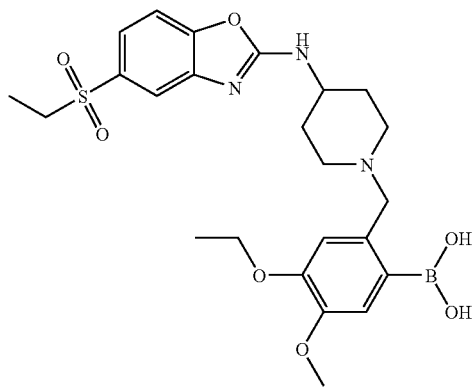

According to the procedure described for the synthesis of example 1/step 3 (benzothiazol-2-yl-[1-(2-ethoxy-naphthalen-1-ylmethyl)-piperidin-4-yl]-amine) the title compound was synthesized from (5-ethanesulfonyl-benzooxazol-2-yl)-piperidin-4-yl-amine dihydrobromide and 2-carbonyl-4-ethoxy 5-methoxy-phenylboronic acid (example 245/step 1) using identical conditions. The solvent was removed by evaporation under reduced pressure and the reaction product directly used without further purification in the next step. MS (ESI): 518.5 $[M+H]^+$.

Step 3:

To a degassed solution of [4-ethoxy-2-[[4-[[5-(ethylsulfonyl)-2-benzooxazolyl]-amino]-1-piperidinyl]methyl]-5-methoxyphenyl]-boronic acid (0.12 g, 0.23 mmol, 1.0 equiv; example 245/step 2) in dimethoxyethane (3 mL) and water (1.5 mL) was added 4-bromopyridine hydrochloride (58.1 mg, 0.3 mmol, 1.3 equiv), potassium tert-butylate (258.1 mg, 2.3 mmol, 10.0 equiv) and tetrakis(triphenylphosphine)palladium(0) (26.6 mg, 0.02 mmol, 0.1 equiv) and the reaction mixture stirred at 85° C. for 72 h. Removal of the solvent under reduced pressure and purification by preparative HPLC on reversed phase eluting with a gradient of acetonitrile/water provided 45.5 mg (28%) of the title compound. MS (ISP): 551.6 $[M+H]^+$.

Example 242

N-{2-[1-(3-Ethoxy-4-methoxy-benzyl)-piperidin-4-ylamino]-benzooxazol-5-yl}-acetamide Step 1:

$N^2$-[1-(3-Ethoxy-4-methoxy-benzyl)-piperidin-4-yl]-benzooxazole-2,5-diamine (intermediate O)

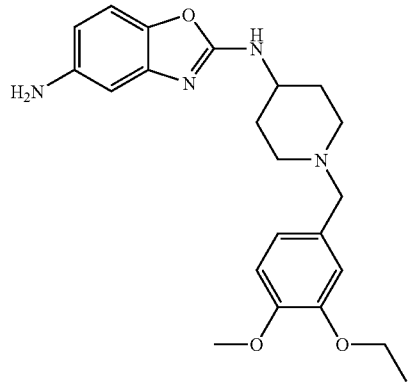

To a solution of [1-(3-ethoxy-4-methoxy-benzyl)-piperidin-4-yl]-(5-nitro-benzooxazol-2-yl)-amine (1.0 g, 2.35 mmol, 1.0 equiv; example 225) in ethanol (10 mL) was added palladium on activated charcoal 10% (0.1 g, 0.10 mmol, 0.04 equiv), the reaction vessel filled with hydrogen (3.5 bar) and stirred at 60° C. for 18 h. The catalyst was removed by filtration over celite and the solvent removed under reduced pressure yielding 0.79 g (85%) of the title compound which was used directly without further purification. MS (ESI): 397.4 $[M+H]^+$.

Step 2:

To a solution of $N^2$-[1-(3-ethoxy-4-methoxy-benzyl)-piperidin-4-yl]-benzooxazole-2,5-diamine (39.8 mg, 0.1 mmol, 1.0 equiv) and acetyl chloride (0.009 mL, 7.9 mg, 0.1 mmol, 1.0 equiv) in anhydrous DMF (1 mL) was added diisopropylethylamine (23.4 μL, 25.9 mg, 0.2 mmol, 2.0 equiv) and the mixture stirred at 100° C. over night. Removal of the solvent under reduced pressure and purification by preparative HPLC on reversed phase eluting with a gradient of acetonitrile/water provided 8.1 mg (19%) of the title compound. MS (ESI): 439.5 [M+H]$^+$.

Examples 243 to 251

According to the procedure described for the synthesis of example 242/step 2 further N-substituted benzooxazole derivatives have been synthesized from N$^2$-[1-(3-ethoxy-4-methoxy-benzyl)-piperidin-4-yl]-benzooxazole-2,5-diamine (intermediate O) and the respective acid chloride or the respective sulfonyl chloride as indicated in Table 4. The results are compiled in Table 4 and comprise example 243 to example 251.

TABLE 4

| No | MW | Name | Starting materials | ISP [M + H]$^+$ or [M − H]$^-$ found |
|---|---|---|---|---|
| 243 | 452.55 | N-{2-[1-(3-ethoxy-4-methoxy-benzyl)-piperidin-4-ylamino]-benzooxazol-5-yl}-propionamide | N$^2$-[1-(3-ethoxy-4-methoxy-benzyl)-piperidin-4-yl]-benzooxazole-2,5-diamine (intermediate O) and propionyl chloride (commercially available) | 453.5 |
| 244 | 478.59 | cyclobutanecarboxylic acid {2-[1-(3-ethoxy-4-methoxy-benzyl)-piperidin-4-ylamino]-benzooxazol-5-yl}-amide | N$^2$-[1-(3-ethoxy-4-4-methoxy-benzyl)-piperidin-4-yl]-benzooxazole-2,5-diamine (intermediate O) and cyclobutanecarbonyl chloride (commercially available) | 479.5 |
| 245 | 492.50 | N-{2-[1-(3-ethoxy-4-methoxy-benzyl)-piperidin-4-ylamino]-benzooxazol-5-yl}-2,2,2-trifluoro-acetamide | N$^2$-[1-(3-ethoxy-4-4-methoxy-benzyl)-piperidin-4-yl]-benzooxazole-2,5-diamine (intermediate O) and trifluoro-acetyl chloride (commercially available) | 493.5 |
| 246 | 519.60 | 3,5-dimethyl-isoxazole-4-carboxylic acid {2-[1-(3-ethoxy-4-methoxy-benzyl)-piperidin-4-ylamino]-benzooxazol-5-yl}-amide | N$^2$-[1-(3-ethoxy-4-4-methoxy-benzyl)-piperidin-4-yl]-benzooxazole-2,5-diamine (intermediate O) and 3,5-dimethyl-isoxazole-4-carbonyl chloride (commercially available) | 520.5 |
| 247 | 474.58 | N-{2-[1-(3-ethoxy-4-methoxy-benzyl)-piperidin-4-ylamino]-benzooxazol-5-yl}-methanesulfonamide | N$^2$-[1-(3-ethoxy-4-4-methoxy-benzyl)-piperidin-4-yl]-benzooxazole-2,5-diamine (intermediate O) and methanesulfonyl chloride (commercially available) | 475.4 |
| 248 | 536.65 | N-{2-[1-(3-ethoxy-4-methoxy-benzyl)-piperidin-4-ylamino]-benzooxazol-5-yl}-benzenesulfonamide | N$^2$-[1-(3-ethoxy-4-4-methoxy-benzyl)-piperidin-4-yl]-benzooxazole-2,5-diamine (intermediate O) and benzenesulfonyl chloride (commercially available) | 535.5 |
| 249 | 555.65 | 3,5-dimethyl-isoxazole-4-sulfonic acid {2-[1-(3-ethoxy-4-methoxy-benzyl)-piperidin-4-ylamino]-benzooxazol-5-yl}-amide | N$^2$-[1-(3-ethoxy-4-4-methoxy-benzyl)-piperidin-4-yl]-benzooxazole-2,5-diamine (intermediate O) and 3,5-dimethyl-isoxazole-4-sulfonyl chloride (commercially available) | [M − H]$^-$ 554.5 |
| 250 | 554.67 | 2,3-dimethyl-3H-imidazole-4-sulfonic acid {2-[1-(3-ethoxy-4-methoxy-benzyl)-piperidin-4-ylamino]-benzooxazol-5-yl}-amide | N$^2$-[1-(3-ethoxy-4-4-methoxy-benzyl)-piperidin-4-yl]-benzooxazole-2,5-diamine (intermediate O) and 2,3-dimethyl-3H-imidazole-4-sulfonyl chloride (commercially available) | [M − H]$^-$ 553.5 |
| 251 | 540.64 | 1-methyl-1H-imidazole-4-sulfonic acid {2-[1-(3-ethoxy-4-methoxy-benzyl)-piperidin-4-ylamino]-benzooxazol-5-yl}-amide | N$^2$-[1-(3-ethoxy-4-4-methoxy-benzyl)-piperidin-4-yl]-benzooxazole-2,5-diamine (intermediate O) and 1-methyl-1H-imidazole-4-sulfonyl chloride (commercially available) | [M − H]$^-$ 539.5 |

Example 252

2-[1-(3-Ethoxy-4-methoxy-benzyl)-piperidin-4-ylamino]-benzooxazole-7-carboxylic acid dimethylamide Step 1:

3-Amino-2-hydroxy-benzoic acid methyl ester

To a solution of 2-hydroxy-3-nitro-benzoic acid methyl ester (2.3 g, 11.67 mmol, 1.0 equiv) in ethanol (50 mL) was added palladium on activated charcoal 10% (0.47 g, 0.47 mmol, 0.04 equiv), the reaction vessel filled with hydrogen (3.5 bar) and stirred at 80° C. for 2 h. The catalyst was removed by filtration over celite and the solvent removed under reduced pressure yielding 1.9 g (95%) of the title compound which was used directly without further purification. $^1$H NMR (300 MHz, CDCl$_3$): δ 3.88 (br s, 2H), 3.93 (s, 3H), 6.71 (t, J=7.9 Hz, 1H), 6.87 (dd, J=7.9 Hz, J=1.5 Hz, 1H), 7.24 (dd, J=7.9 Hz, J=1.5 Hz, 1H). $^{13}$C NMR (75 MHz, CDCl$_3$): δ 52.13, 111.83, 118.71, 118.98, 119.55, 135.85, 149.70, 171.11.

Step 2:

2-Mercapto-benzooxazole-7-carboxylic acid methyl ester

According to the procedure described for the synthesis of example 95/step 1 (2-mercapto-benzooxazole-5-sulfonic acid amide) the title compound was synthesized from 3-amino-2-hydroxy-benzoic acid methyl ester using identical conditions in 80% yield. $^1$H NMR (300 MHz, DMSO): δ 3.94 (s, 3H), 7.40 (t, J=7.9 Hz, 1H), 7.49 (d, J=7.9 Hz, 1H), 7.73 (d, J=7.9 Hz, 1H), 13.5 (br, 1H). MS (ISP): 209.8 [M+H]$^+$.

Step 3:

2-Chloro-benzooxazole-7-carboxylic acid methyl ester

To 2-mercapto-benzooxazole-7-carboxylic acid methyl ester (1.0 g, 4.78 mmol, 1.0 equiv) was added thionyl chloride (8.0 g, 4.9 mL, 67.6 mmol, 14.0 equiv) and anhydrous DMF (0.4 g, 0.4 mL, 5.19 mmol, 1.1 equiv) and the reaction mixture heated to reflux for 15 min. The solvent was removed under reduced pressure, the crude oil azeotroped twice with xylene and the crude material purified with column chromatography on silica eluting with ethyl acetate/hexane (1:1) to afford 0.81 g (81%) of the title compound. $^1$H NMR (300 MHz, CDCl$_3$): δ 4.03 (s, 3H), 7.44 (t, J=7.9 Hz, 1H), 7.87 (dd, J=7.9 Hz, J=1.1 Hz, 1H), 8.01 (dd, J=7.9 Hz, J=1.1 Hz, 1H). $^{13}$C NMR (75 MHz, CDCl$_3$): δ 52.46, 115.07, 124.36, 124.82, 127.54, 142.39, 150.35, 152.24, 163.88. MS (ISP): 212.0 [M+H]$^+$.

Step 4:

2-(1-Ethoxycarbonyl-piperidin-4-ylamino)-benzooxazole-7-carboxylic acid methyl ester To a solution of 2-chloro-benzooxazole-7-carboxylic acid methyl ester (0.43 g, 2.05 mmol, 1.0 equiv) in acetonitrile (30 mL) was added ethyl 4-amino-1-piperidine carboxylate (0.64 g, 3.08 mmol, 1.5 equiv) and the reaction mixture heated to reflux for 30 min. The solvent was removed under reduced pressure and the crude material purified with column chromatography on silica eluting with dichloromethane/methanol (4:1) to afforded 0.68 g (95%) of the title compound. $^1$H NMR (300 MHz, DMSO): δ 1.19 (t, J=7.0 Hz, 3H), 1.38-1.51 (m, 2H), 1.95-2.00 (m, 2H), 2.96-3.03 (m, 2H), 3.78-3.81 (m, 1H), 3.89 (s, 3H), 3.82-3.96 (m, 2H), 4.04 (q, J=7.0 Hz, 2H), 7.23 (t, J=7.9 Hz, 1H), 7.50 (dd, J=7.9 Hz, J=1.9 Hz, 2H), 8.34 (d, J=7.3 Hz, 2H). $^{13}$C NMR (75 MHz, DMSO): δ 14.54, 31.01, 42.04, 49.71, 52.05, 60.63, 112.36, 119.98, 121.27, 123.51, 144.77, 147.00, 154.57, 162.13, 164.17. MS (ISP): 347.9 [M+H]$^+$.

Step 5:

2-(Piperidin-4-ylamino)-benzooxazole-7-carboxylic acid

According to the procedure described for the synthesis of intermediate C/step 2 (piperidin-4-yl-thiazolo[5,4-b]pyridin-2-yl-amine dihydrobromide) the title compound was synthesized from 2-(1-ethoxycarbonyl-piperidin-4-ylamino)-benzooxazole-7-carboxylic acid methyl ester using identical conditions. The product was used in the consecutive step without further purification assuming quantitative deprotection and formation of the zwitterionic salt. MS (ISP): 262.0 [M+H]$^+$.

Step 6:

2-[1-(3-Ethoxy-4-methoxy-benzyl)-piperidin-4-ylamino]-benzooxazole-7-carboxylic acid (Intermediate P)

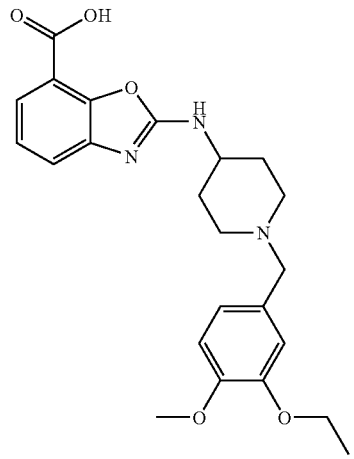

To a solution of 2-(piperidin-4-ylamino)-benzooxazole-7-carboxylic acid (0.35 g, 1.32 mmol, 1.0 equiv) and 3-ethoxy-4-methoxy-benzaldehyde (0.26 g, 1.45 mmol, 1.1 equiv) in ethanol (2 mL) was added diisopropylethylamine (0.39 mL, 0.43 g, 3.3 mmol, 2.5 equiv) and acetic acid (0.16 g, 2.64 mmol, 2.0 equiv) and the mixture stirred at 50° C. After 1.5 h sodium cyano borohydride (0.21 g, 3.3 mmol, 2.5 equiv) was added and the mixture stirred at 50° C. over night. The solvent was removed under reduced pressure and the crude reaction product dissolved in a mixture (1:1, 50 mL) of ethyl acetate and water adjusted to pH 7. The water phase was extracted two more times with ethyl acetate (2×50 mL), the combined organic phases dried over MgSO$_4$ and the solvent evaporated to yield 0.55 g (99%) of the title compound which was used directly in the following step. MS (ISP): 426.0 [M+H]$^+$.

Step 7:

To the crude coupling product 2-[1-(3-ethoxy-4-methoxy-benzyl)-piperidin-4-ylamino]-benzo-oxazole-7-carboxylic acid (42.5 mg, 0.1 mmol, 1.0 equiv) dissolved in anhydrous DMF (1 mL) was added CDI (32.4 mg, 0.2 mmol, 2.0 equiv) and the reaction mixture stirred at 50° C. After 1 h, a solution of dimethylamine 5.6 M in ethanol (71 µL, 0.4 mmol, 4.0 equiv) was added and the reaction mixture stirred at 50° C. for another 24 h. Removal of the solvent under reduced pressure and purification by preparative HPLC on reversed phase eluting with a gradient of acetonitrile/water provided 9.0 mg (20%) of the title compound. MS (ESI): 452.0 [M+H]$^+$.

Examples 253 to 259

According to the procedure described for the synthesis of example 252/step 7 further substituted benzooxazole-derivatives have been synthesized from 2-[1-(3-ethoxy-4-methoxy-benzyl)-piperidin-4-ylamino]-benzooxazole-7-carboxylic acid (intermediate P) and the respective amine as indicated in Table 5. The results are compiled in Table 5 and comprise example 253 to example 259.

Example 260

Cyclobutanecarboxylic acid{2-[1-(3-ethoxy-4-methyl-benzyl)-piperidin-4-ylamino]-benzooxazol-5-yl}-amide Step 1:

4-(5-Nitro-benzooxazol-2-ylamino)-piperidine-1-carboxylic acid tert-butyl ester

A mixture of 2-methylsulfanyl-5-nitro-benzooxazole (10.0 g, 47.57 mmol, 1.0 equiv) and 4-amino-piperidine-1-carboxylic acid tert-butyl ester (14.29 g, 71.36 mmol, 1.5 equiv) in anhydrous DMAc (50 mL) was heated to 140° C. for 72 h. The solution was concentrated by evaporation under reduced pressure and the crude reaction product purified with column chromatography on silica eluting with ethyl acetate/cyclohexane (1:1) to give 4.1 g (24%) of the title compound. $^1$H NMR (300 MHz, CDCl$_3$): δ 1.48 (s, 9H), 1.50-1.53 (m,

TABLE 5

| No | MW | Name | Starting materials | ISP [M + H]$^+$ or [M − H]$^−$ found |
|---|---|---|---|---|
| 253 | 480.61 | 2-[1-(3-ethoxy-4-methoxy-benzyl)-piperidin-4-ylamino]-benzooxazole-7-carboxylic acid diethylamide | 2-[1-(3-ethoxy-4-methoxy-benzyl)-piperidin-4-ylamino]-benzooxazole-7-carboxylic acid (intermediate P) and diethylamine (commercially available) | [M − H]$^−$ 479.6 |
| 254 | 478.59 | 2-[1-(3-ethoxy-4-methoxy-benzyl)-piperidin-4-ylamino]-benzooxazole-7-carboxylic acid cyclopropylmethyl-amide | 2-[1-(3-ethoxy-4-methoxy-benzyl)-piperidin-4-ylamino]-benzooxazole-7-carboxylic acid (intermediate P) and cyclopropylmethylamine (commercially available) | [M − H]$^−$ 477.6 |
| 255 | 494.59 | {2-[1-(3-ethoxy-4-methoxy-benzyl)-piperidin-4-ylamino]-benzooxazol-7-yl}-morpholin-4-yl-methanone | 2-[1-(3-ethoxy-4-methoxy-benzyl)-piperidin-4-ylamino]-benzooxazole-7-carboxylic acid (intermediate P) and morpholine (commercially available) | 495.6 |
| 256 | 520.65 | 2-[1-(3-ethoxy-4-methoxy-benzyl)-piperidin-4-ylamino]-benzooxazole-7-carboxylic acid (thiophen-3-ylmethyl)-amide | 2-[1-(3-ethoxy-4-methoxy-benzyl)-piperidin-4-ylamino]-benzooxazole-7-carboxylic acid (intermediate P) and 3-(aminomethyl)thiophene (commercially available) | [M − H]$^−$ 519.6 |
| 257 | 514.62 | 2-[1-(3-ethoxy-4-methoxy-benzyl)-piperidin-4-ylamino]-benzooxazole-7-carboxylic acid benzylamide | 2-[1-(3-ethoxy-4-methoxy-benzyl)-piperidin-4-ylamino]-benzooxazole-7-carboxylic acid (intermediate P) and benzylamine (commercially available) | [M − H]$^−$ 513.6 |
| 258 | 521.64 | 2-[1-(3-ethoxy-4-methoxy-benzyl)-piperidin-4-ylamino]-benzooxazole-7-carboxylic acid (4-methyl-thiazol-2-yl)-amide | 2-[1-(3-ethoxy-4-methoxy-benzyl)-piperidin-4-ylamino]-benzooxazole-7-carboxylic acid (intermediate P) and 4-methyl-thiazol-2-ylamine (commercially available) | [M − H]$^−$ 520.5 |
| 259 | 521.64 | 2-[1-(3-ethoxy-4-methoxy-benzyl)-piperidin-4-ylamino]-benzooxazole-7-carboxylic acid (5-methyl-thiazol-2-yl)-amide | 2-[1-(3-ethoxy-4-methoxy-benzyl)-piperidin-4-ylamino]-benzooxazole-7-carboxylic acid (intermediate P) and 5-methyl-thiazol-2-ylamine (commercially available) | [M − H]$^−$ 520.6 |

2H), 2.11-2.20 (m, 2H), 2.87-3.05 (m, 2H), 3.89-4.01 (m, 1H), 4.05-4.16 (m, 2H), 5.51 (d, J=7.5 Hz, 1H), 7.30 (d, J=8.7 Hz, 1H), 8.02 (dd, J=8.7 Hz, J=2.3 Hz, 1H), 8.18 (d, J=2.3 Hz, 1H). $^{13}$C NMR (75 MHz, CDCl$_3$): δ 28.40, 32.29, 42.46, 50.88, 79.81, 108.36, 111.99, 116.77, 143.90, 145.23, 152.38, 154.66, 162.69. MS (ISP): 363.5 [M+H]$^+$.

Step 2:

4-(5-Amino-benzooxazol-2-ylamino)-piperidine-1-carboxylic acid tert-butyl ester

According to the procedure described for the synthesis of example 246/step 1 (N-{2-[1-(3-ethoxy-4-methoxy-benzyl)-piperidin-4-ylamino]-benzooxazol-5-yl}-acetamide) the title compound was synthesized from 4-(5-nitro-benzooxazol-2-ylamino)-piperidine-1-carboxylic acid tert-butyl ester using identical conditions in 93% yield. $^1$H NMR (300 MHz, CDCl$_3$): δ 1.47 (s, 9H), 1.45-1.47 (m, 2H), 2.08-2.14 (m, 2H), 2.88-3.01 (m, 2H), 3.87 (br s, 1H), 4.03-4.11 (m, 2H), 5.18 (br s, 1H), 6.36 (dd, J=8.5 Hz, J=2.3 Hz, 1H), 6.70 (d, J=2.3 Hz, 1H), 6.99 (d, J=8.5 Hz, 1H). MS (ISP): 333.1 [M+H]$^+$.

Step 3:

4-[5-(Cyclobutanecarbonyl-amino)-benzooxazol-2-ylamino]-piperidine-1-carboxylic acid tert-butyl ester To a solution of 4-(5-amino-benzooxazol-2-ylamino)-piperidine-1-carboxylic acid tert-butyl ester (1.40 g, 4.21 mmol, 1.0 equiv) in anhydrous DMF (5 mL) was added cyclobutanecarbonyl chloride (0.55 g, 4.63 mmol, 1.1 equiv; commercially available) and diisopropylethylamine (1.03 mL, 1.14 g, 8.84 mmol, 2.1 equiv) and the reaction mixture stirred at rt. After 1 h, water was added (50 mL) and the water phase extracted with dichloromethane (3×50 mL). The combined organic phases were dried over MgSO$_4$, the organic solvent removed under reduced pressure and the crude oil purified with column chromatography on silica eluting with ethyl acetate/heptane (2:1) to afford 1.1 g (64%) of the title compound. $^1$H NMR (300 MHz, CDCl$_3$): δ 1.46-1.50 (m, 2H), 1.47 (s, 9H), 1.94-2.02 (m, 2H), 2.10-2.13 (m, 2H), 2.20-2.26 (m, 2H), 2.34-2.47 (m, 2H), 2.95-2.97 (m, 2H), 3.10-3.22 (m, 1H), 3.90 (br s, 1H), 4.05 (br s, 2H), 5.24 (br s, 1H), 7.14 (d, J=8.6 Hz, 1H), 7.28 (br s, 1H), 7.33 (d, J=8.6 Hz, 1H), 7.41 (br s, 1H). $^{13}$C NMR (75 MHz, CDCl$_3$): δ 18.05, 25.33, 28.41, 32.30, 40.85, 42.49, 50.45, 79.76, 108.41, 108.54, 113.47, 134.57, 143.38, 145.21, 154.70, 161.76, 173.04. MS (ISP): 413.1 [M−H]$^−$.

Step 4:

Cyclobutanecarboxylic acid[2-(piperidin-4-ylamino)-benzooxazol-5-yl]-amide dihydrochloride (Intermediate Q)

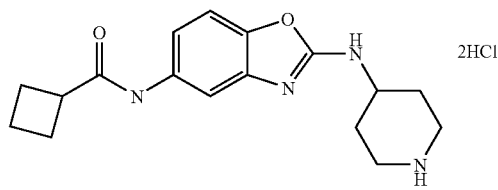

A solution of 4-[5-(cyclobutanecarbonyl-amino)-benzooxazol-2-ylamino]-piperidine-1-carboxylic acid tert-butyl ester (1.10 g, 2.65 mmol) in 4 M HCl (20 mL) was stirred at rt for 2 h. The hydrochloric acid was removed under reduced pressure and the crude material directly used in the following reductive alkylation step. MS (ESI): 315.0 [M+H]$^+$.

Step 5:

According to the procedure described for the synthesis of example 1/step 3 (benzothiazol-2-yl-[1-(2-ethoxy-naphthalen-1-ylmethyl)-piperidin-4-yl]-amine) the title compound was synthesized from cyclobutanecarboxylic acid[2-(piperidin-4-ylamino)-benzooxazol-5-yl]-amide dihydrochloride and 3-ethoxy-4-methyl-benzaldehyde using identical conditions. Isolated yield after purification by preparative HPLC: 13.9 mg (30%). MS (ESI): 461.7 [M−H]$^−$.

Synthesis of Benzooxazole Intermediate R to be Used in Table 6

Intermediate R

Methyl-1H-imidazole-4-sulfonic acid[2-(piperidin-4-ylamino)-benzooxazol-5-yl]-amide dihydrochloride Step 1:

4-[5-(1-Methyl-1H-imidazole-4-sulfonylamino)-benzooxazol-2-ylamino]-piperidine-1-carboxylic acid tert-butyl ester

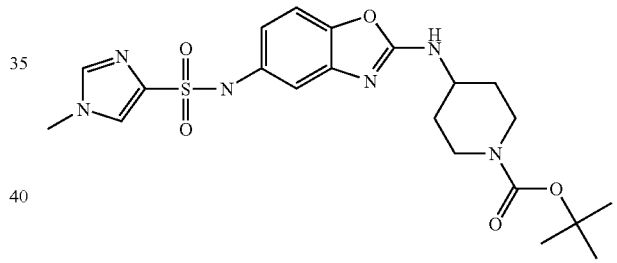

According to the procedure described for the synthesis of example 260/step 3 (4-[5-(cyclobutanecarbonyl-amino)-benzooxazol-2-ylamino]-piperidine-1-carboxylic acid tert-butyl ester) the title compound was synthesized from 4-(5-amino-benzooxazol-2-ylamino)-piperidine-1-carboxylic acid tert-butyl ester and 1-methyl-1H-imidazole-4-sulfonyl chloride (commercially available) using identical conditions in 85% yield. $^1$H NMR (300 MHz, DMSO): δ 1.28-1.37 (m, 2H), 1.33 (s, 9H), 1.80-1.87 (m, 2H), 2.80-2.88 (m, 2H), 3.56 (s, 3H), 3.62-3.69 (m, 1H), 3.79-3.84 (m, 2H), 6.66 (dd, J=8.5 Hz, J=2.1 Hz, 1H), 6.96 (d, J=2.1 Hz, 1H), 7.09 (d, J=8.5 Hz, 1H), 7.64 (s, 1H), 7.66 (s, 1H), 7.85 (d, J=7.6 Hz, 1H), 9.86 (s, 1H). $^{13}$C NMR (75 MHz, DMSO): δ 28.05, 31.26, 33.35, 42.09, 49.59, 78.65, 108.06, 108.38, 113.25, 125.02, 134.02, 138.62, 139.53, 143.47, 144.67, 153.86, 162.05. MS (ISP): 477.3 [M+H]$^+$.

Step 2:

According to the procedure described for the synthesis of example 260/step 4 (cyclobutanecarboxylic acid[2-(piperidin-4-ylamino)-benzooxazol-5-yl]-amide dihydrochloride) the title compound was synthesized from 4-[5-(1-methyl-1H-imidazole-4-sulfonylamino)-benzooxazol-2-ylamino]-piperidine-1-carboxylic acid tert-butyl ester using identical conditions. The product was used in the consecutive step without further purification assuming quantitative deprotection and formation of the dihydrochloride salt. MS (ESI): 377.0 [M+H]⁺.

Examples 261 to 293

According to the procedure described for the synthesis of example 260/step 5 further substituted benzooxazole derivatives have been synthesized from cyclobutanecarboxylic acid [2-(piperidin-4-ylamino)-benzooxazol-5-yl]-amide dihydrochloride (intermediate Q) and 1-methyl-1H-imidazole-4-sulfonic acid[2-(piperidin-4-ylamino)-benzooxazol-5-yl]-amide dihydrochloride (intermediate R) and the respective benzaldehyde as indicated in Table 6. The results are compiled in Table 6 and comprise example 261 to example 293.

TABLE 6

| No | MW | Name | Starting materials | ISP [M + H]⁺ or [M − H]⁻ found |
|---|---|---|---|---|
| 261 | 483.01 | cyclobutanecarboxylic acid {2-[1-(4-chloro-3-ethoxy-benzyl)-piperidin-4-ylamino]-benzooxazol-5-yl}-amide | cyclobutanecarboxylic acid [2-(piperidin-4-ylamino)-benzooxazol-5-yl]-amide dihydrochloride (intermediate Q) and 4-chloro-3-ethoxy-benzaldehyde (intermediate 6) | 483.6 |
| 262 | 466.56 | cyclobutanecarboxylic acid {2-[1-(3-ethoxy-4-fluoro-benzyl)-piperidin-4-ylamino]-benzooxazol-5-yl}-amide | cyclobutanecarboxylic acid [2-(piperidin-4-ylamino)-benzooxazol-5-yl]-amide dihydrochloride (intermediate Q) and 3-ethoxy-4-fluoro-benzaldehyde (intermediate 10) | [M − H]⁻ 465.6 |
| 263 | 516.56 | cyclobutanecarboxylic acid {2-[1-(3-ethoxy-4-trifluoromethyl-benzyl)-piperidin-4-ylamino]-benzooxazol-5-yl}-amide | cyclobutanecarboxylic acid [2-(piperidin-4-ylamino)-benzooxazol-5-yl]-amide dihydrochloride (intermediate Q) and 3-ethoxy-4-trifluoromethyl-benzaldehyde (intermediate 11) | [M − H]⁻ 515.7 |
| 264 | 464.57 | cyclobutanecarboxylic acid {2-[1-(3-ethoxy-4-hydroxy-benzyl)-piperidin-4-ylamino]-benzooxazol-5-yl}-amide | cyclobutanecarboxylic acid [2-(piperidin-4-ylamino)-benzooxazol-5-yl]-amide dihydrochloride (intermediate Q) and 3-ethoxy-4-hydroxy-benzaldehyde (commercially available) | 465.6 |
| 265 | 542.65 | methanesulfonic acid 4-{4-[5-(cyclobutanecarbonyl-amino)-benzooxazol-2-ylamino]-piperidin-1-ylmethyl}-2-ethoxy-phenyl ester | cyclobutanecarboxylic acid [2-(piperidin-4-ylamino)-benzooxazol-5-yl]-amide dihydrochloride (intermediate Q) and methanesulfonic acid 2-ethoxy-4-formyl-phenyl ester (intermediate 32) | [M − H]⁻ 541.6 |
| 266 | 496.58 | cyclobutanecarboxylic acid (2-{1-[3-(2-fluoro-ethoxy)-4-methoxy-benzyl]-piperidin-4-ylamino}-benzooxazol-5-yl)-amide | cyclobutanecarboxylic acid [2-(piperidin-4-ylamino)-benzooxazol-5-yl]-amide dihydrochloride (intermediate Q) and 3-(2-fluoro-ethoxy)-4-methoxy-benzaldehyde (intermediate 3) | 497.6 |
| 267 | 506.65 | cyclobutanecarboxylic acid {2-[1-(3-isobutoxy-4-methoxy-benzyl)-piperidin-4-ylamino]-benzooxazol-5-yl}-amide | cyclobutanecarboxylic acid [2-(piperidin-4-ylamino)-benzooxazol-5-yl]-amide dihydrochloride (intermediate Q) and 3-isobutoxy-4-methoxy-benzaldehyde (intermediate 8) | 507.7 |
| 268 | 520.67 | cyclobutanecarboxylic acid {2-[1-(3-ethoxy-5-isobutoxy-benzyl)-piperidin-4-ylamino]-benzooxazol-5-yl}-amide | cyclobutanecarboxylic acid [2-(piperidin-4-ylamino)-benzooxazol-5-yl]-amide dihydrochloride (intermediate Q) and 3-ethoxy-5-isobutoxy-benzaldehyde (intermediate 38) | 521.6 |
| 269 | 548.68 | cyclobutanecarboxylic acid (2-{1-[3-ethoxy-5-(tetrahydro-pyran-4-yloxy)-benzyl]-piperidin-4-ylamino}-benzooxazol-5-yl)-amide | cyclobutanecarboxylic acid [2-(piperidin-4-ylamino)-benzooxazol-5-yl]-amide dihydrochloride (intermediate Q) and 3-ethoxy-5-(tetrahydro-pyran-4-yloxy)-benzaldehyde (intermediate 20) | 549.7 |

TABLE 6-continued

| No | MW | Name | Starting materials | ISP [M + H]+ or [M − H]− found |
|---|---|---|---|---|
| 270 | 550.70 | cyclobutanecarboxylic acid (2-{1-[3-ethoxy-5-(3-hydroxy-2,2-dimethyl-propoxy)-benzyl]-piperidin-4-ylamino}-benzooxazol-5-yl)-amide | cyclobutanecarboxylic acid [2-(piperidin-4-ylamino)-benzooxazol-5-yl]-amide dihydrochloride (intermediate Q) and 3-ethoxy-5-(3-hydroxy-2,2-dimethyl-propoxy)-benzaldehyde (intermediate 41) | [M − H]− 549.7 |
| 271 | 510.61 | cyclobutanecarboxylic acid {2-[1-(3,5-diethoxy-4-fluoro-benzyl)-piperidin-4-ylamino]-benzooxazol-5-yl}-amide | cyclobutanecarboxylic acid [2-(piperidin-4-ylamino)-benzooxazol-5-yl]-amide dihydrochloride (intermediate Q) and 3,5-diethoxy-4-fluoro-benzaldehyde (intermediate 21) | [M − H]− 509.7 |
| 272 | 554.26 | (±)-cyclobutanecarboxylic acid {2-[1-(3,5-diethoxy-4-methanesulfinyl-benzyl)-piperidin-4-ylamino]-benzooxazol-5-yl}-amide | cyclobutanecarboxylic acid [2-(piperidin-4-ylamino)-benzooxazol-5-yl]-amide dihydrochloride (intermediate Q) and (±)-3,5-diethoxy-4-methanesulfinyl-benzaldehyde (intermediate 43) | 555.7 |
| 273 | 507.63 | cyclobutanecarboxylic acid {2-[1-(4-amino-3,5-diethoxy-benzyl)-piperidin-4-ylamino]-benzooxazol-5-yl}-amide | cyclobutanecarboxylic acid [2-(piperidin-4-ylamino)-benzooxazol-5-yl]-amide dihydrochloride (intermediate Q) and 4-amino-3,5-diethoxy-benzaldehyde (intermediate 23) | 508.6 |
| 274 | 549.67 | cyclobutanecarboxylic acid {2-[1-(4-acetylamino-3,5-diethoxy-benzyl)-piperidin-4-ylamino]-benzooxazol-5-yl}-amide | cyclobutanecarboxylic acid [2-(piperidin-4-ylamino)-benzooxazol-5-yl]-amide dihydrochloride (intermediate Q) and N-(2,6-diethoxy-4-formyl-phenyl)-acetamide (intermediate 24) | 550.7 |
| 275 | 557.69 | cyclobutanecarboxylic acid {2-[1-(3,5-diethoxy-4-pyrrol-1-yl-benzyl)-piperidin-4-ylamino]-benzooxazol-5-yl}-amide | cyclobutanecarboxylic acid [2-(piperidin-4-ylamino)-benzooxazol-5-yl]-amide dihydrochloride (intermediate Q) and 3,5-diethoxy-4-pyrrol-1-yl-benzaldehyde (intermediate 4) | 558.7 |
| 276 | 505.57 | cyclobutanecarboxylic acid {2-[1-(4-ethoxy-2-oxo-2,3-dihydro-benzooxazol-6-ylmethyl)-piperidin-4-ylamino]-benzooxazol-5-yl}-amide | cyclobutanecarboxylic acid [2-(piperidin-4-ylamino)-benzooxazol-5-yl]-amide dihydrochloride (intermediate Q) and 4-ethoxy-2-oxo-2,3-dihydro-benzooxazole-6-carbaldehyde(intermediate 45) | [M − H]− 504.6 |
| 277 | 631.50 | cyclobutanecarboxylic acid {2-[1-(3-acetylamino-5-ethoxy-4-iodo-benzyl)-piperidin-4-ylamino]-benzooxazol-5-yl}-amide | cyclobutanecarboxylic acid [2-(piperidin-4-ylamino)-benzooxazol-5-yl]-amide dihydrochloride (intermediate Q) and N-(3-ethoxy-5-formyl-2-iodo-phenyl)-acetamide (intermediate 26) | 632.5 |
| 278 | 524.64 | 1-methyl-1H-imidazole-4-sulfonic acid {2-[1-(3-ethoxy-4-methyl-benzyl)-piperidin-4-ylamino]-benzooxazol-5-yl}-amide | 1-methyl-1H-imidazole-4-sulfonic acid [2-(piperidin-4-ylamino)-benzooxazol-5-yl]-amide dihydrochloride (intermediate R) and 3-ethoxy-4-methyl-benzaldehyde (intermediate 5) | 525.6 |
| 279 | 545.06 | 1-methyl-1H-imidazole-4-sulfonic acid {2-[1-(4-chloro-3-ethoxy-benzyl)-piperidin-4-ylamino]-benzooxazol-5-yl}-amide | 1-methyl-1H-imidazole-4-sulfonic acid [2-(piperidin-4-ylamino)-benzooxazol-5-yl]-amide dihydrochloride (intermediate R) and 4-chloro-3-ethoxy-benzaldehyde (intermediate 6) | 545.6 |
| 280 | 528.61 | 1-methyl-1H-imidazole-4-sulfonic acid {2-[1-(3-ethoxy-4-fluoro-benzyl)-piperidin-4-ylamino]- | 1-methyl-1H-imidazole-4-sulfonic acid [2-(piperidin-4-ylamino)-benzooxazol-5-yl]-amide dihydrochloride | [M − H]− 527.6 |

TABLE 6-continued

| No | MW | Name | Starting materials | ISP [M + H]+ or [M − H]− found |
|---|---|---|---|---|
| | | benzooxazol-5-yl}-amide | (intermediate R) and 3-ethoxy-4-fluoro-benzaldehyde (intermediate 10) | |
| 281 | 578.61 | 1-methyl-1H-imidazole-4-sulfonic acid {2-[1-(3-ethoxy-4-trifluoromethyl-benzyl)-piperidin-4-ylamino]-benzooxazol-5-yl}-amide | 1-methyl-1H-imidazole-4-sulfonic acid [2-(piperidin-4-ylamino)-benzooxazol-5-yl]-amide dihydrochloride (intermediate R) and 3-ethoxy-4-trifluoromethyl-benzaldehyde (intermediate 11) | [M − H]− 577.6 |
| 282 | 526.62 | 1-methyl-1H-imidazole-4-sulfonic acid {2-[1-(3-ethoxy-4-hydroxy-benzyl)-piperidin-4-ylamino]-benzooxazol-5-yl}-amide | 1-methyl-1H-imidazole-4-sulfonic acid [2-(piperidin-4-ylamino)-benzooxazol-5-yl]-amide dihydrochloride (intermediate R) and 3-ethoxy-4-hydroxy-benzaldehyde (commercially available) | 527.5 |
| 283 | 604.70 | methanesulfonic acid 2-ethoxy-4-{4-[5-(1-methyl-1H-imidazole-4-sulfonylamino)-benzooxazol-2-ylamino]-piperidin-1-ylmethyl}-phenyl ester | 1-methyl-1H-imidazole-4-sulfonic acid [2-(piperidin-4-ylamino)-benzooxazol-5-yl]-amide dihydrochloride (intermediate R) and methanesulfonic acid 2-ethoxy-4-formyl-phenyl ester (intermediate 32) | [M − H]− 603.6 |
| 284 | 558.63 | 1-methyl-1H-imidazole-4-sulfonic acid (2-{1-[3-(2-fluoro-ethoxy)-4-methoxy-benzyl]-piperidin-4-ylamino}-benzooxazol-5-yl)-amide | 1-methyl-1H-imidazole-4-sulfonic acid [2-(piperidin-4-ylamino)-benzooxazol-5-yl]-amide dihydrochloride (intermediate R) and 3-(2-fluoro-ethoxy)-4-methoxy-benzaldehyde (intermediate 3) | 559.5 |
| 285 | 568.70 | 1-methyl-1H-imidazole-4-sulfonic acid {2-[1-(3-isobutoxy-4-methoxy-benzyl)-piperidin-4-ylamino]-benzooxazol-5-yl}-amide | 1-methyl-1H-imidazole-4-sulfonic acid [2-(piperidin-4-ylamino)-benzooxazol-5-yl]-amide dihydrochloride (intermediate R) and 3-isobutoxy-4-methoxy-benzaldehyde (intermediate 8) | [M − H]− 567.6 |
| 286 | 582.72 | 1-methyl-1H-imidazole-4-sulfonic acid {2-[1-(3-ethoxy-5-isobutoxy-benzyl)-piperidin-4-ylamino]-benzooxazol-5-yl}-amide | 1-methyl-1H-imidazole-4-sulfonic acid [2-(piperidin-4-ylamino)-benzooxazol-5-yl]-amide dihydrochloride (intermediate R) and 3-ethoxy-5-isobutoxy-benzaldehyde (intermediate 38) | [M − H]− 581.7 |
| 287 | 610.73 | 1-methyl-1H-imidazole-4-sulfonic acid (2-{1-[3-ethoxy-5-(tetrahydro-pyran-4-yloxy)-benzyl]-piperidin-4-ylamino}-benzooxazol-5yl)-amide | 1-methyl-1H-imidazole-4-sulfonic acid [2-(piperidin-4-ylamino)-benzooxazol-5-yl]-amide dihydrochloride (intermediate R) and 3-ethoxy-5-(tetrahydro-pyran-4-yloxy)-benzaldehyde (intermediate 20) | 611.7 |
| 288 | 612.75 | 1-methyl-1H-imidazole-4-sulfonic acid (2-{1-[3-ethoxy-5-(3-hydroxy-2,2-dimethyl-propoxy)-benzyl]-piperidin-4-ylamino}-benzooxazol-5-yl)-amide | 1-methyl-1H-imidazole-4-sulfonic acid [2-(piperidin-4-ylamino)-benzooxazol-5-yl]-amide dihydrochloride (intermediate R) and 3-ethoxy-5-(3-hydroxy-2,2-dimethyl-propoxy)-benzaldehyde (intermediate 41) | [M − H]− 611.6 |
| 289 | 572.66 | 1-methyl-1H-imidazole-4-sulfonic acid {2-[1-(3,5-diethoxy-4-fluoro-benzyl)-piperidin-4-ylamino]-benzooxazol-5-yl}-amide | 1-methyl-1H-imidazole-4-sulfonic acid [2-(piperidin-4-ylamino)-benzooxazol-5-yl]-amide dihydrochloride (intermediate R) and 3,5-diethoxy-4-fluoro-benzaldehyde (intermediate 21) | [M − H]− 571.6 |
| 290 | 569.68 | 1-methyl-1H-imidazole-4-sulfonic acid {2-[1-(4-amino-3,5-diethoxy-benzyl)-piperidin-4- | 1-methyl-1H-imidazole-4-sulfonic acid [2-(piperidin-4-ylamino)-benzooxazol-5-yl]-amide dihydrochloride | 568.7 |

TABLE 6-continued

| No | MW | Name | Starting materials | ISP [M + H]+ or [M − H]− found |
|---|---|---|---|---|
| | | ylamino]-benzooxazol-5-yl}-amide | (intermediate R) and 4-amino-3,5-diethoxy-benzaldehyde (intermediate 23) | |
| 291 | 611.72 | N-(2,6-diethoxy-4-{4-[5-(1-methyl-1H-imidazole-4-sulfonylamino)-benzooxazol-2-ylamino]-piperidin-1-ylmethyl}-phenyl)-acetamide | 1-methyl-1H-imidazole-4-sulfonic acid [2-(piperidin-4-ylamino)-benzooxazol-5-yl]-amide dihydrochloride (intermediate R) and N-(2,6-diethoxy-4-formyl-phenyl)-acetamide (intermediate 24) | 612.6 |
| 292 | 567.62 | 1-methyl-1H-imidazole-4-sulfonic acid {2-[1-(4-ethoxy-2-oxo-2,3-dihydro-benzooxazol-6-ylmethyl)-piperidin-4-ylamino]-benzooxazol-5-yl}-amide | 1-methyl-1H-imidazole-4-sulfonic acid [2-(piperidin-4-ylamino)-benzooxazol-5-yl]-amide dihydrochloride (intermediate R) and 4-ethoxy-2-oxo-2,3-dihydro-benzooxazole-6-carbaldehyde (intermediate 45) | [M − H]− 566.6 |
| 293 | 693.60 | N-(3-ethoxy-2-iodo-5-{4-[5-(1-methyl-1H-imidazole-4-sulfonylamino)-benzooxazol-2-ylamino]-piperidin-1-ylmethyl}-phenyl)-acetamide | 1-methyl-1H-imidazole-4-sulfonic acid [2-(piperidin-4-ylamino)-benzooxazol-5-yl]-amide dihydrochloride (intermediate R) and N-(3-ethoxy-5-formyl-2-iodo-phenyl)-acetamide (intermediate 26) | [M − H]− 692.5 |

The aldehyde intermediates 53 to 55 were prepared following literature precedents or as described below.

Synthesis of Aldehyde Intermediates 53 to 55 to be Used in Table 7

Intermediate 53

3,5-Diisopropoxy-benzaldehyde [CAS RN 94169-64-9]

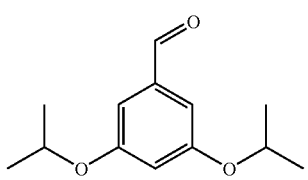

To a solution of 3,5-dihydroxy-benzaldehyde (5.0 g, 36.20 mmol, 1.0 equiv) in anhydrous DMF (30 mL) was added $K_2CO_3$ (15.0 g, 108.60 mmol, 3.0 equiv) and 2-bromo-propane (13.36 g, 10.20 mL, 108.60 mmol, 3.0 equiv) and the mixture stirred at 100° C. for 18 h. The $K_2CO_3$ was removed by filtration and the organic phase concentrated under reduced pressure. To the crude reaction mixture was added a sat. solution of sodium chloride (100 mL) and the solution extracted with ethyl acetate (3×100 mL). The combined organic phases were dried over $MgSO_4$ and the product purified with silica column chromatography using a MPLC system (CombiFlash Companion, Isco Inc.) eluting with a gradient of heptane/ethyl acetate to yield 0.59 g (9%) of 3-hydroxy-5-isopropoxy-benzaldehyde (intermediate 15a) and 6.64 g (83%) of the title compound. $^1$H NMR (300 MHz, CDCl$_3$): δ 1.35 (d, J=6.1 Hz, 6H), 4.59 (quint, J=6.1 Hz, 1H), 6.66-6.68 (m, 1H), 6.96-6.97 (m, 2H), 9.88 (s, 1H). MS (ISP): 223.1 [M+H]+.

Intermediate 54

3,5-Diethoxy-4-methoxy-benzaldehyde

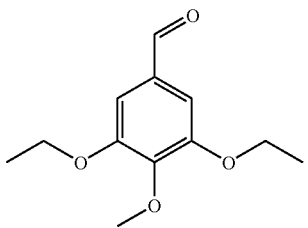

Step 1:

(3,5-Diethoxy-4-methoxy-phenyl)-methanol

To a solution of 3,5-diethoxy-4-methoxy-benzoic acid methyl ester (0.34 g, 1.34 mmol, 1.0 equiv; prepared as described in EP 0 419 905 B1, Eisai Co.) in anhydrous THF (5 mL) was added lithium aluminium hydride (0.15 g, 4.01 mmol, 3.0 equiv) and the reaction mixture stirred at rt for 4 h. The crude reaction mixture was filtered over Hyflo Super Cel, the filtrate extracted with diethyl ether (3×50 mL) and the combined organic phases dried over $MgSO_4$ providing 0.26 g (86%) of the title compound. $^1$H NMR (300 MHz, CDCl$_3$): δ 1.36 (t, J=7.0 Hz, 6H), 3.77 (s, 3H), 4.02 (q, J=7.0 Hz, 4H), 4.53 (s, 2H), 6.51 (s, 2H). MS (EI): 227.3 [M]+.

Step 2:

To a solution of (3,5-diethoxy-4-methoxy-phenyl)-methanol (0.26 g, 1.15 mmol, 1.0 equiv) in THF (10 mL) was added activated MnO$_2$ (1.0 g, 11.49 mmol, 10.0 equiv) and the reaction mixture stirred at rt for 4 h. Filtration through Hyflo Super Cel, concentration by evaporation under reduced pressure and purification with column chromatography on silica eluting with hexane/ethyl acetate (5:1) yielded 0.12 g (48%) of the title compound. $^1$H NMR (300 MHz, CDCl$_3$): δ 1.47 (t, J=7.0 Hz, 6H), 3.94 (s, 3H), 4.14 (q, J=7.0 Hz, 4H), 7.10 (s, 2H), 9.84 (s, 1H). MS (ISP): 225.1 [M+H]$^+$.

Intermediate 55

3,5-Diethoxy-4-[1,2,4]triazol-1-yl-benzaldehyde

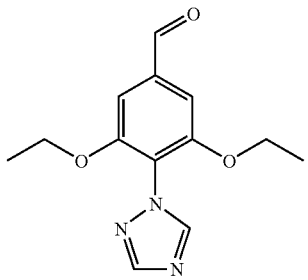

To a solution of 3,5-diethoxy-4-fluoro-benzaldehyde (5.00 g, 23.56 mmol, 1.0 equiv; intermediate 21) in DMSO (50 mL) was added 1H-[1,2,4]triazole (3.26 g, 47.12 mmol, 2.0 equiv) and K$_2$CO$_3$ (6.51 g, 47.12 mmol, 2.0 equiv) and the reaction mixture stirred at 110° C. for 1 h. The solution was poured on crashed ice, the reaction mixture extracted with ethyl acetate (2×50 mL) and the combined organic phases dried over MgSO$_4$. The organic solvent was evaporated under reduced pressure and the crude reaction product purified with column chromatography on silica eluting with a gradient of heptane/ethyl acetate (1:1→0:1) providing 5.28 g (86%) of the title compound. MS (ESI): 261.9 [M+H]$^+$.

Synthesis of Benzooxazole and Oxazolopyridine Intermediates S to U to be Used in Table 7

Intermediate S

Oxazolo[5,4-b]pyridin-2-yl-piperidin-4-yl-amine dihydrochloride

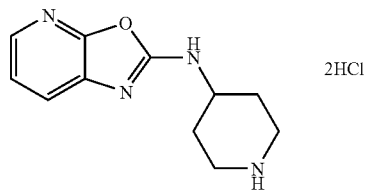

Step 1:

Oxazolo[5,4-b]pyridine-2-thiol

To a solution of 3-amino-pyridin-2-ol (5.51 g, 50.0 mmol, 1.0 equiv) in anhydrous THF (175 mL) was added slowly thiophosgene (6.90 g, 4.57 mL, 60.0 mmol, 1.2 equiv) via syringe pump over a time period of 1 h. After stirring for 24 h at rt, excess thiophosgene was quenched by addition of a conc. solution of ammonium chloride (100 mL) and the majority of solvent was removed by evaporation under reduced pressure. A solution of 10 N NaOH (50 mL) was added and the residue extracted with ethyl acetate (3×100 mL). The combined organic phases were dried over MgSO$_4$ yielding 5.2 g (69%) of crude product, which was used in the subsequent reaction step without further purification. $^1$H NMR (300 MHz, DMSO): δ 6.30 (t, J=7.0 Hz, 1H), 7.29 (dd, J=7.0 Hz, 1=1.8 Hz, 1H), 7.45 (dd, J=7.0 Hz, J=1.8 Hz, 1H), 13.04 (br s, 1H). MS (ISP): 152.9 [M+H]$^+$.

Step 2:

4-(Oxazolo[5,4-b]pyridin-2-ylamino)-piperidine-1-carboxylic acid tert-butyl ester To oxazolo[5,4-b]pyridine-2-thiol (1.0 g, 6.57 mmol, 1.0 equiv) was added thionyl chloride (14.1 g, 8.6 mL, 118.3 mmol, 18.0 equiv) and anhydrous DMF (0.56 g, 0.56 mL, 7.23 mmol, 1.1 equiv) and the reaction mixture heated to reflux for 30 min. The solvent was removed under reduced pressure and the crude oil azeotroped twice with xylene to remove excess thionyl chloride. To the crude reaction product was added 4-amino-piperidine-1-carboxylic acid tert-butyl ester (1.97 g, 9.86 mmol, 1.5 equiv) in anhydrous DMF (5 mL) and the solution heated to 60° C. for 18 h. The solution was concentrated by evaporation under reduced pressure and the crude reaction product purified with column chromatography on silica eluting with ethyl acetate/hexane (1:1) to give 0.40 g (19%) of the title compound. $^1$H NMR (300 MHz, DMSO): δ 1.34 (s, 9H), 1.26-1.40 (m, 2H), 1.84-1.92 (m, 2H), 2.82-2.95 (m, 2H), 3.67-3.76 (m, 1H), 3.82-3.84 (m, 2H), 7.13 (t, J=7.0 Hz, 1H), 7.52 (dd, J=7.0 Hz, J=1.8 Hz, 1H), 7.79 (dd, J=7.0 Hz, J=1.8 Hz, 1H), 8.23 (d, J=7.6 Hz, 1H).

Step 3:

According to the procedure described for the synthesis of example 260/step 4 (cyclobutanecarboxylic acid[2-(piperidin-4-ylamino)-benzooxazol-5-yl]-amide dihydrochloride (intermediate Q)) the title compound was synthesized from 4-(oxazolo[5,4-b]pyridin-2-ylamino)-piperidine-1-carboxylic acid tert-butyl ester using identical conditions. The product was used in the consecutive step without further purification assuming 100% conversion and formation of the dihydrochloride salt. MS (ISP): 219.1 [M+H]$^+$.

Intermediate T 2-(Piperidin-4-ylamino)-benzooxazole-5-carbonitrile

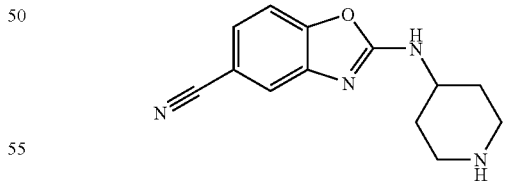

Step 1:

4-(5-Cyano-benzooxazol-2-ylamino)-piperidine-1-carboxylic acid tert-butyl ester

To a solution of 2-chloro-benzooxazole-5-carbonitrile (5.0 g, 28.0 mmol, 1.0 equiv; prepared as described in A. Batista-Parra, S. Venkitachalam, W. D. Wilson, D. W. Boykin Heterocycles 2003, 60, 1367-1376) in acetonitrile (65 mL) was added N-ethyl diisopropylamine (36.0 mL, 27.1 g, 210.0 mmol, 7.5 equiv) and 4-amino-piperidine-1-carboxylic acid tert-butyl ester (5.61 g, 28.0 mmol, 1.0 equiv). The reaction mixture was stirred at rt for 18 h under Ar, poured on crashed ice and the pH adjusted by addition of a solution of 37% HCl to pH 3.0. The reaction mixture was extracted with ethyl acetate (3×100 mL), the combined organic phases washed with water and dried over MgSO$_4$. The organic solvent was evaporated under reduced pressure and the crude reaction product purified with column chromatography on silica eluting with a gradient of dichloromethane/methanol (100:0→95:5) to give 7.31 g (76%) of the title compound. MS (ESI): 343.0 [M+H]$^+$.

Step 2:

To a solution of 4-(5-cyano-benzooxazol-2-ylamino)-piperidine-1-carboxylic acid tert-butyl ester (6.62 g, 19.33 mmol, 1.0 equiv) in dichloromethane (100 mL) was added trifluoro-acetic acid (7.4 mL, 11.03 g, 96.7 mmol, 5.0 equiv). After stirring under Ar at rt for 18 h excess trifluoro-acetic acid was removed under reduced pressure and the crude solid taken up in dichloromethane (100 mL) and water (100 mL). The pH was adjusted to 10 by addition of a conc. solution of K$_2$CO$_3$ and the solution extracted with dichloromethane/2-propanol (4:1, 3×50 mL). The combined organic phases were dried over MgSO$_4$, the organic solvent evaporated under reduced pressure and the crude reaction product purified with column chromatography on silica eluting with a gradient of dichloromethane/methanol (100:0→95:5) containing 33% of NH$_4$OH to yield 4.36 g (93%) of the title compound. MS (ESI): 243.1 [M+H]$^+$.

Intermediate U 2-(Piperidin-4-ylamino)-benzooxazole-5-carboxylic acid amide

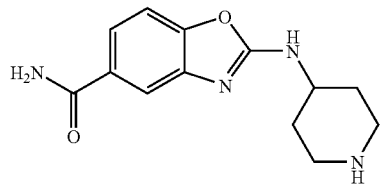

Step 1:

4-(5-Carbamoyl-benzooxazol-2-ylamino)-piperidine-1-carboxylic acid tert-butyl ester To a suspension of 4-(5-cyano-benzooxazol-2-ylamino)-piperidine-1-carboxylic acid tert-butyl ester (1.03 g, 3.01 mmol, 1.0 equiv; intermediate T (2-(piperidin-4-ylamino)-benzooxazole-5-carbonitrile)/step 1) and 0.084 g (0.6 mmol) of potassium carbonate in DMSO (5 mL) was added a solution of 35% hydrogen peroxide in water (0.53 mL, 0.59 g, 6.02 mmol, 2.0 equiv) and the reaction mixture stirred at ambient temperature for 24 h. The solution was poured on crashed ice, the reaction mixture extracted with dichloromethane/2-propanol (4:1, 3×50 mL) and the combined organic phases dried over MgSO$_4$. The organic solvent was evaporated under reduced pressure and the crude reaction product purified with column chromatography on silica eluting with a gradient of dichloromethane/methanol (100:0→95:5) containing 33% of NH$_4$OH to yield 1.05 g (97%) of the title compound. MS (ESI): 361.2 [M+H]$^+$.

Step 2:

According to the procedure described for the synthesis of intermediate T (2-(piperidin-4-ylamino)-benzooxazole-5-carbonitrile)/step 2 the title compound was synthesized from 4-(5-carbamoyl-benzooxazol-2-ylamino)-piperidine-1-carboxylic acid tert-butyl ester using identical conditions in quantitative yield. MS (ESI): 261.0 [M+H]$^+$.

Examples 294 to 307

According to the procedure described for the synthesis of example 37/step 3 further substituted benzooxazole derivatives have been synthesized from benzooxazol-2-yl-piperidin-4-yl-amine dihydrobromide (intermediate D), 2-(piperidin-4-ylamino)-benzooxazole-5-sulfonic acid amide dihydrobromide (intermediate G), oxazolo[5,4-b]pyridin-2-yl-piperidin-4-yl-amine dihydrochloride (intermediate S), 2-(piperidin-4-ylamino)-benzooxazole-5-carbonitrile (intermediate T) and 2-(piperidin-4-ylamino)-benzooxazole-5-carboxylic acid amide (intermediate U) and the respective benzaldehyde as indicated in Table 7. The deproteced piperidines were used either as the free amine, the corresponding dihydrobromide or the corresponding dihydrochloride salt. The results are compiled in Table 7 and comprise example 294 to example 307.

TABLE 7

| No | MW | Name | Starting materials | ISP [M + H]$^+$ or [M − H]$^−$ found |
|---|---|---|---|---|
| 294 | 423.56 | benzooxazol-2-yl-[1-(3,5-diisopropoxy-benzyl)-piperidin-4-yl]-amine | benzooxazol-2-yl-piperidin-4-yl-amine dihydrobromide (intermediate D) and 3,5-diisopropoxy-benzaldehyde (intermediate 53) | 424.3 |
| 295 | 500.62 | 2-[1-(3-cyclopentyloxy-4-methoxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3-cyclopentyloxy-4-methoxy-benzaldehyde (commercially available) | 501.7 |

TABLE 7-continued

| No | MW | Name | Starting materials | ISP [M + H]+ or [M − H]− found |
|---|---|---|---|---|
| 296 | 504.61 | 2-[1-(3,5-diethoxy-4-methoxy-benzyl)-piperidin-4-ylamino]-benzooxazole-5-sulfonic acid amide | 2-(piperidin-4-ylamino)-benzooxazole-5-sulfonic acid amide dihydrobromide (intermediate G) and 3,5-diethoxy-4-methoxy-benzaldehyde (intermediate 54) | 504.5 |
| 297 | 366.46 | [1-(3-ethoxy-4-methyl-benzyl)-piperidin-4-yl]-oxazolo[5,4-b]pyridin-2-yl-amine | oxazolo[5,4-b]pyridin-2-yl-piperidin-4-yl-amine dihydrochloride (intermediate S) and 3-ethoxy-4-methyl-benzaldehyde (intermediate 5) | [M − H]− 365.0 |
| 298 | 386.88 | [1-(4-chloro-3-ethoxy-benzyl)-piperidin-4-yl]-oxazolo[5,4-b]pyridin-2-yl-amine | oxazolo[5,4-b]pyridin-2-yl-piperidin-4-yl-amine dihydrochloride (intermediate S) and 4-chloro-3-ethoxy-benzaldehyde (intermediate 6) | [M − H]− 384.9 |
| 299 | 382.46 | [1-(3-ethoxy-4-methoxy-benzyl)-piperidin-4-yl]-oxazolo[5,4-b]pyridin-2-yl-amine | oxazolo[5,4-b]pyridin-2-yl-piperidin-4-yl-amine dihydrochloride (intermediate S) and 3-ethoxy-4-methoxy-benzaldehyde (commercially available) | [M − H]− 381.1 |
| 300 | 414.48 | [1-(3,5-diethoxy-4-fluoro-benzyl)-piperidin-4-yl]-oxazolo[5,4-b]pyridin-2-yl-amine | oxazolo[5,4-b]pyridin-2-yl-piperidin-4-yl-amine dihydrochloride (intermediate S) and 3,5-diethoxy-4-fluoro-benzaldehyde (intermediate 21) | [M − H]− 413.0 |
| 301 | 411.50 | [1-(4-amino-3,5-diethoxy-benzyl)-piperidin-4-yl]-oxazolo[5,4-b]pyridin-2-yl-amine | oxazolo[5,4-b]pyridin-2-yl-piperidin-4-yl-amine dihydrochloride (intermediate S) and 4-amino-3,5-diethoxy-benzaldehyde (intermediate 23) | [M − H]− 410.1 |
| 302 | 438.50 | 2-[1-(3,5-diethoxy-4-fluoro-benzyl)-piperidin-4-ylamino]-benzooxazole-5-carbonitrile | 2-(piperidin-4-ylamino)-benzooxazole-5-carbonitrile (intermediate T) and 3,5-diethoxy-4-fluoro-benzaldehyde (intermediate 21) | 439.2 |
| 303 | 485.59 | 2-[1-(3,5-diethoxy-4-pyrrol-1-yl-benzyl)-piperidin-4-ylamino]-benzooxazole-5-carbonitrile | 2-(piperidin-4-ylamino)-benzooxazole-5-carbonitrile (intermediate T) and 3,5-diethoxy-4-pyrrol-1-yl-benzaldehyde (intermediate 4) | 486.3 |
| 304 | 487.56 | 2-[1-(3,5-diethoxy-4-[1,2,4]triazol-1-yl-benzyl)-piperidin-4-ylamino]-benzooxazole-5-carbonitrile | 2-(piperidin-4-ylamino)-benzooxazole-5-carbonitrile (intermediate T) and 3,5-diethoxy-4-[1,2,4]triazol-1-yl-benzaldehyde (intermediate 55) | 488.2 |
| 305 | 424.50 | 2-[1-(3-ethoxy-4-methoxy-benzyl)-piperidin-4-ylamino]-benzooxazole-5-carboxylic acid amide | 2-(piperidin-4-ylamino)-benzooxazole-5-carboxylic acid amide (intermediate U) and 3-ethoxy-4-methoxy-benzaldehyde (commercially available) | 425.2 |
| 306 | 456.52 | 2-[1-(3,5-diethoxy-4-fluoro-benzyl)-piperidin-4-ylamino]-benzooxazole-5-carboxylic acid amide | 2-(piperidin-4-ylamino)-benzooxazole-5-carboxylic acid amide (intermediate U) and 3,5-diethoxy-4-fluoro-benzaldehyde (intermediate 21) | 457.2 |
| 307 | 503.60 | 2-[1-(3,5-diethoxy-4-pyrrol-1-yl-benzyl)-piperidin-4-ylamino]-benzooxazole-5-carboxylic acid amide | 2-(piperidin-4-ylamino)-benzooxazole-5-carboxylic acid amide (intermediate U) and 3,5-diethoxy-4-pyrrol-1-yl-benzaldehyde (intermediate 4) | 504.2 |

Example 308

2-[1-(3-Ethoxy-4-methyl-benzyl)-piperidin-4-ylamino]-benzooxazole-7-carboxylic acid methyl ester Step 1:

2-(1-tert-Butoxycarbonyl-piperidin-4-ylamino)-benzooxazole-7-carboxylic acid methyl ester To a solution of 2-chloro-benzooxazole-7-carboxylic acid methyl ester (1.50 g, 7.08 mmol, 1.0 equiv; example 252/step 3) in acetonitrile (23 mL) was added 4-amino-piperidine-1-carboxylic acid tert-butyl ester (1.42 g, 7.08 mmol, 1.0 equiv) and triethylamine (0.79 g, 7.79 mmol, 1.1 equiv). After stirring for 48 h at rt, the reaction mixture was poured on ice, the solution extracted with ethyl acetate (2×100 mL) and the combined organic phases washed with water (2×100 mL) and a conc. solution of sodium chloride (100 mL). The organic phase was dried over $MgSO_4$, concentrated by evaporation under reduced pressure and the crude reaction product purified with column chromatography on silica eluting with hexane/ethyl acetate (1:1) providing 2.27 g (85%) of the title compound. MS (ISP): 376.4 $[M+H]^+$.

Step 2:

2-(Piperidin-4-ylamino)-benzooxazole-7-carboxylic acid methyl ester dihydrotrifluoroacetate (Intermediate V)

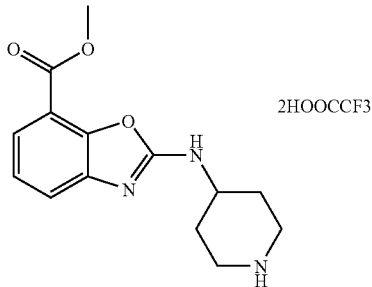

To a solution of 2-(1-tert-butoxycarbonyl-piperidin-4-ylamino)-benzooxazole-7-carboxylic acid methyl ester (2.27 g, 6.05 mmol) in dichloromethane (30 mL) was added trifluoroacetic acid (6.2 mL) and the reaction mixture stirred at rt. After 18 h, volatiles were removed under reduced pressure and the reaction product used in the consecutive step without further purification assuming quantitative deprotection and formation of the dihydrotrifluoroacetate salt. MS (ISP): 276.2 $[M+H]^+$.

Step 3:

To a solution of 2-(piperidin-4-ylamino)-benzooxazole-7-carboxylic acid methyl ester dihydrotrifluoroacetate (100.7 mg, 0.2 mmol, 1.0 equiv) and 3-ethoxy-4-methyl-benzaldehyde (intermediate 5, 32.8 mg, 0.2 mmol, 1.0 equiv) in 2-propanol (2.5 mL) was added titanium(VI) isopropoxide (177.6 μL, 170.5 mg, 0.6 mmol, 3.0 equiv) and sodium cyano borohydride (37.7 mg, 0.6 mmol, 2.0 equiv) and the mixture stirred at rt for 18 h. The crude reaction product was purified with column chromatography on silica eluting with ethyl acetate containing 4% triethylamine to give 25.0 mg (30%) of the title compound. MS (ISP): 424.2 $[M+H]^+$.

The aldehyde intermediates 56 to 60 were prepared following literature precedents or as described below.

Synthesis of Aldehyde Intermediates 56 to 60 to be Used in Table 8

Intermediate 56

4-Chloro-3-(2-fluoro-ethoxy)-benzaldehyde

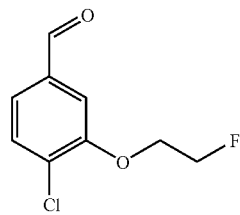

Step 1:

4-Chloro-3-(2-fluoro-ethoxy)-benzoic acid 2-fluoro-ethyl ester

To a solution of 4-chloro-3-hydroxy-benzoic acid (1.04 g, 6.03 mmol, 1.0 equiv) in anhydrous DMF (12 mL) under Ar was added $K_2CO_3$ (2.08 g, 15.07 mmol, 2.5 equiv) and 1-fluoro-2-iodo-ethane (3.67 g, 21.09 mmol, 3.5 equiv) and the mixture stirred at 50° C. for 18 h. The reaction mixture was poured on ice, extracted with ethyl acetate (2×100 mL) and the combined organic phases washed with water (2×100 mL). The organic phase was dried over $Na_2SO_4$, concentrated by evaporation under reduced pressure and the crude reaction product purified with column chromatography on silica eluting with hexane/ethyl acetate (1:3) to give 1.57 g (98%) of the title compound.

Step 2:

[4-Chloro-3-(2-fluoro-ethoxy)-phenyl]-methanol

To a solution of 4-chloro-3-(2-fluoro-ethoxy)-benzoic acid 2-fluoro-ethyl ester (1.57 g, 5.93 mmol, 1.0 equiv) in anhydrous THF (30 mL) was added slowly over a time period of 15 min under cooling to −10° C. a solution of diisobutylaluminium hydride (17.8 mL, 17.80 mmol, 3.0 equiv; 1 M solution in toluene). After 1 h, the reaction mixture was poured on ice, extracted with ethyl acetate (2×100 mL) and the combined organic phases washed with water (2×100 mL). The organic phase was dried over $Na_2SO_4$, concentrated by evaporation under reduced pressure and the crude reaction product purified with column chromatography on silica eluting with hexane/ethyl acetate (2:3) to give 1.19 g (98%) of the title compound.

Step 3:

To a solution of [4-chloro-3-(2-fluoro-ethoxy)-phenyl]-methanol (1.19 g, 5.82 mmol, 1.0 equiv) in dichloromethane (60 mL) was added activated $MnO_2$ (10.1 g, 116.31 mmol, 20.0 equiv). The reaction mixture was stirred vigorously for 6 h at ambient temperature and then filtered through Hyflo Super Cel providing after evaporation of the solvent under reduced pressure 0.91 g (77%) of the title compound. MS (EI): 202.0 $[M]^+$.

Intermediate 57

3-(2-Fluoro-ethoxy)-4-methyl-benzaldehyde

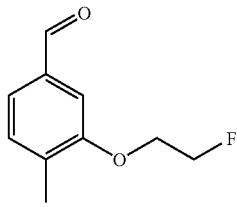

The title compound was prepared according to the procedure described for the synthesis of intermediate 56 (4-chloro-3-(2-fluoro-ethoxy)-benzaldehyde) starting the reaction sequence with 3-hydroxy-4-methyl-benzoic acid instead of 4-chloro-3-hydroxy-benzoic acid. MS (EI): 182.0 $[M]^+$.

Intermediate 58

4-Fluoro-3-(2-fluoro-ethoxy)-benzaldehyde

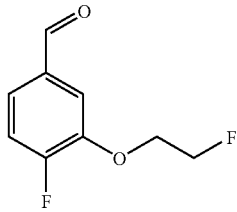

The title compound was prepared according to the procedure described for the synthesis of intermediate 56 (4-chloro-3-(2-fluoro-ethoxy)-benzaldehyde) starting the reaction sequence with 4-fluoro-3-hydroxy-benzoic acid instead of 4-chloro-3-hydroxy-benzoic acid. MS (EI): 186.1 $[M]^+$.

Intermediate 59

Ethoxy-4'-fluoro-biphenyl-4-carbaldehyde

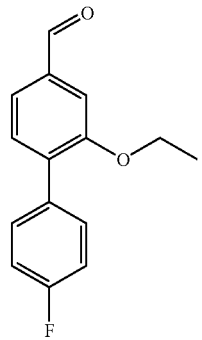

Step 1:

Ethoxy-4'-fluoro-biphenyl-4-carboxylic acid ethyl ester

To a solution of 3-ethoxy-4-iodo-benzoic acid ethyl ester (0.76 g, 2.37 mmol, 1.0 equiv; [CAS RN 741699-04-7], prepared according to WO 04/072 016 A1 (Kissei Pharmaceuticals Co, Ltd.)) in anhydrous DMF (12 mL) under Ar was added 4-fluorophenyl boronic acid (0.40 g, 2.85 mmol, 1.2 equiv), $K_3PO_4$ (0.86 g, 4.04 mmol, 1.7 equiv) and tetrakis (triphenylphosphine) palladium(0) (82.3 mg, 0.071 mmol, 0.03 equiv) and the reaction mixture stirred at 80° C. for 16 h. The reaction mixture was poured on ice, extracted with ethyl acetate (2×100 mL) and the combined organic phases washed with water (2×100 mL). The organic phase was dried over $MgSO_4$, concentrated by evaporation under reduced pressure and the crude reaction product purified with column chromatography on silica eluting with hexane/ethyl acetate (95:5) to give 0.51 g (75%) of the title compound.

Step 2:

(2-Ethoxy-4'-fluoro-biphenyl-4-yl)-methanol

To a solution of 2-ethoxy-4'-fluoro-biphenyl-4-carboxylic acid ethyl ester (0.50 g, 1.73 mmol, 1.0 equiv) in anhydrous THF (10 mL) was added slowly over a time period of 15 min under cooling to −10° C. a solution of diisobutylaluminium hydride (5.2 mL, 5.20 mmol, 3.0 equiv; 1 M solution in hexane). After 1 h, the reaction mixture was poured on ice, the pH adjusted to 4 by addition of a 1 M solution of HCl, the solution extracted with ethyl acetate (2×100 mL) and the combined organic phases washed with water (2×100 mL) and a conc. solution of sodium chloride (100 mL). The organic phase was dried over $MgSO_4$, concentrated by evaporation under reduced pressure to give 0.42 g (99%) of the title compound which was directly used in the consecutive step without further purification.

Step 3:

To a solution of (2-ethoxy-4'-fluoro-biphenyl-4-yl)-methanol (0.42 g, 1.71 mmol, 1.0 equiv) in dichloromethane (20 mL) was added activated $MnO_2$ (2.97 g, 34.11 mmol, 20.0 equiv). The reaction mixture was stirred vigorously for 3 h at ambient temperature and then filtered through Hyflo Super Cel. The organic phase was concentrated by evaporation under reduced pressure and the crude reaction product purified with column chromatography on silica eluting with hexane/ethyl acetate (4:1) providing 0.33 g (79%) of the title compound. MS (EI): 244.1 $[M]^+$.

Intermediate 60

2-Ethoxy-4'-trifluoromethyl-biphenyl-4-carbaldehyde

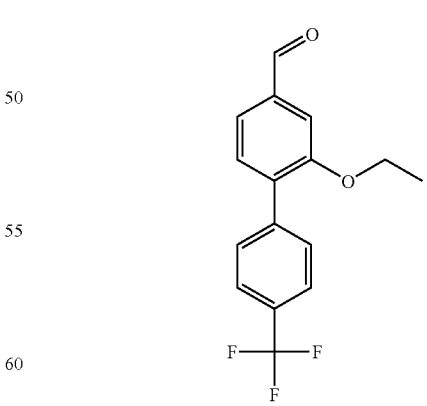

The title compound was prepared according to the procedure described for the synthesis of intermediate 59 (2-ethoxy-4'-fluoro-biphenyl-4-carbaldehyde) using 4-trifluoromethylphenyl boronic acid instead of 4-fluorophenyl boronic acid as the coupling partner in step 1. MS (EI): 294.2 $[M]^+$.

Examples 309 to 317

According to the procedure described for the synthesis of example 308/step 3 further substituted benzooxazole derivatives have been synthesized from 2-(piperidin-4-ylamino)-benzooxazole-7-carboxylic acid methyl ester dihydrotrifluoroacetate (intermediate V) and the respective benzaldehyde as indicated in Table 8. The results are compiled in Table 8 and comprise example 309 to example 317.

TABLE 8

| No | MW | Name | Starting materials | ISP [M + H]+ found |
|---|---|---|---|---|
| 309 | 443.93 | 2-[1-(4-chloro-3-ethoxy-benzyl)-piperidin-4-ylamino]-benzooxazole-7-carboxylic acid methyl ester | 2-(piperidin-4-ylamino)-benzooxazole-7-carboxylic acid methyl ester dihydrotrifluoroacetate (intermediate V) and 4-chloro-3-ethoxy-benzaldehyde (intermediate 6) | 444.2 |
| 310 | 427.47 | 2-[1-(3-ethoxy-4-fluoro-benzyl)-piperidin-4-ylamino]-benzooxazole-7-carboxylic acid methyl ester | 2-(piperidin-4-ylamino)-benzooxazole-7-carboxylic acid methyl ester dihydrotrifluoroacetate (intermediate V) and 3-ethoxy-4-fluoro-benzaldehyde (intermediate 10) | 428.4 |
| 311 | 471.53 | 2-[1-(3,5-diethoxy-4-fluoro-benzyl)-piperidin-4-ylamino]-benzooxazole-7-carboxylic acid methyl ester | 2-(piperidin-4-ylamino)-benzooxazole-7-carboxylic acid methyl ester dihydrotrifluoroacetate (intermediate V) and 3,5-diethoxy-4-fluoro-benzaldehyde (intermediate 21) | 472.0 |
| 312 | 448.52 | 2-[1-(4-ethoxy-1H-indol-6-ylmethyl)-piperidin-4-ylamino]-benzooxazole-7-carboxylic acid methyl ester | 2-(piperidin-4-ylamino)-benzooxazole-7-carboxylic acid methyl ester dihydrotrifluoroacetate (intermediate V) and 4-ethoxy-1H-indole-6-carbaldehyde (intermediate 27) | 449.2 |
| 313 | 461.92 | 2-{1-[4-chloro-3-(2-fluoro-ethoxy)-benzyl]-piperidin-4-ylamino}-benzooxazole-7-carboxylic acid methyl ester | 2-(piperidin-4-ylamino)-benzooxazole-7-carboxylic acid methyl ester dihydrotrifluoroacetate (intermediate V) and 4-chloro-3-(2-fluoro-ethoxy)-benzaldehyde (intermediate 56) | 462.1 |
| 314 | 441.50 | 2-{1-[3-(2-fluoro-ethoxy)-4-methyl-benzyl]-piperidin-4-ylamino}-benzooxazole-7-carboxylic acid methyl ester | 2-(piperidin-4-ylamino)-benzooxazole-7-carboxylic acid methyl ester dihydrotrifluoroacetate (intermediate V) and 3-(2-fluoro-ethoxy)-4-methyl-benzaldehyde (intermediate 57) | 442.2 |
| 315 | 445.46 | 2-{1-[4-fluoro-3-(2-fluoro-ethoxy)-benzyl]-piperidin-4-ylamino}-benzooxazole-7-carboxylic acid methyl ester | 2-(piperidin-4-ylamino)-benzooxazole-7-carboxylic acid methyl ester dihydrotrifluoroacetate (intermediate V) and 4-fluoro-3-(2-fluoro-ethoxy)-benzaldehyde (intermediate 58) | 446.1 |
| 316 | 503.57 | 2-[1-(2-ethoxy-4'-fluoro-biphenyl-4-ylmethyl)-piperidin-4-ylamino]-benzooxazole-7-carboxylic acid methyl ester | 2-(piperidin-4-ylamino)-benzooxazole-7-carboxylic acid methyl ester dihydrotrifluoroacetate (intermediate V) and 2-ethoxy-4'-fluoro-biphenyl-4-carbaldehyde (intermediate 59) | 504.2 |
| 317 | 553.58 | 2-[1-(2-ethoxy-4'-trifluoromethyl-biphenyl-4-ylmethyl)-piperidin-4-ylamino]- | 2-(piperidin-4-ylamino)-benzooxazole-7-carboxylic acid methyl ester dihydrotrifluoroacetate | 554.5 |

TABLE 8-continued

| No | MW | Name | Starting materials | ISP [M + H]+ found |
|---|---|---|---|---|
| | | benzooxazole-7-carboxylic acid methyl ester | (intermediate V) and 2-ethoxy-4'-trifluoromethyl-biphenyl-4-carbaldehyde (intermediate 60) | |

Example 318

2-[1-(3-Ethoxy-4-methyl-benzyl)-piperidin-4-ylamino]-benzooxazole-7-carboxylic acid To a solution of 2-[1-(3-ethoxy-4-methyl-benzyl)-piperidin-4-ylamino]-benzooxazole-7-carboxylic acid methyl ester (22.0 mg, 52.0 mmol, 1.0 equiv; example 308/step 3) in a 1:1 mixture of THF/methanol (0.26 mL) was added a 1 M solution of LiOH in water (0.13 mL, 130.0 mmol, 2.5 equiv). After stirring for 18 h at rt, the pH of the reaction mixture was adjusted to 3.5 by addition of 1 M solution of HCl, the solution extracted with ethyl acetate (2×1 mL) and the combined organic phases washed with water (2×1 mL) and a conc. solution of sodium chloride (1 mL). The organic phase was dried over MgSO$_4$, concentrated by evaporation under reduced pressure and the crude reaction product purified with column chromatography on silica eluting with ethyl acetate/acetone/acetic acid/water (6:2:1:1) providing 21.0 mg (96%) of the title compound. MS (ISP): 410.3 [M+H]+.

Alternatively, after adjusting the pH to approximately 3.5, the reaction mixture is evaporated to dryness, the residue taken up in ethyl acetate, washed with small amounts of brine, and dried. Evaporation of all volatiles leaves then the title compound, not as salt of acetic acid, but as inner salt.

Examples 319 to 324

According to the second procedure described for the synthesis of example 318 further substituted benzooxazole-7-carboxylic acid methyl esters have been hydrolyzed as indicated in Table 9. The results are compiled in Table 9 and comprise example 319 to example 324.

TABLE 9

| No | MW | Name | Starting materials | ISP [M + H]+ found |
|---|---|---|---|---|
| 319 | 429.90 | 2-[1-(4-chloro-3-ethoxy-benzyl)-piperidin-4-ylamino]-benzooxazole-7-carboxylic acid | 2-[1-(4-chloro-3-ethoxy-benzyl)-piperidin-4-ylamino]-benzooxazole-7-carboxylic acid methyl ester (example 309) | 430.3 |
| 320 | 413.45 | 2-[1-(3-ethoxy-4-fluoro-benzyl)-piperidin-4-ylamino]-benzooxazole-7-carboxylic acid | 2-[1-(3-ethoxy-4-fluoro-benzyl)-piperidin-4-ylamino]-benzooxazole-7-carboxylic acid methyl ester (example 310) | 414.3 |
| 321 | 447.89 | 2-{1-[4-chloro-3-(2-fluoro-ethoxy)-benzyl]-piperidin-4-ylamino}-benzooxazole-7-carboxylic acid | 2-{1-[4-chloro-3-(2-fluoro-ethoxy)-benzyl]-piperidin-4-ylamino}-benzooxazole-7-carboxylic acid methyl ester (example 313) | 448.1 |
| 322 | 427.47 | 2-{1-[3-(2-fluoro-ethoxy)-4-methyl-benzyl]-piperidin-4-ylamino}-benzooxazole-7-carboxylic acid | 2-{1-[3-(2-fluoro-ethoxy)-4-methyl-benzyl]-piperidin-4-ylamino}-benzooxazole-7-carboxylic acid methyl ester (example 314) | 428.4 |
| 323 | 431.44 | 2-{1-[4-fluoro-3-(2-fluoro-ethoxy)-benzyl]-piperidin-4-ylamino}-benzooxazole-7-carboxylic acid | 2-{1-[4-fluoro-3-(2-fluoro-ethoxy)-benzyl]-piperidin-4-ylamino}-benzooxazole-7-carboxylic acid methyl ester (example 315) | 432.2 |
| 324 | 489.54 | 2-[1-(2-ethoxy-4'-fluoro-biphenyl-4-ylmethyl)-piperidin-4-ylamino]-benzooxazole-7-carboxylic acid | 2-[1-(2-ethoxy-4'-fluoro-biphenyl-4-ylmethyl)-piperidin-4-ylamino]-benzooxazole-7-carboxylic acid methyl ester (example 316) | 490.3 |

Example 325

Benzooxazol-2-yl-[1-(5-methyl-2-phenyl-1H-imidazol-4-ylmethyl)-piperidin-4-yl]-amine To a solution of benzooxazol-2-yl-piperidin-4-yl-amine (65.2 mg, 0.3 mmol, 1.0 equiv; free amine of intermediate D) and 5-methyl-2-phenyl-3H-imidazole-4-carbaldehyde (61.5 mg, 0.33 mmol, 1.1 equiv; [CAS RN 68282-50-8] prepared as described in L. A. Reiter *J. Org. Chem.* 1987, 52, 2714-2726) in ethanol (2 mL) was added acetic acid (54.1 mg, 0.9 mmol, 3.0 equiv) and the reaction mixture heated under microwave irradiation to 100° C. After 10 min, sodium cyano borohydride (24.5 mg, 0.39 mmol, 1.3 equiv) was added and the mixture heated under microwave irradiation to 100° C. for an additional time period of 20 min. Removal of the solvent under reduced pressure and purification by preparative HPLC on reversed phase eluting with a gradient of acetonitrile/water provided 17.0 mg (15%) of the title compound. MS (ESI): 388.3 [M+H]$^+$.

Example 326

Benzooxazol-2-yl-[1-(5-methyl-2-m-tolyl-1H-imidazol-4-ylmethyl)-piperidin-4-yl]-amine The title compound was prepared according to the procedure described for the synthesis of example 325 (benzooxazol-2-yl-[1-(5-methyl-2-phenyl-1H-imidazol-4-ylmethyl)-piperidin-4-yl]-amine) using 5-methyl-2-m-tolyl-3H-imidazole-4-carbaldehyde ([CAS RN 68283-20-5] prepared as described in U.S. Pat. No. 4,107,307 (American Cyanamid Company)) instead of 5-methyl-2-phenyl-3H-imidazole-4-carbaldehyde. MS (ESI): 402.5 [M+H]$^+$.

Example 327

N-(3-{4-[4-(Benzooxazol-2-ylamino)-piperidin-1-ylmethyl]-5-methyl-1H-imidazol-2-yl}-phenyl)-acetamide Step 1:

N-[3-(5-Hydroxymethyl-4-methyl-1H-imidazol-2-yl)-phenyl]-acetamide

To a solution of N-(3-carbamimidoyl-phenyl)-acetamide hydrochloride (9.75 g, 45.6 mmol, 1.0 equiv; [CAS RN 521269-31-8], prepared according to WO 03/037 327 A1 (Hoffmann-La Roche A G)) in 2-propanol (180 mL) was added butane-2,3-dione (4.91 g, 57.0 mmol, 1.25 equiv). After heating to reflux for 20 h, the solvent was removed by evaporation under reduced pressure, water (20 mL) and 4 M HCl (40 mL) were added and the reaction mixture heated to reflux for an additional time period of 16 h. The reaction mixture was cooled down to rt, concentrated by evaporation under reduced pressure and the crude reaction product purified with column chromatography on silica eluting with dichloromethane/methanol (95:5) to give 2.6 g (23%) of the title compound. MS (ISP): 246.2 [M+H]$^+$.

Step 2:

N-[3-(5-Formyl-4-methyl-1H-imidazol-2-yl)-phenyl]-acetamide

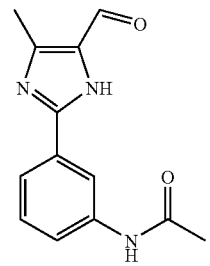

To a solution of N-[3-(5-hydroxymethyl-4-methyl-1H-imidazol-2-yl)-phenyl]-acetamide (0.064 g, 0.23 mmol, 1.0 equiv) in THF (2 mL) was added activated MnO$_2$ (0.20 g, 2.3 mmol, 10.0 equiv). The reaction mixture was stirred vigorously for 18 h at ambient temperature and then filtered through Hyflo Super Cel. The organic phase was concentrated by evaporation under reduced pressure and the crude reaction product directly used in the following reductive alkylation step without further purification assuming quantitative conversion. MS (ESI): 244.3 [M+H]$^+$.

Step 3:

The title compound was prepared according to the procedure described for the synthesis of example 325 (benzooxazol-2-yl-[1-(5-methyl-2-phenyl-1H-imidazol-4-ylmethyl)-piperidin-4-yl]-amine) using N-[3-(5-formyl-4-methyl-1H-imidazol-2-yl)-phenyl]-acetamide instead of 5-methyl-2-phenyl-3H-imidazole-4-carbaldehyde. MS (ESI): 445.3 [M+H]$^+$.

Example 328

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcristalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example 329

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 330

Injection solutions can have the following composition:

| | |
| --- | --- |
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example 331

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 332

Sachets containing the following ingredients can be manufactured in a conventional manner:

| | |
| --- | --- |
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

Example 333

The following tests were carried out in order to determine the activity of the compounds of formula (I).

A CHO cell line stably transfected with a plasmid encoding the human subtype 5 somatostatin receptor (GenBank accession number D16827) was obtained from Euroscreen. Cells were cultured and used for binding and functional assays.

Membranes of these cells were prepared by sonication in the presence of protease inhibitors and subsequent fractionating centrifugation. The protein concentration in the membrane preparation was determined using a commercial kit (BCA kit, Pierce, USA). Membranes were stored at −80° C. until use. After thawing, membranes were diluted in assay buffer (50 mM Tris-HCl at pH 7.4, 5 mM $MgCl_2$ and 0.20% BSA) and subjected to dounce homogenization.

For binding studies, 0.1 mL membrane suspension, corresponding to app. $6 \times 10^{-15}$ mol receptor, was incubated for 1 h at room temperature with 0.05 nM $^{125}$I-labeled tracer (11-Tyr somatostatin-14, Perkin-Elmer) and either test compounds in varying concentrations or, for the determination of non-specific binding, 0.001 mM non-labeled somatostatin-14. The incubation was stopped by filtration through GF/B glassfiber filters and washing with ice-cold wash buffer (50 mM Tris-HCl at pH 7.4). The bound radioactivity was measured after application of a scintillation cocktail (Microscint 40) and expressed as disintegrations per minute (dpm).

The receptor concentration was determined in a prior saturation experiment where a fixed, arbitrary amount of membranes was incubated with a concentration range of radiolabeled tracer. This allows estimating the total number of specific binding sites per amount of protein (i.e., $B_{max}$), typically between 1 and 5 pmol/mg.

The concentration of the test compound required to result in half maximal inhibition of binding of the radio-labeled tracer ($IC_{50}$) was estimated from a concentration-versus-dpm graph. The binding affinity ($K_i$) was calculated from the $IC_{50}$ by applying the Cheng-Prussoff equation for single binding sites.

For functional experiments, 50,000 cells were incubated in Krebs Ringer Hepes buffer (115 mM NaCl, 4.7 mM KCl, 2.56 mM $CaCl_2$, 1.2 mM $KH_2PO_4$, 1.2 mM $MgSO_4$, 20 mM $NaHCO_3$ and 16 mM Hepes, adjusted to pH 7.4) supplemented with 1 mM IBMX and 0.1% BSA, then stimulated with 0.004 mM forskolin. Simultaneously with forskolin, test compounds in varying concentrations were applied. Cells were then incubated for 20 minutes at 37° C. and 5% $CO_2$. Subsequently, cells were lysed and cAMP concentration measured using a fluorescence-based commercial kit according to the manufacturer (HitHunter cAMP, DiscoverX).

The concentration of the test compound to induce a half maximal effect (i.e., $EC_{50}$) as well as the efficacy as compared to 0.15 nM somatostatin-14 were determined from concentration-versus-fluorescence (arbitrary units) graphs. For the determination of potential antagonism, 0.15 nM somatostatin-14 was applied together with the test compounds and the concentration of the test compounds to half maximally reverse the effect of somatostatin-14 (i.e., $IC_{50}$) were deduced from concentration-versus-fluorescence graphs.

The compounds of the present invention exhibit $K_i$ values of 0.1 nM to 10 µM, preferably $K_i$ values of 1 nM to 500 nM and more preferably 0.1 nM to 100 nM for human subtype 5 somatostatin receptor. The following table shows measured values for selected compounds of the present invention.

|  | SSTR5 $K_i$ (nmol/l) |
| --- | --- |
| Example 94 | 59 |
| Example 129 | 4.1 |
| Example 243 | 293 |

It is to be understood that the invention is not limited to the particular embodiments of the invention described above, as variations of the particular embodiments may be made and still fall within the scope of the appended claims.

What is claimed is:

1. A compound of the formula I:

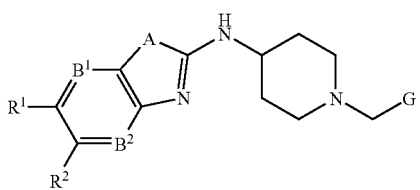

wherein
A is S or O;
$B^1$ is $CR^3$ and $B^2$ is $CR^4$, or
$B^1$ is N and $B^2$ is $CR^4$, or
$B^1$ is $CR^3$ and $B^2$ is N;
one of $R^1$ and $R^2$ is selected from hydrogen or halogen and the other one of $R^1$ and $R^2$ is selected from the group consisting of hydrogen, halogen, cyano, —$NR^5R^6$, —$CONR^7R^8$, —NHCOR$^9$, —$SO_2NR^{10}R^{11}$, —$SO_2R^{12}$, —$NHSO_2R^{13}$, halogen-$C_{1-7}$-alkoxy and nitro;
  $R^5$ and $R^6$ independently from each other are selected from the group consisting of hydrogen, $C_{1-7}$-alkyl and $C_{3-7}$-cycloalkyl;
  $R^7$ is selected from the group consisting of hydrogen, $C_{1-7}$-alkyl and $C_{3-7}$-cycloalkyl;
  $R^8$ is selected from the group consisting of hydrogen, $C_{1-7}$-alkyl, $C_{3-7}$-cycloalkyl, unsubstituted phenyl, phenyl substituted by one to three groups selected from the group consisting of $C_{1-7}$-alkyl, $C_{3-7}$-cycloalkyl, $C_{1-7}$-alkoxy, halogen-$C_{1-7}$-alkyl and halogen, unsubstituted thienyl, thienyl substituted by one or two groups selected from the group consisting of $C_{1-7}$-alkyl and $C_{3-7}$-cycloalkyl, unsubstituted thiazolyl, thiazolyl substituted by one or two groups selected from $C_{1-7}$-alkyl and $C_{3-7}$-cycloalkyl, $C_{1-7}$-alkyl substituted with a group selected from the group consisting of $C_{3-7}$-cycloalkyl, unsubstituted phenyl, phenyl substituted by one to three groups selected from the group consisting of $C_{1-7}$-alkyl, $C_{3-7}$-cycloalkyl, $C_{1-7}$-alkoxy, halogen-$C_{1-7}$-alkyl and halogen, unsubstituted thienyl, thienyl substituted by one or two groups selected from $C_{1-7}$-alkyl and $C_{3-7}$-cycloalkyl, unsubstituted thiazolyl and thiazolyl substituted by one or two groups selected from $C_{1-7}$-alkyl and $C_{3-7}$-cycloalkyl; or
  $R^7$ and $R^8$ together with the nitrogen atom they are attached to form a morpholine ring;
  $R^9$ is selected from the group consisting of $C_{1-7}$-alkyl, $C_{3-7}$-cycloalkyl, halogen-$C_{1-7}$-alkyl unsubstituted phenyl, phenyl substituted by one to three groups selected from the group consisting of $C_{1-7}$-alkyl, $C_{3-7}$-cycloalkyl, $C_{1-7}$-alkoxy, halogen-$C_{1-7}$-alkyl and halogen, unsubstituted heteroaryl, and heteroaryl substituted by one or two groups selected from the group consisting of $C_{1-7}$-alkyl, $C_{3-7}$-cycloalkyl, $C_{1-7}$-alkoxy, halogen-$C_{1-7}$-alkyl and halogen;
  $R^{10}$ and $R^{11}$ independently from each other are selected from the group consisting of hydrogen, $C_{1-7}$-alkyl and $C_{3-7}$-cycloalkyl;
  $R^{12}$ is $C_{1-7}$-alkyl or $C_{3-7}$-cycloalkyl;
  $R^{13}$ is selected from the group consisting of $C_{1-7}$-alkyl, $C_{3-7}$-cycloalkyl, unsubstituted phenyl, phenyl substituted by one to three groups selected from the group consisting of $C_{1-7}$-alkyl, $C_{3-7}$-cycloalkyl, $C_{1-7}$-alkoxy, halogen-$C_{1-7}$-alkyl and halogen, unsubstituted heteroaryl, and heteroaryl substituted by one or two groups selected from the group consisting of $C_{1-7}$-alkyl, $C_{3-7}$-cycloalkyl, $C_{1-7}$-alkoxy, halogen-$C_{1-7}$-alkyl and halogen;
$R^3$ is selected from the group consisting of hydrogen, —$CONR^7R^8$ and —$CO_2R^a$;
$R^a$ is hydrogen or $C_{1-7}$-alkyl;
$R^4$ is hydrogen, and
G is

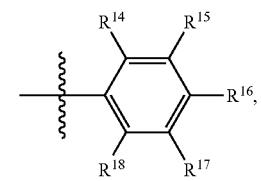
G1

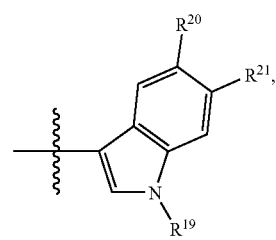
G2

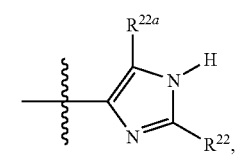
G3

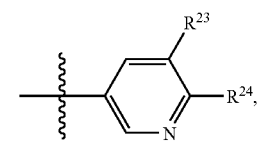
G4

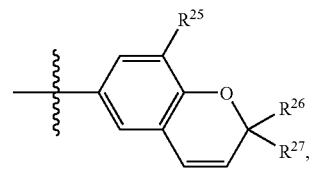
G5

-continued

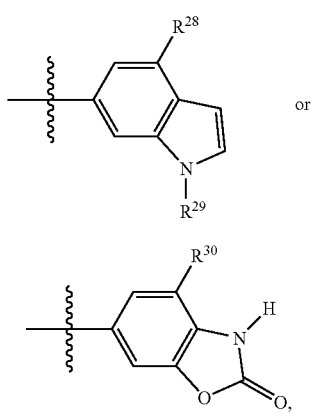

wherein
R$^{14}$ is selected from the group consisting of hydrogen, hydroxy, C$_{1-7}$-alkoxy and halogen;
R$^{15}$ is selected from the group consisting of C$_{1-7}$-alkoxy, C$_{2-7}$-alkenyloxy, C$_{3-7}$-cycloalkyloxy, —NR$^{31}$R$^{32}$, halogen-C$_{1-7}$-alkoxy, C$_{1-7}$-alkoxy-C$_{1-7}$-alkoxy, C$_{1-7}$-alkoxy-C$_{1-7}$-alkyl, and hydrogen, provided that not both of R$^{14}$ and R$^{15}$ are hydrogen;
R$^{31}$ and R$^{32}$ independently from each other are hydrogen or C$_{1-7}$-alkyl;
R$^{16}$ is selected from the group consisting of hydrogen, C$_{1-7}$-alkyl, halogen-C$_{1-7}$-alkyl, hydroxy, C$_{1-7}$-alkoxy, hydroxy-C$_{1-7}$-alkoxy, C$_{3-7}$-cycloalkyloxy, halogen, —NR$^{33}$R$^{34}$, C$_{1-7}$-alkylthio, pyrrolo, triazolo, —CO$_2$R$^{35}$, —NHCOR$^{35}$, —OSO$_2$R$^{35}$, —SOR$^{35}$, —SO$_2$R$^{35}$, unsubstituted phenyl, and phenyl substituted by halogen-C$_{1-7}$-alkyl or halogen;
R$^{33}$ and R$^{34}$ independently from each other are hydrogen or C$_{1-7}$-alkyl;
R$^{35}$ is C$_{1-7}$-alkyl;
or R$^{15}$ and R$^{16}$ together with the carbon atoms to which they are attached to form a phenyl ring;
R$^{17}$ is selected from the group consisting of hydrogen, hydroxy, C$_{1-7}$-alkoxy, halogen-C$_{1-7}$-alkoxy, hydroxy-C$_{1-7}$-alkoxy, nitro, —NR$^{36}$R$^{37}$, —NHCOR$^{38}$, —NHSO$_2$R$^{38}$, —SOR$^{38}$, —SO$_2$R$^{38}$, —O-tetrahydropyranyl, pyridyl, morpholinyl, thiomorpholinyl and 1,1-dioxothiomorpholinyl;
R$^{36}$ and R$^{37}$ independently from each other are hydrogen or C$_{1-7}$-alkyl;
R$^{38}$ is C$_{1-7}$-alkyl;
R$^{18}$ is selected from the group consisting of hydrogen, halogen, pyridyl, hydroxy, C$_{1-7}$-alkoxy and benzyloxy;
or R$^{17}$ and R$^{18}$ together with the carbon atoms to which they are attached to form a phenyl ring;
R$^{19}$ is C$_{1-7}$-alkyl or —CO$_2$R$^{39}$;
R$^{39}$ is C$_{1-7}$-alkyl;
R$^{20}$ and R$^{21}$ independently from each other are hydrogen or C$_{1-7}$-alkoxy;
R$^{22}$ is phenyl unsubstituted or substituted by C$_{1-7}$-alkyl or —NHCOR$^{38}$;
R$^{22a}$ is hydrogen or C$_{1-7}$-alkyl;
R$^{23}$ and R$^{24}$ are hydrogen or C$_{1-7}$-alkoxy, provided that at least one of R$^{23}$ and R$^{24}$ is C$_{1-7}$-alkoxy;
R$^{25}$ is C$_{1-7}$-alkoxy;
R$^{26}$ and R$^{27}$ independently from each other are C$_{1-7}$-alkyl;
R$^{28}$ is C$_{1-7}$-alkoxy;
R$^{29}$ is hydrogen or C$_{1-7}$-alkyl;
R$^{30}$ is C$_{1-7}$-alkoxy;
and pharmaceutically acceptable salts thereof.

2. The compound according to claim 1, wherein
A is S or O;
B$^1$ is CR$^3$ and B$^2$ is CR$^4$, or
B$^1$ is N and B$^2$ is CH, or
B$^1$ is CH and B$^2$ is N;
one of R$^1$ and R$^2$ is selected from hydrogen or halogen and the other one of R$^1$ and R$^2$ is selected from the group consisting of hydrogen, halogen, —NR$^5$R$^6$, —CONR$^7$R$^8$, —NHCOR$^9$, —SO$_2$NR$^{10}$R$^{11}$, —SO$_2$R$^{12}$, —NHSO$_2$R$^{13}$, halogen-C$_{1-7}$-alkoxy and nitro;
R$^5$ and R$^6$ independently from each other are selected from the group consisting of hydrogen, C$_{1-7}$-alkyl and C$_{3-7}$-cycloalkyl;
R$^7$ is selected from the group consisting of hydrogen, C$_{1-7}$-alkyl and C$_{3-7}$-cycloalkyl;
R$^8$ is selected from the group consisting of hydrogen, C$_{1-7}$-alkyl, C$_{3-7}$-cycloalkyl, unsubstituted phenyl or phenyl substituted by one to three groups selected from C$_{1-7}$-alkyl, C$_{3-7}$-cycloalkyl, C$_{1-7}$-alkoxy, halogen-C$_{1-7}$-alkyl or halogen, unsubstituted thienyl or thienyl substituted by one or two groups selected from C$_{1-7}$-alkyl or C$_{3-7}$-cycloalkyl, unsubstituted thiazolyl or thiazolyl substituted by one or two groups selected from C$_{1-7}$-alkyl or C$_{3-7}$-cycloalkyl, C$_{1-7}$-alkyl substituted with a group selected from the group consisting of C$_{3-7}$-cycloalkyl, unsubstituted phenyl or phenyl substituted by one to three groups selected from C$_{1-7}$-alkyl, C$_{3-7}$-cycloalkyl, C$_{1-7}$-alkoxy, halogen-C$_{1-7}$-alkyl or halogen, unsubstituted thienyl or substituted thienyl substituted by one or two groups selected from C$_{1-7}$-alkyl or C$_{3-7}$-cycloalkyl, unsubstituted thiazolyl and thiazolyl substituted by one or two groups selected from C$_{1-7}$-alkyl or C$_{3-7}$-cycloalkyl; or
R$^7$ and R$^8$ together with the nitrogen atom they are attached to form a morpholine ring;
R$^9$ is selected from the group consisting of C$_{1-7}$-alkyl, C$_{3-7}$-cycloalkyl, halogen-C$_{1-7}$-alkyl, unsubstituted phenyl, phenyl substituted by one to three groups selected from the group consisting of C$_{1-7}$-alkyl, C$_{3-7}$-cycloalkyl, C$_{1-7}$-alkoxy, halogen-C$_{1-7}$-alkyl and halogen, unsubstituted heteroaryl and heteroaryl substituted by one or two groups selected from C$_{1-7}$-alkyl, C$_{3-7}$-cycloalkyl, C$_{1-7}$-alkoxy, halogen-C$_{1-7}$-alkyl or halogen;
R$^{10}$ and R$^{11}$ independently from each other are selected from the group consisting of hydrogen, C$_{1-7}$-alkyl and C$_{3-7}$-cycloalkyl;
R$^{12}$ is C$_{1-7}$-alkyl or C$_{3-7}$-cycloalkyl;
R$^{13}$ is selected from the group consisting of C$_{1-7}$-alkyl, C$_{3-7}$-cycloalkyl, unsubstituted phenyl, phenyl substituted by one to three groups selected from C$_{1-7}$-alkyl, C$_{3-7}$-cycloalkyl, C$_{1-7}$-alkoxy, halogen-C$_{1-7}$-alkyl or halogen, unsubstituted heteroaryl and heteroaryl substituted by one or two groups selected from C$_{1-7}$-alkyl, C$_{3-7}$-cycloalkyl, C$_{1-7}$-alkoxy, halogen-C$_{1-7}$-alkyl or halogen;
R$^3$ is hydrogen or —CONR$^7$R$^8$;
R$^4$ is hydrogen, and
G is selected from the groups

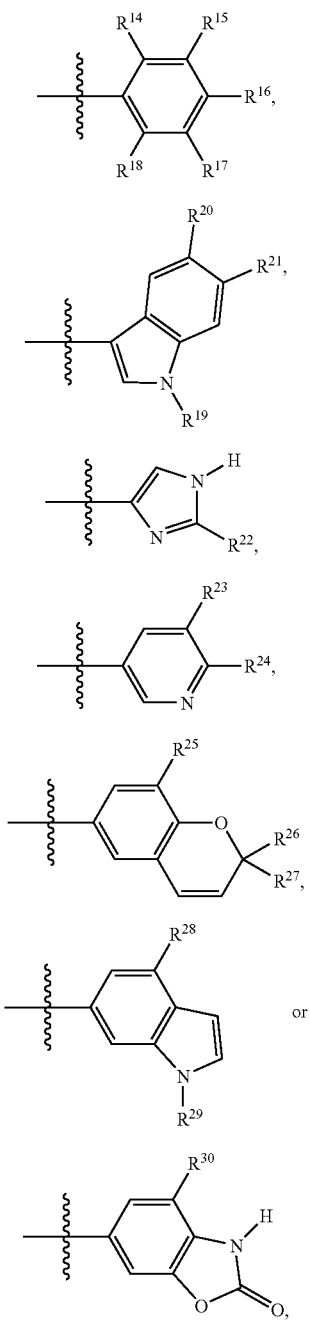

wherein
R$^{14}$ is selected from the group consisting of hydrogen, hydroxy, C$_{1-7}$-alkoxy and halogen;
R$^{15}$ is selected from the group consisting of C$_{1-7}$-alkoxy, C$_{2-7}$-alkenyloxy, C$_{3-7}$-cycloalkyloxy, —NR$^{31}$R$^{32}$, halogen-C$_{1-7}$-alkoxy, C$_{1-7}$-alkoxy-C$_{1-7}$-alkoxy, C$_{1-7}$-alkoxy-C$_{1-7}$-alkyl, and hydrogen, provided that not both of R$^{14}$ and R$^{15}$ are hydrogen;
R$^{31}$ and R$^{32}$ independently from each other are hydrogen or C$_{1-7}$-alkyl;
R$^{16}$ is selected from the group consisting of hydrogen, C$_{1-7}$-alkyl, halogen-C$_{1-7}$-alkyl, hydroxy, C$_{1-7}$-alkoxy, hydroxy-C$_{1-7}$-alkoxy, C$_{3-7}$-cycloalkyloxy, halogen, —NR$^{33}$R$^{34}$, C$_{1-7}$-alkylthio, pyrrolo, —CO$_2$R$^3$, —NHCOR$^{35}$, —OSO$_2$R$^{35}$, —SOR$^{35}$ and —SO$_2$R$^{35}$;
R$^{33}$ and R$^{34}$ independently from each other are hydrogen or C$_{1-7}$-alkyl;
R$^{35}$ is C$_{1-7}$-alkyl;
or R$^{15}$ and R$^{16}$ together with the carbon atoms to which they are attached to form a phenyl ring;
R$^{17}$ is selected from the group consisting of hydrogen, hydroxy, C$_{1-7}$-alkoxy, halogen-C$_{1-7}$-alkoxy, hydroxy-C$_{1-7}$-alkoxy, nitro, —NR$^{36}$R$^{37}$, —NHCOR$^{38}$, —NHSO$_2$R$^{38}$, —SOR$^{38}$, —SO$_2$R$^{38}$—O-tetrahydropyranyl, pyridyl, morpholinyl, thiomorpholinyl and 1,1-dioxothiomorpholinyl;
R$^{36}$ and R$^{37}$ independently from each other are hydrogen or C$_{1-7}$-alkyl;
R$^{31}$ is C$_{1-7}$-alkyl;
R$^{18}$ is selected from the group consisting of hydrogen, halogen, pyridyl, hydroxy, C$_{1-7}$-alkoxy and benzyloxy;
or R$^{17}$ and R$^{18}$ together with the carbon atoms to which they are attached to form a phenyl ring;
R$^{19}$ is C$_{1-7}$-alkyl or —CO$_2$R$^{39}$;
R$^{39}$ is C$_{1-7}$-alkyl;
R$^{20}$ and R$^{21}$ independently from each other are hydrogen or C$_{1-7}$-alkoxy,
R$^{22}$ is phenyl;
R$^{23}$ and R$^{24}$ are hydrogen or C$_{1-7}$-alkoxy, provided that at least one of R$^{23}$ and R$^{24}$ is C$_{1-7}$-alkoxy;
R$^{25}$ is C$_{1-7}$-alkoxy;
R$^{26}$ and R$^{27}$ independently from each other are C$_{1-7}$-alkyl;
R$^{28}$ is C$_{1-7}$-alkoxy;
R$^{29}$ is hydrogen or C$_{1-7}$-alkyl;
R$^{30}$ is C$_{1-7}$-alkoxy;
and pharmaceutically acceptable salts thereof.

3. The compound according to claim 1, wherein A is O.

4. The compound according to claim 1, wherein A is S.

5. The compound according to claim 1, wherein B$^1$ is CR$^3$ and B$^2$ is CR$^4$ and wherein R$^3$ is hydrogen or —CONR$^7$R$^8$ and R$^4$ is hydrogen.

6. The compound according to claim 1, wherein B$^1$ is CR$^3$ and B$^2$ is CR$^4$ and wherein R$^4$ is hydrogen and R$^3$ is —CO$_2$R$^a$ with R$^a$ being hydrogen or C$_{1-7}$-alkyl.

7. The compound according to claim 1, wherein R$^3$ and R$^4$ are hydrogen.

8. The compound according to claim 1, wherein B$^1$ is N and B$^2$ is CH.

9. The compound according to claim 1, wherein B$^1$ is CH and B$^2$ is N.

10. The compound according to claim 1, wherein R$^1$ and R$^2$ are hydrogen.

11. The compound according to claim 1, wherein one of R$^1$ and R$^2$ is selected from hydrogen or halogen and the other one of R$^1$ and R$^2$ is selected from the group consisting of —NHCOR$^9$, —SO$_2$NR$^{10}$R$^{11}$, —SO$_2$R$^{12}$, and —NHSO$_2$R$^{13}$.

12. The compound according to claim 1, wherein one of R$^1$ and R$^2$ is selected from hydrogen or halogen and the other one of R$^1$ and R$^2$ is —CONR$^7$R$^8$.

13. The compound according to claim 1, wherein G is

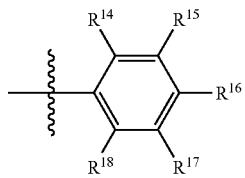

and wherein
R$^{14}$ is selected from the group consisting of hydrogen, hydroxy, C$_{1-7}$-alkoxy and halogen;
R$^{15}$ is selected from the group consisting of C$_{1-7}$-alkoxy, C$_{2-7}$-alkenyloxy, C$_{3-7}$-cycloalkyloxy, —NR$^{31}$R$^{32}$, halogen-C$_{1-7}$-alkyl, C$_{1-7}$-alkoxy-C$_{1-7}$-alkoxy, C$_{1-7}$-alkoxy-C$_{1-7}$-alkyl, and hydrogen, provided that not both of R$^{14}$ and R$^{15}$ are hydrogen;
R$^{31}$ and R$^{32}$ independently from each other are hydrogen or C$_{1-7}$-alkyl;
R$^{16}$ is selected from the group consisting of hydrogen, C$_{1-7}$-alkyl, halogen-C$_{1-7}$-alkyl, hydroxy, C$_{1-7}$-alkoxy, hydroxy-C$_{1-7}$-alkoxy, C$_{3-7}$-cycloalkyloxy, halogen, —NR$^{33}$R$^{34}$, C$_{1-7}$-alkylthio, pyrrolo, [1,2,4]triazolo, —CO$_2$R$^{35}$, —NHCOR$^{35}$, —OSO$_2$R$^{31}$, —SOR$^{35}$, —SO$_2$R$^{35}$, unsubstituted phenyl, and phenyl substituted by halogen-C$_{1-7}$-alkyl or halogen;
R$^{33}$ and R$^{34}$ independently from each other are hydrogen or C$_{1-7}$-alkyl;
R$^{35}$ is C$_{1-7}$-alkyl;
or R$^{15}$ and R$^{16}$ together with the carbon atoms to which they are attached to form a phenyl ring;
R$^{17}$ is selected from the group consisting of hydrogen, hydroxy, C$_{1-7}$-alkoxy, halogen-C$_{1-7}$-alkoxy, hydroxy-C$_{1-7}$-alkoxy, nitro, —NR$^{36}$R$^{37}$, —NHCOR$^{38}$, —NHSO$_2$R$^{38}$, —SOR$^{38}$, —SO$_2$R$^{38}$, —O-tetrahydropyranyl, pyridyl, morpholinyl, thiomorpholinyl and 1,1-dioxothiomorpholinyl;
R$^{36}$ and R$^{37}$ independently from each other are hydrogen or C$_{1-7}$-alkyl;
R$^{38}$ is C$_{1-7}$-alkyl;
R$^{18}$ is selected from the group consisting of hydrogen, halogen, pyridyl, hydroxy, C$_{1-7}$-alkoxy and benzyloxy;
or R$^{17}$ and R$^{18}$ together with the carbon atoms to which they are attached to form a phenyl ring.

14. The compound according to claim 1, wherein R$^{16}$ is selected from the group consisting of hydrogen, C$_{1-7}$-alkyl, halogen-C$_{1-7}$-alkyl, hydroxy, C$_{1-7}$-alkoxy, hydroxy-C$_{1-7}$-alkoxy, C$_{3-7}$-cycloalkyloxy, halogen, —NR$^{33}$R$^{34}$, C$_{1-7}$-alkylthio, pyrrolo, —CO$_2$R$^{35}$, —NHCOR$^{35}$, —OSO$_2$R$^{35}$, —SOR$^{35}$ and —SO$_2$R$^{35}$.

15. The compound according to claim 1, wherein R$^{14}$ is hydrogen.

16. The compound according to claim 1, wherein R$^{15}$ is selected from the group consisting of C$_{1-7}$-alkoxy, C$_{2-7}$-alkenyloxy, C$_{3-7}$-cycloalkyloxy, halogen-C$_{1-7}$-alkoxy, hydroxy-C$_{1-7}$-alkoxy and C$_{1-7}$-alkoxy-C$_{1-7}$-alkyl.

17. The compound according to claim 1, wherein R$^{15}$ is C$_{1-7}$-alkoxy.

18. The compound according to claim 1, wherein R$^{15}$ is ethoxy.

19. The compound according to claim 1, wherein R$^{16}$ is selected from the group consisting of hydrogen, C$_{1-7}$-alkyl, halogen-C$_{1-7}$-alkyl, C$_{1-7}$-alkoxy, halogen, —NR$^{33}$R$^{34}$ and pyrrolo, and R$^{33}$ and R$^{34}$ independently from each other are hydrogen or —C$_{1-7}$-alkyl.

20. The compound according to claim 1, wherein R$^{16}$ is pyrrolo.

21. The compound according to claim 1, wherein R$^{17}$ is selected from the group consisting of hydrogen, C$_{1-7}$-alkoxy and —O-tetrahydropyranyl.

22. The compound according to claim 1, wherein R$^{18}$ is hydrogen or pyridyl.

23. The compound according to claim 1, wherein G is

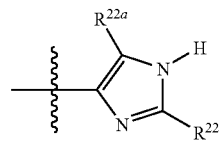

and wherein R$^{22}$ is phenyl unsubstituted or substituted by C$_{1-7}$-alkyl or —NHCOR$^{38}$ and R$^{22a}$ is hydrogen or C$_{1-7}$-alkyl.

24. The compound according to claim 1, selected from the group consisting of [1-(4-chloro-3-ethoxy-benzyl)-piperidin-4-yl]-thiazolo[5,4-b]pyridin-2-yl-amine,
benzooxazol-2-yl-[1-(3-ethoxy-4-methoxy-benzyl)-piperidin-4-yl]-amine,
benzooxazol-2-yl-{1-[3-ethoxy-5-(tetrahydro-pyran-4-yloxy)-benzyl]-piperidin-4-yl}-amine,
benzooxazol-2-yl-[1-(3,5-diethoxy-4-fluoro-benzyl)-piperidin-4-yl]-amine,
benzooxazol-2-yl-[1-(2-phenyl-3H-imidazol-4-ylmethyl)-piperidin-4-yl]-amine,
2-[1-(3-ethoxy-4-methyl-benzyl)-piperidin-4-ylamino]-benzooxazole-5-sulfonic acid amide,
2-[1-(3-ethoxy-4-fluoro-benzyl)-piperidin-4-ylamino]-benzooxazole-5-sulfonic acid amide,
2-[1-(3-ethoxy-4-trifluoromethyl-benzyl)-piperidin-4-ylamino]-benzooxazole-5-sulfonic acid amide,
2-[1-(3-ethoxy-4-methoxy-benzyl)-piperidin-4-ylamino]-benzooxazole-5-sulfonic acid amide,
2-[1-(3,5-diethoxy-4-fluoro-benzyl)-piperidin-4-ylamino]-benzooxazole-5-sulfonic acid amide,
2-[1-(4-amino-3,5-diethoxy-benzyl)-piperidin-4-ylamino]-benzooxazole-5-sulfonic acid amide,
2-[1-(3,5-diethoxy-4-pyrrol-1-yl-benzyl)-piperidin-4-ylamino]-benzooxazole-5-sulfonic acid amide,
5-chloro-2-[1-(4-chloro-3-ethoxy-benzyl)-piperidin-4-ylamino]-benzooxazole-6-sulfonic acid amide,
5-chloro-2-[1-(3-ethoxy-4-trifluoromethyl-benzyl)-piperidin-4-ylamino]-benzooxazole-6-sulfonic acid amide,
[1-(4-chloro-3-ethoxy-benzyl)-piperidin-4-yl]-(5-ethanesulfonyl-benzooxazol-2-yl)-amine,
[1-(4-chloro-3-ethoxy-benzyl)-piperidin-4-yl]-oxazolo[4,5-b]pyridin-2-yl-amine,
[1-(3,5-diethoxy-benzyl)-piperidin-4-yl]-oxazolo[4,5-b]pyridin-2-yl-amine,
[1-(3,5-diethoxy-4-pyrrol-1-yl-benzyl)-piperidin-4-yl]-oxazolo[4,5-b]pyridin-2-yl-amine,
(5-ethanesulfonyl-benzooxazol-2-yl)-[1-(5-ethoxy-4-methoxy-2-pyridin-4-yl-benzyl)-piperidin-4-yl]-amine,
3,5-dimethyl-isoxazole-4-sulfonic acid{2-[1-(3-ethoxy-4-methoxy-benzyl)-piperidin-4-ylamino]-benzooxazol-5-yl}-amide,
2-[1-(3-ethoxy-4-methoxy-benzyl)-piperidin-4-ylamino]-benzooxazole-7-carboxylic acid (4-methyl-thiazol-2-yl)-amide,
2-[1-(3-ethoxy-4-methoxy-benzyl)-piperidin-4-ylamino]-benzooxazole-7-carboxylic acid (5-methyl-thiazol-2-yl)-amide, cyclobutanecarboxylic acid{2-[1-(3-ethoxy-4-methyl-benzyl)-piperidin-4-ylamino]-benzooxazol-5-yl}-amide,
1-methyl-1H-imidazole-4-sulfonic acid{2-[1-(4-chloro-3-ethoxy-benzyl)-piperidin-4-ylamino]-benzooxazol-5-yl}-amide,
benzooxazol-2-yl-[1-(3,5-diisopropoxy-benzyl)-piperidin-4-yl]-amine,
[1-(4-chloro-3-ethoxy-benzyl)-piperidin-4-yl]-oxazolo[5,4-b]pyridin-2-yl-amine,
2-[1-(3,5-diethoxy-4-fluoro-benzyl)-piperidin-4-ylamino]-benzooxazole-5-carboxylic acid amide,
and pharmaceutically acceptable salts thereof.

25. The compound according to claim 1, selected from the group consisting of 2-[1-(3-ethoxy-4-methyl-benzyl)-piperidin-4-ylamino]-benzooxazole-5-sulfonic acid amide,
2-[1-(3-ethoxy-4-fluoro-benzyl)-piperidin-4-ylamino]-benzooxazole-5-sulfonic acid amide,
2-[1-(3-ethoxy-4-trifluoromethyl-benzyl)-piperidin-4-ylamino]-benzooxazole-5-sulfonic acid amide,
2-[1-(3,5-diethoxy-4-fluoro-benzyl)-piperidin-4-ylamino]-benzooxazole-5-sulfonic acid amide,
2-[1-(4-amino-3,5-diethoxy-benzyl)-piperidin-4-ylamino]-benzooxazole-5-sulfonic acid amide,
2-[1-(3,5-diethoxy-4-pyrrol-1-yl-benzyl)-piperidin-4-ylamino]-benzooxazole-5-sulfonic acid amide,
[1-(3,5-diethoxy-4-pyrrol-1-yl-benzyl)-piperidin-4-yl]-oxazolo[4,5-b]pyridin-2-yl-amine,
cyclobutanecarboxylic acid{2-[1-(3-ethoxy-4-methyl-benzyl)-piperidin-4-ylamino]-benzooxazol-5-yl}-amide,
1-methyl-1H-imidazole-4-sulfonic acid{2-[1-(4-chloro-3-ethoxy-benzyl)-piperidin-4-ylamino]-benzooxazol-5-yl}-amide,
benzooxazol-2-yl-[1-(3,5-diisopropoxy-benzyl)-piperidin-4-yl]-amine,
[1-(4-chloro-3-ethoxy-benzyl)-piperidin-4-yl]-oxazolo[5,4-b]pyridin-2-yl-amine,
2-[1-(3,5-diethoxy-4-fluoro-benzyl)-piperidin-4-ylamino]-benzooxazole-5-carboxylic acid amide,
and pharmaceutically acceptable salts thereof.

26. A process for the manufacture of a compound according to claim 1, comprising the steps of:

reacting a compound of the general formula

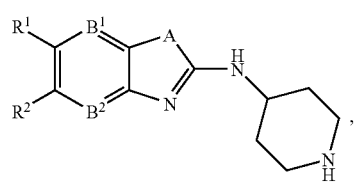

wherein A, $B^1$, $B^2$, $R^1$ and $R^2$ are as defined in claim 1, with an aldehyde of the formula

wherein G is as defined in claim 1, by employing a reducing agent to obtain a compound of the formula

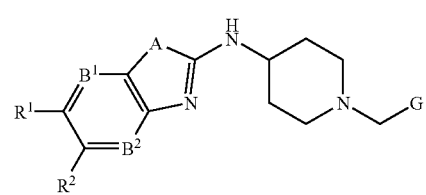

and, if desired, converting the compound of formula I into a pharmaceutically acceptable salt.

27. A pharmaceutical composition, comprising a therapeutically effective amount of a compound according to claim 1 and a pharmaceutically acceptable carrier and/or adjuvant.

* * * * *

UNITED STATES PATENT AND TRADEMARK OFFICE
CERTIFICATE OF CORRECTION

PATENT NO. : 7,645,753 B2  Page 1 of 1
APPLICATION NO. : 11/366516
DATED : January 12, 2010
INVENTOR(S) : Alfred Binggeli et al.

It is certified that error appears in the above-identified patent and that said Letters Patent is hereby corrected as shown below:

In Column 168, Claim 2, Line 1, please delete

"-$NR^{33}R^{34}$, $C_{1-7}$-alkylthio, pyrrolo, -$CO_2R^3$, -NH –"

And insert

-- -$NR^{33}R^{34}$, $C_{1-7}$-alkylthio, pyrrolo, -$CO_2R^{35}$, -NH – --

Signed and Sealed this

Fifteenth Day of June, 2010

David J. Kappos
*Director of the United States Patent and Trademark Office*